United States Patent
Hopkins et al.

(10) Patent No.: US 10,961,237 B2
(45) Date of Patent: *Mar. 30, 2021

(54) INHIBITING AGENTS FOR BRUTON'S TYROSINE KINASE

(71) Applicant: BIOGEN MA INC., Cambridge, MA (US)

(72) Inventors: Brian T. Hopkins, Newton, MA (US); Bin Ma, Arlington, MA (US); Robin Prince, Sharon, MA (US); Isaac Marx, Arlington, MA (US); Joseph P. Lyssikatos, Piedmont, CA (US); Fengmei Zheng, Quincy, MA (US); Matthew Peterson, Hopkinton, MA (US); Daniel B. Patience, Arlington, MA (US)

(73) Assignee: BIOGEN MA INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/534,540

(22) Filed: Aug. 7, 2019

(65) Prior Publication Data

US 2020/0239459 A1 Jul. 30, 2020

Related U.S. Application Data

(63) Continuation of application No. 16/246,986, filed on Jan. 14, 2019, now abandoned, which is a continuation of application No. 15/952,505, filed on Apr. 13, 2018, now Pat. No. 10,227,341.

(60) Provisional application No. 62/485,745, filed on Apr. 14, 2017.

(51) Int. Cl.
| | | |
|---|---|---|
| *C07D 417/14* | (2006.01) |
| *C07D 403/14* | (2006.01) |
| *C07D 413/14* | (2006.01) |
| *C07D 405/14* | (2006.01) |
| *C07D 471/04* | (2006.01) |
| *A61P 43/00* | (2006.01) |
| *A61P 1/16* | (2006.01) |

(52) U.S. Cl.
CPC ............ *C07D 417/14* (2013.01); *A61P 1/16* (2018.01); *A61P 43/00* (2018.01); *C07D 403/14* (2013.01); *C07D 405/14* (2013.01); *C07D 413/14* (2013.01); *C07D 471/04* (2013.01); *C07B 2200/13* (2013.01)

(58) Field of Classification Search
CPC .. C07D 417/14; C07D 403/14; C07D 405/14; C07D 413/14; C07D 471/04; A61P 43/00
See application file for complete search history.

(56) References Cited

U.S. PATENT DOCUMENTS

| | | |
|---|---|---|
| 9,809,577 B2 | 11/2017 | Hopkins et al. |
| 10,081,619 B2 | 9/2018 | Hopkins et al. |
| 10,189,829 B2 | 1/2019 | Hopkins et al. |
| 10,227,341 B2 | 3/2019 | Hopkins et al. |
| 2011/0009421 A1 | 1/2011 | Setoh et al. |
| 2016/0096834 A1 | 4/2016 | Gaillard et al. |
| 2016/0311802 A1 | 10/2016 | Hopkins et al. |
| 2019/0218204 A1 | 7/2019 | Hopkins et al. |

FOREIGN PATENT DOCUMENTS

| | | |
|---|---|---|
| WO | 2009/158571 A1 | 12/2009 |
| WO | 2011/090760 A1 | 7/2011 |
| WO | 2014/130856 A2 | 8/2014 |
| WO | 2015/061247 A2 | 4/2015 |

OTHER PUBLICATIONS

International Search Report and Written Opinion for Application No. PCT/US2018/027415 dated Jun. 11, 2018, 13 pages.

*Primary Examiner* — Rebecca L Anderson
(74) *Attorney, Agent, or Firm* — McCarter & English, LLP; Steven G. Davis; Xin Zhang

(57) ABSTRACT

Provided are compounds of Formula (I), or pharmaceutically acceptable salts thereof, and methods for their use and production.

6 Claims, 6 Drawing Sheets

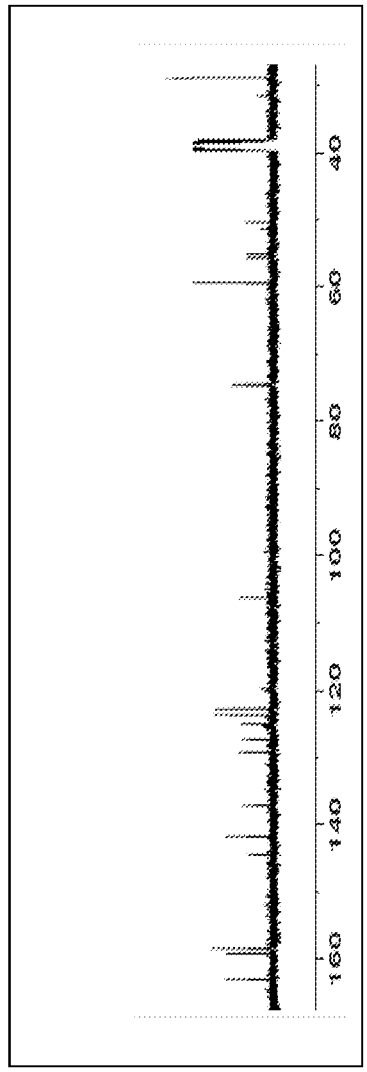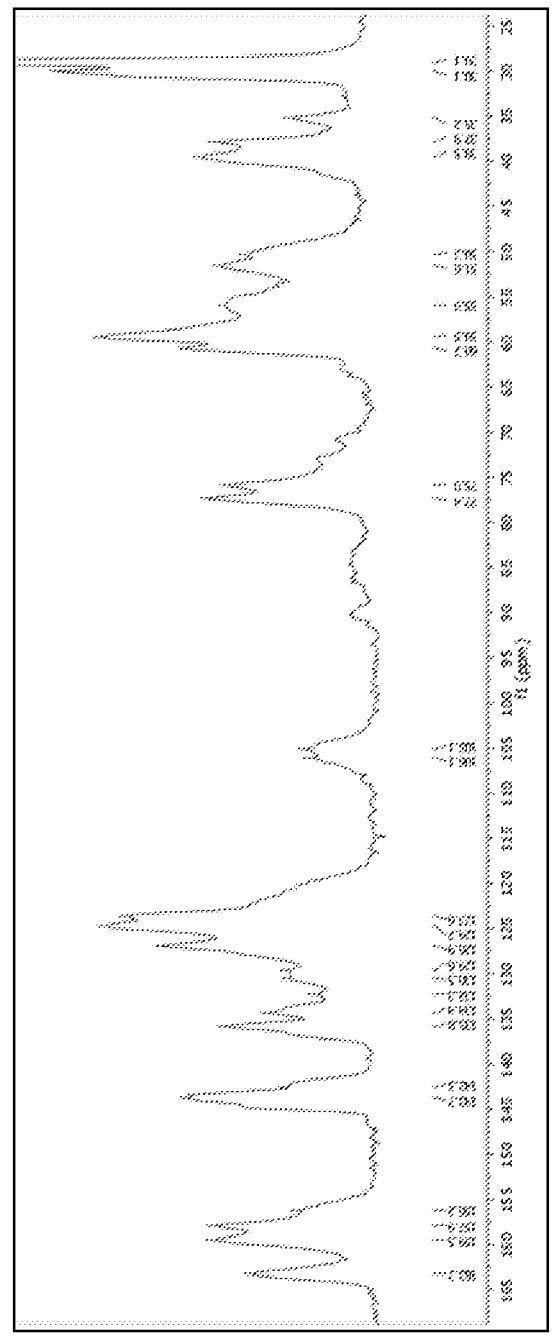
FIG. 3A
FIG. 3B

INHIBITING AGENTS FOR BRUTON'S TYROSINE KINASE

RELATED APPLICATIONS

This application is a continuation of U.S. patent application Ser. No. 16/246,986, filed Jan. 14, 2019, which is a continuation of U.S. patent application Ser. No. 15/952,505, filed Apr. 13, 2018, now U.S. Pat. No. 10,227,341, which claims the benefit of the filing date, under 35 U.S.C. § 119(e), of U.S. Provisional Application No. 62/485,745, filed on Apr. 14, 2017. The entire contents of each of the above-referenced applications are incorporated herein by reference.

TECHNICAL FIELD

Provided are certain agents that inhibit Bruton's tyrosine kinase (Btk), and methods of making and using such agents.

BACKGROUND

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)) and are primarily expressed in haematopoietic cells, although expression of Bmx and Tec has been detected in endothelial and liver cells. Tec kinases (Itk, Rlk and Tec) are expressed in T cell and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCy), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors of Btk.

SUMMARY

A first embodiment of the invention is a compound of Formula (I):

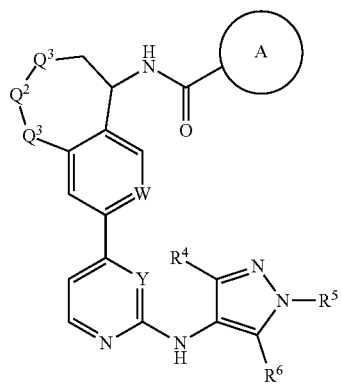

Formula (I)

or a pharmaceutically acceptable salt, wherein:

Ring A is 5-membered monocyclic heteroaryl containing 3 heteroatoms independently selected from N, O and S, wherein said 5-membered monocyclic heteroaryl is optionally substituted with one or more $R^1$;

$Q^1$, $Q^2$, and $Q^3$ are each, independently, selected from O, N($R^2$), and CH—$R^3$, wherein at least two of $Q^1$, $Q^2$, and $Q^3$ are C—$R^3$;

W is selected from CH and N;

Y is selected from CH and N;

$R^1$ in each occurrence is independently selected from $C_{1-6}$alkyl and 3- to 5-membered carbocyclyl, wherein said $C_{1-6}$alkyl and 3- to 5-membered carbocyclyl are optionally substituted with one or more $R^{10}$;

$R^{10}$ in each occurrence is independently selected from halo, —CN, $C_{1-6}$alkyl, and 3- to 5-membered carbocyclyl;

$R^2$ is selected from H, $C_{1-6}$alkyl, $C_{2-6}$alkenyl, $C_{2-6}$alkynyl, 4- to 6-membered monocyclic carbocyclyl, 4- to 6-membered monocyclic heterocyclyl, —CN, —C(O)$R^{2a}$, —C(O)$_2R^{2a}$, —C(O)N($R^{2a}$)$_2$, —S(O)$_2R^{2a}$, and —S(O)$_2$N($R^{2a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl are optionally substituted with one or more $R^{20}$;

$R^{2a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{20}$;

$R^{20}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{20a}$, —C(O)$_2R^{20a}$, —C(O)N($R^{20a}$)$_2$, —N($R^{20a}$)$_2$, —N($R^{20a}$)C(O)$R^{20a}$, —N($R^{20a}$)C(O)$_2 R^{20a}$, —N($R^{20a}$)C(O)N($R^{20a}$)$_2$, —N($R^{20a}$)S(O)$_2R^{20a}$, —O$R^{20a}$, —OC(O)$R^{20a}$, —OC(O)N($R^{20a}$)$_2$, —S$R^{20a}$, —S(O)$R^{20a}$, —S(O)$_2R^{20a}$, —S(O)N($R^{20a}$)$_2$, and —S(O)$_2$N($R^{20a}$)$_2$;

$R^{20a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^3$ is selected from H, $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{3a}$, —C(O)$_2R^{3a}$, —C(O)N($R^{3a}$)$_2$, —N($R^{3a}$)$_2$, —N($R^{3a}$)C (O)R$^{3a}$, —N(R$^{3a}$)C(O)$_2$R$^{3a}$, —N(R$^{3a}$)C(O)N(R$^{3a}$)$_2$, —N(R$^{3a}$)S(O)$_2$R$^{3a}$, —OR$^{3a}$, —OC(O)R$^{3a}$, —OC(O)N(R$^{3a}$)$_2$, —SR$^{3a}$, —S(O)R$^{3a}$, —S(O)$_2$R$^{3a}$, —S(O)N(R$^{3a}$)$_2$, and —S(O)$_2$N(R$^{3a}$)$_2$, wherein said C$_{1-6}$alkyl, C$_{2-6}$alkenyl, C$_{2-6}$alkynyl, 4- to 6-membered monocyclic carbocyclyl, and 4- to 6-membered monocyclic heterocyclyl are optionally substituted with one or more R$^{30}$;

R$^{3a}$ in each occurrence is independently selected from H, C$_{1-6}$alkyl, C$_{2-6}$alkenyl, C$_{2-6}$alkynyl, 4- to 6-membered monocyclic carbocyclyl, and 4- to 6-membered monocyclic heterocyclyl, wherein said C$_{1-6}$alkyl, C$_{2-6}$alkenyl, C$_{2-6}$alkynyl, 4- to 6-membered monocyclic carbocyclyl, and 4- to 6-membered monocyclic heterocyclyl in each occurrence are optionally and independently substituted with one or more R$^{30}$;

R$^{30}$ in each occurrence is independently selected from C$_{1-6}$alkyl, C$_{2-6}$alkenyl, C$_{2-6}$alkynyl, 4- to 6-membered monocyclic carbocyclyl, 4- to 6-membered monocyclic heterocyclyl, halo, —CN, —C(O)R$^{30a}$, —C(O)$_2$R$^{30a}$, —C(O)N(R$^{30a}$)$_2$, —N(R$^{30a}$)$_2$, —N(R$^{30a}$)C(O)R$^{30a}$, —N(R$^{30a}$)C(O)$_2$R$^{30a}$, —N(R$^{30a}$)C(O)N(R$^{30a}$)$_2$, —N(R$^{30a}$)S(O)$_2$R$^{30a}$, —OR$^{30a}$, —OC(O)R$^{30a}$, —OC(O)N(R$^{30a}$)$_2$, —SR$^{30a}$, —S(O)R$^{30a}$, —S(O)$_2$R$^{30a}$, —S(O)N(R$^{30a}$)$_2$, and —S(O)$_2$N(R$^{30a}$)$_2$;

R$^{30a}$ in each occurrence is independently selected from H, C$_{1-6}$alkyl, C$_{2-6}$alkenyl, C$_{2-6}$alkynyl, 4- to 6-membered monocyclic carbocyclyl, and 4- to 6-membered monocyclic heterocyclyl;

R$^4$ is selected from H and C$_{1-6}$alkyl, wherein said C$_{1-6}$alkyl is optionally substituted with one or more halo;

R$^5$ is selected from H and C$_{1-6}$alkyl wherein said C$_{1-6}$alkyl is optionally substituted with one or more halo;

R$^6$ is selected from H and C$_{1-6}$alkyl, wherein said C$_{1-6}$alkyl is optionally substituted with one or more halo;

or R$^5$ and R$^6$, together with the atoms to which they are attached, form a ring containing one or two heteroatoms selected from O, N, and S, wherein the ring is optionally substituted with one or more R$^{50}$; and R$^{50}$ is C$_{1-6}$alkyl.

The present invention also provides a pharmaceutical composition comprising at least one compound described herein, or a pharmaceutically acceptable salt thereof, and at least one pharmaceutically acceptable excipient.

In one embodiment, the invention is a method of treating a disorder responsive to inhibition of Btk in a subject comprising administering to said subject an effective amount of at least one compound described herein, or a pharmaceutically acceptable salt thereof.

The present invention also includes the use of at least one compound described herein, or a pharmaceutically acceptable salt thereof, for the manufacture of a medicament for the treatment of a disorder responsive to inhibition of Btk. Also provided is a compound described herein, or a pharmaceutically acceptable salt thereof for use in treating a disorder responsive to inhibition of Btk.

Other features or advantages will be apparent from the following detailed description of several embodiments, and also from the appended claims.

BRIEF DESCRIPTION OF THE FIGURES

FIG. 3A shows solution $^{13}$C NMR spectrum of crystalline Form A of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. FIG. 3B shows solid state $^{13}$NMR spectrum of crystalline Form A.

DETAILED DESCRIPTION

Figure 1:
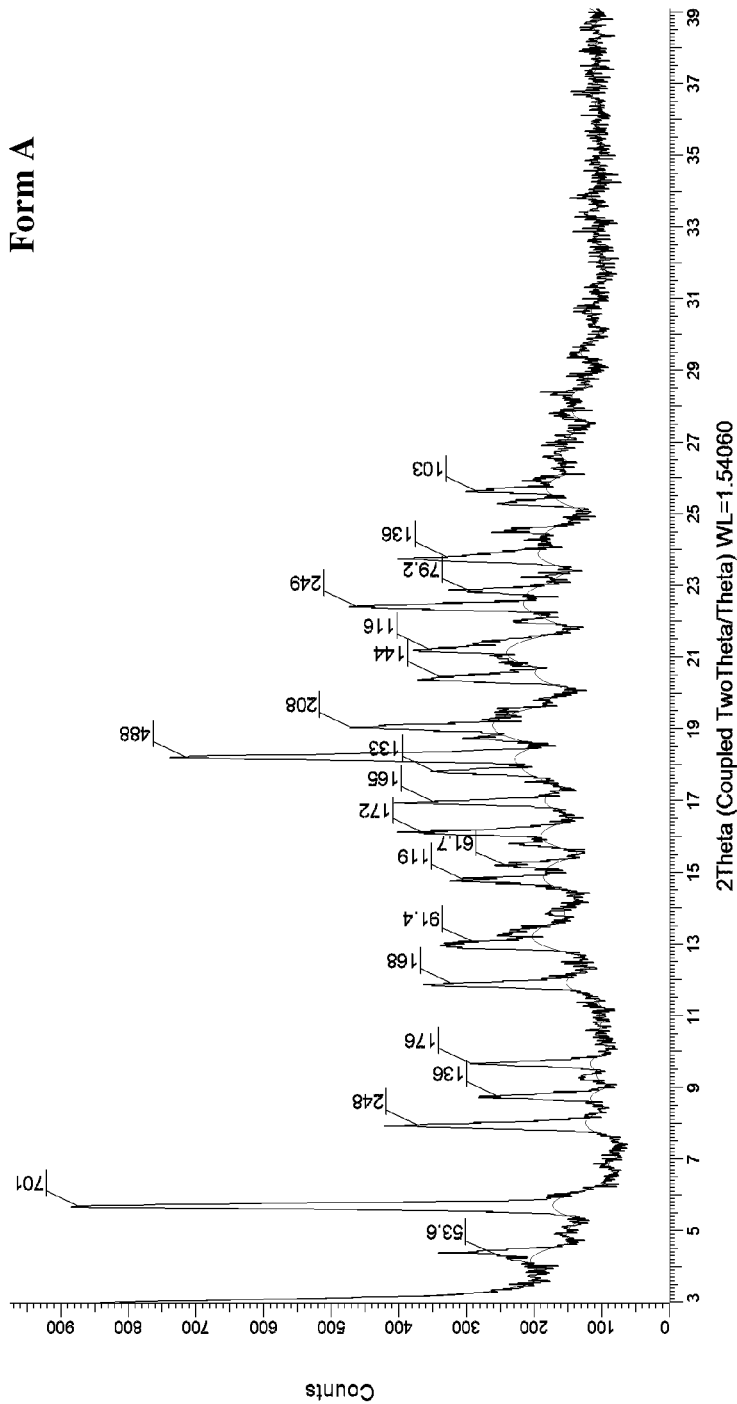
FIG. 1 depicts an powder X-ray diffraction (PXRD) pattern of crystalline Form A of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

The compounds or pharmaceutically acceptable salts thereof as described herein, can have activity as Btk modulators. In particular, compounds or pharmaceutically acceptable salts thereof as described herein, can be Btk inhibitors.

In a second embodiment of the present invention, the compound is represented by formula (I), or a pharmaceutically acceptable salt thereof, wherein Q$^1$, Q$^2$ and Q$^3$ are each independently CH—R$^3$ and the definitions for the other variables are as defined in the first embodiment.

In a third embodiment of the present invention, the compound is represented by formula (I), or a pharmaceutically acceptable salt thereof, wherein Q$^2$ is N(R$^2$), Q$^1$ and Q$^3$ are each independently CH—R$^3$, and the definitions for the other variables are as defined in the first embodiment.

In a fourth embodiment of the present invention, the compound is represented by formula (I), or a pharmaceutically acceptable salt thereof, wherein Q$^3$ is N(R$^2$), Q$^1$ and Q$^2$ are each independently CH—R$^3$, and the definitions for the other variables are as defined in the first embodiment.

In a fifth embodiment of the present invention, the compound is represented by formula (I), or a pharmaceutically acceptable salt thereof, wherein Q$^1$ is O, Q$^2$ and Q$^3$ are each independently CH—R$^3$; and the definitions for the other variables are as defined in the first embodiment.

In a sixth embodiment of the present invention, the compound is represented by formula (I), or a pharmaceutically acceptable salt thereof, W is CH; and the definitions for the other variables are as defined in the first, second, third, fourth or fifth embodiment.

In a seventh embodiment of the present invention, the compound is represented by formula (I), or a pharmaceutically acceptable salt thereof, wherein Y is N; and the definitions for the other variables are as defined in the first, second, third, fourth, fifth or sixth embodiment.

In an eighth embodiment of the present invention, the compound of the present invention is represented by any one of the following formulas:

(II)
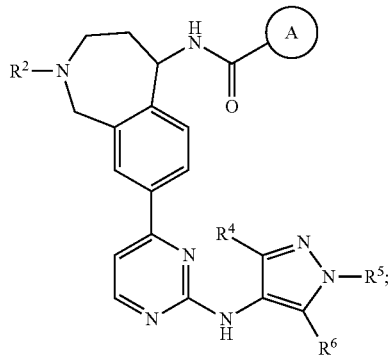

(III)
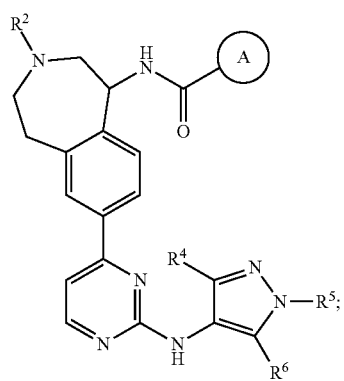

(IV)
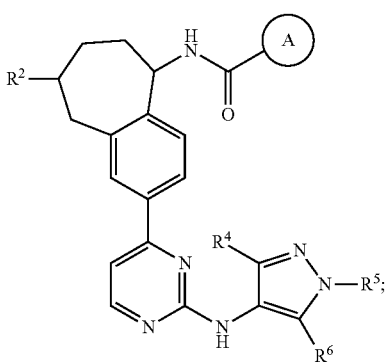

(V)
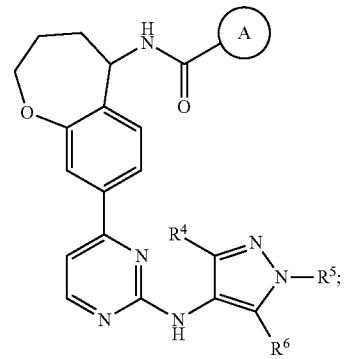

(II')
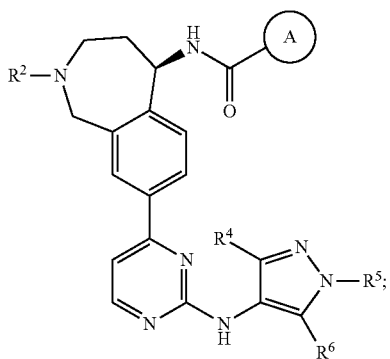

(III')
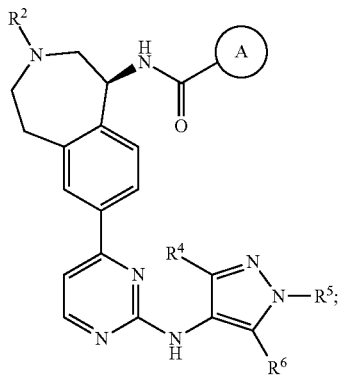

(IV')
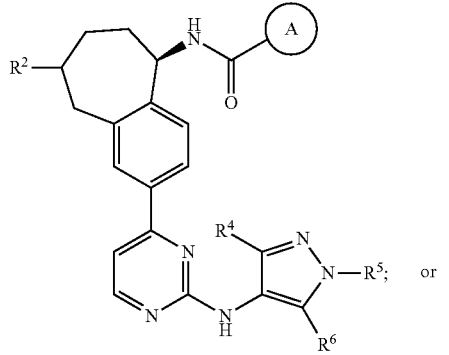

or (V')
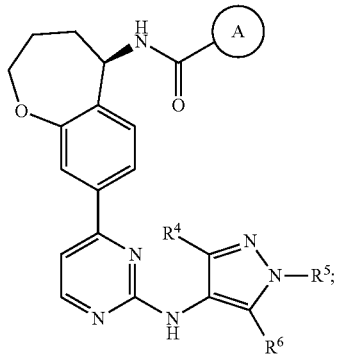

or a pharmaceutically acceptable salt thereof; and the definitions for the variables are as defined in the first embodiment.

In a ninth embodiment of the present invention, the compound is represented by formula (I), (II), (III), (IV), (V), (II'), (III'), (IV') or (V'), or a pharmaceutically acceptable salt thereof, wherein ring A is selected from 1,2,3-oxadiazole, 1,3,4-oxadiazole, 1,2,4-oxadiazole, 1,2,3-thiadiazole, 1,3,4-thiadiazole, 1,2,4-thiadiazole, 1,2,3-triazole, and 1,2,4-triazole, each of which is optionally substituted with one or two $R^1$; and the definitions for the other variables are as defined in the first, second, third, fourth, fifth, sixth, seventh or eighth embodiment.

In a tenth embodiment of the present invention, the compounds is represented by formula (I), (II), (III), (IV), (V), (II'), (III'), (IV') or (V'), or a pharmaceutically acceptable salt thereof, wherein ring A is represented by one of the following formula:

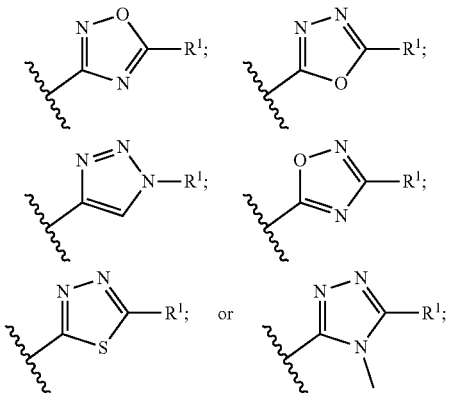

and the definitions for the other variables are as defined in the first, second, third, fourth, fifth, sixth, seventh or eighth embodiment.

In a eleventh embodiment of the present invention, the compound is represented by formula (I), (II), (III), (IV), (V), (II'), (III'), (IV') or (V'), or a pharmaceutically acceptable salt thereof, wherein:

$R^1$ in each occurrence is independently $C_{1-6}$alkyl or $C_{3-5}$cycloalkyl; wherein said $C_{1-6}$alkyl and $C_{3-5}$cycloalkyl are optionally substituted with one to three $R^{10}$;

$R^{10}$ in each occurrence is independently selected from halo, —CN and $C_{1-6}$alkyl; and the definitions for the other variables are as defined in the first, second, third, fourth, fifth, sixth, seventh, eighth, ninth or tenth embodiment.

In a twelfth embodiment of the present invention, the compound is represented by formula (I), (II), (III), (IV), (V), (II'), (III'), (IV') or (V'), or a pharmaceutically acceptable salt thereof, wherein:

$R^1$ in each occurrence is independently $C_{1-4}$alkyl, cyclopropyl, or cyclobutyl; wherein said $C_{1-4}$alkyl, cyclopropyl and cyclobutyl are optionally substituted with one to three $R^{10}$;

$R^{10}$ in each occurrence is independently selected from halo, —CN and $C_{1-3}$alkyl; and the definitions for the other variables are as defined in the first, second, third, fourth, fifth, sixth, seventh, eighth, ninth or tenth embodiment.

In a thirteenth embodiment of the present invention, the compound is represented by formula (I), (II), (III), (IV), (V), (II'), (III'), (IV') or (V'), or a pharmaceutically acceptable salt thereof, wherein:

$R^1$ in each occurrence is independently selected from $C(CH_3)_3$, —$CH(CH_3)_2$, —$C(CH_3)_2CHF_2$, —$C(CH_3)_2CF_3$, —$C(CH_3)_2CH_2F$, —$C(CH_3)_2CN$, 1-methylcyclopropyl, cyclobutyl, and 3,3-difluorocyclobutyl; and the definitions for the other variables are as defined in the first, second, third, fourth, fifth, sixth, seventh, eighth, ninth or tenth embodiment.

In a fourteenth embodiment of the present invention, the compound is represented by formula (I), (II), (III), (IV), (V), (II'), (III'), (IV') or (V'), or a pharmaceutically acceptable salt thereof, wherein $R^1$ is —$C(CH_3)_3$; and the definitions for the other variables are as defined in the first, second, third, fourth, fifth, sixth, seventh, eighth, ninth or tenth embodiment.

In a fifteenth embodiment of the present invention, the compound is represented by formula (I), (II), (III), (IV), (V), (II'), (III'), (IV') or (V'), or a pharmaceutically acceptable salt thereof, wherein:

$R^2$ is selected from H, $C_{1-6}$alkyl, $C_{4-6}$cycloalkyl, saturated 4- to 6-membered monocyclic heterocyclyl, —$C(O)R^{2a}$, —$C(O)_2R^{2a}$, and —$S(O)_2R^{2a}$, wherein said $C_{1-6}$alkyl, $C_{4-6}$cycloalkyl, and saturated 4- to 6-membered monocyclic heterocyclyl are optionally substituted with one to three $R^{20}$;

$R^{2a}$ in each occurrence is independently selected from H, $C_{1-6}$alkyl, $C_{4-6}$alkyl, and saturated 4- to 6-membered monocyclic heterocyclyl, wherein said $C_{1-6}$alkyl, 4- to 6-membered monocyclic carbocyclyl, and saturated 4- to 6-membered monocyclic heterocyclyl in each occurrence are optionally and independently substituted with one or more $R^{20}$;

$R^{20}$ in each occurrence is independently selected from $C_{1-6}$alkyl, $C_{4-6}$cycloalkyl, saturated 4- to 6-membered monocyclic heterocyclyl, halo, —CN, —$N(R^{20a})_2$, and —$OR^{20a}$;

$R^{20a}$ in each occurrence is independently H or $C_{1-6}$alkyl; and the definitions for the other variables are as defined in the first, second, third, fourth, fifth, sixth, seventh, eighth, ninth, tenth, eleventh, twelfth, thirteenth or fourteen embodiment.

In a sixteenth embodiment, the compound is represented by formula (I), (II), (III), (IV), (V), (II'), (III'), (IV') or (V'), or a pharmaceutically acceptable salt thereof, wherein:

$R^2$ is selected from H, $C_{1-6}$alkyl, $C_{4-6}$cycloalkyl selected from cyclobutyl, cyclopentyl and cyclohexyl, saturated 4- to 6-membered monocyclic heterocyclyl selected from azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, and dioxanyl, —$C(O)R^{2a}$, —$C(O)_2R^{2a}$, and —$S(O)_2R^{2a}$, wherein said $C_{1-6}$alkyl, $C_{4-6}$cycloalkyl and saturated 4- to 6-membered monocyclic heterocyclyl are optionally substituted with one to three $R^{20}$;

$R^{2a}$ is $C_{1-6}$alkyl optionally and independently substituted with one to three $R^{20}$;

$R^{20}$ in each occurrence is independently selected from $C_{1-3}$alkyl, cyclopropyl, cyclobutyl, cyclopentyl, cyclohexyl, halo, —$N(R^{20a})_2$, and —$OR^{20a}$;

$R^{20a}$ in each occurrence is independently H or $C_{1-3}$alkyl; and the definitions for the other variables are as defined in the first, second, third, fourth, fifth, sixth, seventh, eighth, ninth, tenth, eleventh, twelfth, thirteenth, fourteen or fifteenth embodiment.

In a seventeenth embodiment of the present invention, the compound is represented by formula (I), (II), (III), (IV), (V), (II'), (III'), (IV') or (V'), or a pharmaceutically acceptable salt thereof, wherein:

$R^2$ is selected from H, $C_{1-6}$alkyl, cyclobutyl, cyclopentyl and cyclohexyl, oxetanyl, tetrahydrofuranyl, tetrahydropyranyl, —$C(O)R^{2a}$, —$C(O)_2R^{2a}$, and —$S(O)_2R^{2a}$, wherein said $C_{1-6}$alkyl, cyclobutyl, cyclopentyl and cyclohexyl, oxetanyl, tetrahydrofuranyl, and tetrahydropyranyl are optionally substituted with one to three $R^{20}$;

$R^{2a}$ is $C_{1-6}$alkyl optionally substituted with one $R^{20}$;

$R^{20}$ in each occurrence is independently selected from $C_{1-3}$alkyl, cyclopropyl, cyclobutyl, cyclopentyl, cyclohexyl, halo, $-N(R^{20a})_2$, and $-OR^{20a}$;

$R^{20a}$ in each occurrence is independently H or methyl; the definitions for the other variables are as defined in the first, second, third, fourth, fifth, sixth, seventh, eighth, ninth, tenth, eleventh, twelfth, thirteenth, fourteen or fifteenth embodiment.

In a eighteenth embodiment of the present invention, the compound is represented by formula (I), (II), (III), (IV), (V), (II'), (III'), (IV') or (V'), or a pharmaceutically acceptable salt thereof, wherein $R^2$ is selected from $-H$, $-SO_2CH_3$, $-C(=O)OC(CH_3)_3$, $-C(=O)CH_2N(CH_3)_2$, $-CH_3$, $-CH_2CH_3$, $-CH_2CH_2OH$, $-CH_2CH_2OCH_3$, $-CH_2CH_2OCH_2CH_3$, $-CH_2CH(CH_3)OH$, $-CH_2C(CH_3)_2OH$, $-CH_2CH_2CH_2OH$, $-CH_2CHF_2$, $-CH_2CF_3$,

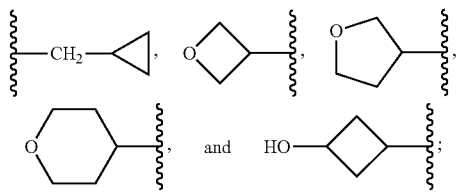

and the definitions for the other variables are as defined in the first, second, third, fourth, fifth, sixth, seventh, eighth, ninth, tenth, eleventh, twelfth, thirteenth, fourteen or fifteenth embodiment.

In a nineteenth embodiment of the present invention, the compound is represented by formula (I), (II), (III), (IV), (V), (II'), (III'), (IV') or (V'), or a pharmaceutically acceptable salt thereof, wherein $R^2$ is selected from $-CH_2CHF_2$, $-CH_2CF_3$, $-CH_2CH_2OH$, $-CH_2CH(CH_3)OH$, $-CH_2CH_2OCH_3$,

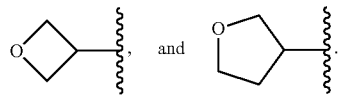 [SMILES: *C1COC1 ; *C1CCOC1]

In a twentieth embodiment of the present invention, the compound is represented by formula (I), (II), (III), (IV), (V), (II'), (III'), (IV') or (V'), or a pharmaceutically acceptable salt thereof, wherein:

$R^3$ is selected from H, $C_{1-6}$alkyl, $C_{4-6}$cycloalkyl, saturated 4- to 6-membered monocyclic heterocyclyl, halo, $-OR^{3a}$, $-OC(O)R^{3a}$, $-OC(O)N(R^{3a})_2$, and $-SR^{3a}$, wherein said $C_{1-6}$alkyl, $C_{4-6}$cycloalkyl, and saturated 4- to 6-membered monocyclic heterocyclyl are optionally substituted with one to three $R^{30}$;

$R^{3a}$ in each occurrence is independently H or $C_{1-6}$alkyl, wherein said $C_{1-6}$alkyl in each occurrence is optionally and independently substituted with one $R^{30}$;

$R^{30}$ in each occurrence is independently selected from $C_{1-6}$alkyl;

and the definitions for the other variables are as defined in the first, second, third, fourth, fifth, sixth, seventh, eighth, ninth, tenth, eleventh, twelfth, thirteenth, fourteen, fifteenth, seventeenth, eighteenth, or nineteenth embodiment.

In a twenty-first embodiment of the present invention, the compound is represented by formula (I), (II), (III), (IV), (V), (II'), (III'), (IV') or (V'), or a pharmaceutically acceptable salt thereof, wherein $R^3$ is selected from H, halo, and $-OR^{3a}$; $R^{3a}$ is independently H or $C_{1-3}$alkyl; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, or nineteenth embodiment.

In a twenty-second embodiment of the present invention, the compound is represented by formula (I), (II), (III), (IV), (V), (II'), (III'), (IV') or (V'), or a pharmaceutically acceptable salt thereof, wherein $R^3$ is selected from H, $-F$ and OH; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, or nineteenth embodiment.

In a twenty-third embodiment of the present invention, the compound is represented by formula (I), (II), (III), (IV), (V), (II'), (III'), (IV') or (V'), or a pharmaceutically acceptable salt thereof, wherein $R^4$ is H or $C_{1-3}$alkyl optionally substituted with one to three fluoro; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first or twenty-second embodiment.

In a twenty-fourth embodiment of the present invention, the compound is represented by formula (I), (II), (III), (IV), (V), (II'), (III'), (IV') or (V'), or a pharmaceutically acceptable salt thereof, wherein $R^4$ is H or methyl; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first or twenty-second embodiment.

In a twenty-fifth embodiment of the present invention, the compound is represented by formula (I), (II), (III), (IV), (V), (II'), (III'), (IV') or (V'), or a pharmaceutically acceptable salt thereof, wherein $R^5$ is H or $C_{1-3}$alkyl optionally substituted with one to three fluoro; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first, twenty-second, twenty-third or twenty-fourth embodiment.

In a twenty-sixth embodiment of the present invention, the compound is represented by formula (I), (II), (III), (IV), (V), (II'), (III'), (IV') or (V'), or a pharmaceutically acceptable salt thereof, wherein $R^5$ is H, methyl, ethyl or isopropyl; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first, twenty-second, twenty-third or twenty-fourth embodiment.

In a twenty-seventh embodiment of the present invention, the compound is represented by formula (I), (II), (III), (IV), (V), (II'), (III'), (IV') or (V'), or a pharmaceutically acceptable salt thereof, wherein $R^6$ is H or $C_{1-3}$alkyl optionally substituted with one to three fluoro; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first, twenty-second, twenty-third, twenty-fourth, twenty-fifth or twenty-sixth embodiment.

In a twenty-eighth embodiment of the present invention, the compound is represented by formula (I), (II), (III), (IV), (V), (II'), (III'), (IV') or (V'), or a pharmaceutically acceptable salt thereof, wherein $R^6$ is H, methyl or trifluoromethyl;

and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first, twenty-second, twenty-third, twenty-fourth, twenty-fifth or twenty-sixth embodiment.

In a twenty-ninth embodiment of the present invention, the compound is represented by formula (I), (II), (III), (IV), (V), (II'), (III'), (IV') or (V'), or a pharmaceutically acceptable salt thereof, wherein $R^5$ and $R^6$ together with the atoms to which they are attached, form a 5- to 6-membered saturated heterocyclic ring containing one or two heteroatoms selected from O, N, and S, wherein the ring is optionally substituted with one $R^{50}$; $R^{50}$ is a $C_{1-3}$alkyl; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first, twenty-second, twenty-third, or twenty-fourth embodiment. In a more specific embodiment, the 5- to 6-membered saturated heterocyclic ring heterocyclic ring is pyrrolidine, piperazine or N-methylpiperazine.

In a thirtieth embodiment of the present invention, the compound is represented by the following formula:

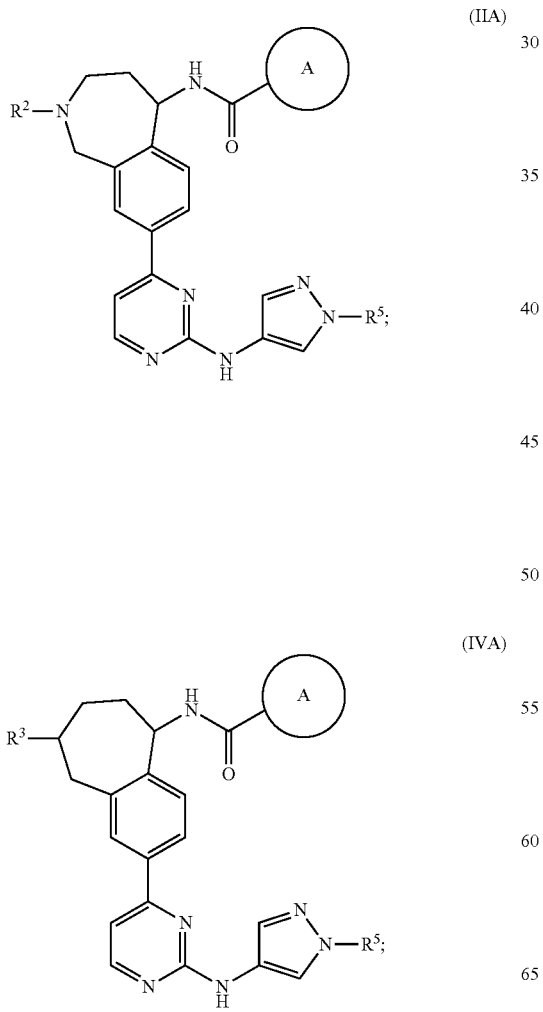
(IIA)

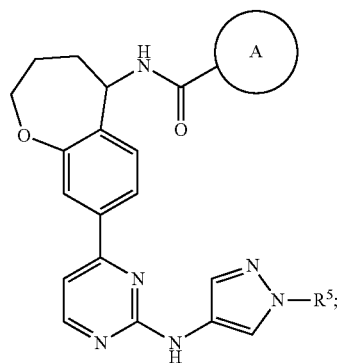
(VA)

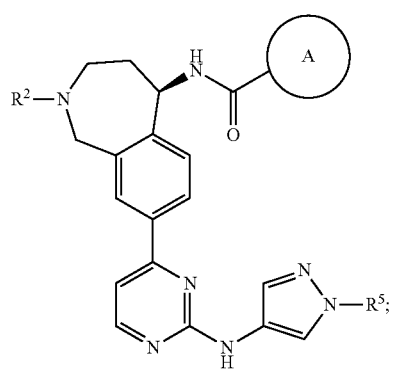
(IIA')

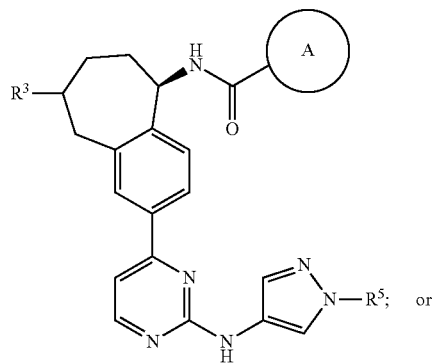
(IVA')

or

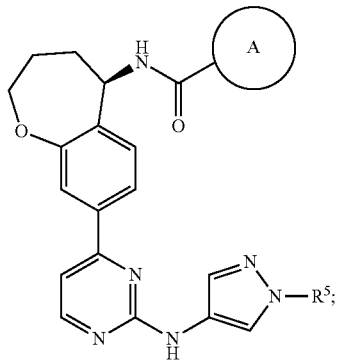
(VA')

or a pharmaceutically acceptable salt thereof, wherein:
ring A is represented by one of the following formula:

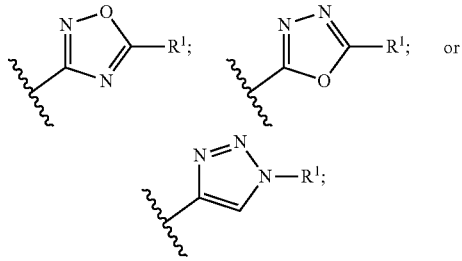

R¹ is $C_{1-6}$alkyl;
R² is $C_{1-6}$alkyl, oxetanyl, tetrahydrofuranyl, or tetrahydropyranyl, wherein said $C_{1-6}$alkyl is optionally substituted with one to three $R^{20}$;
$R^{20}$ for each occurrence is independently halo or —$OR^{20a}$;
$R^{20a}$ H or $C^{1-3}$alkyl;
R³ is H; and
R⁵ is H or $C_{1-3}$alkyl.

In a thirty-first embodiment of the present invention, the compound is represented by formula (IIA), (IVA), (VA), (IIA'), (IVA'), or (VA'), or a pharmaceutically acceptable salt thereof, wherein R¹ is tert-butyl; and the definitions for the other variables are as defined in the thirtieth embodiment.

In a thirty-second embodiment of the present invention, the compound is represented by formula (IIA) or (IIA'), or a pharmaceutically acceptable salt thereof, wherein R² is

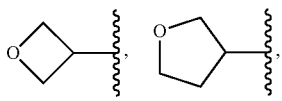

—CH₂CHF₂, —CH₂CF₃, —CH₂CH₂OH, —CH₂CH₂OCH₃, or —CH₂C(CH₃)OH; and the definitions for the other variables are as defined in the thirtieth or thirty-first embodiment.

In a thirty-third embodiment of the present invention, the compound is represented by formula (IVA) to (IVA'), or a pharmaceutically acceptable salt thereof, wherein R³ is H; and the definitions for the other variables are as defined in the thirtieth, or thirty-first embodiment.

In a thirty-fourth embodiment of the present invention, the compound is represented by formula (IIA), (IVA), (VA), (IIA'), (IVA'), or (VA'), or a pharmaceutically acceptable salt thereof, wherein R⁵ is methyl or isopropyl; and the definitions for the other variables are as defined in the thirtieth, thirty-first, thirty-second or thirty-third embodiment.

In a thirty-fifth embodiment of the present invention, the compound of the present invention is selected from:
5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,2,4-oxadiazole-3-carboxamide,
(S)-5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,2,4-oxadiazole-3-carboxamide,
(R)-5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,2,4-oxadiazole-3-carboxamide,
5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide,
(R)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide,
(S)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide,
5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide,
(R)-5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide,
(S)-5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide,
5-(tert-butyl)-N-(8-(2-((1-methyl-1H-pyrazol-4-yl)amino)pyrimidin-4-yl)-2-(methylsulfonyl)-2,3,4,5-tetrahydro-1H-benzo[c]azepin-5-yl)-1,2,4-oxadiazole-3-carboxamide,
(R)-5-(tert-butyl)-N-(8-(2-((1-methyl-1H-pyrazol-4-yl)amino)pyrimidin-4-yl)-2-(methylsulfonyl)-2,3,4,5-tetrahydro-1H-benzo[c]azepin-5-yl)-1,2,4-oxadiazole-3-carboxamide,
(S)-5-(tert-butyl)-N-(8-(2-((1-methyl-1H-pyrazol-4-yl)amino)pyrimidin-4-yl)-2-(methylsulfonyl)-2,3,4,5-tetrahydro-1H-benzo[c]azepin-5-yl)-1,2,4-oxadiazole-3-carboxamide, 5-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide,
(R)-5-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide,
(S)-5-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide,
5-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide,
(R)-5-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide,
(S)-5-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide,
5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,2,4-oxadiazole-3-carboxamide,
(R)-5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,2,4-oxadiazole-3-carboxamide, (S)-5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,2,4-oxadiazole-3-carboxamide, 5-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1,2,4-oxadiazole-3-carboxamide, (R)-5-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1,2,4-oxadiazole-3-carboxamide, (S)-5-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1,2,4-oxadiazole-3-carboxamide, 5-(tert-butyl)-N-(8-(2-((1-methyl-1H-pyrazol-4-yl)amino)pyrimidin-4-yl)-2-(tetrahydrofuran-3-yl)-2,3,4,5-tetrahydro-1H-benzo[c]azepin-5-yl)-1,2,4-oxadiazole-3-carboxamide, 5-(tert-butyl)-N—((R)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1,2,4-oxadiazole-3-carboxamide, 5-(tert-butyl)-N—((R)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1,2,4-oxadiazole-3-carboxamide, 5-(tert-butyl)-N—((S)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1,2,4-oxadiazole-3-carboxamide, 5-(tert-butyl)-N—((S)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1,2,4-oxadiazole-3-carboxamide, 5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,2,4-oxadiazole-3-carboxamide (R)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,2,4-oxadiazole-3-carboxamide, (S)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,2,4-oxadiazole-3-carboxamide, 5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,3,4-oxadiazole-2-carboxamide, (R)-5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,3,4-oxadiazole-2-carboxamide, (S)-5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,3,4-oxadiazole-2-carboxamide, 5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide, (R)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide, (S)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide, 5-(tert-butyl)-N-(8-(2-((1-methyl-1H-pyrazol-4-yl)amino)pyrimidin-4-yl)-2-(methylsulfonyl)-2,3,4,5-tetrahydro-1H-benzo[c]azepin-5-yl)-1,3,4-oxadiazole-2-carboxamide (R)-5-(tert-butyl)-N-(8-(2-((1-methyl-1H-pyrazol-4-yl)amino)pyrimidin-4-yl)-2-(methylsulfonyl)-2,3,4,5-tetrahydro-1H-benzo[c]azepin-5-yl)-1,3,4-oxadiazole-2-carboxamide, (S)-5-(tert-butyl)-N-(8-(2-((1-methyl-1H-pyrazol-4-yl)amino)pyrimidin-4-yl)-2-(methylsulfonyl)-2,3,4,5-tetrahydro-1H-benzo[c]azepin-5-yl)-1,3,4-oxadiazole-2-carboxamide, 5-(tert-butyl)-N-(2-(2-hydroxyethyl)-8-(2-((1-isopropyl-1H-pyrazol-4-yl)amino)pyrimidin-4-yl)-2,3,4,5-tetrahydro-1H-benzo[c]azepin-5-yl)-1,3,4-oxadiazole-2-carboxamide (R)-5-(tert-butyl)-N-(2-(2-hydroxyethyl)-8-(2-((1-isopropyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(tert-butyl)-N-(2-(2-hydroxyethyl)-8-(2-((1-isopropyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(8-(2-((1-isopropyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide (R)-5-(tert-butyl)-N-(8-(2-((1-isopropyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide, (S)-5-(tert-butyl)-N-(8-(2-((1-isopropyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide, 5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,3,4-oxadiazole-2-carboxamide (R)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,3,4-oxadiazole-2-carboxamide, (S)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,3,4-oxadiazole-2-carboxamide 5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(8-(2-((1-methyl-1H-pyrazol-4-yl)amino) pyrimidin-4-yl)-2-(tetrahydrofuran-3-yl)-2,3,4,5-tetrahydro-1H-benzo[c]azepin-5-yl)-1,3,4-oxadiazole-2-carboxamide, 5-(tert-butyl)-N—((R)-8-(2-((1-methyl-1H-pyrazol-4-yl) amino)pyrimidin-4-yl)-2-((R)-tetrahydrofuran-3-yl)-2,3,4,5-tetrahydro-1H-benzo[c]azepin-5-yl)-1,3,4-oxadiazole-2-carboxamide, 5-(tert-butyl)-N—((R)-8-(2-((1-methyl-1H-pyrazol-4-yl) amino)pyrimidin-4-yl)-2-((S)-tetrahydrofuran-3-yl)-2,3,4,5-tetrahydro-1H-benzo[c]azepin-5-yl)-1,3,4-oxadiazole-2-carboxamide, 5-(tert-butyl)-N—((S)-8-(2-((1-methyl-1H-pyrazol-4-yl) amino)pyrimidin-4-yl)-2-((R)-tetrahydrofuran-3-yl)-2,3,4,5-tetrahydro-1H-benzo[c]azepin-5-yl)-1,3,4-oxadiazole-2-carboxamide, 5-(tert-butyl)-N—((S)-8-(2-((1-methyl-1H-pyrazol-4-yl) amino)pyrimidin-4-yl)-2-((S)-tetrahydrofuran-3-yl)-2,3,4,5-tetrahydro-1H-benzo[c]azepin-5-yl)-1,3,4-oxadiazole-2-carboxamide, 5-(tert-butyl)-N-(2-(2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N—((R)-2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N—((R)-2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide 5-(tert-butyl)-N—((S)-2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N—((S)-2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N—((R)-2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N—((S)-2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide 5-(tert-butyl)-N—((S)-2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide, (R)-1-(tert-butyl)-N-(8-(2-((1-ethyl-1H-pyrazol-4-yl) amino)pyrimidin-4-yl)-2-(oxetan-3-yl)-2,3,4,5-tetrahydro-1H-benzo[c]azepin-5-yl)-1H-1,2,3-triazole-4-carboxamide (S)-1-(tert-butyl)-N-(8-(2-((1-ethyl-1H-pyrazol-4-yl)amino) pyrimidin-4-yl)-2-(oxetan-3-yl)-2,3,4,5-tetrahydro-1H-benzo[c]azepin-5-yl)-1H-1,2,3-triazole-4-carboxamide 1-(tert-butyl)-N-(8-(2-((1-isopropyl-1H-pyrazol-4-yl) amino)pyrimidin-4-yl)-2-(oxetan-3-yl)-2,3,4,5-tetrahydro-1H-benzo[c]azepin-5-yl)-1H-1,2,3-triazole-4-carboxamide, (R)-1-(tert-butyl)-N-(8-(2-((1-isopropyl-1H-pyrazol-4-yl) amino)pyrimidin-4-yl)-2-(oxetan-3-yl)-2,3,4,5-tetrahydro-1H-benzo[c]azepin-5-yl)-1H-1,2,3-triazole-4-carboxamide, (S)-1-(tert-butyl)-N-(8-(2-((1-isopropyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, 1-(tert-butyl)-N-(8-(2-((1-methyl-1H-pyrazol-4-yl)amino) pyrimidin-4-yl)-2-(tetrahydrofuran-3-yl)-2,3,4,5-tetrahydro-1H-benzo[c]azepin-5-yl)-1H-1,2,3-triazole-4-carboxamide, 1-(tert-butyl)-N-((5R)-8-(2-((1-methyl-1H-pyrazol-4-yl) amino)pyrimidin-4-yl)-2-(tetrahydrofuran-3-yl)-2,3,4,5-tetrahydro-1H-benzo[c]azepin-5-yl)-1H-1,2,3-triazole-4-carboxamide, 1-(tert-butyl)-N—((R)-8-(2-((1-methyl-1H-pyrazol-4-yl) amino)pyrimidin-4-yl)-2-((R)-tetrahydrofuran-3-yl)-2,3,4,5-tetrahydro-1H-benzo[c]azepin-5-yl)-1H-1,2,3-triazole-4-carboxamide, 1-(tert-butyl)-N—((R)-8-(2-((1-methyl-1H-pyrazol-4-yl) amino)pyrimidin-4-yl)-2-((S)-tetrahydrofuran-3-yl)-2,3,4,5-tetrahydro-1H-benzo[c]azepin-5-yl)-1H-1,2,3-triazole-4-carboxamide, 1-(tert-butyl)-N—((S)-8-(2-((1-methyl-1H-pyrazol-4-yl) amino)pyrimidin-4-yl)-2-((S)-tetrahydrofuran-3-yl)-2,3,4,5-tetrahydro-1H-benzo[c]azepin-5-yl)-1H-1,2,3-triazole-4-carboxamide, 1-(tert-butyl)-N—((S)-8-(2-((1-methyl-1H-pyrazol-4-yl) amino)pyrimidin-4-yl)-2-((R)-tetrahydrofuran-3-yl)-2,3,4,5-tetrahydro-1H-benzo[c]azepin-5-yl)-1H-1,2,3-triazole-4-carboxamide, 1-(tert-butyl)-N-(8-(2-((1-methyl-1H-pyrazol-4-yl)amino) pyrimidin-4-yl)-2-(oxetan-3-yl)-2,3,4,5-tetrahydro-1H-benzo[c]azepin-5-yl)-1H-1,2,3-triazole-4-carboxamide, (R)-1-(tert-butyl)-N-(8-(2-((1-methyl-1H-pyrazol-4-yl) amino)pyrimidin-4-yl)-2-(oxetan-3-yl)-2,3,4,5-tetrahydro-1H-benzo[c]azepin-5-yl)-1H-1,2,3-triazole-4-carboxamide, (S)-1-(tert-butyl)-N-(8-(2-((1-methyl-1H-pyrazol-4-yl) amino)pyrimidin-4-yl)-2-(oxetan-3-yl)-2,3,4,5-tetrahydro-1H-benzo[c]azepin-5-yl)-1H-1,2,3-triazole-4-carboxamide, 1-(tert-butyl)-N-(8-(2-((1-methyl-1H-pyrazol-4-yl)amino) pyrimidin-4-yl)-2-(2,2,2-trifluoroethyl)-2,3,4,5-tetrahydro-1H-benzo[c]azepin-5-yl)-1H-1,2,3-triazole-4-carboxamide, (R)-1-(tert-butyl)-N-(8-(2-((1-methyl-1H-pyrazol-4-yl) amino)pyrimidin-4-yl)-2-(2,2,2-trifluoroethyl)-2,3,4,5-tetrahydro-1H-benzo[c]azepin-5-yl)-1H-1,2,3-triazole-4-carboxamide, (S)-1-(tert-butyl)-N-(8-(2-((1-methyl-1H-pyrazol-4-yl) amino)pyrimidin-4-yl)-2-(2,2,2-trifluoroethyl)-2,3,4,5-tetrahydro-1H-benzo[c]azepin-5-yl)-1H-1,2,3-triazole-4-carboxamide, 1-(tert-butyl)-N-(2-(2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, 1-(tert-butyl)-N—((R)-2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, 1-(tert-butyl)-N—((R)-2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, 1-(tert-butyl)-N—((S)-2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, 1-(tert-butyl)-N—((S)-2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, 1-(tert-butyl)-N-(2-(2-methoxyethyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (R)-1-(tert-butyl)-N-(2-(2-methoxyethyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (S)-1-(tert-butyl)-N-(2-(2-methoxyethyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, 5-(tert-butyl)-N-(2-(2,2-difluoroethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(tert-butyl)-N-(2-(2,2-difluoroethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (5)-5-(tert-butyl)-N-(2-(2,2-difluoroethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,2,4-oxadiazole-3-carboxamide, (R)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,2,4-oxadiazole-3-carboxamide, (S)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,2,4-oxadiazole-3-carboxamide, N-(2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide (R)—N-(2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide, (S)—N-(2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide, 5-(tert-butyl)-N-(2-(2-((1-methyl-1H-pyrazol-4-yl)amino)pyridin-4-yl)-6,7,8,9-tetrahydro-5H-benzo[7]annulen-5-yl)-1,2,4-oxadiazole-3-carboxamide, (R)-5-(tert-butyl)-N-(2-(2-((1-methyl-1H-pyrazol-4-yl)amino)pyridin-4-yl)-6,7,8,9-tetrahydro-5H-benzo[7]annulen-5-yl)-1,2,4-oxadiazole-3-carboxamide, (S)-5-(tert-butyl)-N-(2-(2-((1-methyl-1H-pyrazol-4-yl)amino)pyridin-4-yl)-6,7,8,9-tetrahydro-5H-benzo[7]annulen-5-yl)-1,2,4-oxadiazole-3-carboxamide, 5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, (R)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, (S)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, 3-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,2,4-oxadiazole-5-carboxamide, (R)-3-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,2,4-oxadiazole-5-carboxamide, (S)-3-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,2,4-oxadiazole-5-carboxamide, 5-(tert-butyl)-N-(8-(2-((1-methyl-1H-pyrazol-4-yl)amino)pyrimidin-4-yl)-2,3,4,5-tetrahydrobenzo[b]oxepin-5-yl)-1,3,4-oxadiazole-2-carboxamide, (R)-5-(tert-butyl)-N-(8-(2-((1-methyl-1H-pyrazol-4-yl)amino)pyrimidin-4-yl)-2,3,4,5-tetrahydrobenzo[b]oxepin-5-yl)-1,3,4-oxadiazole-2-carboxamide, (S)-5-(tert-butyl)-N-(8-(2-((1-methyl-1H-pyrazol-4-yl)amino)pyrimidin-4-yl)-2,3,4,5-tetrahydrobenzo[b]oxepin-5-yl)-1,3,4-oxadiazole-2-carboxamide, 5-(tert-butyl)-N-(8-(2-((1-methyl-1H-pyrazol-4-yl)amino)pyrimidin-4-yl)-2,3,4,5-tetrahydrobenzo[b]oxepin-5-yl)-1,2,4-oxadiazole-2-carboxamide, (R)-5-(tert-butyl)-N-(8-(2-((1-methyl-1H-pyrazol-4-yl)amino)pyrimidin-4-yl)-2,3,4,5-tetrahydrobenzo[b]oxepin-5-yl)-1,2,4-oxadiazole-2-carboxamide, (S)-5-(tert-butyl)-N-(8-(2-((1-methyl-1H-pyrazol-4-yl)amino)pyrimidin-4-yl)-2,3,4,5-tetrahydrobenzo[b]oxepin-5-yl)-1,2,4-oxadiazole-2-carboxamide, 5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,3,4-oxadiazole-2-carboxamide, (R)-5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,3,4-oxadiazole-2-carboxamide, (S)-5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,3,4-oxadiazole-2-carboxamide, 5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,2,4-oxadiazole-3-carboxamide, (R)-5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,2,4-oxadiazole-3-carboxamide, (S)-5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,2,4-oxadiazole-3-carboxamide, 1-(tert-butyl)-N-(3-(2-((1-methyl-1H-pyrazol-4-yl)amino)pyridin-4-yl)-6,7,8,9-tetrahydro-5H-cyclohepta[c]pyridin-9-yl)-1H-1,2,3-triazole-4-carboxamide, (R)-1-(tert-butyl)-N-(3-(2-((1-methyl-1H-pyrazol-4-yl)amino)pyridin-4-yl)-6,7,8,9-tetrahydro-5H-cyclohepta[c]pyridin-9-yl)-1H-1,2,3-triazole-4-carboxamide, (S)-1-(tert-butyl)-N-(3-(2-((1-methyl-1H-pyrazol-4-yl)amino)pyridin-4-yl)-6,7,8,9-tetrahydro-5H-cyclohepta[c]pyridin-9-yl)-1H-1,2,3-triazole-4-carboxamide, 5-(tert-butyl)-N-(3-(2-hydroxyethyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (R)-5-(tert-butyl)-N-(3-(2-hydroxyethyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (S)-5-(tert-butyl)-N-(3-(2-hydroxyethyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, 5-(tert-butyl)-N-(7-(2-((1-methyl-1H-pyrazol-4-yl)amino)pyrimidin-4-yl)-3-(methylsulfonyl)-2,3,4,5-tetrahydro-1H-benzo[d]azepin-1-yl)-1,3,4-oxadiazole-2-carboxamide, (R)-5-(tert-butyl)-N-(7-(2-((1-methyl-1H-pyrazol-4-yl)amino)pyrimidin-4-yl)-3-(methylsulfonyl)-2,3,4,5-tetrahydro-1H-benzo[d]azepin-1-yl)-1,3,4-oxadiazole-2-carboxamide, (S)-5-(tert-butyl)-N-(7-(2-((1-methyl-1H-pyrazol-4-yl)amino)pyrimidin-4-yl)-3-(methylsulfonyl)-2,3,4,5-tetrahydro-1H-benzo[d]azepin-1-yl)-1,3,4-oxadiazole-2-carboxamide 5-(tert-butyl)-N-(7-(2-((1-methyl-1H-pyrazol-4-yl)amino)pyrimidin-4-yl)-3-(oxetan-3-yl)-2,3,4,5-tetrahydro-1H-benzo[d]azepin-1-yl)-1,3,4-oxadiazole-2-carboxamide, (R)-5-(tert-butyl)-N-(7-(2-((1-methyl-1H-pyrazol-4-yl)amino)pyrimidin-4-yl)-3-(oxetan-3-yl)-2,3,4,5-tetrahydro-1H-benzo[d]azepin-1-yl)-1,3,4-oxadiazole-2-carboxamide, (S)-5-(tert-butyl)-N-(7-(2-((1-methyl-1H-pyrazol-4-yl)amino)pyrimidin-4-yl)-3-(oxetan-3-yl)-2,3,4,5-tetrahydro-1H-benzo[d]azepin-1-yl)-1,3,4-oxadiazole-2-carboxamide, 5-(tert-butyl)-N-(7-(2-((1-methyl-1H-pyrazol-4-yl)amino)pyrimidin-4-yl)-3-(tetrahydrofuran-3-yl)-2,3,4,5-tetrahydro-1H-benzo[d]azepin-1-yl)-1,3,4-oxadiazole-2-carboxamide, 5-(tert-butyl)-N—((R)-7-(2-((1-methyl-1H-pyrazol-4-yl)amino)pyrimidin-4-yl)-3-((S)-tetrahydrofuran-3-yl)-2,3,4,5-tetrahydro-1H-benzo[d]azepin-1-yl)-1,3,4-oxadiazole-2-carboxamide 5-(tert-butyl)-N—((R)-7-(2-((1-methyl-1H-pyrazol-4-yl)amino)pyrimidin-4-yl)-3-((R)-tetrahydrofuran-3-yl)-2,3,4,5-tetrahydro-1H-benzo[d]azepin-1-yl)-1,3,4-oxadiazole-2-carboxamide 5-(tert-butyl)-N—((S)-7-(2-((1-methyl-1H-pyrazol-4-yl)amino)pyrimidin-4-yl)-3-((S)-tetrahydrofuran-3-yl)-2,3,4,5-tetrahydro-1H-benzo[d]azepin-1-yl)-1,3,4-oxadiazole-2-carboxamide 5-(tert-butyl)-N—((S)-7-(2-((1-methyl-1H-pyrazol-4-yl)amino)pyrimidin-4-yl)-3-((R)-tetrahydrofuran-3-yl)-2,3,4,5-tetrahydro-1H-benzo[d]azepin-1-yl)-1,3,4-oxadiazole-2-carboxamide 5-(tert-butyl)-N-(3-(2-hydroxy-2-methylpropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (R)-5-(tert-butyl)-N-(3-(2-hydroxy-2-methylpropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (S)-5-(tert-butyl)-N-(3-(2-hydroxy-2-methylpropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, 1-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1H-1,2,3-triazole-4-carboxamide, (R)-1-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1H-1,2,3-triazole-4-carboxamide, (S)-1-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1H-1,2,3-triazole-4-carboxamide, 1-(tert-butyl)-N-(3-methyl-7-(2-((1-methyl-1H-pyrazol-4-yl)amino)pyrimidin-4-yl)-2,3,4,5-tetrahydro-1H-benzo[d]azepin-1-yl)-1H-1,2,3-triazole-4-carboxamide, (R)-1-(tert-butyl)-N-(3-methyl-7-(2-((1-methyl-1H-pyrazol-4-yl)amino)pyrimidin-4-yl)-2,3,4,5-tetrahydro-1H-benzo[d]azepin-1-yl)-1H-1,2,3-triazole-4-carboxamide, (S)-1-(tert-butyl)-N-(3-methyl-7-(2-((1-methyl-1H-pyrazol-4-yl)amino)pyrimidin-4-yl)-2,3,4,5-tetrahydro-1H-benzo[d]azepin-1-yl)-1H-1,2,3-triazole-4-carboxamide, 1-(tert-butyl)-N-(3-(2-hydroxyethyl)-7-(2-((1-methyl-1H-pyrazol-4-yl)amino)pyrimidin-4-yl)-2,3,4,5-tetrahydro-1H-benzo[d]azepin-1-yl)-1H-1,2,3-triazole-4-carboxamide, (R)-1-(tert-butyl)-N-(3-(2-hydroxyethyl)-7-(2-((1-methyl-1H-pyrazol-4-yl)amino)pyrimidin-4-yl)-2,3,4,5-tetrahydro-1H-benzo[d]azepin-1-yl)-1H-1,2,3-triazole-4-carboxamide, (S)-1-(tert-butyl)-N-(3-(2-hydroxyethyl)-7-(2-((1-methyl-1H-pyrazol-4-yl)amino)pyrimidin-4-yl)-2,3,4,5-tetrahydro-1H-benzo[d]azepin-1-yl)-1H-1,2,3-triazole-4-carboxamide, 5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,2,4-oxadiazole-3-carboxamide, (R)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,2,4-oxadiazole-3-carboxamide (S)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,2,4-oxadiazole-3-carboxamide 5-(tert-butyl)-N-(2-(2-(dimethylamino)acetyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide, (R)-5-(tert-butyl)-N-(2-(2-(dimethylamino)acetyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide, (S)-5-(tert-butyl)-N-(2-(2-(dimethylamino)acetyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide, N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-5-(1,1,1-trifluoro-2-methylpropan-2-yl)-1,3,4-oxadiazole-2-carboxamide, (R)—N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-5-(1,1,1-trifluoro-2-methylpropan-2-yl)-1,3,4-oxadiazole-2-carboxamide, (S)—N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-5-(1,1,1-trifluoro-2-methylpropan-2-yl)-1,3,4-oxadiazole-2-carboxamide, N-(2-methyl-8-(2-((1-methyl-1H-pyrazol-4-yl)amino)pyrimidin-4-yl)-2,3,4,5-tetrahydro-1H-benzo[c]azepin-5-yl)-5-(1,1,1-trifluoro-2-methylpropan-2-yl)-1,3,4-oxadiazole-2-carboxamide, (R)—N-(2-methyl-8-(2-((1-methyl-1H-pyrazol-4-yl)amino)pyrimidin-4-yl)-2,3,4,5-tetrahydro-1H-benzo[c]azepin-5-yl)-5-(1,1,1-trifluoro-2-methylpropan-2-yl)-1,3,4-oxadiazole-2-carboxamide, (S)—N-(2-methyl-8-(2-((1-methyl-1H-pyrazol-4-yl)amino)pyrimidin-4-yl)-2,3,4,5-tetrahydro-1H-benzo[c]azepin-5-yl)-5-(1,1,1-trifluoro-2-methylpropan-2-yl)-1,3,4-oxadiazole-2-carboxamide, 5-(1,1-difluoro-2-methylpropan-2-yl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide, (R)-5-(1,1-difluoro-2-methylpropan-2-yl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide, (S)-5-(1,1-difluoro-2-methylpropan-2-yl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide, 5-(1,1-difluoro-2-methylpropan-2-yl)-N-(2-(2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(1,1-difluoro-2-methylpropan-2-yl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(1,1-difluoro-2-methylpropan-2-yl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(1,1-difluoro-2-methylpropan-2-yl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(1,1-difluoro-2-methylpropan-2-yl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(1,1-difluoro-2-methylpropan-2-yl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(1-fluoro-2-methylpropan-2-yl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide, (R)-5-(1-fluoro-2-methylpropan-2-yl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide (S)-5-(1-fluoro-2-methylpropan-2-yl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide, 5-(1-fluoro-2-methylpropan-2-yl)-N-(2-(2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(1-fluoro-2-methylpropan-2-yl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(1-fluoro-2-methylpropan-2-yl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(1-fluoro-2-methylpropan-2-yl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(1-fluoro-2-methylpropan-2-yl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(1-fluoro-2-methylpropan-2-yl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-cyclobutyl-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-cyclobutyl-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-cyclobutyl-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(2-cyanopropan-2-yl)-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(2-cyanopropan-2-yl)-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(2-cyanopropan-2-yl)-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(2-cyanopropan-2-yl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(2-cyanopropan-2-yl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(2-cyanopropan-2-yl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 1-isopropyl-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, (R)-1-isopropyl-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, (S)-1-isopropyl-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, 1-cyclobutyl-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, (R)-1-cyclobutyl-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, (S)-1-cyclobutyl-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, 5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-thiadiazole-2-carboxamide (R)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-thiadiazole-2-carboxamide, (S)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-thiadiazole-2-carboxamide, 3-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-5-carboxamide, (R)-3-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-5-carboxamide, (S)-3-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-5-carboxamide, 1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (R)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (S)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, 1-(tert-butyl)-N-(2-ethyl-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (R)-1-(tert-butyl)-N-(2-ethyl-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (S)-1-(tert-butyl)-N-(2-ethyl-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, 1-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (R)-1-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (S)-1-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, 1-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1H-1,2,3-triazole-4-carboxamide, (R)-1-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1H-1,2,3-triazole-4-carboxamide, (S)-1-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1H-1,2,3-triazole-4-carboxamide, 1-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (R)-1-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (S)-1-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, 1-(tert-butyl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (R)-1-(tert-butyl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (R)-1-(tert-butyl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (S)-1-(tert-butyl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, (S)-1-(tert-butyl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide, 5-(tert-butyl)-N-(2-(2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide 5-(tert-butyl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide, (R)-5-(tert-butyl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide, (R)-5-(tert-butyl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide, (S)-5-(tert-butyl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide, (S)-5-(tert-butyl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide, 5-(tert-butyl)-N-(2-(2-methoxyethyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide, (R)-5-(tert-butyl)-N-(2-(2-methoxyethyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide, (S)-5-(tert-butyl)-N-(2-(2-methoxyethyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide, 5-(tert-butyl)-N-(8-(2-((1-methyl-1H-pyrazol-4-yl)amino)pyrimidin-4-yl)-2-(tetrahydrofuran-3-yl)-2,3,4,5-tetrahydro-1H-benzo[c]azepin-5-yl)-1,3,4-oxadiazole-2-carboxamide, 5-(tert-butyl)-N—((R)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1,3,4-oxadiazole-2-carboxamide, 5-(tert-butyl)-N—((R)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1,3,4-oxadiazole-2-carboxamide, 5-(tert-butyl)-N—((S)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1,3,4-oxadiazole-2-carboxamide, 5-(tert-butyl)-N—((S)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1,3,4-oxadiazole-2-carboxamide, 5-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(2-ethyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(tert-butyl)-N-(2-ethyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(tert-butyl)-N-(2-ethyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(2-(2-hydroxy-2-methylpropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-tert-butyl-1,3,4-oxadiazole-2-carboxylic acid {(R)-2-(2-hydroxy-2-methyl-propyl)-8-[2-(1-methyl-1H-pyrazol-4-ylamino)-pyrimidin-4-yl]-2,3,4,5-tetrahydro-1H-2-benzazepin-5-yl}-amide, (S)-5-(tert-butyl)-N-(2-(2-hydroxy-2-methylpropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(2-(3-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(tert-butyl)-N-(2-(3-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(tert-butyl)-N-(2-(3-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide N-(8-(2-((1H-pyrazol-4-yl)amino)pyrimidin-4-yl)-2-(oxetan-3-yl)-2,3,4,5-tetrahydro-1H-benzo[c]azepin-5-yl)-5-(tert-butyl)-1,3,4-oxadiazole-2-carboxamide, (R)—N-(8-(2-((1H-pyrazol-4-yl)amino)pyrimidin-4-yl)-2-(oxetan-3-yl)-2,3,4,5-tetrahydro-1H-benzo[c]azepin-5-yl)-5-(tert-butyl)-1,3,4-oxadiazole-2-carboxamide, (S)—N-(8-(2-((1H-pyrazol-4-yl)amino)pyrimidin-4-yl)-2-(oxetan-3-yl)-2,3,4,5-tetrahydro-1H-benzo[c]azepin-5-yl)-5-(tert-butyl)-1,3,4-oxadiazole-2-carboxamide, (R)-5-(tert-butyl)-N-(8-(2-((5,6-dihydro-4H-pyrrolo[1,2-b]pyrazol-3-yl)amino)pyrimidin-4-yl)-2-(2-hydroxyethyl)-2,3,4,5-tetrahydro-1H-benzo[c]azepin-5-yl)-1,3,4-oxadiazole-2-carboxamide, (S)-5-(tert-butyl)-N-(8-(2-((5,6-dihydro-4H-pyrrolo[1,2-b]pyrazol-3-yl)amino)pyrimidin-4-yl)-2-(2-hydroxyethyl)-2,3,4,5-tetrahydro-1H-benzo[c]azepin-5-yl)-1,3,4-oxadiazole-2-carboxamide, 5-(tert-butyl)-N-(8-(2-((5,6-dihydro-4H-pyrrolo[1,2-b]pyrazol-3-yl)amino)pyrimidin-4-yl)-2-(2-hydroxyethyl)-2,3,4,5-tetrahydro-1H-benzo[c]azepin-5-yl)-1,3,4-oxadiazole-2-carboxamide, (R)-1-(tert-butyl)-N-(8-(2-((5,6-dihydro-4H-pyrrolo[1,2-b]pyrazol-3-yl)amino)pyrimidin-4-yl)-2-(2-hydroxyethyl)-2,3,4,5-tetrahydro-1H-benzo[c]azepin-5-yl)-1H-1,2,3-triazole-4-carboxamide, (S)-1-(tert-butyl)-N-(8-(2-((5,6-dihydro-4H-pyrrolo[1,2-b]pyrazol-3-yl)amino)pyrimidin-4-yl)-2-(2-hydroxyethyl)-2,3,4,5-tetrahydro-1H-benzo[c]azepin-5-yl)-1H-1,2,3-triazole-4-carboxamide, 1-(tert-butyl)-N-(8-(2-((5,6-dihydro-4H-pyrrolo[1,2-b]pyrazol-3-yl)amino)pyrimidin-4-yl)-2-(2-hydroxyethyl)-2,3,4,5-tetrahydro-1H-benzo[c]azepin-5-yl)-1H-1,2,3-triazole-4-carboxamide, N-(2-methyl-8-(2-((1-methyl-1H-pyrazol-4-yl)amino)pyrimidin-4-yl)-2,3,4,5-tetrahydro-1H-benzo[c]azepin-5-yl)-5-(1-methylcyclopropyl)-1,3,4-oxadiazole-2-carboxamide, (R)—N-(2-methyl-8-(2-((1-methyl-1H-pyrazol-4-yl)amino)pyrimidin-4-yl)-2,3,4,5-tetrahydro-1H-benzo[c]azepin-5-yl)-5-(1-methylcyclopropyl)-1,3,4-oxadiazole-2-carboxamide, (S)—N-(2-methyl-8-(2-((1-methyl-1H-pyrazol-4-yl)amino)pyrimidin-4-yl)-2,3,4,5-tetrahydro-1H-benzo[c]azepin-5-yl)-5-(1-methylcyclopropyl)-1,3,4-oxadiazole-2-carboxamide, 5-(tert-butyl)-N-(8-(2-((1-ethyl-1H-pyrazol-4-yl)amino)pyrimidin-4-yl)-2-(tetrahydrofuran-3-yl)-2,3,4,5-tetrahydro-1H-benzo[c]azepin-5-yl)-1,3,4-oxadiazole-2-carboxamide, 5-(tert-butyl)-N—((R)-8-(2-((1-ethyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1,3,4-oxadiazole-2-carboxamide, 5-(tert-butyl)-N—((R)-8-(2-((1-ethyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1,3,4-oxadiazole-2-carboxamide, 5-(tert-butyl)-N—((S)-8-(2-((1-ethyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1,3,4-oxadiazole-2-carboxamide, 5-(tert-butyl)-N—((S)-8-(2-((1-ethyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1,3,4-oxadiazole-2-carboxamide, 5-(tert-butyl)-N-(8-(2-((1-ethyl-1H-pyrazol-4-yl)amino)pyrimidin-4-yl)-2-(2-hydroxyethyl)-2,3,4,5-tetrahydro-1H-benzo[c]azepin-5-yl)-1,3,4-oxadiazole-2-carboxamide, (R)-5-(tert-butyl)-N-(8-(2-((1-ethyl-1H-pyrazol-4-yl)amino)pyrimidin-4-yl)-2-(2-hydroxyethyl)-2,3,4,5-tetrahydro-1H-benzo[c]azepin-5-yl)-1,3,4-oxadiazole-2-carboxamide, (S)-5-(tert-butyl)-N-(8-(2-((1-ethyl-1H-pyrazol-4-yl)amino)pyrimidin-4-yl)-2-(2-hydroxyethyl)-2,3,4,5-tetrahydro-1H-benzo[c]azepin-5-yl)-1,3,4-oxadiazole-2-carboxamide, 5-(tert-butyl)-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(tert-butyl)-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(tert-butyl)-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1,3,4-oxadiazole-2-carboxamide, (R)-5-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1,3,4-oxadiazole-2-carboxamide, (S)-5-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1,3,4-oxadiazole-2-carboxamide, 1-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1H-1,2,3-triazole-4-carboxamide, (R)-1-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1H-1,2,3-triazole-4-carboxamide, (S)-1-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1H-1,2,3-triazole-4-carboxamide, 5-(tert-butyl)-N-(8-(2-((1,3-dimethyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide, (R)-5-(tert-butyl)-N-(8-(2-((1,3-dimethyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide, (S)-5-(tert-butyl)-N-(8-(2-((1,3-dimethyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide, 1-(tert-butyl)-N-(8-(2-((1,3-dimethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, (R)-1-(tert-butyl)-N-(8-(2-((1,3-dimethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, (S)-1-(tert-butyl)-N-(8-(2-((1,3-dimethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, 5-(tert-butyl)-N-(8-(2-((1,3-dimethyl-1H-pyrazol-4-yl)amino)pyrimidin-4-yl)-2-(2-hydroxyethyl)-2,3,4,5-tetrahydro-1H-benzo[c]azepin-5-yl)-1,2,4-oxadiazole-3-carboxamide, (R)-5-(tert-butyl)-N-(8-(2-((1,3-dimethyl-1H-pyrazol-4-yl)amino)pyrimidin-4-yl)-2-(2-hydroxyethyl)-2,3,4,5-tetrahydro-1H-benzo[c]azepin-5-yl)-1,2,4-oxadiazole-3-carboxamide, (S)-5-(tert-butyl)-N-(8-(2-((1,3-dimethyl-1H-pyrazol-4-yl)amino)pyrimidin-4-yl)-2-(2-hydroxyethyl)-2,3,4,5-tetrahydro-1H-benzo[c]azepin-5-yl)-1,2,4-oxadiazole-3-carboxamide, 1-(tert-butyl)-N-(2-(2-hydroxyethyl)-8-(2-((1-isopropyl-1H-pyrazol-4-yl)amino)pyrimidin-4-yl)-2,3,4,5-tetrahydro-1H-benzo[c]azepin-5-yl)-1H-1,2,3-triazole-4-carboxamide, (R)-1-(tert-butyl)-N-(2-(2-hydroxyethyl)-8-(2-((1-isopropyl-1H-pyrazol-4-yl)amino)pyrimidin-4-yl)-2,3,4,5-tetrahydro-1H-benzo[c]azepin-5-yl)-1H-1,2,3-triazole-4-carboxamide, (S)-1-(tert-butyl)-N-(2-(2-hydroxyethyl)-8-(2-((1-isopropyl-1H-pyrazol-4-yl)amino)pyrimidin-4-yl)-2,3,4,5-tetrahydro-1H-benzo[c]azepin-5-yl)-1H-1,2,3-triazole-4-carboxamide, 5-(tert-butyl)-N-(2-(cyclopropylmethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(tert-butyl)-N-(2-(cyclopropylmethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(tert-butyl)-N-(2-(cyclopropylmethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(8-(2-((1,3-dimethyl-1H-pyrazol-4-yl)amino)pyrimidin-4-yl)-2-(2,2,2-trifluoroethyl)-2,3,4,5-tetrahydro-1H-benzo[c]azepin-5-yl)-1,3,4-oxadiazole-2-carboxamide, (R)-5-(tert-butyl)-N-(8-(2-((1,3-dimethyl-1H-pyrazol-4-yl)amino)pyrimidin-4-yl)-2-(2,2,2-trifluoroethyl)-2,3,4,5-tetrahydro-1H-benzo[c]azepin-5-yl)-1,3,4-oxadiazole-2-carboxamide, (S)-5-(tert-butyl)-N-(8-(2-((1,3-dimethyl-1H-pyrazol-4-yl)amino)pyrimidin-4-yl)-2-(2,2,2-trifluoroethyl)-2,3,4,5-tetrahydro-1H-benzo[c]azepin-5-yl)-1,3,4-oxadiazole-2-carboxamide, 5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, (R)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, (S)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, N-(2-(2-((1H-pyrazol-4-yl)amino)pyrimidin-4-yl)-6,7,8,9-tetrahydro-5H-benzo[7]annulen-5-yl)-5-(tert-butyl)-1,2,4-oxadiazole-3-carboxamide, (R)—N-(2-(2-((1H-pyrazol-4-yl)amino)pyrimidin-4-yl)-6,7,8,9-tetrahydro-5H-benzo[7]annulen-5-yl)-5-(tert-butyl)-1,2,4-oxadiazole-3-carboxamide, (S)—N-(2-(2-((1H-pyrazol-4-yl)amino)pyrimidin-4-yl)-6,7,8,9-tetrahydro-5H-benzo[7]annulen-5-yl)-5-(tert-butyl)-1,2,4-oxadiazole-3-carboxamide, 5-(tert-butyl)-N-(2-(2-((5-methyl-4,5,6,7-tetrahydropyrazolo[1,5-a]pyrazin-3-yl)amino)pyrimidin-4-yl)-6,7,8,9-tetrahydro-5H-benzo[7]annulen-5-yl)-1,2,4-oxadiazole-3-carboxamide, (R)-5-(tert-butyl)-N-(2-(2-((5-methyl-4,5,6,7-tetrahydropyrazolo[1,5-a]pyrazin-3-yl)amino)pyrimidin-4-yl)-6,7,8,9-tetrahydro-5H-benzo[7]annulen-5-yl)-1,2,4-oxadiazole-3-carboxamide, (S)-5-(tert-butyl)-N-(2-(2-((5-methyl-4,5,6,7-tetrahydropyrazolo[1,5-a]pyrazin-3-yl)amino)pyrimidin-4-yl)-6,7,8,9-tetrahydro-5H-benzo[7]annulen-5-yl)-1,2,4-oxadiazole-3-carboxamide, N-(2-(2-((1H-pyrazol-4-yl)amino)pyrimidin-4-yl)-6,7,8,9-tetrahydro-5H-benzo[7]annulen-5-yl)-5-(tert-butyl)-1,3,4-oxadiazole-2-carboxamide, (R)—N-(2-(2-((1H-pyrazol-4-yl)amino)pyrimidin-4-yl)-6,7,8,9-tetrahydro-5H-benzo[7]annulen-5-yl)-5-(tert-butyl)-1,3,4-oxadiazole-2-carboxamide, (S)—N-(2-(2-((1H-pyrazol-4-yl)amino)pyrimidin-4-yl)-6,7,8,9-tetrahydro-5H-benzo[7]annulen-5-yl)-5-(tert-butyl)-1,3,4-oxadiazole-2-carboxamide, 1-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1H-1,2,3-triazole-4-carboxamide, (R)-1-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1H-1,2,3-triazole-4-carboxamide, (S)-1-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1H-1,2,3-triazole-4-carboxamide, 5-(tert-butyl)-4-methyl-N-(2-(2-((1-methyl-1H-pyrazol-4-yl)amino)pyrimidin-4-yl)-6,7,8,9-tetrahydro-5H-benzo[7]annulen-5-yl)-4H-1,2,4-triazole-3-carboxamide, (R)-5-(tert-butyl)-4-methyl-N-(2-(2-((1-methyl-1H-pyrazol-4-yl)amino)pyrimidin-4-yl)-6,7,8,9-tetrahydro-5H-benzo[7]annulen-5-yl)-4H-1,2,4-triazole-3-carboxamide, (S)-5-(tert-butyl)-4-methyl-N-(2-(2-((1-methyl-1H-pyrazol-4-yl)amino)pyrimidin-4-yl)-6,7,8,9-tetrahydro-5H-benzo[7]annulen-5-yl)-4H-1,2,4-triazole-3-carboxamide, 2-isopropyl-N-(2-(2-((1-methyl-1H-pyrazol-4-yl)amino)pyrimidin-4-yl)-6,7,8,9-tetrahydro-5H-benzo[7]annulen-5-yl)-2H-1,2,3-triazole-4-carboxamide, (R)-2-isopropyl-N-(2-(2-((1-methyl-1H-pyrazol-4-yl)amino)pyrimidin-4-yl)-6,7,8,9-tetrahydro-5H-benzo[7]annulen-5-yl)-2H-1,2,3-triazole-4-carboxamide, (S)-2-isopropyl-N-(2-(2-((1-methyl-1H-pyrazol-4-yl)amino)pyrimidin-4-yl)-6,7,8,9-tetrahydro-5H-benzo[7]annulen-5-yl)-2H-1,2,3-triazole-4-carboxamide, 5-(tert-butyl)-N-(8-fluoro-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, 5-(tert-butyl)-N-((8S)-8-fluoro-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, 5-(tert-butyl)-N-((8R)-8-fluoro-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, 5-(tert-butyl)-N-((5R,8S)-8-fluoro-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, 5-(tert-butyl)-N-((5S,8R)-8-fluoro-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, 5-(tert-butyl)-N-((5R,8R)-8-fluoro-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, 5-(tert-butyl)-N-((5S,8S)-8-fluoro-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, N-(8-fluoro-2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide, N-((8S)-8-fluoro-2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide, N-((8R)-8-fluoro-2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide N-((5R,8S)-8-fluoro-2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide N-((5S,8R)-8-fluoro-2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide N-((5S,8S)-8-fluoro-2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide N-((5S,8R)-8-fluoro-2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide N-(2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,3,4-oxadiazole-2-carboxamide, (R)—N-(2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,3,4-oxadiazole-2-carboxamide, (S)—N-(2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,3,4-oxadiazole-2-carboxamide, 5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-cyclobutyl-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-cyclobutyl-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-cyclobutyl-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(2-(2-ethoxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(tert-butyl)-N-(2-(2-ethoxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(tert-butyl)-N-(2-(2-ethoxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (R)-5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (S)-5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, 1-(tert-butyl)-N-(7-(2-((1-methyl-1H-pyrazol-4-yl)amino)pyrimidin-4-yl)-3-(oxetan-3-yl)-2,3,4,5-tetrahydro-1H-benzo[d]azepin-1-yl)-1H-1,2,3-triazole-4-carboxamide, (R)-1-(tert-butyl)-N-(7-(2-((1-methyl-1H-pyrazol-4-yl)amino)pyrimidin-4-yl)-3-(oxetan-3-yl)-2,3,4,5-tetrahydro-1H-benzo[d]azepin-1-yl)-1H-1,2,3-triazole-4-carboxamide, (S)-1-(tert-butyl)-N-(7-(2-((1-methyl-1H-pyrazol-4-yl)amino)pyrimidin-4-yl)-3-(oxetan-3-yl)-2,3,4,5-tetrahydro-1H-benzo[d]azepin-1-yl)-1H-1,2,3-triazole-4-carboxamide, 5-(tert-butyl)-N-(8-(2-((1-methyl-1H-pyrazol-4-yl)amino)pyrimidin-4-yl)-2-(tetrahydrofuran-3-yl)-2,3,4,5-tetrahydro-1H-benzo[c]azepin-5-yl)-1,3,4-thiadiazole-2-carboxamide, 5-(tert-butyl)-N—((R)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1,3,4-thiadiazole-2-carboxamide, 5-(tert-butyl)-N—((R)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1,3,4-thiadiazole-2-carboxamide, 5-(tert-butyl)-N—((S)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1,3,4-thiadiazole-2-carboxamide, 5-(tert-butyl)-N—((S)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1,3,4-thiadiazole-2-carboxamide, 5-(tert-butyl)-N-(3-methyl-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (R)-5-(tert-butyl)-N-(3-methyl-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (S)-5-(tert-butyl)-N-(3-methyl-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, 5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-thiadiazole-2-carboxamide, (R)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-thiadiazole-2-carboxamide, (S)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-thiadiazole-2-carboxamide, 5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,2,4-oxadiazole-3-carboxamide, tert-butyl 1-(5-(tert-butyl)-1,3,4-oxadiazole-2-carboxamido)-7-(2-((1-methyl-1H-pyrazol-4-yl)amino)pyrimidin-4-yl)-1,2,4,5-tetrahydro-3H-benzo[d]azepine-3-carboxylate, (R)-tert-butyl 1-(5-(tert-butyl)-1,3,4-oxadiazole-2-carboxamido)-7-(2-((1-methyl-1H-pyrazol-4-yl)amino)pyrimidin-4-yl)-1,2,4,5-tetrahydro-3H-benzo[d]azepine-3-carboxylate, (S)-tert-butyl 1-(5-(tert-butyl)-1,3,4-oxadiazole-2-carboxamido)-7-(2-((1-methyl-1H-pyrazol-4-yl)amino)pyrimidin-4-yl)-1,2,4,5-tetrahydro-3H-benzo[d]azepine-3-carboxylate, 5-(tert-butyl)-N-(7-(2-((1-methyl-1H-pyrazol-4-yl)amino)pyrimidin-4-yl)-3-(2,2,2-trifluoroethyl)-2,3,4,5-tetrahydro-1H-benzo[d]azepin-1-yl)-1,3,4-oxadiazole-2-carboxamide, (R)-5-(tert-butyl)-N-(7-(2-((1-methyl-1H-pyrazol-4-yl)amino)pyrimidin-4-yl)-3-(2,2,2-trifluoroethyl)-2,3,4,5-tetrahydro-1H-benzo[d]azepin-1-yl)-1,3,4-oxadiazole-2-carboxamide, (S)-5-(tert-butyl)-N-(7-(2-((1-methyl-1H-pyrazol-4-yl)amino)pyrimidin-4-yl)-3-(2,2,2-trifluoroethyl)-2,3,4,5-tetrahydro-1H-benzo[d]azepin-1-yl)-1,3,4-oxadiazole-2-carboxamide, 5-(tert-butyl)-N-(3-(2-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, 5-(tert-butyl)-N-(3-((S)-2-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (R)-5-(tert-butyl)-N-(3-((S)-2-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (S)-5-(tert-butyl)-N-(3-((S)-2-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, 5-(tert-butyl)-N-(3-((R)-2-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (R)-5-(tert-butyl)-N-(3-((R)-2-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (S)-5-(tert-butyl)-N-(3-((R)-2-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, 5-(tert-butyl)-N-(7-(2-((1-methyl-1H-pyrazol-4-yl)amino)pyrimidin-4-yl)-3-(tetrahydro-2H-pyran-4-yl)-2,3,4,5-tetrahydro-1H-benzo[d]azepin-1-yl)-1,3,4-oxadiazole-2-carboxamide, (R)-5-(tert-butyl)-N-(7-(2-((1-methyl-1H-pyrazol-4-yl)amino)pyrimidin-4-yl)-3-(tetrahydro-2H-pyran-4-yl)-2,3,4,5-tetrahydro-1H-benzo[d]azepin-1-yl)-1,3,4-oxadiazole-2-carboxamide, (S)-5-(tert-butyl)-N-(7-(2-((1-methyl-1H-pyrazol-4-yl)amino)pyrimidin-4-yl)-3-(tetrahydro-2H-pyran-4-yl)-2,3,4,5-tetrahydro-1H-benzo[d]azepin-1-yl)-1,3,4-oxadiazole-2-carboxamide, 5-(tert-butyl)-N-(3-(3-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (S)-5-(tert-butyl)-N-(3-(3-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, (R)-5-(tert-butyl)-N-(3-(3-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide, 5-(3,3-difluorocyclobutyl)-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(3,3-difluorocyclobutyl)-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(3,3-difluorocyclobutyl)-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(3,3-difluorocyclobutyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (R)-5-(3,3-difluorocyclobutyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, (S)-5-(3,3-difluorocyclobutyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide, 5-(tert-butyl)-N-(8-(2-((5,6-dihydro-4H-pyrrolo[1,2-b]pyrazol-3-yl)amino)pyrimidin-4-yl)-2-(2-hydroxyethyl)-2,3,4,5-tetrahydro-1H-benzo[c]azepin-5-yl)-1,2,4-oxadiazole-3-carboxamide, (R)-5-(tert-butyl)-N-(8-(2-((5,6-dihydro-4H-pyrrolo[1,2-b]pyrazol-3-yl)amino)pyrimidin-4-yl)-2-(2-hydroxyethyl)-2,3,4,5-tetrahydro-1H-benzo[c]azepin-5-yl)-1,2,4-oxadiazole-3-carboxamide, (S)-5-(tert-butyl)-N-(8-(2-((5,6-dihydro-4H-pyrrolo[1,2-b]pyrazol-3-yl)amino)pyrimidin-4-yl)-2-(2-hydroxyethyl)-2,3,4,5-tetrahydro-1H-benzo[c]azepin-5-yl)-1,2,4-oxadiazole-3-carboxamide, 5-(tert-butyl)-N-(8-hydroxy-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, (R)-5-(tert-butyl)-N-(8-hydroxy-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, (S)-5-(tert-butyl)-N-(8-hydroxy-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide, 5-(tert-butyl)-N-(2-(2-((1,5-dimethyl-1H-pyrazol-4-yl)amino)pyrimidin-4-yl)-6,7,8,9-tetrahydro-5H-benzo[7]annulen-5-yl)-1,2,4-oxadiazole-3-carboxamide, (R)-5-(tert-butyl)-N-(2-(2-((1,5-dimethyl-1H-pyrazol-4-yl)amino)pyrimidin-4-yl)-6,7,8,9-tetrahydro-5H-benzo[7]annulen-5-yl)-1,2,4-oxadiazole-3-carboxamide, (S)-5-(tert-butyl)-N-(2-(2-((1,5-dimethyl-1H-pyrazol-4-yl)amino)pyrimidin-4-yl)-6,7,8,9-tetrahydro-5H-benzo[7]annulen-5-yl)-1,2,4-oxadiazole-3-carboxamide, 5-(tert-butyl)-N-(2-(2-((5,6-dihydro-4H-pyrrolo[1,2-b]pyrazol-3-yl)amino)pyrimidin-4-yl)-6,7,8,9-tetrahydro-5H-benzo[7]annulen-5-yl)-1,2,4-oxadiazole-3-carboxamide, (R)-5-(tert-butyl)-N-(2-(2-((5,6-dihydro-4H-pyrrolo[1,2-b]pyrazol-3-yl)amino)pyrimidin-4-yl)-6,7,8,9-tetrahydro-5H-benzo[7]annulen-5-yl)-1,2,4-oxadiazole-3-carboxamide, (S)-5-(tert-butyl)-N-(2-(2-((5,6-dihydro-4H-pyrrolo[1,2-b]pyrazol-3-yl)amino)pyrimidin-4-yl)-6,7,8,9-tetrahydro-5H-benzo[7]annulen-5-yl)-1,2,4-oxadiazole-3-carboxamide, 5-(tert-butyl)-N-(2-(2-((1-methyl-5-(trifluoromethyl)-1H-pyrazol-4-yl)amino)pyrimidin-4-yl)-6,7,8,9-tetrahydro-5H-benzo[7]annulen-5-yl)-1,2,4-oxadiazole-3-carboxamide, (R)-5-(tert-butyl)-N-(2-(2-((1-methyl-5-(trifluoromethyl)-1H-pyrazol-4-yl)amino)pyrimidin-4-yl)-6,7,8,9-tetrahydro-5H-benzo[7]annulen-5-yl)-1,2,4-oxadiazole-3-carboxamide, (S)-5-(tert-butyl)-N-(2-(2-((1-methyl-5-(trifluoromethyl)-1H-pyrazol-4-yl)amino)pyrimidin-4-yl)-6,7,8,9-tetrahydro-5H-benzo[7]annulen-5-yl)-1,2,4-oxadiazole-3-carboxamide, 1-(tert-butyl)-N-(2-(2-((1-methyl-1H-pyrazol-4-yl)amino)pyridin-4-yl)-6,7,8,9-tetrahydro-5H-benzo[7]annulen-5-yl)-1H-1,2,3-triazole-4-carboxamide, (R)-1-(tert-butyl)-N-(2-(2-((1-methyl-1H-pyrazol-4-yl)amino)pyridin-4-yl)-6,7,8,9-tetrahydro-5H-benzo[7]annulen-5-yl)-1H-1,2,3-triazole-4-carboxamide, (S)-1-(tert-butyl)-N-(2-(2-((1-methyl-1H-pyrazol-4-yl)amino)pyridin-4-yl)-6,7,8,9-tetrahydro-5H-benzo[7]annulen-5-yl)-1H-1,2,3-triazole-4-carboxamide, N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-5-(1-methylcyclopropyl)-1,3,4-oxadiazole-2-carboxamide, (R)—N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-5-(1-methylcyclopropyl)-1,3,4-oxadiazole-2-carboxamide, and (S)—N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-5-(1-methylcyclopropyl)-1,3,4-oxadiazole-2-carboxamide, or a pharmaceutically acceptable salt thereof.

The present invention also provides crystalline forms of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide (compound 27):

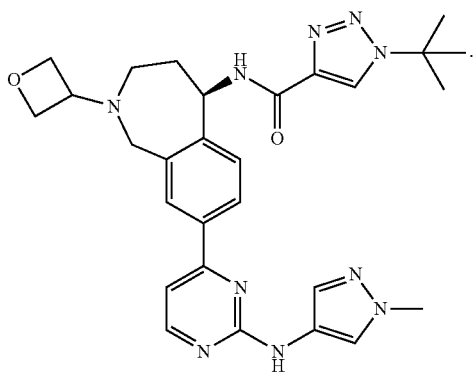 [SMILES: Cn1cc(Nc2nccc(-c3ccc4c(c3)CN(C3COC3)CC[C@H]4NC(=O)c3cn(C(C)(C)C)nn3)n2)cn1]

As used herein, the term "crystalline" refers to a solid form having a crystal structure wherein the individual molecules have a highly homogeneous regular locked-in chemical configuration.

Form A

In one embodiment, the present invention provides crystalline Form A of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one aspect, crystalline Form A is characterized by at least three, at least four, or at least five powder X-ray diffraction (PXRD) peaks at 2θ angles selected from 5.7°, 7.9°, 9.7°, 18.2°, 19.0° and 22.4°. In one embodiment, crystalline Form A is characterized by powder X-ray diffraction peaks at 2θ angles selected from 5.7°, 7.9°, 9.7°, 18.2°, 19.0° and 22.4°. In some embodiments, the peaks described above for crystalline Form A have a relative intensity of at least 5%, at least 10%, or at least 15%. In another embodiment, crystalline Form A is characterized by at least three, at least four, at least five, at least six, at least seven, at least eight, at least nine, at least ten, at least eleven, at least twelve, at least thirteen, at least fourteen, at least fifteen, at least sixteen, at least seventeen, or at least nineteen PXRD peaks at 2θ angles selected from 4.3°, 5.7°, 7.9°, 8.7°, 9.7°, 11.9°, 13.1°, 14.8°, 15.2°, 16.1°, 17.0°, 17.8°, 18.2°, 19.0°, 20.5°, 21.2°, 22.4°, 22.8°, 23.8°, and 25.6°.

As used herein, the term "relative intensity" refers to a ratio of the peak intensity for the peak of interest versus the peak intensity for the largest peak.

In another aspect, crystalline Form A has a PXRD pattern that is substantially the same as PXRD pattern shown in FIG. 1.

Figure 2:
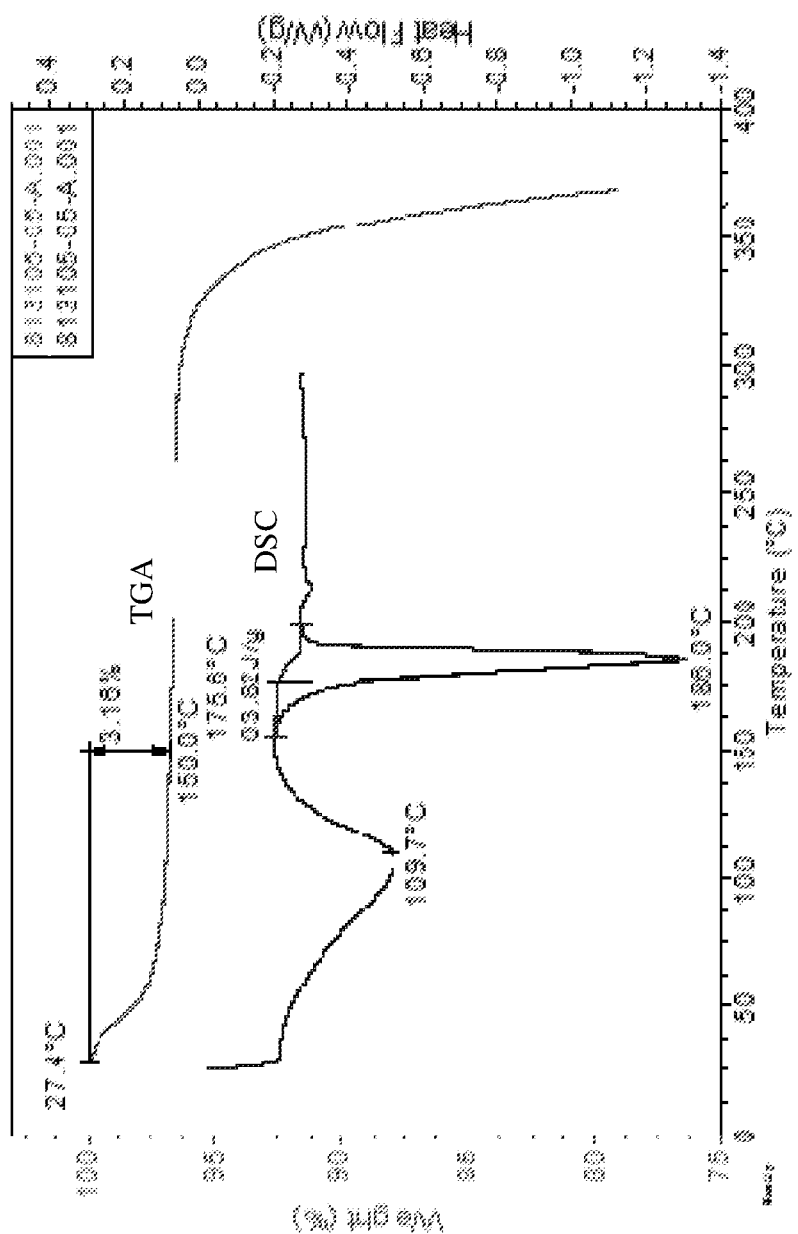
FIG. 2 depicts differential scanning calorimetry (DSC) and thermal gravimetric analysis (TGA) profiles of crystalline Form A of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one aspect, crystalline Form A has a differential scanning calorimetry (DSC) profile that is substantially the same as the DSC profile shown in FIG. 2. In particular, crystalline Form A is characterized by an onset temperature at 175.6° C.±2° C. in the DSC profile. In one embodiment, crystalline Form A has a melting temperature of 186° C.±2° C.

In one aspect, crystalline Form A has a TGA profile that is substantially the same as the TGA profile shown in FIG. 2. In particular, the TGA profile indicates that crystalline Form A is a hydrate.

As used herein, "hydrate" refers to refers to a crystalline solid adduct containing (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide and either stoichiometric or nonstoichiometric amounts of a water incorporated within the crystal structure. Techniques known in the art to determine the to determine the amount of water present include, for example, TGA and Karl Fisher (KF) analysis.

In another aspect, crystalline Form A has a solid state $^{13}$C NMR spectrum that is substantially the same as that shown in FIG. 3B. In one embodiment, crystalline Form A is characterized by chemical shifts at 143.7 ppm and/or 134.4 ppm in solid state $^{13}$C NMR spectrum. The spectrum of Form A exhibit broader signals without showing clear duplicated signals. The Form A spectrum also suggests that there may be two independent molecules with different geometry. In another embodiments, crystalline Form A is characterized by chemical shifts in solid state $^{13}$C NMR spectrum as shown in Table 3.

In some embodiments, crystalline Form A is characterized by, for example, PXRD, DSC, TGA or $^{13}$NMR described above or any combination thereof. In one embodiment, crystalline Form A is characterized by PXRD alone or PXRD in combination with one or more of DSC, TGA and $^{13}$NMR described above.

In some embodiments, crystalline Form A is at least 70%, 80%, 85%, 90%, 95%, 97%, 99%, 99.5% or 99.9% pure. The purity of Form A is determined by dividing the weight of crystalline Form A in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form A of the compound.

In one embodiment, the present invention provides a method for preparing crystalline Form A of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. Such method includes, e.g., forming crystalline Form A from a slurry comprising (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide and ethanol (EtOH). In one embodiment, the method comprises stirring the slurry containing (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide and EtOH at room temperature for 1 hour to 1 week, e.g., 1 hour, 2 hours, 3 hours, 4 hours, 5 hours, 10 hours, 15 hours, 24 hours, or 48 hours.

Form G

In one embodiment, the present invention provides crystalline Form G of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one aspect, crystalline Form G is characterized by at least three, at least four or at least five PXRD peaks at 2θ angles selected from 3.6°, 8.9°, 10.9°, 12.6°, 20.2° and 21.8°. In one embodiment, crystalline Form G is characterized by PXRD peaks at 2θ angles selected from 3.6°, 8.9°, 10.9°, 12.6°, 20.2° and 21.8°. In some embodiments, the peaks described above for crystalline Form G have a relative intensity of at least 5%, at least 10%, or at least 15%. In another embodiment, crystalline Form G is characterized by at least three, at least four, at least five, at least six, at least seven, at least eight, at least nine, at least ten, at least eleven, at least twelve, or at least thirteen PXRD peaks at 2θ angles selected from 3.6°, 8.9°, 11.0°, 12.6°, 14.5°, 15.4°, 16.3°, 18.4°, 20.2°, 21.8°, 23.4°, 25.4°, 26.8°, and 34.2°. In another embodiment, crystalline Form A is characterized by PXRD peaks at 2θ angles selected from 3.6°, 8.9°, 11.0°, 12.6°, 14.5°, 15.4°, 16.3°, 18.4°, 20.2°, 21.8°, 23.4°, 25.4°, 26.8°, and 34.2°.

Figure 4:
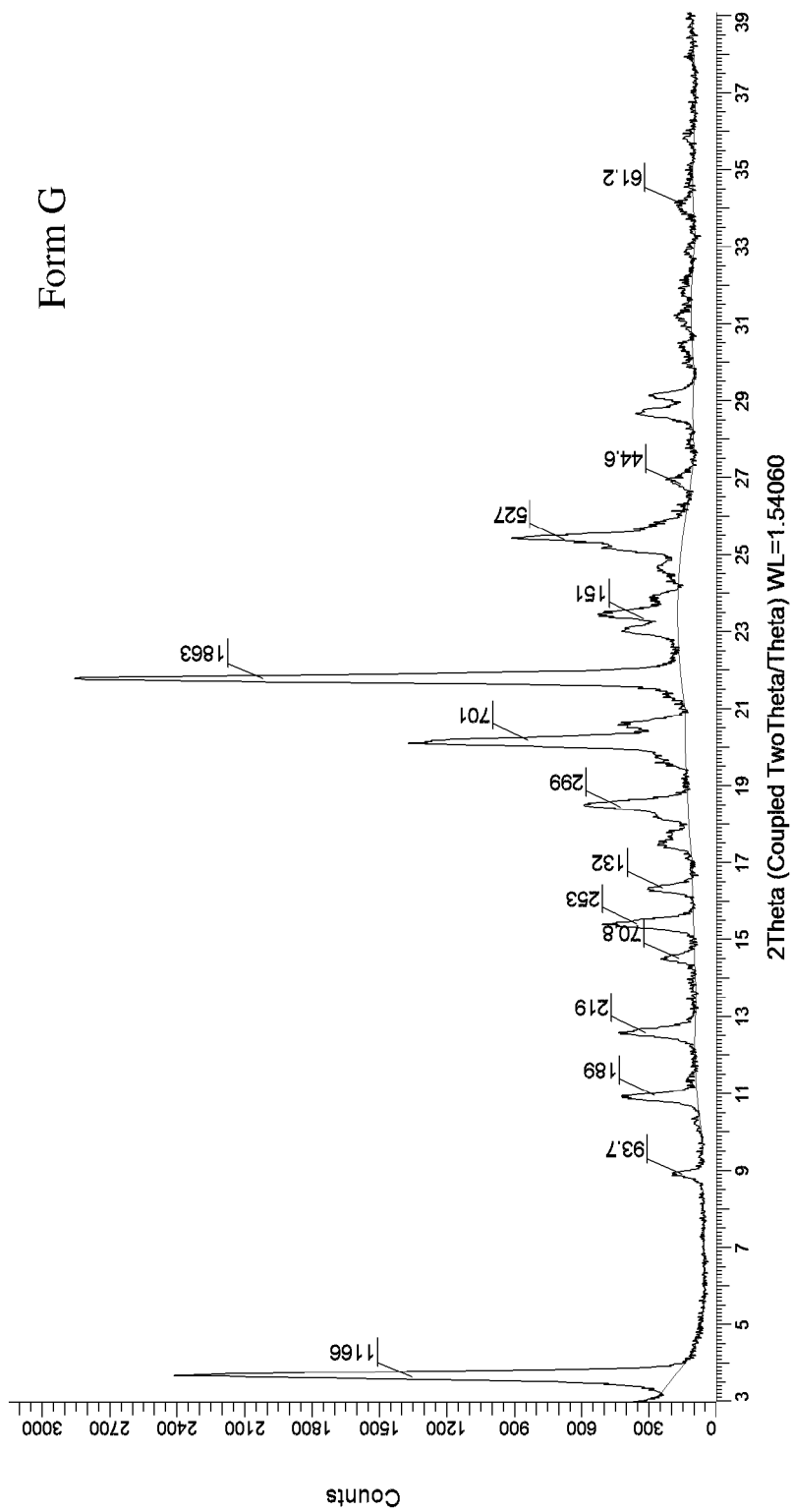
FIG. 4 depicts an powder X-ray diffraction (PXRD) pattern of crystalline Form G of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In another aspect, crystalline Form G has a PXRD pattern that is substantially the same as PXRD pattern shown in FIG. 4.

Figure 5:
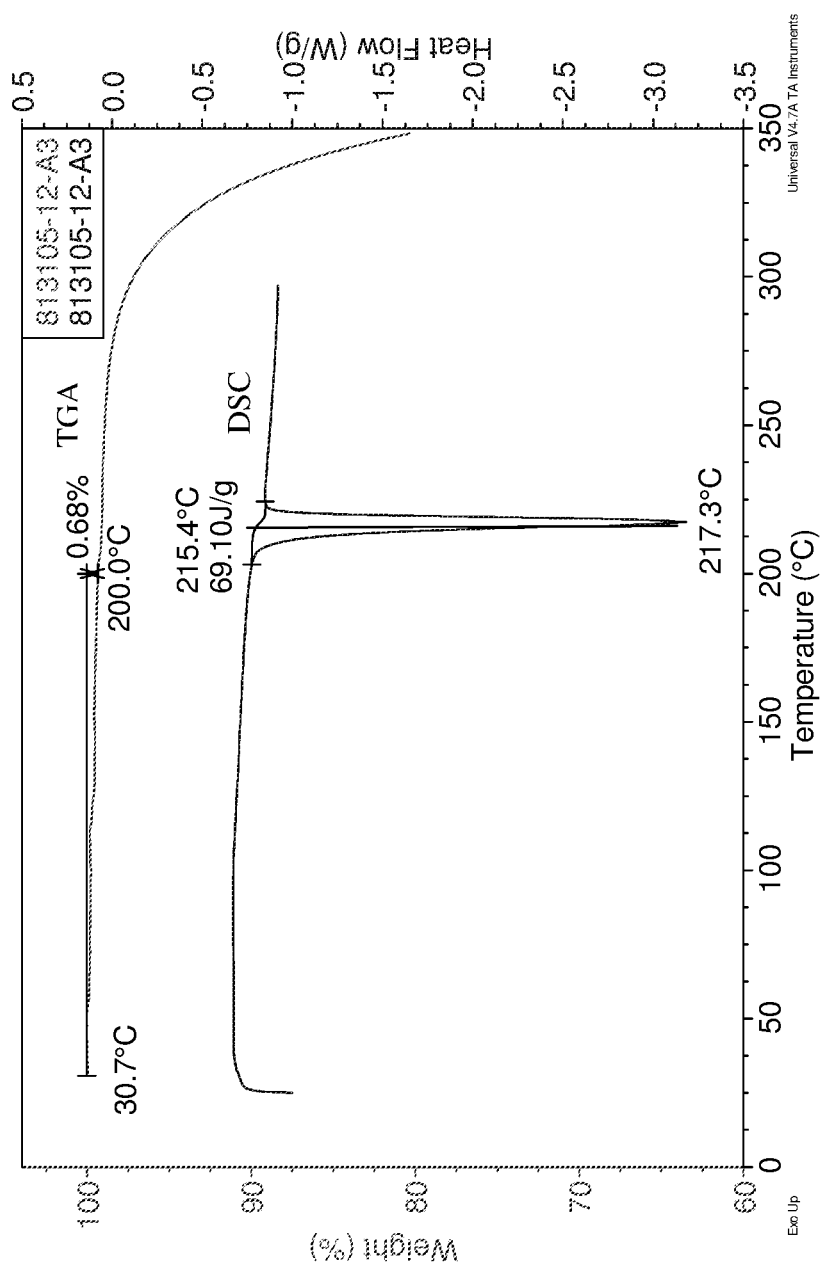
FIG. 5 depicts differential scanning calorimetry (DSC) and thermal gravimetric analysis (TGA) profiles of crystalline Form G of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one aspect, crystalline Form G has a DSC profile that is substantially the same as the DSC profile shown in FIG. 5. In particular, crystalline Form G is characterized by an onset temperature at 215.4° C.±2° C. in the DSC profile. In another embodiment, crystalline Form G has a melting temperature of 217° C.±2° C.

In one aspect, crystalline Form G has a TGA profile that is substantially the same as the TGA profile shown in FIG. 5. In particular, the TGA profile indicates that crystalline Form G is an anhydrate.

"Anhydrate" as used herein, means that the crystalline form comprises substantially no water in the crystal lattice e.g., less than 1% by weight as determined by, for example, TGA analysis or other quantitative analysis.

Figure 6A:
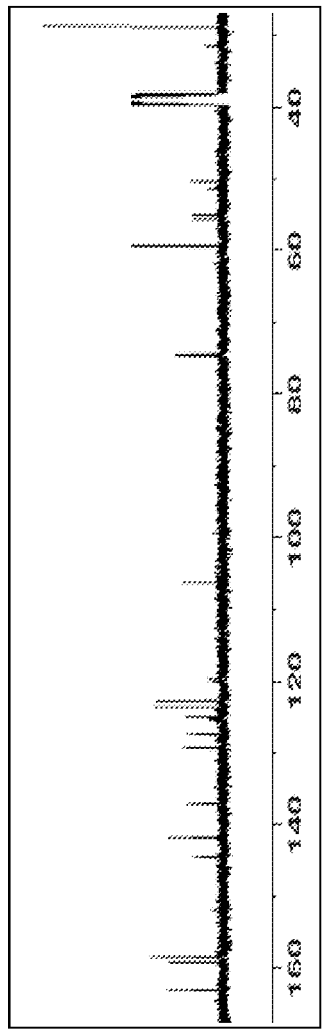
FIG. 6A shows solution $^{13}$C NMR spectrum of crystalline Form G of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.
Figure 6B:
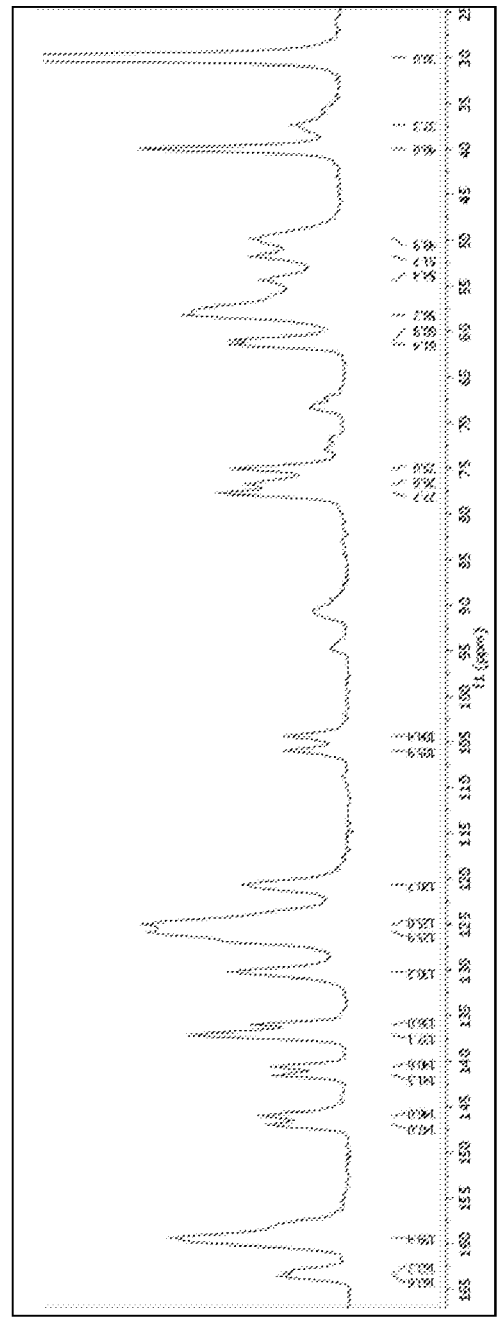
FIG. 6B shows solid state $^{13}$NMR spectrum of crystalline Form G.

In another aspect, crystalline Form G has a solid state $^{13}$C NMR spectrum that is substantially the same as that shown in FIG. 6B. In one embodiment, crystalline Form G is characterized by chemical shifts at 147.0 ppm, 146.0 ppm and/or 140.6 ppm in solid state $^{13}$C NMR spectrum. The spectrum of Form G shows peak splitting (duplicate signals) in aromatic regions when compared to the solution $^{13}$C NMR spectrum suggesting there are two independent molecules in the asymmetric unit. In another embodiment, crystalline Form G is characterized by chemical shifts in solid state $^{13}$C NMR spectrum as shown in Table 3.

In some embodiments, crystalline Form G is at least 70%, 80%, 85%, 90%, 95%, 97%, 99%, 99.5% or 99.9% pure. The purity of Form G is determined by dividing the weight of crystalline Form G in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form G of the compound.

In one embodiment, the present invention provides a method for preparing crystalline Form G of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. Such method includes, e.g., forming crystalline Form G from a slurry comprising (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide and isopropyl acetate (IPAc). In one embodiment, the method comprises stirring the slurry containing (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide and isopropyl acetate (IPAc) at an elevated temperature (e.g., between 30° C. and 70° C., between 40° C. and 60° C., between 45° C. and 55° C., or at 50° C.), for 1 hour to 1 week, e.g., 1 hour, 2 hours, 3 hours, 4 hours, 5 hours, 10 hours, 15 hours, 24 hours, or 48 hours.

Alternatively, crystalline Form G can be prepared by a method comprising the steps of (i) removing at least a portion of dichloromethane by distillation from a mixture containing (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide and dichloromethane; (ii) adding isopropyl acetate (IPAc) to the mixture; (iii) heating the mixture containing IPAc to an elevated temperature (e.g., between 50° C. and 70° C., between 55° C. and 65° C. or 60° C.) followed by cooling to near room temperature (e.g., 20° C.) to form a slurry containing the compound and IPAc; and (iv) isolating crystalline Form G from the slurry. In one embodiment, steps (i) and (ii) can be repeated for one or more times (e.g. two, three, four, or five times). In one embodiment, steps (i) and (ii) are repeated until substantially all (e.g., at least 60%, at least 70%, at least 80%, at least 90%, or at least 95% by volume) of dichloromethane is removed. In one embodiment, the heating and the cooling in step (iii) can be repeated for one or more times (e.g. two, three, four, five, ten, fifteen, twenty, or more times).

It will be understood that the 2θ values of the PXRD pattern for crystalline Form A or crystalline Form G may vary slightly from one instrument to another and may depend on variations in sample preparation. Therefore, the PXRD peak positions for crystalline Form A or crystalline Form G are not to be construed as absolute and can vary ±0.2°.

As intended herein, "substantially the same PXRD pattern as shown in FIG. 1", "substantially the same PXRD pattern as shown in FIG. 4", "substantially the same as that shown in FIG. 3B" or "substantially the same as that shown in FIG. 6B" mean that for comparison purposes, at least 80%, at least 90%, or at least 95% of the peaks shown in FIG. 1, FIG. 4, FIG. 3B and FIG. 6B are present. It is to be further understood that for comparison purposes some variability in peak position from those shown in FIG. 1 and FIG. 4 are allowed, such as ±0.2°. Similarly, for comparison purposes some variability in peak position from those shown in FIG. 3B and FIG. 6B are allowed, such as ±0.5 ppm.

As used herein, the term "alkyl" refers to a fully saturated branched or unbranched hydrocarbon moiety. Preferably the alkyl comprises 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, iso-propenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

The number of carbon atoms in a group is specified herein by the prefix "$C_{x-xx}$", wherein x and xx are integers. For example, "$C_{1-4}$alkyl" is an alkyl group which has from 1 to 4 carbon atoms.

"Halogen" or "halo" may be fluoro, chloro, bromo or iodo.

As used herein, the term "heterocyclyl" refers to a saturated or unsaturated, monocyclic or bicyclic (e.g., fused, bridged or spiro ring systems) ring system which has from 3- to 10-ring members, or in particular 3- to 8-ring members, 3- to 7-ring members, 3- to 6-ring members or 5- to 7-ring members or 4- to 7-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings. As used herein, the term "heteroaryl" refers to an aromatic 5- or 6-membered monocyclic ring system, having 1 to 4 heteroatoms independently selected from O, S and N, and wherein N can be oxidized (e.g., N(O)) or quaternized, and S can be optionally oxidized to sulfoxide and sulfone. In one embodiment, a heterocyclyl is a 3- to 7-membered saturated monocyclic or a 3- to 6-membered saturated monocyclic or a 5- to 7-membered saturated monocyclic ring or a 4- to 6-membered saturated monocyclic ring. In one embodiment, a heterocyclyl is a 3- to 7-membered monocyclic or a 3- to 6-membered monocyclic or a 4- to 6-membered monocyclic ring or a 5- to 7-membered monocyclic ring. In another embodiment, a heterocyclyl is a 6- or 7-membered bicyclic ring. In yet another embodiment, a heterocyclyl is a 4- to 7-membered monocyclic non-aromatic ring. In another embodiment, a heterocyclyl is 6- to 8-membered spiro or bridged bicyclic ring. The heterocyclyl group can be attached at a heteroatom or a carbon atom. Examples of heterocyclyls include, but are not limited to, aziridinyl, oxiranyl, thiiranyl, oxaziridinyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, and heteroaryl rings including azetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl and the like.

The term "fused ring system", as used herein, is a ring system that has two rings each of which are independently selected from a carbocyclyl or a heterocyclyl, wherein the two ring structures share two adjacent ring atoms. A fused ring system may have from 9 to 12 ring members.

The term "bridged ring system", as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system may have from 6 to 8 ring members.

The term "spiro ring system," as used herein, is a ring system that has two rings each of which are independently selected from a carbocyclyl or a heterocyclyl, wherein the two ring structures having one ring atom in common. Spiro ring systems have from 5 to 8 ring members.

In one embodiment, a heterocyclyl is a 4- to 6-membered monocyclic heterocyclyl. Examples of 4- to 6-membered monocyclic heterocyclic ring systems include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl.

In another embodiment, a heterocyclyl is a saturated 4- to 6-membered monocyclic heterocyclyl. Examples of saturated 4- to 6-membered monocyclic heterocyclic ring systems include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, and dithiinyl. In one embodiment, a saturated 4- to 6-membered monocyclic heterocyclyl is azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, or dioxinyl. In another embodiment, a saturated 4- to 6-membered monocyclic heterocyclyl is oxetanyl, tetrahydrofuranyl, or tetrahydropyranyl.

As used herein, the term "carbocyclyl" refers to saturated or unsaturated monocyclic or bicyclic hydrocarbon groups of 3-7 carbon atoms, 3-5, 3-6, 4-6, or 5-7 carbon atoms. The term "carbocyclyl" encompasses cycloalkyl groups and aromatic groups. The term "cycloalkyl" refers to completely saturated monocyclic or bicyclic or spiro hydrocarbon groups of 3-7 carbon atoms, 3-6 carbon atoms, or 5-7 carbon atoms. Exemplary monocyclic carbocyclyl groups include, but are not limited to, cyclopropyl, cyclobutyl, cyclopentyl, cyclohexyl, cycloheptyl, cyclopropenyl, cyclobutenyl, cyclopentenyl, cyclohexenyl, cycloheptenyl, cyclobutadienyl, cyclopentadienyl, cyclohexadienyl, cycloheptadienyl, phenyl and cycloheptatrienyl. Exemplary bicyclic carbocyclyl groups include bicyclo[2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, or 2,6,6-trimethylbicyclo[3.1.1]heptyl, spiro[2.2]pentanyl, and spiro[3.3]heptanyl. In one embodiment, the carbocyclyl is a 4- to 6-membered monocyclic carbocyclyl. In another embodiment, the carbocyclyl is a 3- to 5-membered carbocyclyl. In one embodiment, the carbocyclyl is a $C_{4-6}$ cycloalkyl. In yet another embodiment, the carbocyclyl is cyclobutyl, cyclopentyl or cyclohexyl.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, trimethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

The compounds or pharmaceutically acceptable salts thereof as described herein, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase).

When a particular stereoisomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired stereoisomer relative to the combined weight of all stereoisomers.

When a particular enantiomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired enantiomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 20%, 30%, 40%, 50%, 60%, 70%, 80%, 90%, 95%, 97%, 99%, 99.5% or 99.9%. The stereoisomeric purity the weight percent of the desired stereoisomers encompassed by the name or structure relative to the combined weight of all of the stereoisomers.

When a disclosed compound is named or depicted by structure without indicating the stereochemistry, and the compound has one chiral center, it is to be understood that the name or structure encompasses one enantiomer of compound in pure or substantially pure form, as well as mixtures thereof (such as a racemic mixture of the compound and mixtures enriched in one enantiomer relative to its corresponding optical isomer).

When a disclosed compound is named or depicted by structure without indicating the stereochemistry and, e.g., the compound has at least two chiral centers, it is to be understood that the name or structure encompasses one stereoisomer in pure or substantially pure form, as well as mixtures thereof (such as mixtures of stereoisomers, and mixtures of stereoisomers in which one or more stereoisomers is enriched relative to the other stereoisomer(s)).

The disclosed compounds may exist in tautomeric forms and mixtures and separate individual tautomers are contemplated. In addition, some compounds may exhibit polymorphism.

In one embodiment, the compounds of the invention or a pharmaceutically acceptable salt thereof include deuterium.

Another embodiment is a pharmaceutical composition comprising at least one compound described herein, or a pharmaceutically acceptable salt thereof, and at least one pharmaceutically acceptable carrier.

The compounds, or pharmaceutically acceptable salts thereof described herein may be used to decrease the activity of Btk, or to otherwise affect the properties and/or behavior of Btk, e.g., stability, phosphorylation, kinase activity, interactions with other proteins, etc.

In some embodiments, the present invention provides methods of decreasing Btk enzymatic activity. In some embodiments, such methods include contacting a Btk with an effective amount of a Btk inhibitor. Therefore, the present invention further provides methods of inhibiting Btk enzymatic activity by contacting a Btk with a Btk inhibitor of the present invention.

One embodiment of the invention includes a method of treating a disorder responsive to inhibition of Btk in a subject comprising administering to said subject an effective amount of at least one compound described herein, or a pharmaceutically acceptable salt thereof.

In one embodiment, the present invention provides methods of treating autoimmune disorders, inflammatory disorders, and cancers in a subject in need thereof comprising administering to said subject an effective amount of at least one compound described herein, or a pharmaceutically acceptable salt thereof.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barre syndrome (GBS), Hashimoto's disease, idiopathic thrombocytopenic purpura, lupus erythematosus, mixed connective tissue disease, multiple sclerosis, myasthenia gravis, pemphigus vulgaris, pernicious anaemia, polymyositis, primary biliary cirrhosis, Sjogren's syndrome, temporal arteritis, and Wegener's granulomatosis. The term "inflammatory disorders" includes diseases or disorders involving acute or chronic inflammation such as allergies, asthma, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis. In some embodiments, the present invention provides a method of treating rheumatoid arthritis or lupus. In some embodiments, the present invention provides a method of treating multiple sclerosis.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present invention provides a method of treating leukemia or lymphoma.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The effective dose of a compound provided herein, or a pharmaceutically acceptable salt thereof, administered to a subject can be 10 µg-500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of nontoxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The a compound or pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

EXEMPLIFICATIONS

LCMS methods: Samples were analyzed on a Waters Acquity UPLC BEH C18 1.7 uM 2.1×50 mm, part number 186002350 machine, MS mode: MS:ESI+ scan range 100-1000 daltons. PDA detection 210-400 nm. The method utilized was 95% water/5% MeCN (initial conditions) linear gradient to 5% $H_2O$/95% MeCN at 1 min, HOLD 5% $H_2O$/95% MeCN to 1.3 min at 0.7 ml/min in 0.1% trifluoroacetic acid (0.1% v/v) and the injection volume was 0.5 uL.

SFC separations: Each separation was run with conditions as specified in the examples below, including column name/part number, separation method, backpressure regulator setting on the SFC system, flowrate, detection wavelength, injection volume, sample concentration, and sample diluent.

Example 1: 5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,2,4-oxadiazole-3-carboxamide

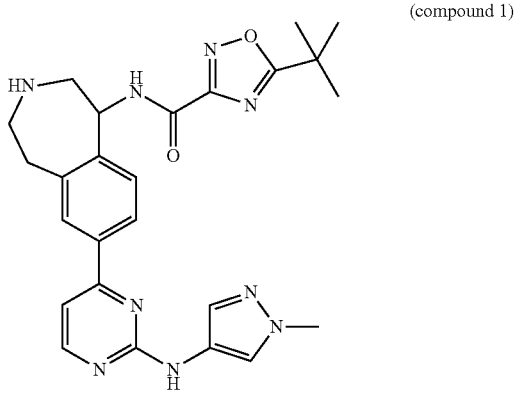 [SMILES: Cn1cc(Nc2nccc(-c3ccc4c(c3)CCNCC4NC(=O)c3noc(C(C)(C)C)n3)n2)cn1]

(compound 1)

I. Synthesis of N-(3-bromophenethyl)-4-methylbenzenesulfonamide

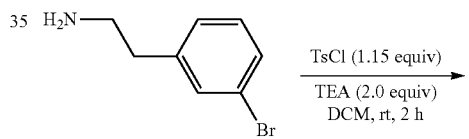

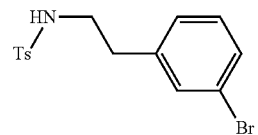

To a mixture of 2-(3-bromophenyl)ethanamine (2 g, 10 mmol) in $CH_2Cl_2$ (10 mL), triethylamine (2.02 g, 20 mmol) and TsCl (2.18 g, 11.5 mmol) were added at 0° C. The mixture was stirred at rt for 2 h, diluted with NaOH (1N, 100 mL) and extracted with $CH_2Cl_2$ (100 mL). The organic layer was washed with water (100 mL), brine (100 mL), dried ($Na_2SO_4$) and concentrated in vacuo to give N-(3-bromophenethyl)-4-methylbenzenesulfonamide (3.5 g, yield: 100%) as a yellow oil. ESI-MS (M+H)$^+$: 354.0. $^1$H NMR (400 MHz, $CDCl_3$) δ: 7.69 (d, J=8.0 Hz, 2H), 7.34 (d, J=8.4 Hz, 1H), 7.30 (d, J=8.0 Hz, 2H), 7.17 (t, J=1.6 Hz, 1H), 7.13 (t, J=8.0 Hz, 1H), 7.03-7.02 (m, 1H), 4.52 (t, J=6.0 Hz, 1H), 3.22-3.17 (m, 2H), 2.73 (t, J=6.8 Hz, 2H), 2.45 (s, 3H).

2. Synthesis of ethyl 2-(N-(3-bromophenethyl)-4-methylphenylsulfonamido)acetate

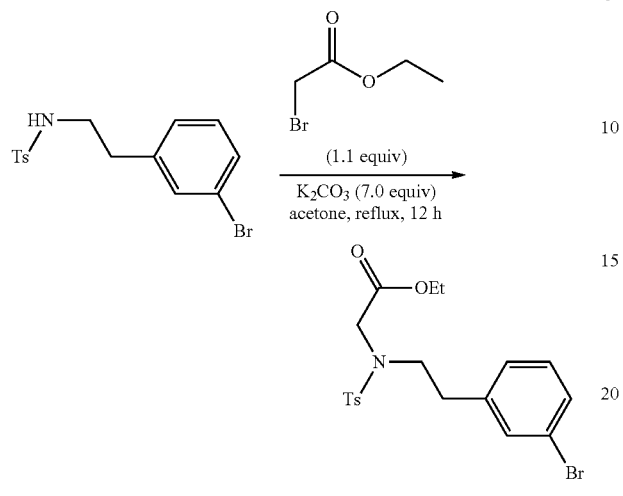

To a mixture of N-(3-bromophenethyl)-4-methylbenzenesulfonamide (7.2 g, 20 mmol) in (CH$_3$)$_2$CO (80 mL), K$_2$CO$_3$ (19.3 g, 140 mmol) and ethyl 2-bromoacetate (3.67 g, 22 mmol) were added. The mixture was stirred at 60° C. for 12 h, cooled to rt and the salt was filtered out. The resulting filtrate was concentrated in vacuo to give ethyl 2-(N-(3-bromophenethyl)-4-methylphenylsulfonamido)acetate (8.78 g, yield: 100%) as a yellow oil. ESI-MS (M+H)$^+$: 440.0. $^1$H NMR (400 MHz, CDCl$_3$) δ: 7.70 (d, J=8.4 Hz, 2H), 7.34 (d, J=8.4 Hz, 1H), 7.28 (d, J=8.0 Hz, 2H), 7.14 (t, J=7.6 Hz, 1H), 7.10-7.08 (m, 2H), 4.08 (q, J=7.6 Hz, 2H), 3.98 (s, 2H), 3.44 (t, J=7.6 Hz, 2H), 2.85 (t, J=7.2 Hz, 2H), 2.42 (s, 3H), 1.19 (t, J=7.2 Hz, 3H).

3. Synthesis of 2-(N-(3-bromophenethyl)-4-methylphenylsulfonamido)acetic Acid

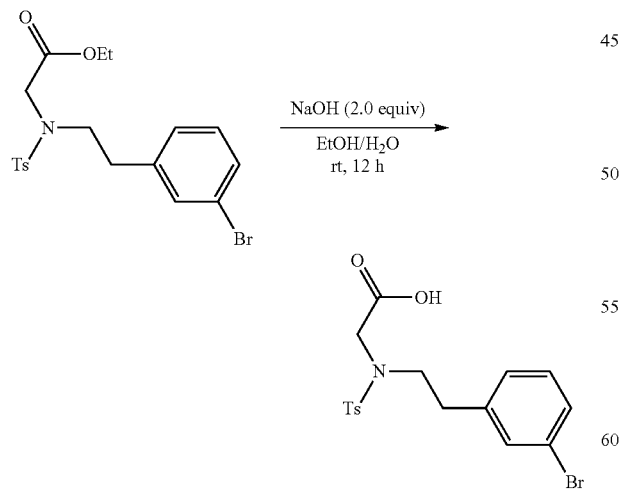

To a solution of ethyl 2-(N-(3-bromophenethyl)-4-methylphenylsulfonamido)acetate (8.78 mg, 20 mmol) in EtOH (40 mL) and H$_2$O (40 mL) was added NaOH (1.6 g, 40 mmol). The reaction mixture was stirred at rt for 12 h. Then the solvent was reduced and the residue was adjusted to pH=3 with HCl (1 N). The mixture was extracted with EtOAc (100 mL×3). The organic layers were dried over (Na$_2$SO$_4$) and concentrated in vacuo to give 2-(N-(3-bromophenethyl)-4-methylphenylsulfonamido)acetic acid as a yellow solid (8.2 g, yield: 100%). ESI-MS (M+H)$^+$: 412.0. $^1$H NMR (400 MHz, CDCl$_3$) δ: 7.69 (d, J=8.0 Hz, 2H), 7.34 (d, J=7.6 Hz, 1H), 7.29 (d, J=8.4 Hz, 2H), 7.22 (s, 1H), 7.14 (t, J=8.0 Hz, 1H), 7.08-7.06 (m, 1H), 4.00 (s, 2H), 3.45 (t, J=7.6 Hz, 2H), 2.83 (t, J=7.6 Hz, 2H), 2.42 (s, 3H).

4. Synthesis of 7-bromo-3-tosyl-2,3,4,5-tetrahydro-1H-benzo[d]azepin-1-one

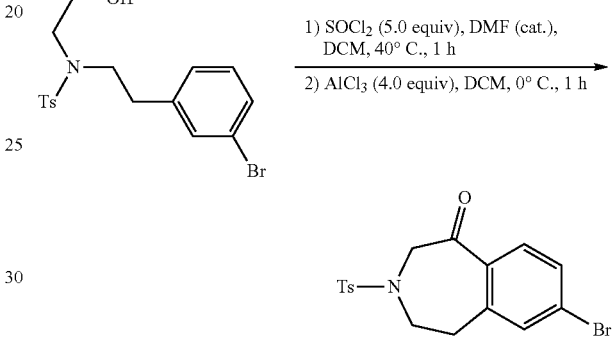

To a solution of 2-(N-(3-bromophenethyl)-4-methylphenylsulfonamido)acetic acid (8.2 g, 20 mmol) in CH$_2$Cl$_2$ (100 mL) was added SOCl$_2$ (11.9 g, 100 mmol) and DMF (cat.). The reaction mixture was stirred at 40° C. for 1 h. Then the solvent was removed under reduced pressure and dried in vacuo for 2 h. The residue was dissolved in CH$_2$Cl$_2$ (100 mL) and cooled in an ice bath. AlCl$_3$ (10.56 g, 80 mmol) was added and the mixture was stirred at 0° C.-rt for 12 h. The mixture was poured into conc. HCl (20 mL) and extracted with EtOAc (100 mL×2). The organic layers were washed with water (100 mL), brine (100 mL), dried (Na$_2$SO$_4$), and concentrated in vacuo to afford a residue which was purified by silica gel column (petroleum ether:EtOAc=4:1) to give 7-bromo-3-tosyl-2,3,4,5-tetrahydro-1H-benzo[d]azepin-1-one as a yellow solid (1.88 g, yield: 24%). ESI-MS (M+H)$^+$: 394.1. $^1$H NMR (400 MHz, CDCl$_3$) δ: 7.42 (d, J=8.4 Hz, 2H), 7.38 (dd, J=8.4, 1.6 Hz, 1H), 7.31-7.29 (m, 2H), 7.14 (d, J=8.0 Hz, 2H), 4.21 (s, 2H), 3.68 (t, J=6.8 Hz, 2H), 2.93 (t, J=7.2 Hz, 2H), 2.39 (s, 3H).

5. Synthesis of 7-bromo-3-tosyl-2,3,4,5-tetrahydro-1H-benzo[d]azepin-1-amine

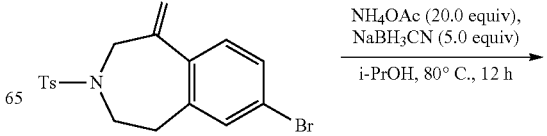

7. Synthesis of tert-butyl 1-amino-7-bromo-4,5-dihydro-1H-benzo[d]azepine-3(2H)-carboxylate

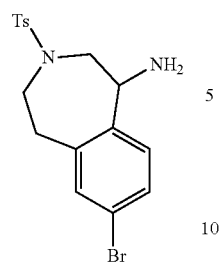

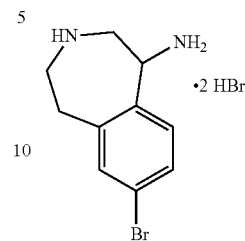

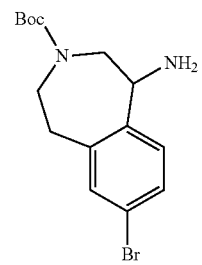

Synthesis of 7-bromo-3-tosyl-2,3,4,5-tetrahydro-1H-benzo[d]azepin-1-amine was similar to that of Example 2. The residue was purified by silica gel column (CH$_2$Cl$_2$: MeOH=20:1) to give 7-bromo-3-tosyl-2,3,4,5-tetrahydro-1H-benzo[d]azepin-1-amine as a yellow solid (154 mg, yield: 64%). ESI-MS (M+H)$^+$: 395.1. $^1$H NMR (400 MHz, CDCl$_3$) δ: 7.66 (d, J=8.4 Hz, 2H), 7.37 (d, J=8.4 Hz, 2H), 7.31 (dd, J=8.4, 1.6 Hz, 1H), 7.27 (d, J=1.6 Hz, 1H), 7.18 (d, J=8.4 Hz, 1H), 4.12-4.40 (m, 1H), 3.42-3.36 (m, 2H), 3.19-3.12 (m, 2H), 2.96-2.89 (m, 2H), 2.41 (s, 3H).

To a mixture of 7-bromo-3-tosyl-2,3,4,5-tetrahydro-1H-benzo[d]azepin-1-amine (680 mg, 1.7 mmol) and triethylamine (515 mg, 5.1 mmol) in CH$_2$Cl$_2$ (10 mL), Boc$_2$O (333 mg, 1.0 mmol) was added. The mixture was stirred at rt for 2 h. After diluting with CH$_2$Cl$_2$ (100 mL), the organic layer was washed with water (30 mL) and brine (30 mL), dried (Na$_2$SO$_4$), filtered and concentrated in vacuo to give tert-butyl 1-amino-7-bromo-4,5-dihydro-1H-benzo[d]azepine-3(2H)-carboxylate (450 mg, yield: 77%) as a yellow oil. ESI-MS (M+H)$^+$: 341.0. $^1$H NMR (400 MHz, CDCl$_3$) δ: 7.31 (d, J=8.0 Hz, 1H), 7.26 (s, 1H), 7.19-7.11 (m, 1H), 4.17-4.10 (m, 1H), 3.83-3.66 (m, 2H), 3.48-3.45 (m, 1H), 3.37-3.14 (m, 2H), 2.78-2.73 (m, 1H), 1.47 (s, 9H).

6. Synthesis of 7-bromo-3-tosyl-2,3,4,5-tetrahydro-1H-benzo[d]azepin-1-amine

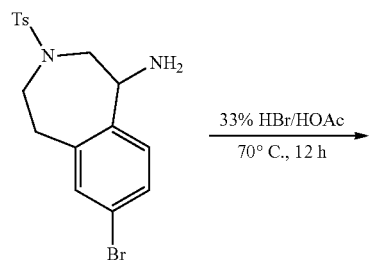

A mixture of 7-bromo-3-tosyl-2,3,4,5-tetrahydro-1H-benzo[d]azepin-1-amine (1.2 g, 3.04 mmol) in HBr/HOAc (33%, 20 mL) was stirred at 70° C. for 12 h. After cooling down, the mixture was diluted with EtOAc (60 mL) and the resulting precipitate was filtered and dried under vacuum to give 7-bromo-3-tosyl-2,3,4,5-tetrahydro-1H-benzo[d]azepin-1-amine (870 mg, yield: 71%) as a white solid. ESI-MS (M+H)$^+$: 241.1. $^1$H NMR (400 MHz, CDCl$_3$) δ: 7.65-7.63 (m, 2H), 7.25 (d, J=8.8 Hz, 1H), 5.17-5.14 (m, 1H), 3.84-3.80 (m, 1H), 3.69-3.65 (m, 1H), 3.44-3.40 (m, 2H), 3.27-3.14 (m, 2H).

8. Synthesis of tert-butyl 7-bromo-1-(5-(tert-butyl)-1,2,4-oxadiazole-3-carboxamido)-4,5-dihydro-1H-benzo[d]azepine-3(2H)-carboxylate

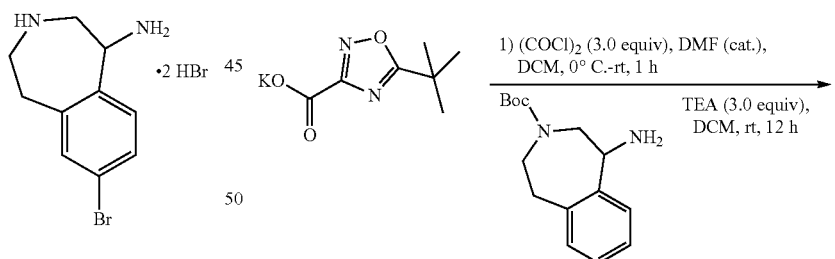

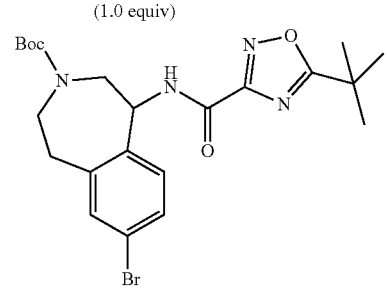

To a mixture of potassium 5-(tert-butyl)-1,2,4-oxadiazole-3-carboxylate (358 mg, 1.5 mmol) in CH$_2$Cl$_2$ (10 mL), (COCl)$_2$ (567 mg, 4.5 mmol) and DMF (cat.) were added at 0° C. The mixture was stirred at room temperature for 1 h. The mixture was concentrated. The residue was dried in vacuo, then dissolved in CH$_2$Cl$_2$ (10 mL), tert-butyl 1-amino-7-bromo-4,5-dihydro-1H-benzo[d]azepine-3(2H)-carboxylate (408 mg, 1.5 mmol) and triethylamine (454 mg, 4.5 mmol) were added. The mixture was stirred at rt for 12 h and diluted with CH$_2$Cl$_2$ (100 mL). The organic phase was washed with water (50 mL) and brine (50 mL) and concentrated. The residue was purified by silica gel column (PE (petroleum ether):EtOAc (ethyl acetate)=4:1) to give tert-butyl 7-bromo-1-(5-(tert-butyl)-1,2,4-oxadiazole-3-carboxamido)-4,5-dihydro-1H-benzo[d]azepine-3(2H)-carboxylate (290 mg, yield: 38%) as a white solid. ESI-MS (M+H−56)$^+$: 437.0. $^1$H NMR (400 MHz, CD$_3$OD) δ: 7.42-7.38 (m, 2H), 7.26 (d, J=7.6 Hz, 1H), 5.39 (d, J=5.2 Hz, 1H), 4.14-4.08 (m, 1H), 4.01-3.87 (m, 1H), 3.75-3.70 (m, 2H), 3.56-3.46 (m, 1H), 3.24-3.15 (m, 1H), 3.00-2.91 (m, 1H), 1.48 (s, 9H), 1.38 (s, 9H).

9. Synthesis of 2-chloro-4-methoxypyrimidine

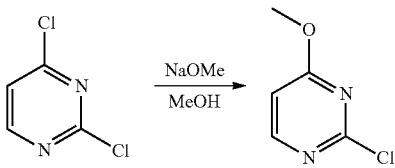

To a solution of 2,4-dichloropyrimidine (7.5 g, 50 mmol,) in MeOH (80 mL) was added dropwise into a solution of NaOMe (2.84 g, 52.5 mmol) in MeOH (20 mL) at 0° C. The reaction mixture was stirred at 0° C. for 2 h. The reaction mixture was concentrated in vacuo to give crude product. The crude product was poured into 150 mL of water. The aqueous phase was extracted with EtOAc (100 mL). The organic layer was dried with Na$_2$SO$_4$ and concentrated in vacuum to give 2-chloro-4-methoxypyrimidine (5.9 g, yield: 82%) as a light yellow solid. ESI-MS (M+H)$^+$: 145.0. $^1$H NMR (400 MHz, CDCl$_3$) δ: 8.27 (d, J=6.0 Hz, 1H), 6.65 (d, J=6.0 Hz, 1H), 3.99 (s, 3H).

10. Synthesis of 4-methoxy-N-(1-methyl-1H-pyrazol-4-yl)pyrimidin-2-amine

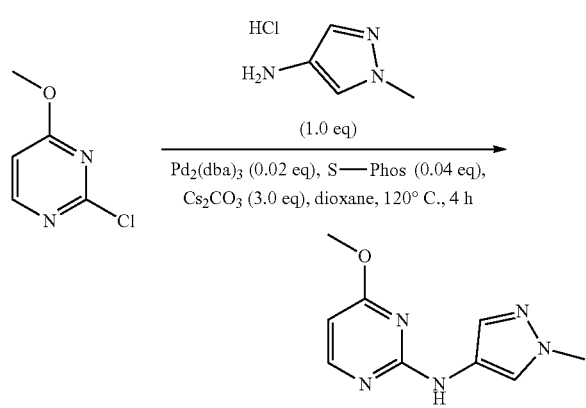

To a solution of 2-chloro-4-methoxypyrimidine (120 g, 0.83 mol) in dioxane (2 L) was added 1-methyl-1H-pyrazol-4-amine hydrochloride (111 g, 0.83 mol), Cs$_2$CO$_3$ (0.83 kg, 2.5 mol), S-Phos (13.3 g, 0.03 mol) and Pd$_2$(dba)$_3$ (16.7 g, 0.02 mol). The reaction mixture was stirred at 120° C. under N$_2$ for 4 h. The reaction mixture was cooled to room temperature and water (4 L) was added. The layers were separated and the aqueous phase was extracted with EtOAc (3×2 L). The combined organic layers were washed with brine (3 L), dried (Na$_2$SO$_4$) and concentrated. The crude material was purified by silica gel chromatography (PE:EtOAc=5:1 to 1:1) to give 4-methoxy-N-(1-methyl-1H-pyrazol-4-yl)pyrimidin-2-amine (73 g, yield: 43%) as a tan solid. ESI-MS (M+H)$^+$: 205.8.

11. Synthesis of 4-chloro-N-(1-methyl-1H-pyrazol-4-yl)pyrimidin-2-amine

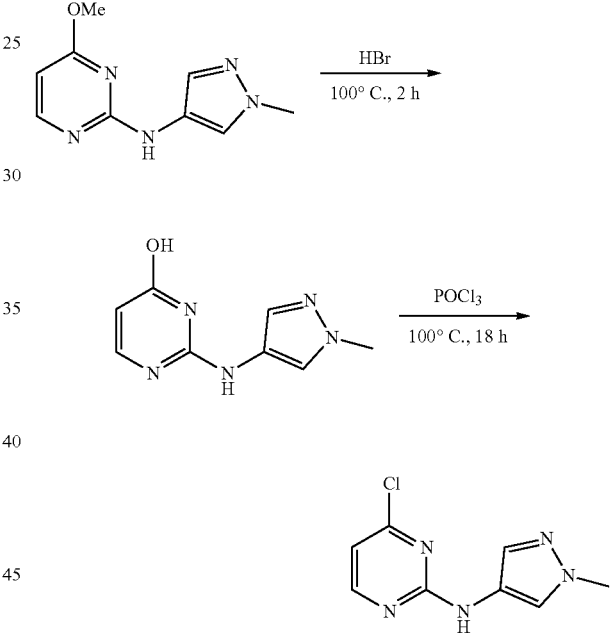

To 4-methoxy-N-(1-methyl-1H-pyrazol-4-yl)pyrimidin-2-amine (1.4 kg, 6.8 mol) was added HBr (11.2 L, 38% aqueous). The reaction mixture was heated to 100° C. and stirred at that temperature for 2 h. The reaction mixture was concentrated and then POCl$_3$ (11.2 L) was added. The reaction mixture was heated to 100° C. and stirred at that temperature for 16 h. The reaction mixture was cooled to room temperature and concentrated. Water (10 L) was added to the residue and the pH of the solution was adjusted to pH=14 with aqueous NaOH (4 M). The basic aqueous phase was extracted with EtOAc (3×10 L). The combined organic layers were washed with brine (9 L), dried (Na$_2$SO$_4$) and concentrated. The crude material was purified by silica gel chromatography (PE:EtOAc=5:1 to 2:1) to give 4-chloro-N-(1-methyl-1H-pyrazol-4-yl)pyrimidin-2-amine as a white solid (770 g, yield: 54%). ESI-MS (M+H)$^+$: 210.0.

12. Synthesis of tert-butyl 1-(5-(tert-butyl)-1,2,4-oxadiazole-3-carboxamido)-7-(2-((1-methyl-1H-pyrazol-4-yl)amino)pyrimidin-4-yl)-4,5-dihydro-1H-benzo[d]azepine-3(2H)-carboxylate

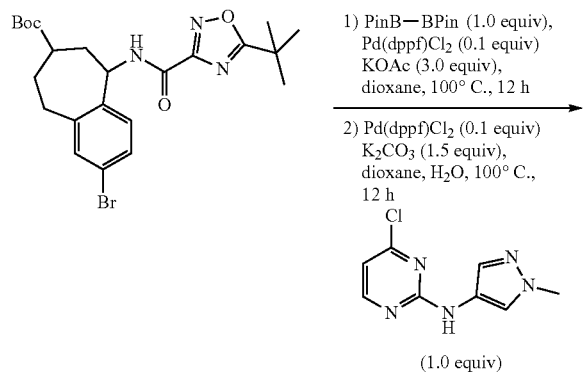

To a mixture of tert-butyl 7-bromo-1-(5-(tert-butyl)-1,2,4-oxadiazole-3-carboxamido)-4,5-dihydro-1H-benzo[d]azepine-3(2H)-carboxylate (510 mg, 1.03 mmol) and PinB-BPin (263 mg, 1.0 mmol) in dry 1,4-dioxane (10 mL), KOAc (303 mg, 3.09 mmol) and Pd(dppf)Cl$_2$CH$_2$Cl$_2$ (81 mg, 0.1 mmol) were added quickly under N$_2$. The mixture was stirred at 100° C. for 12 h under N$_2$. After cooling down, 4-chloro-N-(1-methyl-1H-pyrazol-4-yl)pyrimidin-2-amine (237 mg, 1.13 mmol), K$_2$CO$_3$ (213 mg, 1.54 mmol) and H$_2$O (2.5 mL) were added. The mixture was stirred at 100° C. for 12 h under N$_2$. After cooling down, the mixture was concentrated and purified by silica gel column (CH$_2$Cl$_2$:PE:EtOAc=1:1:1) to give tert-butyl 1-(5-(tert-butyl)-1,2,4-oxadiazole-3-carboxamido)-7-(2-((1-methyl-1H-pyrazol-4-yl)amino)pyrimidin-4-yl)-4,5-dihydro-1H-benzo[d]azepine-3(2H)-carboxylate (250 mg, yield: 41%) as a yellow solid. ESI-MS (M+H)$^+$: 588.2. $^1$H NMR (400 MHz, CD$_3$OD) δ: 8.41 (d, J=4.8 Hz, 1H), 7.99-7.98 (m, 3H), 7.64 (s, 1H), 7.49 (d, J=8.4 Hz, 1H), 7.21 (d, J=5.2 Hz, 1H), 5.54-5.47 (m, 1H), 4.18-4.05 (m, 1H), 3.97-3.90 (m, 4H), 3.87-3.76 (m, 2H), 3.65-3.57 (m, 1H), 3.15-3.11 (m, 1H), 1.49 (s, 9H), 1.39 (s, 9H).

13. Synthesis of 5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,2,4-oxadiazole-3-carboxamide

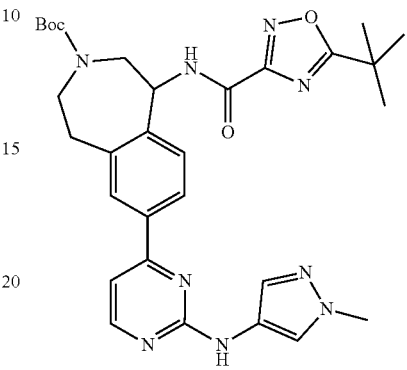

To a solution of TFA (1 mL) in CH$_2$Cl$_2$ (2 mL) was added tert-butyl 1-(5-(tert-butyl)-1,2,4-oxadiazole-3-carboxamido)-7-(2-((1-methyl-1H-pyrazol-4-yl)amino)pyrimidin-4-yl)-4,5-dihydro-1H-benzo[d]azepine-3(2H)-carboxylate (230 mg, 0.39 mmol). The mixture was stirred at rt for 1 h, then concentrated and purified by prep-HPLC (CH$_3$CN/water NH$_4$HCO$_3$ 0.05% as mobile phrase) to give 5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,2,4-oxadiazole-3-carboxamide (120 mg, yield: 58%). ESI-MS (M+H)$^+$: 488.3. $^1$H NMR (400 MHz, CD$_3$OD) δ: 8.37-8.35 (m, 1H), 7.95 (s, 1H), 7.91-7.88 (m, 2H), 7.63 (s, 1H), 7.46 (d, J=7.6 Hz, 1H), 7.15 (d, J=4.8 Hz, 1H), 5.34 (d, J=7.2 Hz, 1H), 3.95 (s, 3H), 3.24-3.19 (m, 1H), 3.11-3.08 (m, 3H), 2.99-2.94 (m, 2H), 1.49 (s, 9H).

Example 2. (R)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide (Compound 2)

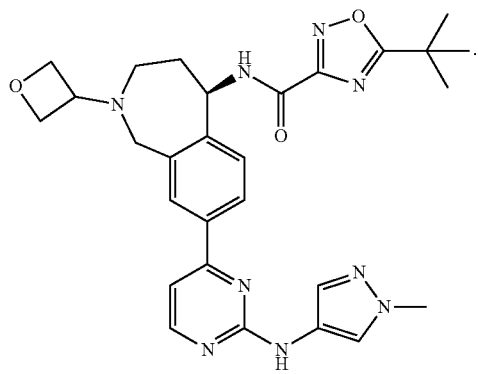 [SMILES: Cn1cc(Nc2nccc(-c3ccc4c(c3)CN(C3COC3)CC[C@H]4NC(=O)c3noc(C(C)(C)C)n3)n2)cn1]

Method 1:

I. Preparation of 3-(3-Bromo-benzylamino)-propionic Acid Ethyl Ester

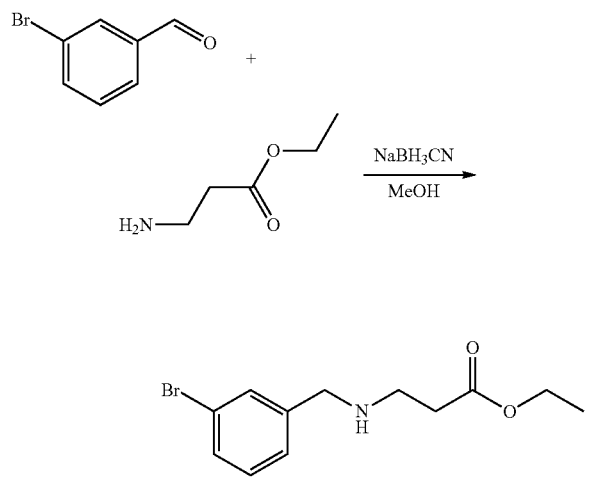

To a solution of ethyl 3-aminopropanoate (46.0 g, 0.3 mol) and 3-bromobenzaldehyde (55.5 g, 0.3 mol) in MeOH (1.2 L) were added triethylamine (60.7 g, 0.6 mol) and NaCNBH₃ (56.5 g, 0.9 mol) portion-wise. The resulting mixture was stirred at rt for 4 h. The reaction mixture was concentrated in vacuo and the residue was diluted with water (600 mL). The mixture was extracted with EtOAc (3×500 mL). The combined organic layer was washed with brine (100 mL), dried over anhydrous Na₂SO₄, filtered and concentrated in vacuo to give 3-(3-bromo-benzylamino)-propionic acid ethyl ester (46.5 g, yield: 54%) as a light yellow oil. ¹H NMR (DMSO-d₆, 300 MHz): δ 7.52 (s, 1H), 7.40 (d, J=7.5 Hz, 1H), 7.31-7.25 (m, 2H), 4.04 (q, J=7.2 Hz, 2H), 3.67 (s, 2H), 2.69 (t, J=7.2 Hz, 2H), 2.42 (t, J=6.9 Hz, 2H), 1.17 (t, J=6.9 Hz, 3H).

2. Preparation of 3-[(3-Bromo-benzyl)-(toluene-4-sulfonyl)-amino]-propionic Acid Ethyl Ester

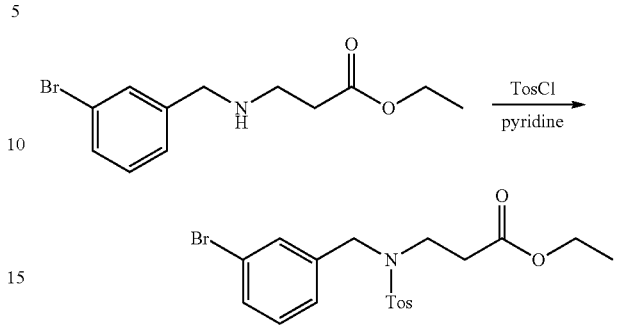

To a solution of 3-(3-bromo-benzylamino)-propionic acid ethyl ester (45.6 g, 0.16 mol) in pyridine (500 mL) was added TosCl (61.0 g, 0.32 mol) at rt. The reaction mixture was stirred at 120° C. for 16 h. The solvent was removed in vacuo to give the crude product. The crude product was purified by column chromatography on silica gel (petroleum ether:EtOAc=10:1 to 5:1) to afford 3-[(3-Bromo-benzyl)-(toluene-4-sulfonyl)-amino]-propionic acid ethyl ester (61 g, yield: 88%) as a light yellow oil. ¹H NMR (DMSO-d₆, 300 MHz): δ 7.74 (d, J=8.4 Hz, 2H), 7.49-7.41 (m, 4H), 7.31 (d, J=5.1 Hz, 2H), 4.33 (s, 2H), 3.93 (q, J=7.2 Hz, 2H), 3.32 (t, J=7.2 Hz, 2H), 2.41 (s, 3H), 2.36 (t, J=6.9 Hz, 2H), 1.10 (t, J=6.9 Hz, 3H).

3. Preparation of 3-[(3-Bromo-benzyl)-(toluene-4-sulfonyl)-amino]-propionic Acid

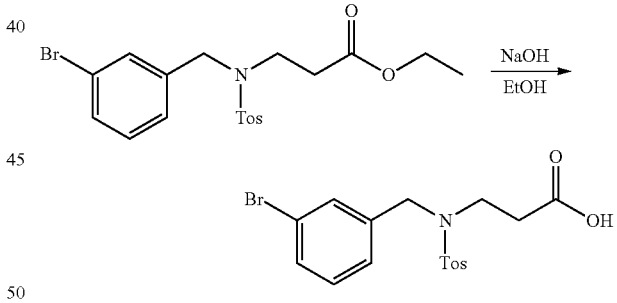

To a solution of 3-[(3-Bromo-benzyl)-(toluene-4-sulfonyl)-amino]-propionic acid ethyl ester (60.0 g, 0.14 mol) in a mixed solvent of EtOH (600 mL) and H₂O (60 mL) was added NaOH (11.2 g, 0.28 mol) portion-wise, the reaction solution was stirred at 60° C. for 4 h. The reaction solution was cooled to 0° C. and acidified to pH=5 with concentrated HCl. The solvent was concentrated in vacuo to give a residue which was extracted with EtOAc (3×150 mL). The organic layer was dried with Na₂SO₄, filtered, and concentrated in vacuo to give 3-[(3-Bromo-benzyl)-(toluene-4-sulfonyl)-amino]-propionic acid (45.2 g, yield: 78.6%) as a white solid. ¹H NMR (DMSO-d₆, 300 MHz): δ 12.28 (br, 1H), 7.74 (d, J=8.1 Hz, 2H), 7.49-7.41 (m, 4H), 7.32 (d, J=5.1 Hz, 2H), 4.33 (s, 2H), 3.29 (t, J=6.9 Hz, 2H), 2.41 (s, 3H), 2.27 (t, J=7.5 Hz, 2H).

4. Preparation of 3-[(3-Bromo-benzyl)-(toluene-4-sulfonyl)-amino]-propionyl Chloride

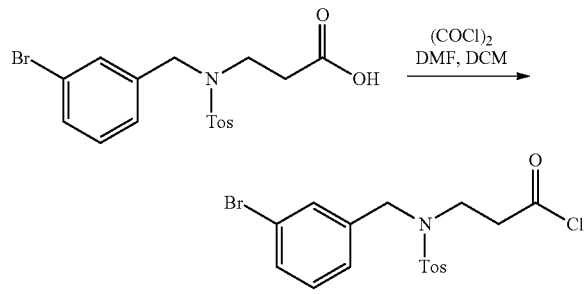

To a solution of 3-[(3-Bromo-benzyl)-(toluene-4-sulfonyl)-amino]-propionic acid (45.2 g, 0.11 mol) in CH$_2$Cl$_2$ (1000 mL) were added dropwise DMF (1 mL) and oxalyl chloride (27.9 g, 0.22 mol) portion-wise. The reaction solution was stirred at 55° C. for 2 h. The mixture was concentrated in vacuo to give the crude 3-[(3-Bromo-benzyl)-(toluene-4-sulfonyl)-amino]-propionyl chloride (47.2 g, yield: 99%) as a black oil which was used in the next step without further purification.

5. Preparation of 8-Bromo-2-(toluene-4-sulfonyl)-1,2,3,4-tetrahydro-benzo[c]azepin-5-one

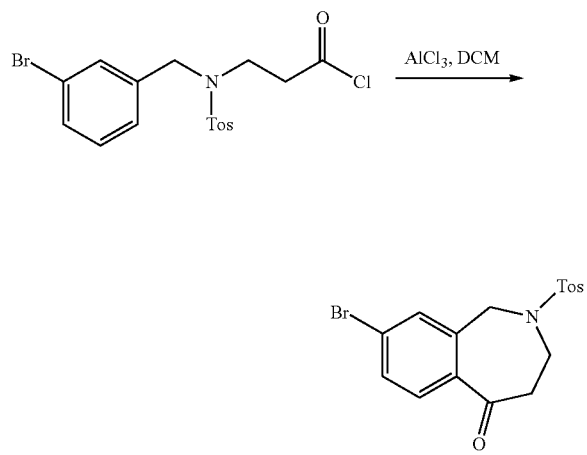

To a solution of 3-[(3-Bromo-benzyl)-(toluene-4-sulfonyl)-amino]-propionyl chloride (47.0 g, 0.11 mol) in anhydrous CH$_2$Cl$_2$ (1200 mL) was added AlCl$_3$ (29.3 g, 0.22 mol) portion-wise at rt. The reaction mixture was stirred at 55° C. for 2 h. The reaction mixture was poured into ice water (1.2 L) and extracted with (500 mL). The organic layer was concentrated in vacuo to give the crude product. The crude product was purified by column chromatography on silica gel (petroleum ether:EtOAc=5:1 to 2:1) to afford 8-bromo-2-(toluene-4-sulfonyl)-1,2,3,4-tetrahydro-benzo[c]azepin-5-one (35 g, yield: 81%) as a white solid. $^1$H NMR (DMSO-d$_6$, 300 MHz): δ 7.65 (d, J=8.4 Hz, 3H), 7.60-7.51 (m, 2H), 7.36 (d, J=8.1 Hz, 2H), 4.68 (s, 2H), 3.42 (t, J=9.2 Hz, 2H), 2.96 (t, J=6.3 Hz, 2H), 2.37 (s, 3H).

6. Preparation of [8-Bromo-2-(toluene-4-sulfonyl)-2,3,4,5-tetrahydro-1H-benzo[c]azepin-5-yl]-carbamic Acid Tert-Butyl Ester

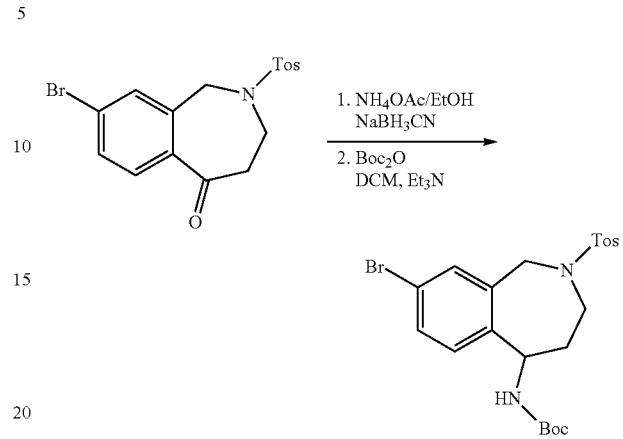

To a solution of 8-bromo-2-(toluene-4-sulfonyl)-1,2,3,4-tetrahydro-benzo[c]azepin-5-one (32.0 g, 0.08 mol) in EtOH (600 mL) were added NH$_4$OAc (18.5 g, 0.24 mol) and NaCNBH$_3$ (14.9 g, 0.24 mol) portion-wise at rt. Then the reaction mixture was stirred at 95° C. for 16 h. The mixture was poured into ice water (500 mL) and then EtOH was removed in vacuo. The residue was extracted with CH$_2$Cl$_2$ (3×500 mL). The combined solvent was concentrated. The residue was redissolved in CH$_2$Cl$_2$ (300 mL) and were added triethylamine (12.2 g, 0.12 mol) and (Boc)$_2$O (34.6 g, 0.12 mol) at rt. The mixture was stirred at rt for 4 h and then concentrated in vacuo to give the crude product. The crude product was purified by column chromatography on silica gel (petroleum ether:EtOAc=8:1 to 2:1) to afford [8-bromo-2-(toluene-4-sulfonyl)-2,3,4,5-tetrahydro-1H-benzo[c]azepin-5-yl]-carbamic acid tert-butyl ester (16.7 g, yield: 42%) as a white solid. $^1$H NMR (DMSO d$_6$, 300 MHz): δ 7.62-7.51 (m, 2H), 7.47 (d, J=9.9 Hz, 1H), 7.41-7.34 (m, 3H), 7.10 (d, J=8.4 Hz, 1H), 4.81-4.74 (m, 1H), 4.53 (d, J=15.0 Hz, 1H), 4.28 (d, J=15.3 Hz, 1H), 3.64-3.57 (m, 1H), 3.41-3.30 (m, 1H), 2.35 (s, 3H), 1.85-1.77 (m, 1H), 1.69-1.63 (m, 1H), 1.36 (s, 9H).

7. Preparation of 8-Bromo-2-(toluene-4-sulfonyl)-2,3,4,5-tetrahydro-1H-benzo[c]azepin-5-ylamine

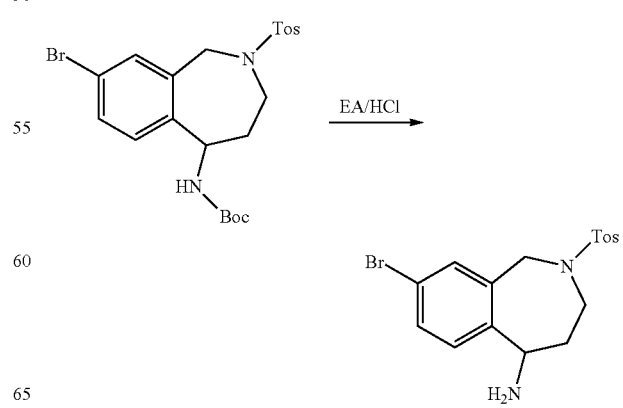

A solution of [8-bromo-2-(toluene-4-sulfonyl)-2,3,4,5-tetrahydro-1H-benzo[c]azepin-5-yl]-carbamic acid tert-butyl ester (14.8 g, 0.03 mol) in HCl/EtOAc (150 mL) was stirred at 25° C. for 4 h. The resulting solid was filtered and washed with MeOH and Et₂O to give the product 8-bromo-2-(toluene-4-sulfonyl)-2,3,4,5-tetrahydro-1H-benzo[c]azepin-5-ylamine (10.5 g, yield: 89%) as a white solid. ¹H NMR (DMSO-d₆, 300 MHz): δ 8.79 (br, 3H), 7.64-7.58 (m, 3H), 7.53 (s, 1H), 7.36 (d, J=8.4 Hz, 2H), 7.15 (d, J=8.4 Hz, 1H), 4.71-4.61 (m, 2H), 4.31 (d, J=15.3 Hz, 1H), 3.82 (d, J=18.3 Hz, 1H), 2.38 (s, 3H), 2.14-2.07 (m, 1H), 1.77-1.71 (m, 1H). LC-MS: m/z 395.0/397.0 [M+H]⁺.

8. Synthesis of 8-bromo-2,3,4,5-tetrahydro-1H-benzo[c]azepin-5-amine

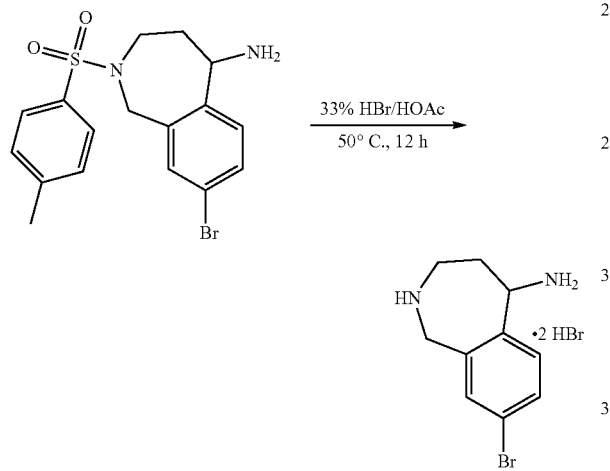

A solution of 8-bromo-2-(toluene-4-sulfonyl)-2,3,4,5-tetrahydro-1H-benzo[c]azepin-5-ylamine (2.00 g, 5.06 mmol) in HBr (33% solution in acetic acid, 20 mL) was heated at 50° C. for 12 h. After cooling to rt, the mixture was diluted EtOAc (50 mL). The white solid was collected by filtration and dried in vacuo to afford crude product 8-bromo-2,3,4,5-tetrahydro-1H-benzo[c]azepin-5-amine (1.66 g, yield: 82%), which was used directly in the next step. ESI-MS (M+H)⁺241.1. ¹H NMR (400 MHz, CD₃OD) δ: 7.72-7.55 (m, 2H), 7.18 (d, J=8.4 Hz, 1H), 4.99-4.98 (m, 1H), 4.51 (d, J=14.4 Hz, 1H), 4.39 (d, J=14.4 Hz, 1H), 3.62-3.49 (m, 2H), 2.38-2.24 (m, 1H), 2.16-2.00 (m, 1H).

9. Synthesis of tert-butyl 5-amino-8-bromo-4,5-dihydro-1H-benzo[c]azepine-2(3H)-carboxylate

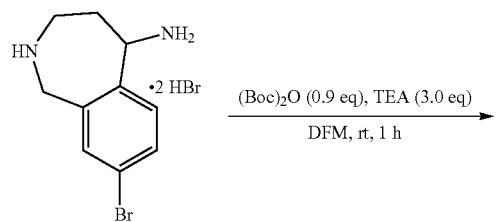

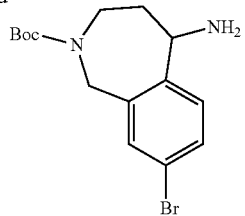

To a solution of 8-bromo-2,3,4,5-tetrahydro-1H-benzo[c]azepin-5-amine (640 mg, 1.60 mmol) and triethylamine (490 mg, 4.8 mmol) in CH₂Cl₂ (20 mL) was added (Boc)₂O (314 mg, 1.44 mmol). The mixture was stirred at rt for 1 h. After diluting with CH₂Cl₂ (100 mL), the mixture was washed with brine (20 mL×2). The organic phase was concentrated in vacuo and the residue was purified by prep-HPLC (CH₃CN/H₂O with 0.05% NH₃.H₂O as mobile phase) to give tert-butyl 5-amino-8-bromo-4,5-dihydro-1H-benzo[c]azepine-2(3H)-carboxylate as a colorless oil (364 mg, yield: 67%). ESI-MS (M+H)⁺: 341.1.

10. The Preparation of tert-butyl 8-bromo-5-(5-(tert-butyl)-1,2,4-oxadiazole-3-carboxamido)-4,5-dihydro-1H-benzo[c]azepine-2(3H)-carboxylate

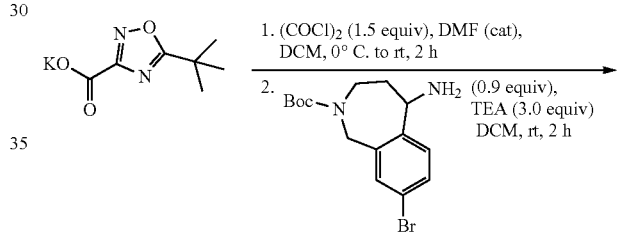

Synthesis of tert-butyl 8-bromo-5-(5-(tert-butyl)-1,2,4-oxadiazole-3-carboxamido)-4,5-dihydro-1H-benzo[c]azepine-2(3H)-carboxylate was similar to that of tert-butyl 7-bromo-1-(5-(tert-butyl)-1,2,4-oxadiazole-3-carboxamido)-4,5-dihydro-1H-benzo[d]azepine-3(2H)-carboxylate in Example 1, Step 8. The crude product was purified by prep-HPLC (CH₃CN/H₂O with 0.05% NH₄HCO₃ as mobile phase) to give tert-butyl 8-bromo-5-(5-(tert-butyl)-1,2,4-oxadiazole-3-carboxamido)-4,5-dihydro-1H-benzo[c]azepine-2(3H)-carboxylate as a yellow solid (4.5 g, yield: 70%). ESI-MS (M+H)⁺: 493.3.

11. The Preparation of tert-butyl 5-(5-(tert-butyl)-1,2,4-oxadiazole-3-carboxamido)-8-(2-((1-methyl-1H-pyrazol-4-yl)amino)pyrimidin-4-yl)-4,5-dihydro-1H-benzo[c]azepine-2(3H)-carboxylate

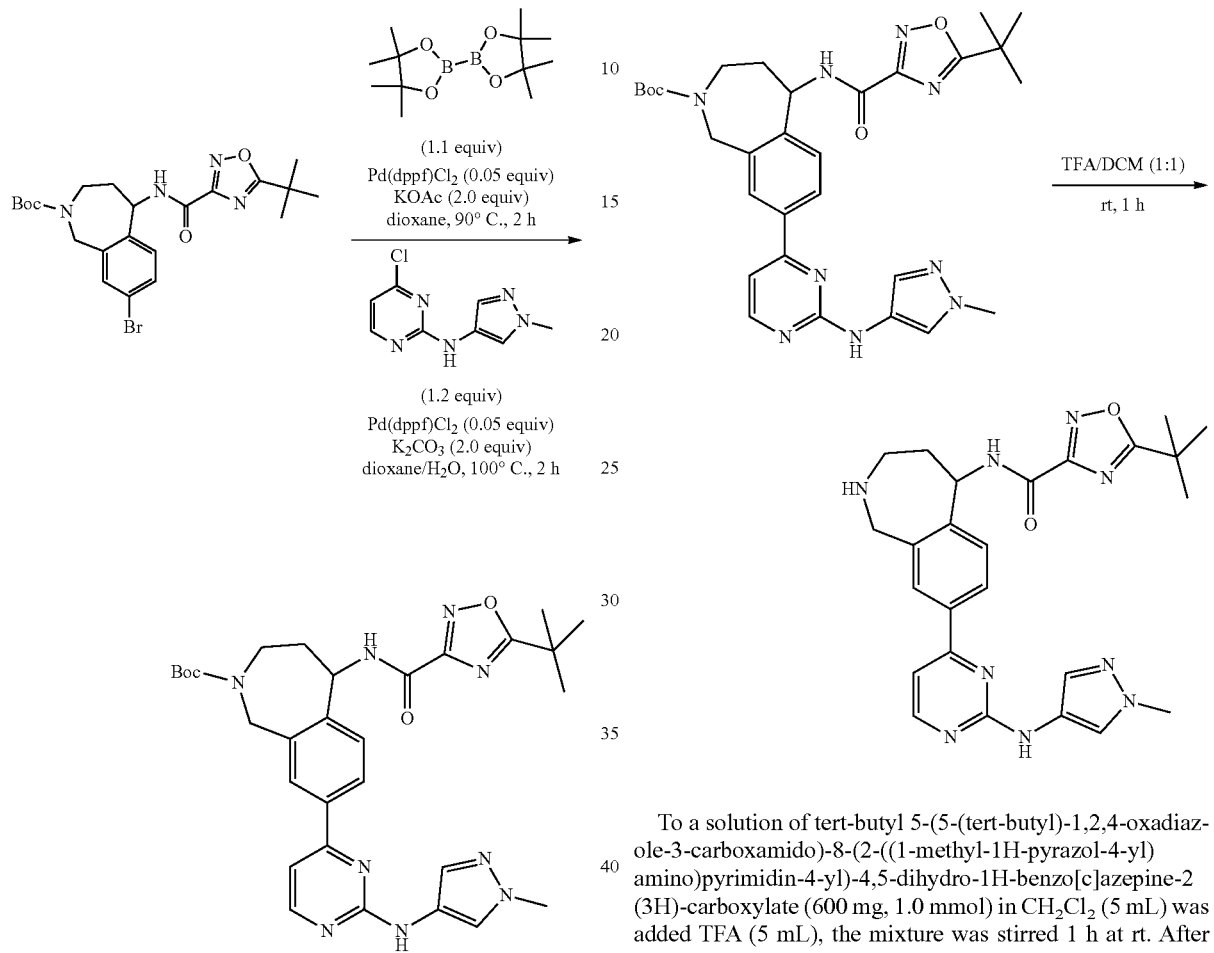

Synthesis of tert-butyl 5-(5-(tert-butyl)-1,2,4-oxadiazole-3-carboxamido)-8-(2-((1-methyl-1H-pyrazol-4-yl)amino)pyrimidin-4-yl)-4,5-dihydro-1H-benzo[c]azepine-2(3H)-carboxylate was similar to that of tert-butyl 1-(5-(tert-butyl)-1,2,4-oxadiazole-3-carboxamido)-7-(2-((1-methyl-1H-pyrazol-4-yl)amino)pyrimidin-4-yl)-4,5-dihydro-1H-benzo[d]azepine-3(2H)-carboxylate in Example 1, Step 12. The crude product was purified by silica gel column chromatograph (EtOAc/MeOH=15:1) to give tert-butyl 5-(5-(tert-butyl)-1,2,4-oxadiazole-3-carboxamido)-8-(2-((1-methyl-1H-pyrazol-4-yl)amino)pyrimidin-4-yl)-4,5-dihydro-1H-benzo[c]azepine-2(3H)-carboxylate as yellow solid (1.2 g, yield: 28%). ESI-MS (M+H)$^+$: 588.3. $^1$H NMR (400 MHz, CD$_3$OD) δ: 8.43-8.38 (m, 1H), 8.11-7.95 (m, 3H), 7.67-7.48 (m, 2H), 7.25-7.24 (m, 1H), 5.67-5.63 (m, 1H), 4.84-4.77 (m, 1H), 4.55-4.50 (m, 1H), 4.17-4.09 (m, 1H), 3.94-3.88 (m, 3H), 3.64-3.54 (m, 1H), 2.11-2.08 (m, 2H), 1.43-1.34 (m, 9H), 1.22 (s, 9H).

12. The Preparation of 5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide To a solution of tert-butyl 5-(5-(tert-butyl)-1,2,4-oxadiazole-3-carboxamido)-8-(2-((1-methyl-1H-pyrazol-4-yl)amino)pyrimidin-4-yl)-4,5-dihydro-1H-benzo[c]azepine-2(3H)-carboxylate (600 mg, 1.0 mmol) in CH$_2$Cl$_2$ (5 mL) was added TFA (5 mL), the mixture was stirred 1 h at rt. After concentration, the crude product (440 mg, yield: 85%) was used in the next step without further purification. ESI-MS (M+H)$^+$: 488.3.

13. The Preparation of 5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide

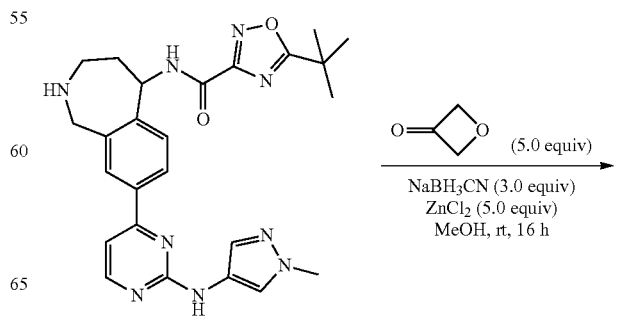

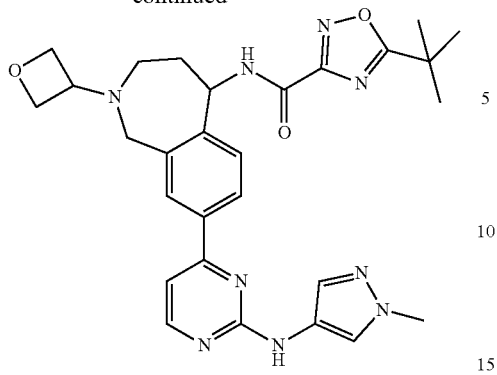

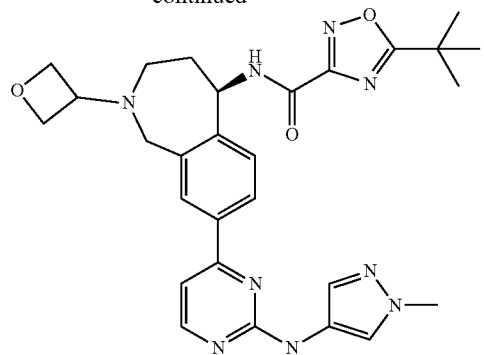

To a solution of 5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide (180 mg, 0.36 mmol) and dihydrofuran-3(2H)-one (132 mg, 1.8 mmol) in MeOH (20 mL) were added NaBH$_3$CN (66 mg, 1.08 mmol) and ZnCl$_2$ (246 mg, 1.8 mmol). The mixture was stirred at rt for 16 h. After concentration and diluting with water (30 mL), the mixture was extracted with EtOAc (80 mL×2). The combined organic layer was washed with H$_2$O (60 mL) and concentrated. The crude product was purified by prep-HPLC (CH$_3$CN/H$_2$O with 0.05% NH$_4$HCO$_3$ as mobile phase) to give 5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide as a yellow solid (114 mg, yield: 49%). ESI-MS (M+H)$^+$: 544.3. $^1$H NMR (400 MHz, CD$_3$OD) δ: 8.30 (d, J=5.2 Hz, 1H), 7.92-7.85 (m, 3H), 7.51 (s, 1H), 7.35 (d, J=8.4 Hz, 1H), 7.11 (d, J=5.2 Hz, 1H), 5.50 (d, J=9.6 Hz, 1H), 4.67-4.55 (m, 4H), 3.84-3.70 (m, 3H), 3.80 (s, 3H), 2.95-2.89 (m, 1H), 2.76-2.72 (m, 1H), 2.15-2.12 (m, 1H), 1.95-1.92 (m, 1H), 1.40 (s, 9H).

14. The Preparation of (R)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide

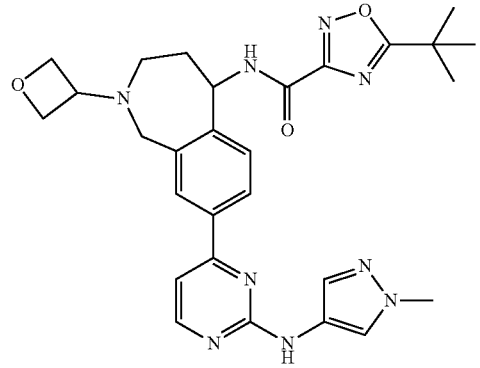

5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide was subjected to SFC separation (OD-H (2×25 cm), 30% methanol/CO$_2$, 100 bar, 60 mL/min, 220 nm, inj vol.: 1.5 mL, 9 mg/mL, methanol) and yielded 34.8 mg of peak-1 (chemical purity 99%, ee>99%) and 37.1 mg of peak-2 (chemical purity 99%, ee>99%).

Peak 2 was assigned as 5-tert-butyl-1,2,4-oxadiazole-3-carboxylic acid {(R)-8-[2-(1-methyl-1H-pyrazol-4-ylamino)-pyrimidin-4-yl]-2-oxetan-3-yl-2,3,4,5-tetrahydro-1H-2-benzazepin-5-yl}-amide: LCMS: Rt 0.88 min, m/z 544.00. 1H NMR (400 MHz, METHANOL-d4) δ 8.40 (d, J=5.02 Hz, 1H), 7.87-8.09 (m, 3H), 7.63 (s, 1H), 7.45 (d, J=8.28 Hz, 1H), 7.20 (d, J=5.27 Hz, 1H), 5.60 (s, 1H), 4.55-4.77 (m, 4H), 3.89 (s, 3H), 3.75-3.85 (m, 3H), 2.75-3.10 (m, 2H), 1.89-2.42 (m, 2H), 1.51 (s, 9H).

Method 2

1. Chiral Resolution of tert-butyl 5-amino-8-bromo-4,5-dihydro-1H-benzo[c]azepine-2(3H)-carboxylate to Give tert-butyl (R)-5-amino-8-bromo-1,3,4,5-tetrahydro-2H-benzo[c]azepine-2-carboxylate Compound with (11bS)-4-hydroxydinaphtho[2,1-d:1',2'-f][1,3,2]dioxaphosphepine 4-oxide (1:1)

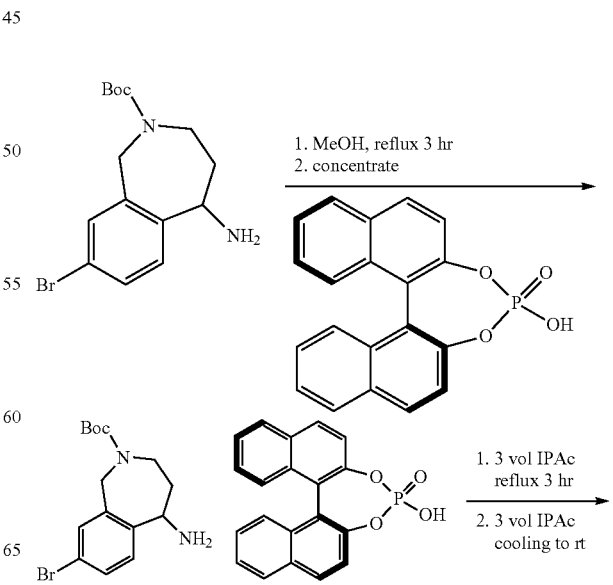

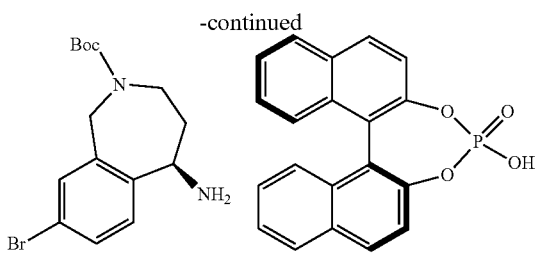

To tert-butyl 5-amino-8-bromo-4,5-dihydro-1H-benzo[c]azepine-2(3H)-carboxylate (800 g, 2.34 mol) was added MeOH (4.8 L) and (S)-(−)-1,1'-binaphthyl-2,2'-diyl hydrogenphosphate (816.6 g, 2.34 mol). The mixture was stirred at 25° C. for 30 min and formed a yellow slurry. The slurry was stirred at reflux (70° C.) to give a yellow solution. The mixture was concentrated to dryness and IPAc (3.44 L) was added. The mixture was heated to 70° C. and was stirred at that temperature for 3 h. The reaction mixture was cooled to room temperature and an additional portion of IPAc (3.44 L) was added. The reaction mixture continued to stir at room temperature for 16 h. The slurry was filtered on centrifuge and the cake was washed three times, each with 7 vol IPAc. The wet cake was briefly dried to give tert-butyl (R)-5-amino-8-bromo-1,3,4,5-tetrahydro-2H-benzo[c]azepine-2-carboxylate compound with (11bS)-4-hydroxydinaphtho[2,1-d:1',2'-f][1,3,2]dioxaphosphepine 4-oxide (1:1) (515 g. yield: 64% ([assuming maximum recovery of 50%], 91.3% ee) as a white solid. The recrystallization process can be repeated to increase the ee to 97.2%.

2. The Preparation of tert-butyl (R)-8-bromo-5-(5-(tert-butyl)-1,2,4-oxadiazole-3-carboxamido)-1,3,4,5-tetrahydro-2H-benzo[c]azepine-2-carboxylate

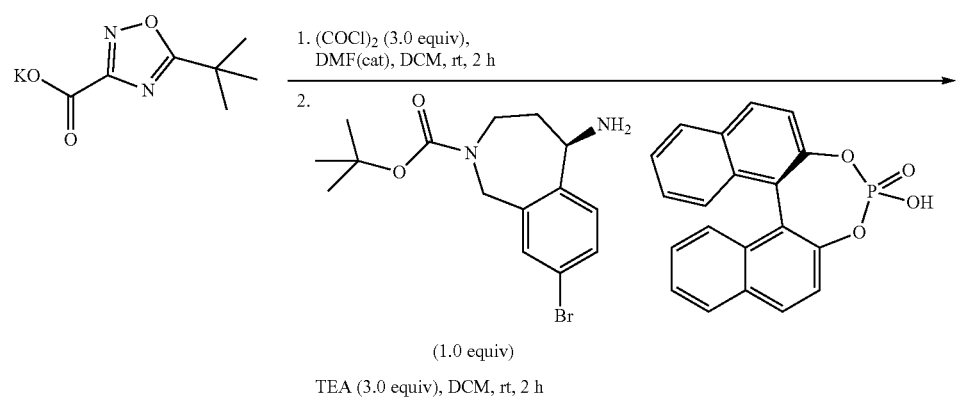

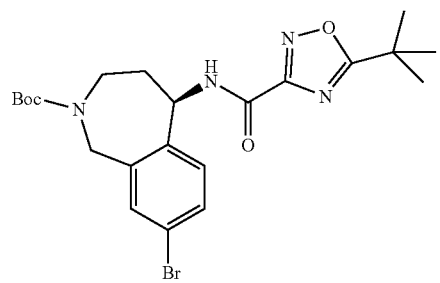

To a solution of potassium 5-(tert-butyl)-1,2,4-oxadiazole-3-carboxylate (800 mg, 4.0 mmol) and oxalyl chloride (2.0 g, 16 mmol) in CH$_2$Cl$_2$ (10 mL) was added DMF (cat.). The mixture was stirred at room temperature for 2 h, and then was concentrated with CH$_2$Cl$_2$ twice. The residue was diluted with CH$_2$Cl$_2$ (20 mL) and tert-butyl (R)-5-amino-8-bromo-1,3,4,5-tetrahydro-2H-benzo[c]azepine-2-carboxylate compound with (11bR)-4-hydroxydinaphtho[2,1-d:1',2'-f][1,3,2]dioxaphosphepine 4-oxide (1:1) (2.0 g, 3.0 mmol) and triethylamine (900 mg, 9.0 mmol) were added. The mixture was stirred at room temperature for 2 h and concentrated. The crude product was purified by silica gel chromatography (PE:EtOAc=2:1) to give tert-butyl (R)-8-bromo-5-(5-(tert-butyl)-1,2,4-oxadiazole-3-carboxamido)-1,3,4,5-tetrahydro-2H-benzo[c]azepine-2-carboxylate as a yellow solid (1.2 g, yield: 80%). ESI-MS (M+Na)$^+$: 515.1. $^1$H NMR (400 MHz, CDCl$_3$) δ: 7.48-7.36 (m, 2H), 7.24-7.18 (m, 1H), 5.61-5.50 (m, 1H), 4.70-4.51 (m, 1H), 4.38-4.29 (m, 1H), 4.05-3.85 (m, 1H), 3.53-3.48 (m, 1H), 2.24-2.16 (m, 2H), 1.48 (s, 9H), 1.40-1.37 (m, 9H).

3. Synthesis of tert-butyl (R)-5-(5-(tert-butyl)-1,2,4-oxadiazole-3-carboxamido)-8-(2-((1-methyl-1H-pyrazol-4-yl)amino)pyrimidin-4-yl)-1,3,4,5-tetrahydro-2H-benzo[c]azepine-2-carboxylate Synthesis of tert-butyl (R)-5-(5-(tert-butyl)-1,2,4-oxadiazole-3-carboxamido)-8-(2-((1-methyl-1H-pyrazol-4-yl)amino)pyrimidin-4-yl)-1,3,4,5-tetrahydro-2H-benzo[c]azepine-2-carboxylate was similar to that of tert-butyl 1-(5-(tert-butyl)-1,2,4-oxadiazole-3-carboxamido)-7-(2-((1-methyl-1H-pyrazol-4-yl)amino)pyrimidin-4-yl)-4,5-dihydro-1H-benzo[d]azepine-3(2H)-carboxylate in Example 1, Step 12. The crude material was purified by silica gel chromatography (EtOAc:MeOH=15:1) to give tert-butyl (R)-5-(5-(tert-butyl)-1,2,4-oxadiazole-3-carboxamido)-8-(2-((1-methyl-1H-pyrazol-4-yl)amino)pyrimidin-4-yl)-1,3,4,5-tetrahydro-2H-benzo[c]azepine-2-carboxylate as a yellow solid (1.5 g, yield: 43%). ESI-MS (M+H)$^+$: 588.3.

4. Synthesis of (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide

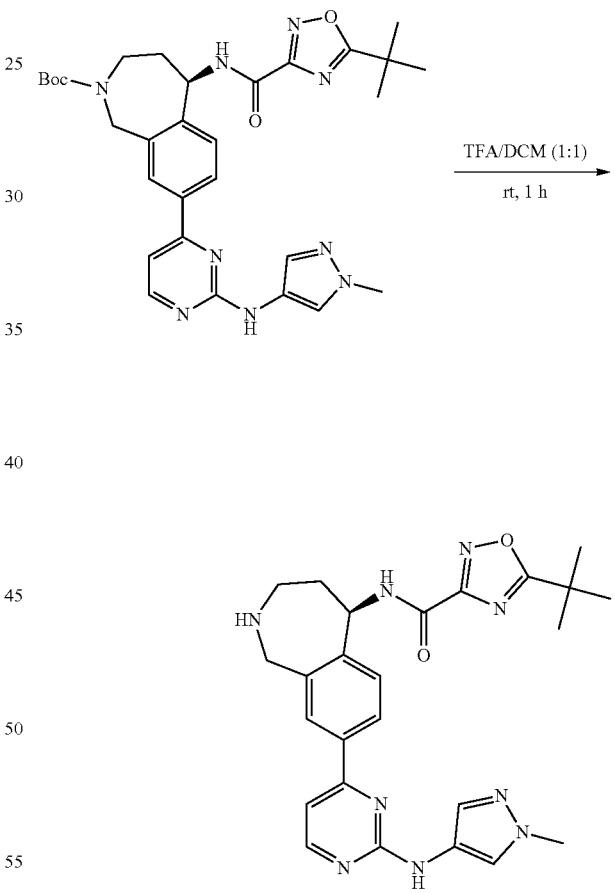

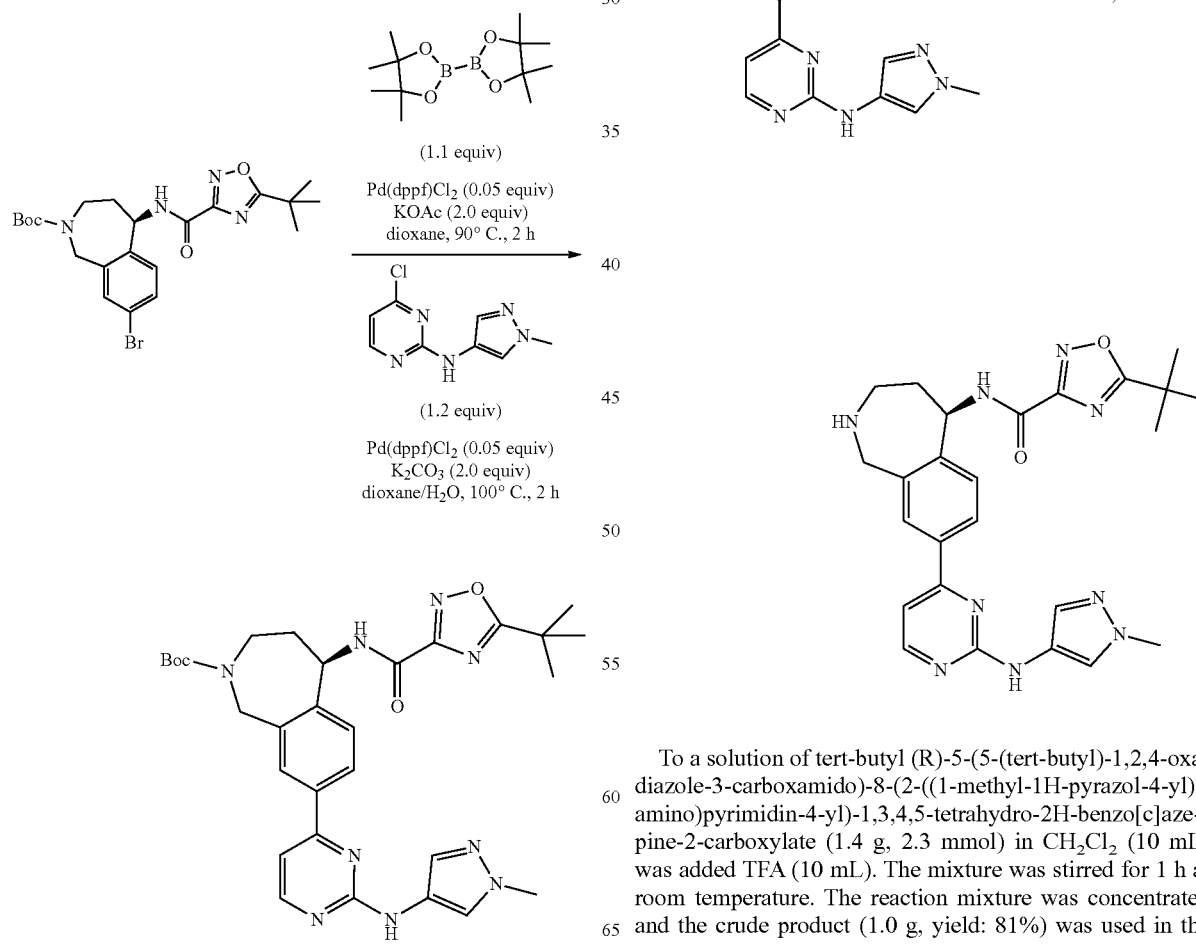

To a solution of tert-butyl (R)-5-(5-(tert-butyl)-1,2,4-oxadiazole-3-carboxamido)-8-(2-((1-methyl-1H-pyrazol-4-yl)amino)pyrimidin-4-yl)-1,3,4,5-tetrahydro-2H-benzo[c]azepine-2-carboxylate (1.4 g, 2.3 mmol) in CH$_2$Cl$_2$ (10 mL) was added TFA (10 mL). The mixture was stirred for 1 h at room temperature. The reaction mixture was concentrated and the crude product (1.0 g, yield: 81%) was used in the next step without further purification. ESI-MS (M+H)$^+$: 488.3.

5. Synthesis of (R)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide (I-RP33)

Example 3. 5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide (compound 3)

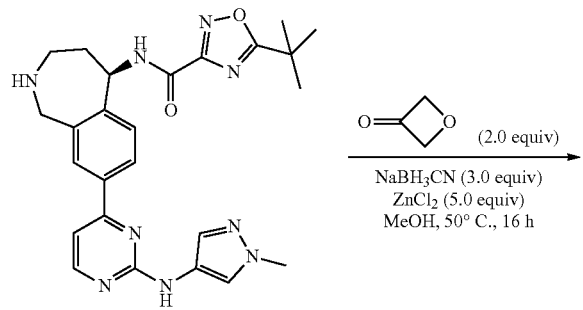

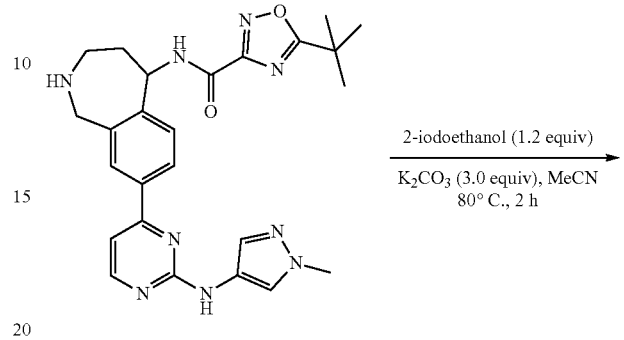

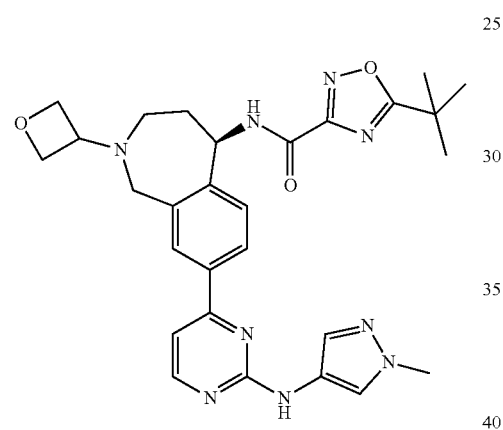

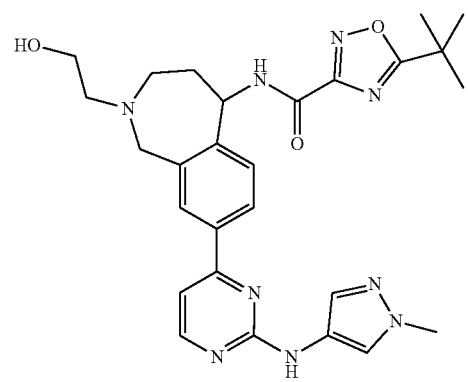

Synthesis of (R)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide was similar to that of 5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide described above in method 1, step 13. The crude material was purified by silica gel chromatography (EtOAc:MeOH=20:1) to give (R)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide as a yellow solid (746 mg, Y: 67%). ESI-MS (M+H)$^+$: 544.3. $^1$H NMR (400 MHz, CD$_3$OD) δ: 8.42 (d, J=5.2 Hz, 1H), 8.03-7.96 (m, 3H), 7.63 (s, 1H), 7.48 (d, J=8.0 Hz, 1H), 7.23 (d, J=5.2 Hz, 1H), 5.61 (d, J=9.6 Hz, 1H), 4.78-4.67 (m, 4H), 3.96-3.82 (m, 3H), 3.90 (s, 3H), 3.06-3.02 (m, 1H), 2.89-2.80 (m, 1H), 2.29-2.22 (m, 1H), 2.07-2.03 (m, 1H), 1.52 (s, 9H).

To a solution of 5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide (200 mg, 0.41 mmol) in CH$_3$CN (20 mL) were added 2-iodoethanol (141 mg, 0.82 mmol) and K$_2$CO$_3$ (170 mg, 1.23 mmol). The mixture was stirred at 80° C. for 2 h. The mixture was diluted with EtOAc (100 mL), washed with water (60 mL) and concentrated. The crude product was purified by prep-HPLC (CH$_3$CN/H$_2$O with 0.05% NH$_4$HCO$_3$ as mobile phase) to give 5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide as a yellow solid (90 mg, yield: 32%). ESI-MS (M+H)$^+$: 532.3. $^1$H NMR (400 MHz, CD$_3$OD) δ: 8.43 (d, J=5.2 Hz, 1H), 8.04-8.00 (m, 3H), 7.64 (s, 1H), 7.47 (d, J=8.0 Hz, 1H), 7.25 (d, J=5.0 Hz, 1H), 5.60 (d, J=9.6 Hz, 1H), 4.22-4.10 (m, 2H), 3.91 (s, 3H), 3.75 (t, J=6.0 Hz, 2H), 3.28-3.21 (m, 2H), 2.69-2.65 (m, 2H), 2.31-2.27 (m, 1H), 2.00-1.97 (m, 1H), 1.53 (s, 9H).

Example 4. 5-(tert-butyl)-N-(8-(2-((1-methyl-1H-pyrazol-4-yl)amino)pyrimidin-4-yl)-2-(methylsulfonyl)-2,3,4,5-tetrahydro-1H-benzo[c]azepin-5-yl)-1,2,4-oxadiazole-3-carboxamide (Compound 4)

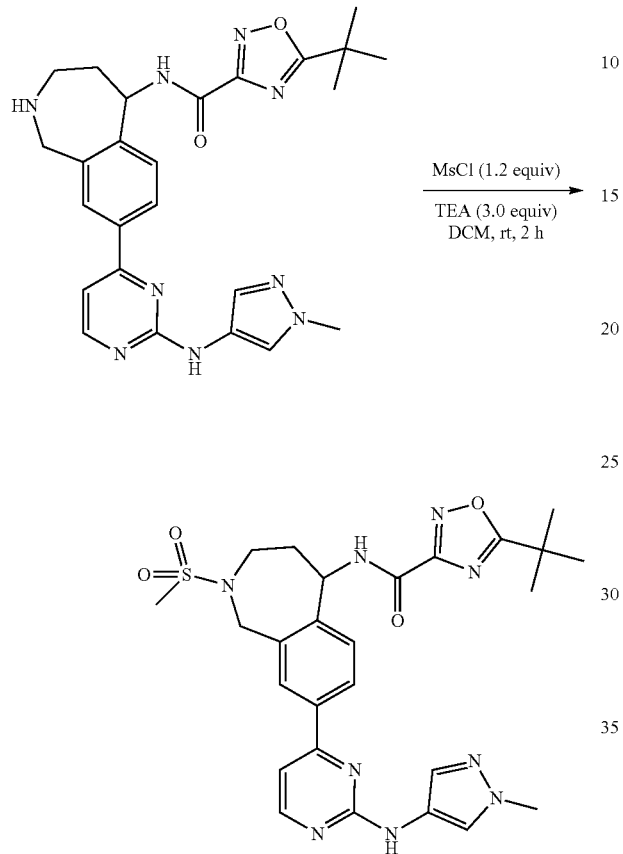

Synthesis of 5-(tert-butyl)-N-(8-(2-((1-methyl-1H-pyrazol-4-yl)amino)pyrimidin-4-yl)-2-(methylsulfonyl)-2,3,4,5-tetrahydro-1H-benzo[c]azepin-5-yl)-1,2,4-oxadiazole-3-carboxamide was similar to that of 5-(tert-butyl)-N-(8-(2-((1-methyl-1H-pyrazol-4-yl)amino)pyrimidin-4-yl)-2-(methylsulfonyl)-2,3,4,5-tetrahydro-1H-benzo[c]azepin-5-yl)-1,3,4-oxadiazole-2-carboxamide in Example 15. The crude product was purified by prep-HPLC (CH$_3$CN/H$_2$O with 0.05% NH$_4$HCO$_3$ as mobile phase) to give 5-(tert-butyl)-N-(8-(2-((1-methyl-1H-pyrazol-4-yl)amino)pyrimidin-4-yl)-2-(methylsulfonyl)-2,3,4,5-tetrahydro-1H-benzo[c]azepin-5-yl)-1,2,4-oxadiazole-3-carboxamide as a yellow solid (98 mg, yield: 60%). ESI-MS (M+H)$^+$: 566.2. $^1$H NMR (400 MHz, CDCl$_3$) δ: 8.45 (d, J=4.8 Hz, 1H), 8.02 (s, 1H), 7.94-7.92 (m, 2H), 7.57-7.48 (m, 3H), 7.07 (d, J=5.2 Hz, 1H), 6.96 (s, 1H), 5.72 (t, J=8.8 Hz, 1H), 4.85-4.81 (m, 1H), 4.57-4.53 (m, 1H), 4.03-3.97 (m, 1H), 3.93 (s, 3H), 3.66-3.63 (m, 1H), 2.74 (s, 3H), 2.39-2.21 (m, 2H), 1.49 (s, 9H).

Example 5. 5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide (Compound 5)

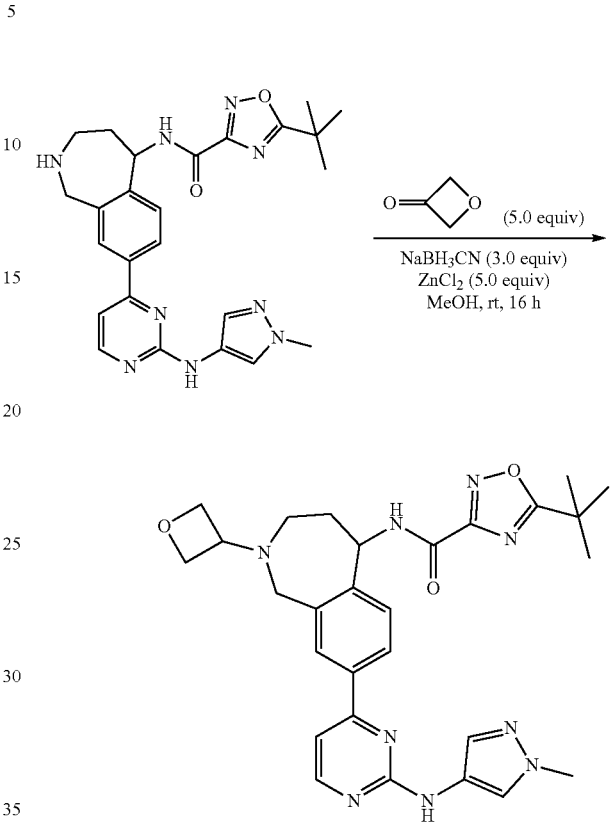

To a solution of 5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide (180 mg, 0.36 mmol) and dihydrofuran-3(2H)-one (132 mg, 1.8 mmol) in MeOH (20 mL) were added NaBH$_3$CN (66 mg, 1.08 mmol) and ZnCl$_2$ (246 mg, 1.8 mmol). The mixture was stirred at rt for 16 h. After concentration and diluting with water (30 mL), the mixture was extracted with EtOAc (80 mL×2). The combined organic layer was washed with H$_2$O (60 mL) and concentrated. The crude product was purified by prep-HPLC (CH$_3$CN/H$_2$O with 0.05% NH$_4$HCO$_3$ as mobile phase) to give 5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide as a yellow solid (114 mg, yield: 49%). ESI-MS (M+H)$^+$: 544.3. $^1$H NMR (400 MHz, CD$_3$OD) δ: 8.30 (d, J=5.2 Hz, 1H), 7.92-7.85 (m, 3H), 7.51 (s, 1H), 7.35 (d, J=8.4 Hz, 1H), 7.11 (d, J=5.2 Hz, 1H), 5.50 (d, J=9.6 Hz, 1H), 4.67-4.55 (m, 4H), 3.84-3.70 (m, 3H), 3.80 (s, 3H), 2.95-2.89 (m, 1H), 2.76-2.72 (m, 1H), 2.15-2.12 (m, 1H), 1.95-1.92 (m, 1H), 1.40 (s, 9H).

Example 6. 5-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide (Compound 6)

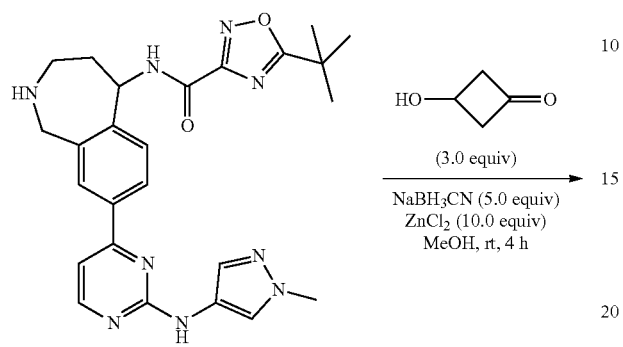

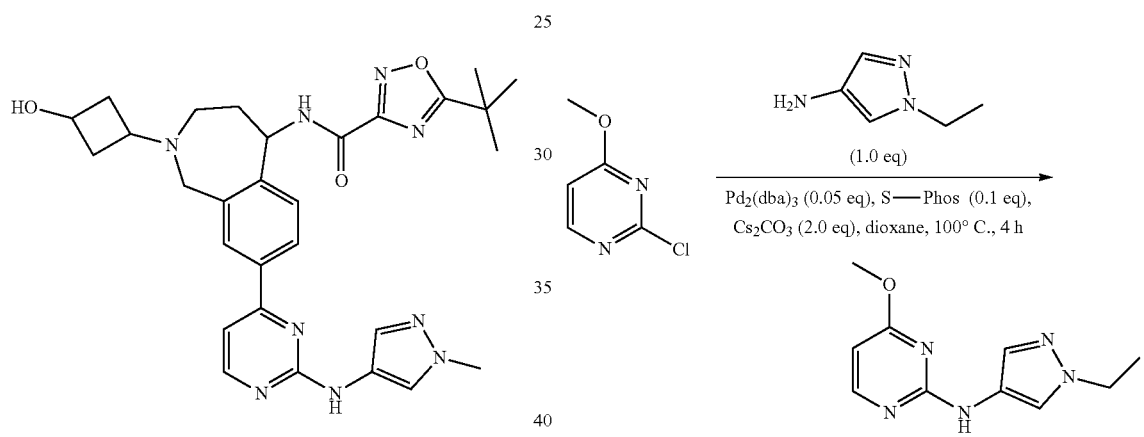

Synthesis of 5-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide was similar to that of 5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide in Example 5. The crude product was purified by silica gel chromatography (EtOAc:MeOH=10:1) to give 5-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide as a yellow solid (102 mg, yield: 53%). ESI-MS (M+H)+: 557.7. 1H NMR (400 MHz, CD3OD) δ: 8.29 (d, J=5.2 Hz, 1H), 7.87 (s, 3H), 7.50 (s, 1H), 7.32 (d, J=8.8 Hz, 1H), 7.09 (d, J=5.6 Hz, 1H), 5.45 (d, J=10.0 Hz, 1H), 3.86-3.78 (m, 3H), 3.75 (s, 3H), 3.09-3.06 (m, 1H), 2.80-2.74 (m, 1H), 2.50-2.39 (m, 3H), 2.14-2.05 (m, 1H), 1.88-1.85 (m, 1H), 1.72-1.69 (m, 2H), 1.41 (s, 9H).

Example 7. 5-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide (Compound 7)

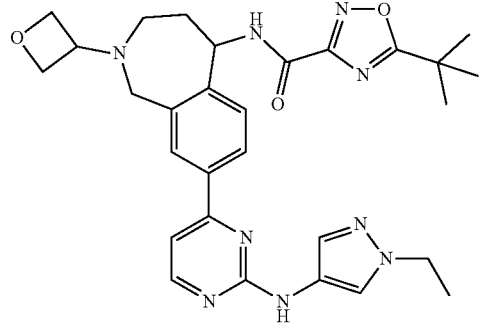 [SMILES: CCn1cc(Nc2nccc(-c3ccc4c(c3)CN(C3COC3)CCC4NC(=O)c3noc(C(C)(C)C)n3)n2)cn1]

I. Synthesis of 4-methoxy-N-(1-ethyl-1H-pyrazol-4-yl)pyrimidin-2-amine

Synthesis of 4-methoxy-N-(1-methyl-1H-pyrazol-4-yl)pyrimidin-2-amine was similar to that of 4-methoxy-N-(1-methyl-1H-pyrazol-4-yl)pyrimidin-2-amine in Example 1, Step 10. The crude material was purified by silica gel chromatography (PE:EtOAc=1:1) to give 4-methoxy-N-(1-ethyl-1H-pyrazol-4-yl)pyrimidin-2-amine (420 mg, yield: 43%) as a tan solid. ESI-MS (M+H)+: 220.1.

2. Synthesis of 4-chloro-N-(1-eethyl-1H-pyrazol-4-yl)pyrimidin-2-amine

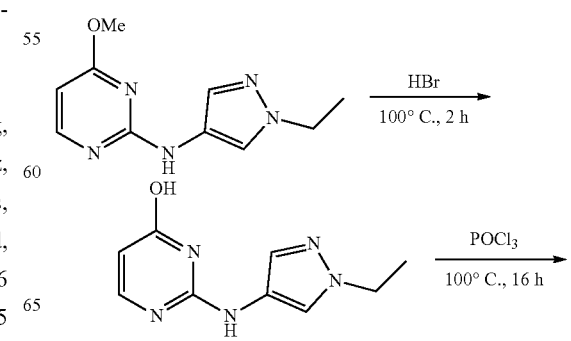

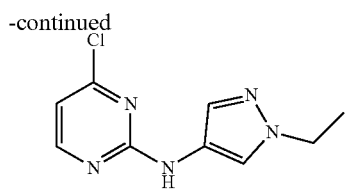

To 4-methoxy-N-(1-ethyl-1H-pyrazol-4-yl)pyrimidin-2-amine (420 mg, 1.9 mmol) was added HBr (5 mL, 48% aqueous). The reaction mixture was heated to 100° C. and stirred at that temperature for 2 h. The reaction mixture was concentrated and then POCl₃ (5 mL) was added. The reaction mixture was heated to 100° C. and stirred at that temperature for 16 h. The reaction mixture was cooled to room temperature and poured into ice-water. The pH of the solution was adjusted to pH=8 with aqueous NaOH (5 M). The basic aqueous phase was extracted with EtOAc (2×30 mL). The combined organic layers were washed with brine (100 mL), dried (Na₂SO₄) and concentrated. The crude material was purified by silica gel chromatography (PE:EtOAc=1:1) to give 4-chloro-N-(1-ethyl-1H-pyrazol-4-yl)pyrimidin-2-amine as a white solid (220 mg, yield: 51%). ESI-MS (M+H)⁺: 224.1.

3. Synthesis of tert-butyl 5-(5-(tert-butyl)-1,2,4-oxadiazole-3-carboxamido)-8-(2-((1-ethyl-1H-pyrazol-4-yl)amino)pyrimidin-4-yl)-1,3,4,5-tetrahydro-2H-benzo[c]azepine-2-carboxylate

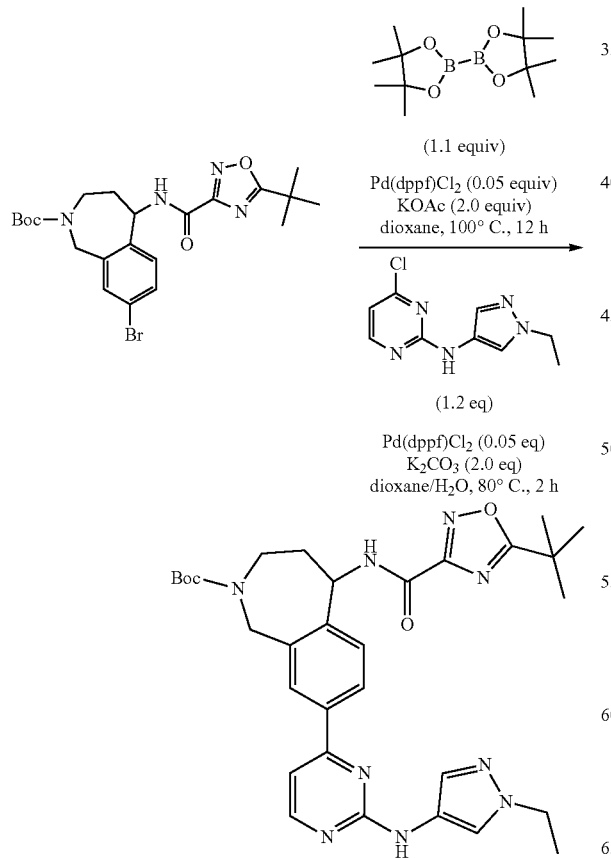

To a mixture of tert-butyl 8-bromo-5-(5-(tert-butyl)-1,2,4-oxadiazole-3-carboxamido)-1,3,4,5-tetrahydro-2H-benzo[c]azepine-2-carboxylate (560 mg, 1.13 mmol) and PinB-BPin (288 mg, 1.10 mmol) in dry 1,4-dioxane (11 mL), KOAc (332 mg, 3.39 mmol) and Pd(dppf)Cl₂CH₂Cl₂ (89 mg, 0.11 mmol) were added quickly under N₂. The mixture was stirred at 100° C. for 12 h under N₂. After cooling down, 4-chloro-N-(1-ethyl-1H-pyrazol-4-yl)pyrimidin-2-amine (301 mg, 1.35 mmol), K₂CO₃ (312 mg, 2.26 mmol), Pd(dppf)Cl₂CH₂Cl₂ (89 mg, 0.11 mmol) and H₂O (2.5 mL) were added. The mixture was stirred at 80° C. for 2 h under N₂. After cooling down, the mixture was concentrated and purified by silica gel column (PE:EtOAc=3:1) to give tert-butyl 5-(5-(tert-butyl)-1,2,4-oxadiazole-3-carboxamido)-8-(2-((1-ethyl-1H-pyrazol-4-yl)amino)pyrimidin-4-yl)-1,3,4,5-tetrahydro-2H-benzo[c]azepine-2-carboxylate (200 mg, yield: 29%) as a yellow solid. ESI-MS (M+H)⁺: 602.2.

4. The Preparation of 5-(tert-butyl)-N-(8-(2-((1-ethyl-1H-pyrazol-4-yl)amino)pyrimidin-4-yl)-2,3,4,5-tetrahydro-1H-benzo[c]azepin-5-yl)-1,2,4-oxadiazole-3-carboxamide

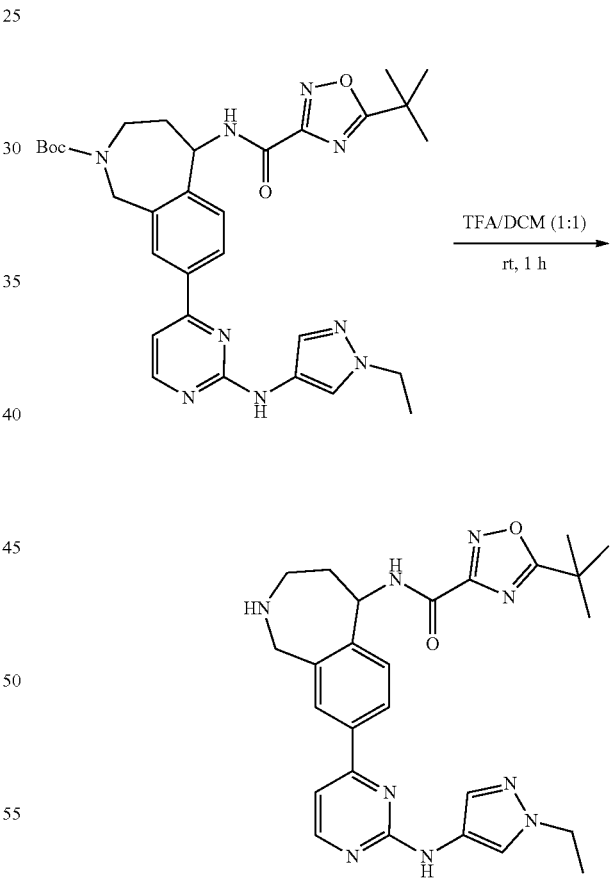

To a solution of tert-butyl 5-(5-(tert-butyl)-1,2,4-oxadiazole-3-carboxamido)-8-(2-((1-ethyl-1H-pyrazol-4-yl)amino)pyrimidin-4-yl)-1,3,4,5-tetrahydro-2H-benzo[c]azepine-2-carboxylate (200 mg, 0.33 mmol) in CH₂Cl₂ (5 mL) was added TFA (5 mL), the mixture was stirred 1 h at rt. After concentration, the crude product (166 mg, yield: 100%) was used in the next step without further purification. ESI-MS (M+H)⁺: 502.7.

5. Synthesis of 5-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide (I-RP1)

Example 8. 5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,2,4-oxadiazole-3-carboxamide (Compound 8)

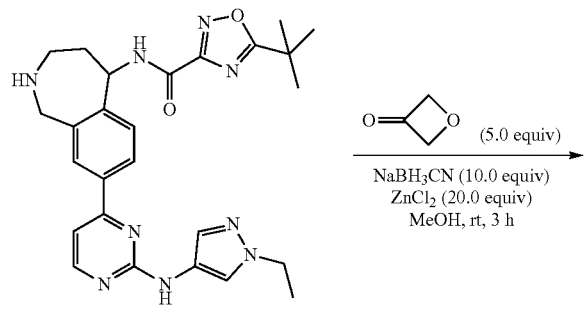

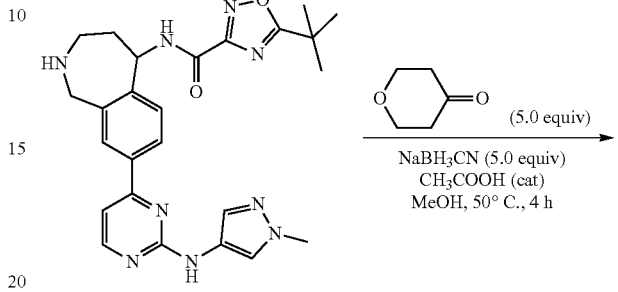

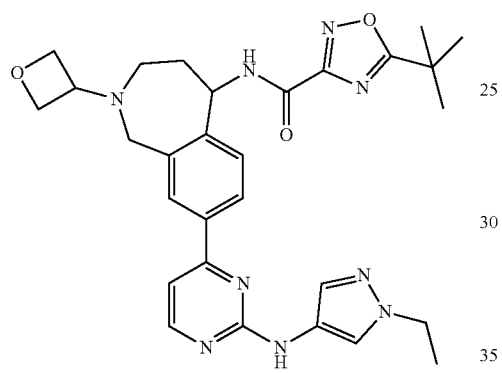

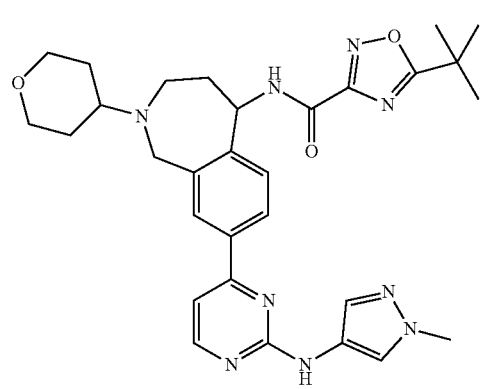

To a solution of 5-(tert-butyl)-N-(8-(2-((1-ethyl-1H-pyrazol-4-yl)amino)pyrimidin-4-yl)-2,3,4,5-tetrahydro-1H-benzo[c]azepin-5-yl)-1,2,4-oxadiazole-3-carboxamide (166 mg, 0.33 mmol) and dihydrofuran-3(2H)-one (119 mg, 1.65 mmol) in MeOH (18 mL) were added NaBH$_3$CN (21 mg, 0.33 mmol) and ZnCl$_2$ (90 mg, 0.66 mmol). The mixture was stirred at rt for 3 h. After concentration and diluting with water (30 mL), the mixture was extracted with EtOAc (80 mL×2). The combined organic layer was washed with H$_2$O (60 mL) and concentrated. The crude product was purified by prep-TLC (CH$_2$Cl$_2$:MeOH=20:1) to give 5-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide as a yellow solid (60 mg, yield: 32%). ESI-MS (M+H)$^+$: 557.7. $^1$H NMR (400 MHz, CDCl$_3$) δ: 8.42 (d, J=5.2 Hz, 2H), 7.90 (s, 1H), 7.85 (d, J=8.0 Hz, 1H), 7.79 (s, 1H), 7.57-7.53 (m, 2H), 7.04 (d, J=5.2 Hz, 1H), 5.71 (t, J=8.4 Hz, 1H), 4.82-4.66 (m, 4H), 4.17 (q, J=7.2 Hz, 2H), 3.91-3.72 (m, 3H), 2.99-2.92 (m, 1H), 2.63-2.58 (m, 1H), 2.40-2.34 (m, 1H), 2.15-2.07 (m, 1H), 1.51 (t, J=7.6 Hz, 3H), 1.45 (s, 9H).

Synthesis of 5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,2,4-oxadiazole-3-carboxamide was similar to that of 5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,3,4-oxadiazole-2-carboxamide in Example 12, Step 4. The crude product was purified by prep-HPLC (CH$_3$CN/H$_2$O with 0.05% NH$_4$HCO$_3$ as mobile phase) to give 5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,2,4-oxadiazole-3-carboxamide as a yellow solid (20 mg, yield: 14%). ESI-MS (M+H)$^+$: 572.3. $^1$H NMR (400 MHz, CD$_3$OD) δ: 8.30 (s, 1H), 7.91-7.86 (m, 3H), 7.53 (s, 1H), 7.36 (d, J=8.0 Hz, 1H), 7.10 (d, J=5.6 Hz, 1H), 5.48 (d, J=9.2 Hz, 1H), 4.19-3.88 (m, 4H), 3.78 (s, 3H), 3.30-3.21 (m, 2H), 3.16-3.03 (m, 2H), 2.67-2.62 (m, 1H), 2.16-2.11 (m, 1H), 1.96-1.83 (m, 3H), 1.64-1.52 (m, 2H), 1.38 (s, 9H).

Example 9. (R)-5-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1,2,4-oxadiazole-3-carboxamide
(Compound 9)

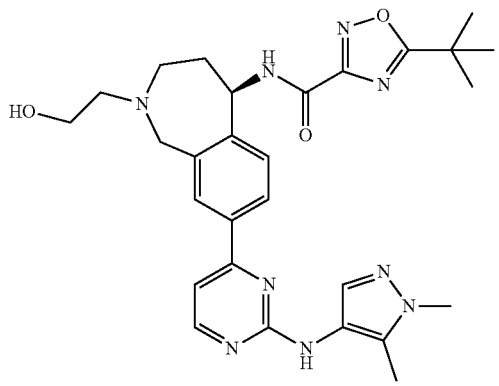 [SMILES: Cc1c(Nc2nccc(-c3ccc4c(c3)CN(CCO)CC[C@H]4NC(=O)c3noc(C(C)(C)C)n3)n2)cnn1C]

I. Synthesis of tert-butyl (R)-5-(5-(tert-butyl)-1,2,4-oxadiazole-3-carboxamido)-8-(4,4,5,5-tetramethyl-1,3,2-dioxaborolan-2-yl)-1,3,4,5-tetrahydro-2H-benzo[c]azepine-2-carboxylate

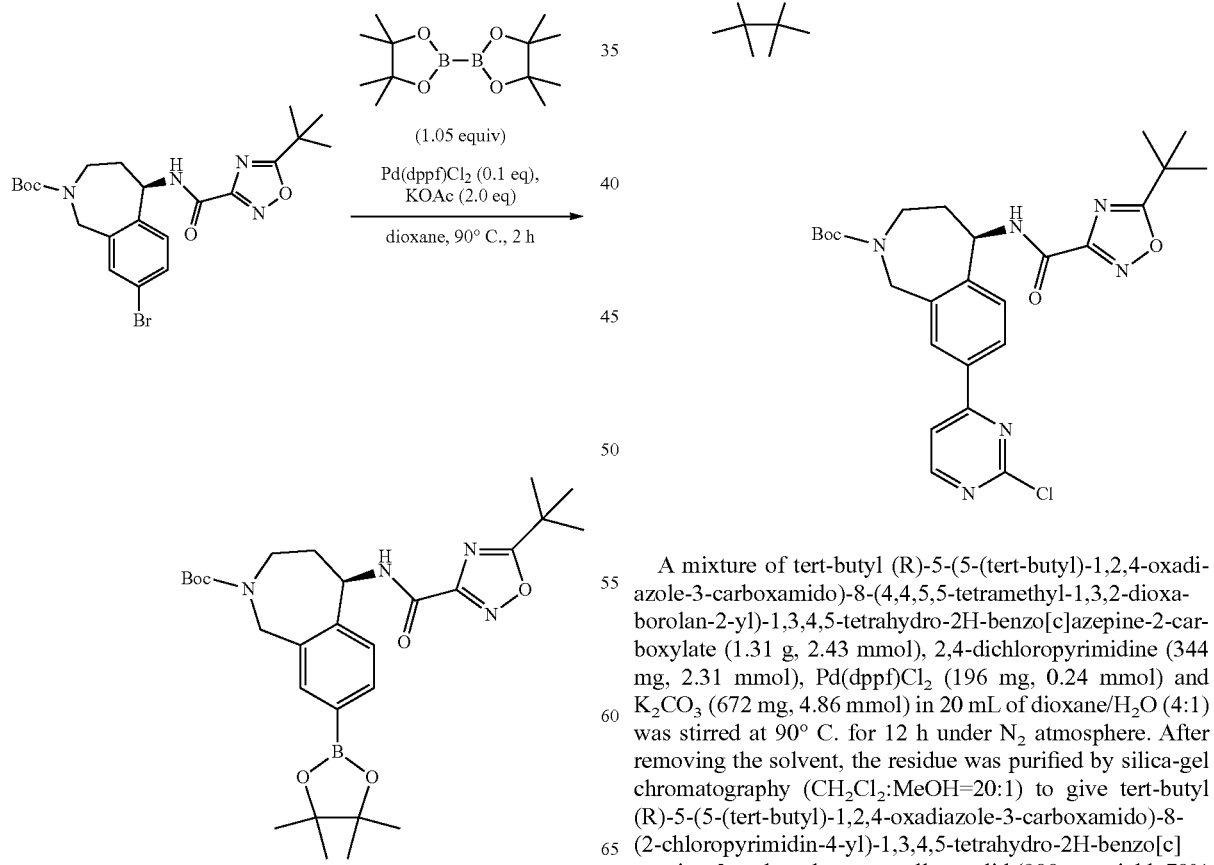

A mixture of tert-butyl (R)-8-bromo-5-(5-(tert-butyl)-1,2,4-oxadiazole-3-carboxamido)-1,3,4,5-tetrahydro-2H-benzo[c]azepine-2-carboxylate (1.2 g, 2.43 mmol), 4,4,4',4',5,5,5',5'-octamethyl-2,2'-bi(1,3,2-dioxaborolane) (650 mg, 2.56 mmol), KOAc (477 mg, 4.86 mmol) and Pd(dppf)Cl$_2$.DCM (196 mg, 0.24 mmol) in 30 mL 1,4-dioxane was stirred at 90° C. for 2 h under nitrogen. After cooling to room temperature, the mixture was diluted with EtOAc (200 mL), washed with water (50 mL×2), dried with Na$_2$SO$_4$ and concentrated to give tert-butyl (R)-5-(5-(tert-butyl)-1,2,4-oxadiazole-3-carboxamido)-8-(4,4,5,5-tetramethyl-1,3,2-dioxaborolan-2-yl)-1,3,4,5-tetrahydro-2H-benzo[c]azepine-2-carboxylate which was used for the next step without further purification. ESI-MS (M+H)$^+$: 541.3.

2. Synthesis of tert-butyl (R)-5-(5-(tert-butyl)-1,2,4-oxadiazole-3-carboxamido)-8-(2-chloropyrimidin-4-yl)-1,3,4,5-tetrahydro-2H-benzo[c]azepine-2-carboxylate

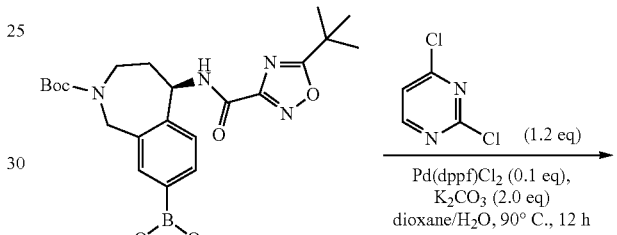

A mixture of tert-butyl (R)-5-(5-(tert-butyl)-1,2,4-oxadiazole-3-carboxamido)-8-(4,4,5,5-tetramethyl-1,3,2-dioxaborolan-2-yl)-1,3,4,5-tetrahydro-2H-benzo[c]azepine-2-carboxylate (1.31 g, 2.43 mmol), 2,4-dichloropyrimidine (344 mg, 2.31 mmol), Pd(dppf)Cl$_2$ (196 mg, 0.24 mmol) and K$_2$CO$_3$ (672 mg, 4.86 mmol) in 20 mL of dioxane/H$_2$O (4:1) was stirred at 90° C. for 12 h under N$_2$ atmosphere. After removing the solvent, the residue was purified by silica-gel chromatography (CH$_2$Cl$_2$:MeOH=20:1) to give tert-butyl (R)-5-(5-(tert-butyl)-1,2,4-oxadiazole-3-carboxamido)-8-(2-chloropyrimidin-4-yl)-1,3,4,5-tetrahydro-2H-benzo[c]azepine-2-carboxylate as a yellow solid (900 mg, yield: 70% for two steps). ESI-MS (M+H)$^+$: 527.2.

3. Synthesis of tert-butyl (R)-5-(5-(tert-butyl)-1,2,4-oxadiazole-3-carboxamido)-8-(2-((1,5-dimethyl-1H-pyrazol-4-yl)amino)pyrimidin-4-yl)-1,3,4,5-tetrahydro-2H-benzo[c]azepine-2-carboxylate

4. Synthesis of (R)-5-(tert-butyl)-N-(8-(2-((1,5-dimethyl-1H-pyrazol-4-yl)amino)pyrimidin-4-yl)-2,3,4,5-tetrahydro-1H-benzo[c]azepin-5-yl)-1,2,4-oxadiazole-3-carboxamide

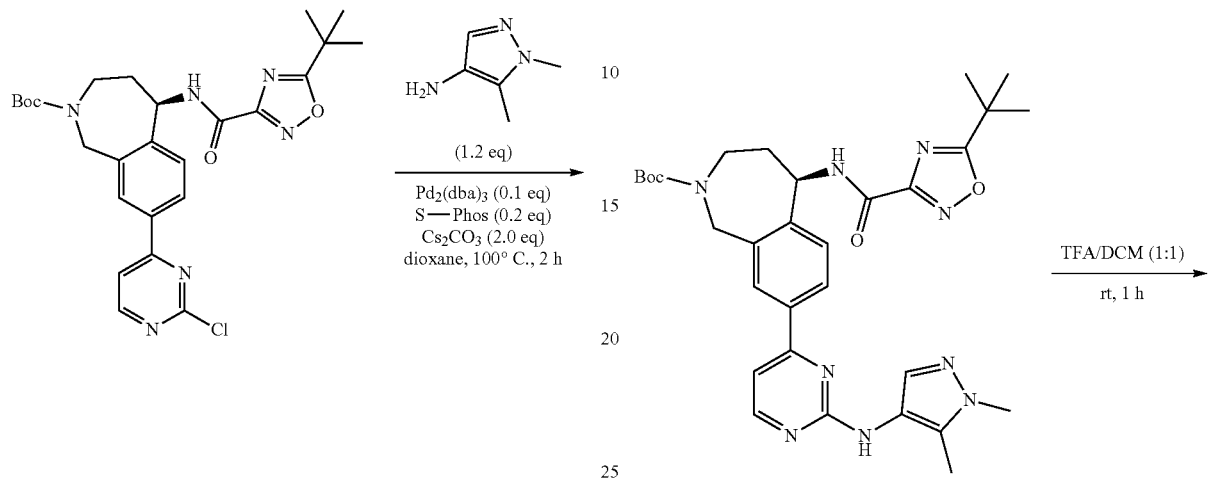

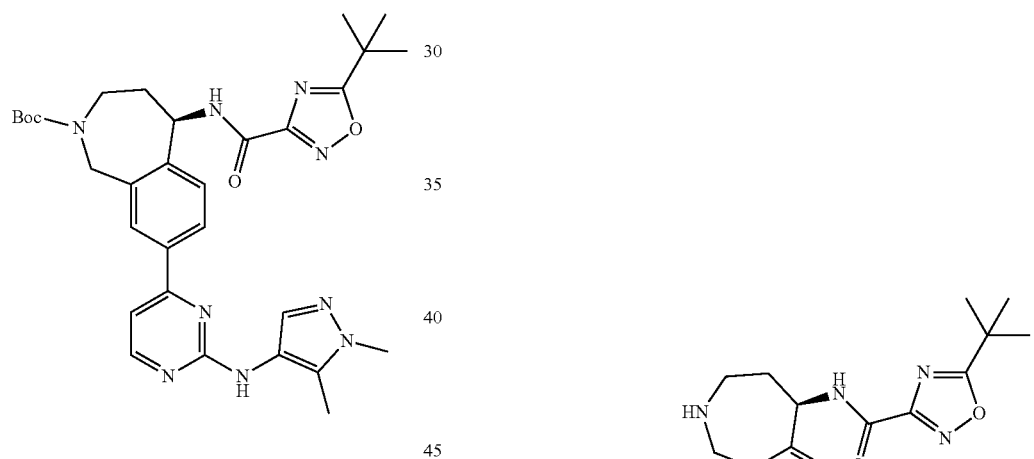

A mixture of tert-butyl (R)-5-(5-(tert-butyl)-1,2,4-oxadiazole-3-carboxamido)-8-(2-chloropyrimidin-4-yl)-1,3,4,5-tetrahydro-2H-benzo[c]azepine-2-carboxylate (900 mg, 1.71 mmol), 1,5-dimethyl-1H-pyrazol-4-amine (228 mg, 2.05 mmol), $Cs_2CO_3$ (1.11 g, 3.42 mmol), $Pd_2(dba)_3$ (157 mg, 0.17 mmol) and S-Phos (140 mg, 0.34 mmol) in 15 mL 1,4-dioxane was stirred at 100° C. for 2 h under nitrogen. The mixture was diluted with EtOAc (200 mL) and washed with water (60 mL×2). The organic phase was dried with $Na_2SO_4$ and concentrated. The crude product was purified by silica gel chromatography (DCM/MeOH=20:1) to give tert-butyl (R)-5-(5-(tert-butyl)-1,2,4-oxadiazole-3-carboxamido)-8-(2-((1,5-dimethyl-1H-pyrazol-4-yl)amino)pyrimidin-4-yl)-1,3,4,5-tetrahydro-2H-benzo[c]azepine-2-carboxylate as a yellow solid (110 mg, yield: 11%). ESI-MS $(M+H)^+$: 602.3. $^1H$ NMR (400 MHz, $CDCl_3$) δ: 8.39-8.38 (m, 1H), 7.93-7.90 (m, 2H), 7.67 (s, 1H), 7.46-7.44 (m, 2H), 7.05 (d, J=4.2 Hz, 1H), 6.48-6.41 (m, 1H), 5.69-5.59 (m, 1H), 4.81-4.66 (m, 1H), 4.50-4.41 (m, 1H), 4.10-4.03 (m, 1H), 3.81 (s, 3H), 3.61-3.52 (m, 1H), 2.23 (s, 3H), 2.20-2.16 (m, 2H), 1.40 (s, 9H), 1.34-1.30 (m, 9H).

Synthesis of (R)-5-(tert-butyl)-N-(8-(2-((1,5-dimethyl-1H-pyrazol-4-yl)amino)pyrimidin-4-yl)-2,3,4,5-tetrahydro-1H-benzo[c]azepin-5-yl)-1,2,4-oxadiazole-3-carboxamide was like that of 5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide in Example 2. The crude material was carried forward without further purification. ESI-MS $(M+H)^+$: 502.2.

5. Synthesis of (R)-5-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1,2,4-oxadiazole-3-carboxamide Example 10. 5-(tert-butyl)-N-(8-(2-((1-methyl-1H-pyrazol-4-yl)amino)pyrimidin-4-yl)-2-(tetrahydrofuran-3-yl)-2,3,4,5-tetrahydro-1H-benzo[c]azepin-5-yl)-1,2,4-oxadiazole-3-carboxamide (Compound 10)

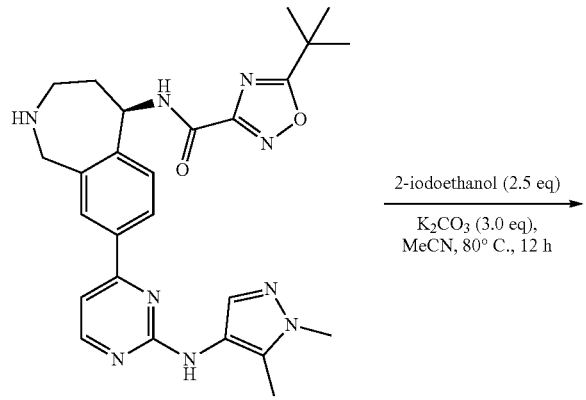

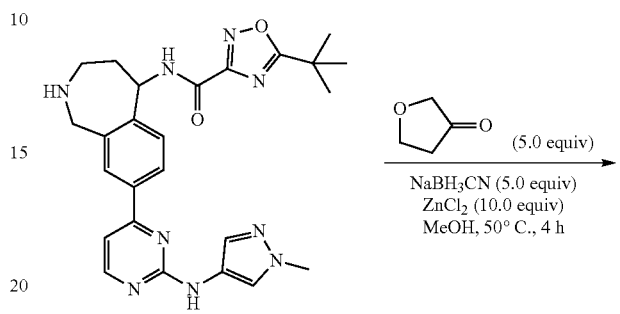

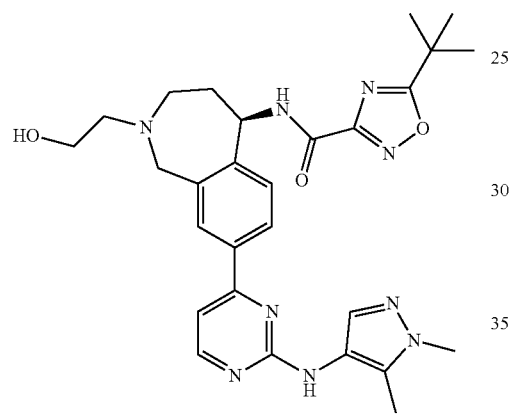

Synthesis of (R)-5-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1,2,4-oxadiazole-3-carboxamide was similar to that of 5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide in Example 3. The crude material was purified by silica gel chromatography ($CH_2Cl_2$:MeOH=10:1) to give (R)-5-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1,2,4-oxadiazole-3-carboxamide as a yellow solid (43 mg, yield 42%). ESI-MS (M+H)$^+$: 546.3. $^1$H NMR (400 MHz, CD$_3$OD) δ: 8.32 (d, J=5.2 Hz, 1H), 8.00-7.98 (m, 2H), 7.60 (s, 1H), 7.42 (d, J=8.0 Hz, 1H), 7.23 (d, J=5.2 Hz, 1H), 5.58-5.56 (m, 1H), 4.16-4.10 (m, 2H), 3.82 (s, 3H), 3.73 (t, J=6.0 Hz, 2H), 3.30-3.21 (m, 2H), 2.67-2.65 (m, 2H), 2.30-2.27 (m, 1H), 2.25 (s, 3H), 2.02-1.96 (m, 1H), 1.52 (s, 9H).

Synthesis of 5-(tert-butyl)-N-(8-(2-((1-methyl-1H-pyrazol-4-yl)amino)pyrimidin-4-yl)-2-(tetrahydrofuran-3-yl)-2,3,4,5-tetrahydro-1H-benzo[c]azepin-5-yl)-1,2,4-oxadiazole-3-carboxamide was similar to that described in Example 7, Step 3. The crude material was purified by prep-HPLC (CH$_3$CN/H$_2$O with 0.05% NH$_4$HCO$_3$ as mobile phase) to give 5-(tert-butyl)-N-(8-(2-((1-methyl-1H-pyrazol-4-yl)amino)pyrimidin-4-yl)-2-(tetrahydrofuran-3-yl)-2,3,4,5-tetrahydro-1H-benzo[c]azepin-5-yl)-1,2,4-oxadiazole-3-carboxamide as a yellow solid (97 mg, yield: 57%). ESI-MS (M+H)$^+$: 558.3. $^1$H NMR (400 MHz, CD$_3$OD) δ: 8.43 (d, J=5.2 Hz, 1H), 8.04-7.99 (m, 3H), 7.64-7.63 (m, 1H), 7.48 (d, J=8.0 Hz, 1H), 7.24 (d, J=5.2 Hz, 1H), 5.61 (d, J=9.6 Hz, 1H), 4.10-3.91 (m, 4H), 3.90 (s, 3H), 3.78-3.71 (m, 2H), 3.36-3.10 (m, 3H), 2.33-2.20 (m, 2H), 2.06-1.96 (m, 2H), 1.52 (s, 9H).

Example 11. (R)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,2,4-oxadiazole-3-carboxamide (Compound 11)

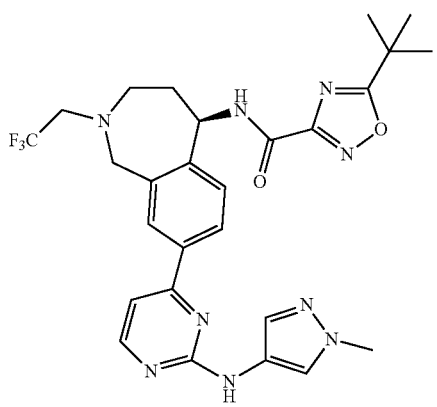 [SMILES: Cn1cc(Nc2nccc(-c3ccc4c(c3)CN(CC(F)(F)F)CC[C@H]4NC(=O)c3noc(C(C)(C)C)n3)n2)cn1]

I. Synthesis of tert-butyl (R)-5-(5-(tert-butyl)-1,2,4-oxadiazole-3-carboxamido)-8-(2-((1-methyl-1H-pyrazol-4-yl)amino)pyrimidin-4-yl)-1,3,4,5-tetrahydro-2H-benzo[c]azepine-2-carboxylate

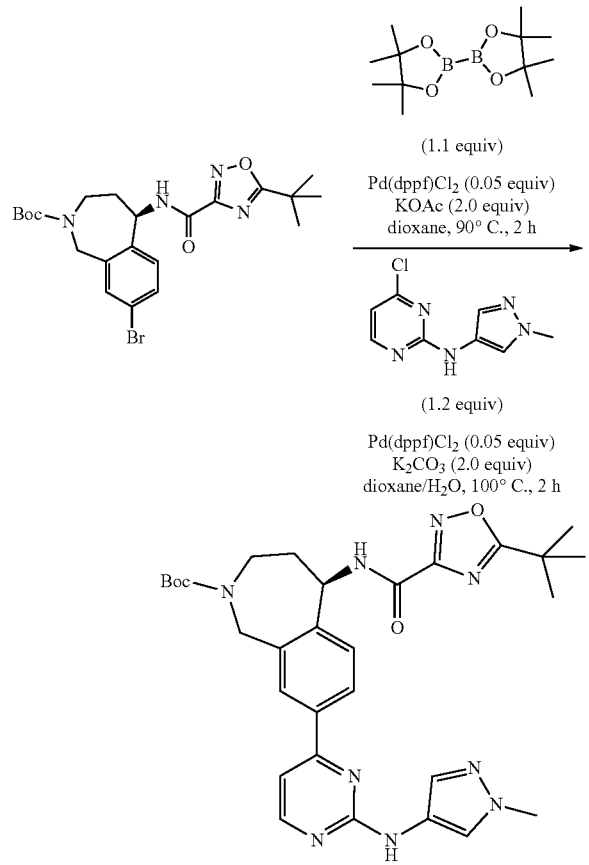

Synthesis of tert-butyl (R)-5-(5-(tert-butyl)-1,2,4-oxadiazole-3-carboxamido)-8-(2-((1-methyl-1H-pyrazol-4-yl)amino)pyrimidin-4-yl)-1,3,4,5-tetrahydro-2H-benzo[c]azepine-2-carboxylate was similar to that of tert-butyl 1-(5-(tert-butyl)-1,2,4-oxadiazole-3-carboxamido)-7-(2-((1-methyl-1H-pyrazol-4-yl)amino)pyrimidin-4-yl)-4,5-dihydro-1H-benzo[d]azepine-3 (2H)-carboxylate in Example 1, Step 12. The crude material was purified by silica gel chromatography (EtOAc:MeOH=15:1) to give tert-butyl (R)-5-(5-(tert-butyl)-1,2,4-oxadiazole-3-carboxamido)-8-(2-((1-methyl-1H-pyrazol-4-yl)amino)pyrimidin-4-yl)-1,3,4,5-tetrahydro-2H-benzo[c]azepine-2-carboxylate as a yellow solid (1.5 g, yield: 43%). ESI-MS (M+H)$^+$: 588.3.

2. Synthesis of (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide

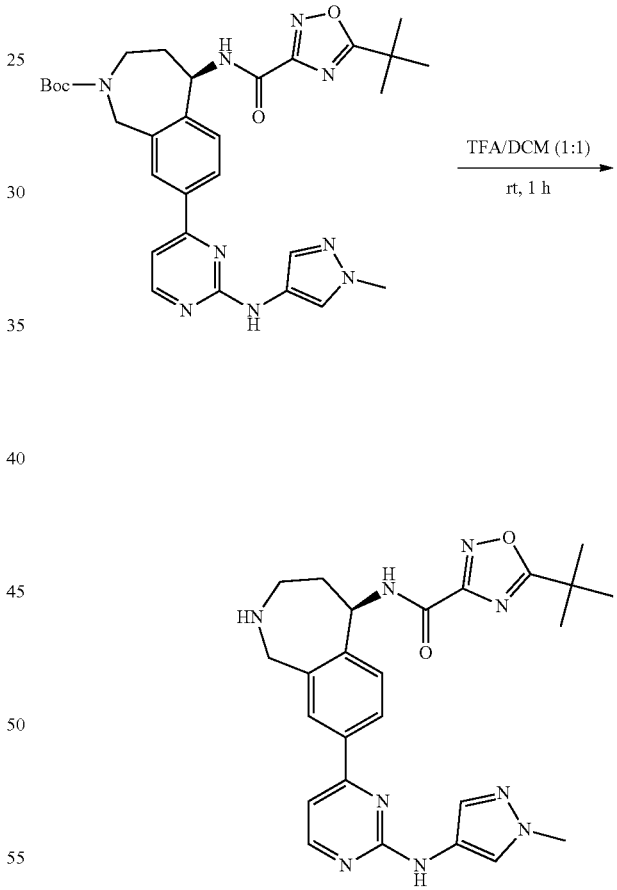

To a solution of tert-butyl (R)-5-(5-(tert-butyl)-1,2,4-oxadiazole-3-carboxamido)-8-(2-((1-methyl-1H-pyrazol-4-yl)amino)pyrimidin-4-yl)-1,3,4,5-tetrahydro-2H-benzo[c]azepine-2-carboxylate (1.4 g, 2.3 mmol) in CH$_2$Cl$_2$ (10 mL) was added TFA (10 mL). The mixture was stirred for 1 h at room temperature. The reaction mixture was concentrated and the crude product (1.0 g, yield: 81%) was used in the next step without further purification. ESI-MS (M+H)$^+$: 488.3.

3. Synthesis of (R)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,2,4-oxadiazole-3-carboxamide

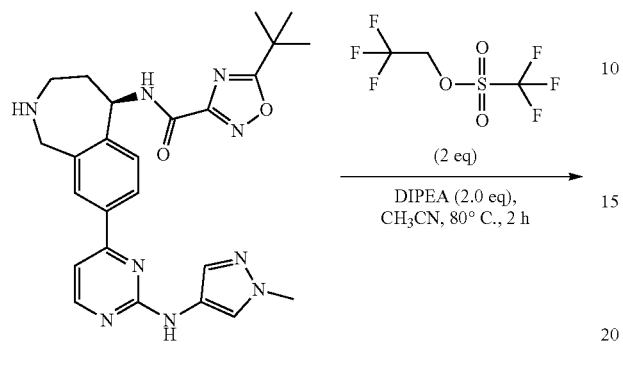

To a solution of (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide (75 mg, 0.15 mmol) in CH$_3$CN (5 mL) were added 2,2,2-trifluoroethyl trifluoromethanesulfonate (60 mg, 0.3 mmol) and DIPEA (34 mg, 0.3 mmol). The mixture was stirred at 80° C. for 2 h under microwave. The mixture was concentrated and purified by prep-TLC (DCM/MeOH=10:1) to give (R)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,2,4-oxadiazole-3-carboxamide as a yellow solid (45 mg, yield: 58%). ESI-MS (M+H)$^+$: 570.2. $^1$H NMR (400 MHz, CD$_3$OD) δ: 8.30 (d, J=5.6 Hz, 1H), 7.92-7.86 (m, 3H), 7.50 (s, 1H), 7.35 (d, J=8.0 Hz, 1H), 7.10 (d, J=5.6 Hz, 1H), 5.48-5.50 (m, 1H), 4.26-4.22 (m, 1H), 4.02-3.98 (m, 1H), 3.78 (s, 3H), 3.32-3.27 (m, 1H), 3.21-3.17 (m, 1H), 3.05-2.98 (m, 2H), 2.17-2.07 (m, 1H), 1.91-1.82 (m, 1H), 1.40 (s, 9H).

Example 12. 5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,3,4-oxadiazole-2-carboxamide
(Compound 12)

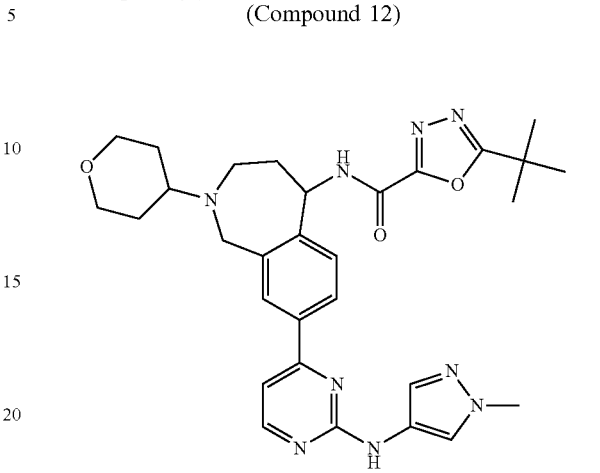

I. The Preparation of tert-butyl 8-bromo-5-(5-(tert-butyl)-1,3,4-oxadiazole-2-carboxamido)-4,5-dihydro-1H-benzo[c]azepine-2(3H)-carboxylate

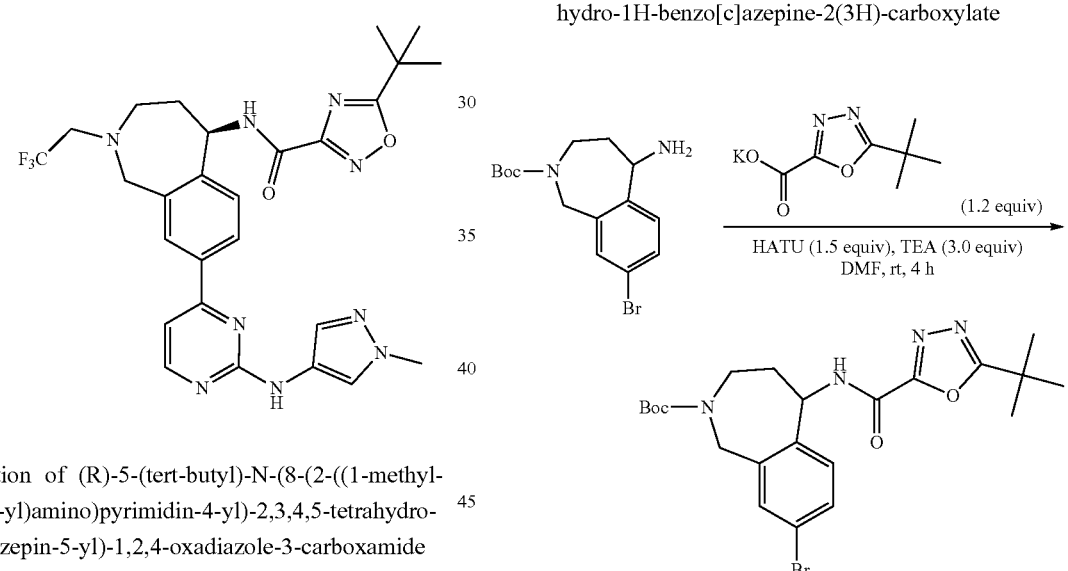

To a solution of potassium 5-(tert-butyl)-1,3,4-oxadiazole-2-carboxylate (1.4 g, 6.7 mmol) and HATU (3.2 g, 8.4 mmol) in DMF (20 mL) were added triethylamine (1.69 g, 16.8 mmol) and tert-butyl 5-amino-8-bromo-4,5-dihydro-1H-benzo[c]azepine-2(3H)-carboxylate (1.9 g, 5.6 mmol). The mixture was stirred at rt for 4 h. After diluting with water (80 mL), the mixture was extracted with EtOAc (100 mL×2). The combined organics were washed with brine (80 mL), dried, and concentrated. The crude product was purified by silica gel column chromatograph (PE/EtOAc=2:1) to give tert-butyl 8-bromo-5-(5-(tert-butyl)-1,3,4-oxadiazole-2-carboxamido)-4,5-dihydro-1H-benzo[c]azepine-2(3H)-carboxylate as yellow solid (1.8 g, yield: 62%). ESI-MS (M+H−56)$^+$: 437.3. $^1$H NMR (400 MHz, CD$_3$OD) δ: 7.51-7.43 (m, 2H), 7.28-7.26 (m, 1H), 5.52-5.45 (m, 1H), 4.65-4.61 (m, 1H), 4.43-4.39 (m, 1H), 4.15-4.09 (m, 1H), 3.65-3.43 (m, 1H), 2.08-2.03 (m, 2H), 1.50 (s, 9H), 1.43-1.42 (m, 9H).

2. The Preparation of tert-butyl 5-(5-(tert-butyl)-1,3,4-oxadiazole-2-carboxamido)-8-(2-((1-methyl-1H-pyrazol-4-yl)amino)pyrimidin-4-yl)-4,5-dihydro-1H-benzo[c]azepine-2(3H)-carboxylate

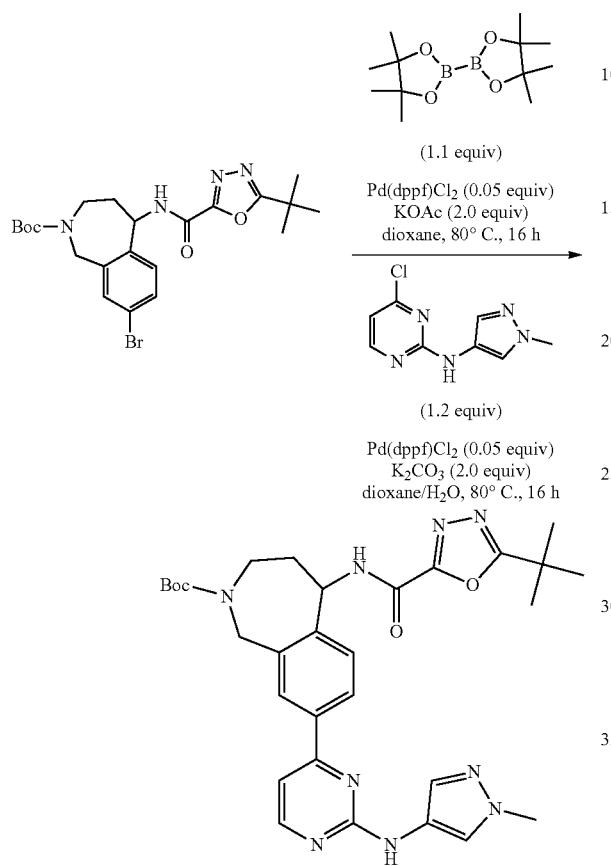

A mixture of tert-butyl 8-bromo-5-(5-(tert-butyl)-1,3,4-oxadiazole-2-carboxamido)-4,5-dihydro-1H-benzo[c]azepine-2(3H)-carboxylate (1.6 g, 3.2 mmol), PinB-BPin (802 mg, 3.84 mmol), KOAc (640 mg, 6.4 mmol) and Pd(dppf)Cl$_2$.CH$_2$Cl$_2$ (130 mg, 0.16 mmol) in 20 mL dry 1,4-dioxane was stirred at 80° C. for 16 h under nitrogen. After the mixture was cooled to rt, 4-chloro-N-(1-methyl-1H-pyrazol-4-yl)pyrimidin-2-amine (802 mg, 3.84 mmol), Pd(dppf)Cl$_2$CH$_2$Cl$_2$ (130 mg, 0.16 mmol), K$_2$CO$_3$(1.3 g, 9.6 mmol), and H$_2$O (5 mL) were added and the resulting mixture was stirred at 80° C. for another 16 h. The mixture was diluted with EtOAc (200 mL), washed with water (80 mL×2), dried with Na$_2$SO$_4$, and concentrated. The crude product was purified by silica gel column chromatography (EtOAc/MeOH=20:1) to give tert-butyl 5-(5-(tert-butyl)-1,3,4-oxadiazole-2-carboxamido)-8-(2-((1-methyl-1H-pyrazol-4-yl)amino)pyrimidin-4-yl)-4,5-dihydro-1H-benzo[c]azepine-2(3H)-carboxylate as yellow solid (1.4 g, yield: 86%). ESI-MS (M+H)$^+$: 588.3. $^1$H NMR (400 MHz, CD$_3$OD) δ: 8.42-8.38 (m, 1H), 8.11-7.95 (m, 3H), 7.66-7.50 (m, 2H), 7.24-7.21 (m, 1H), 5.64-5.62 (m, 1H), 4.85-4.47 (m, 2H), 3.93-3.88 (m, 1H), 3.57-3.54 (m, 1H), 2.12-2.10 (m, 2H), 1.51 (s, 9H), 1.43-1.34 (m, 9H)

3. The Preparation of 5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide

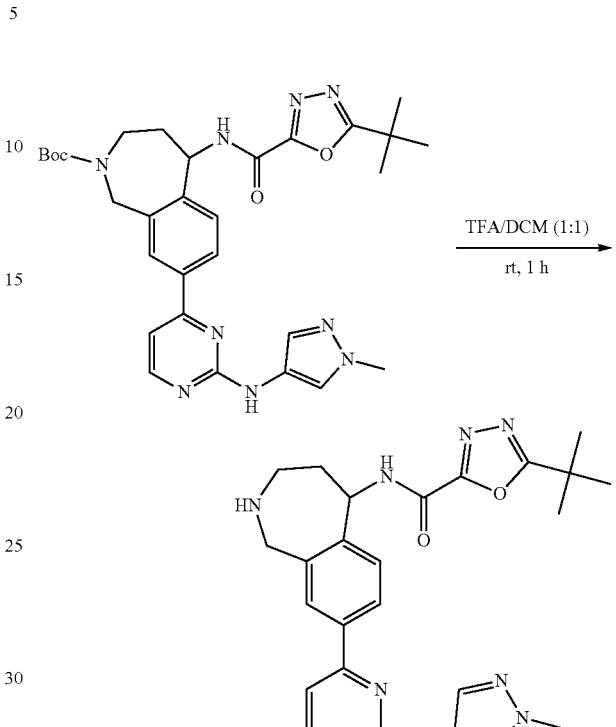

To a solution of tert-butyl 5-(5-(tert-butyl)-1,3,4-oxadiazole-2-carboxamido)-8-(2-((1-methyl-1H-pyrazol-4-yl)amino)pyrimidin-4-yl)-4,5-dihydro-1H-benzo[c]azepine-2(3H)-carboxylate (600 mg, 1.02 mmol) in CH$_2$Cl$_2$ (5 mL) was added TFA (5 mL). The mixture was stirred 1 h at rt. After removal of the solvent, the residue was dried in vacuo to give crude title product (460 mg, yield: 80%), which was used in the next step without further purification. ESI-MS (M+H)$^+$: 488.3.

4. Synthesis of 5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,3,4-oxadiazole-2-carboxamide

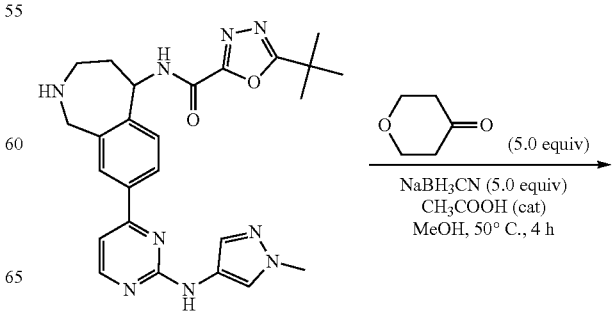

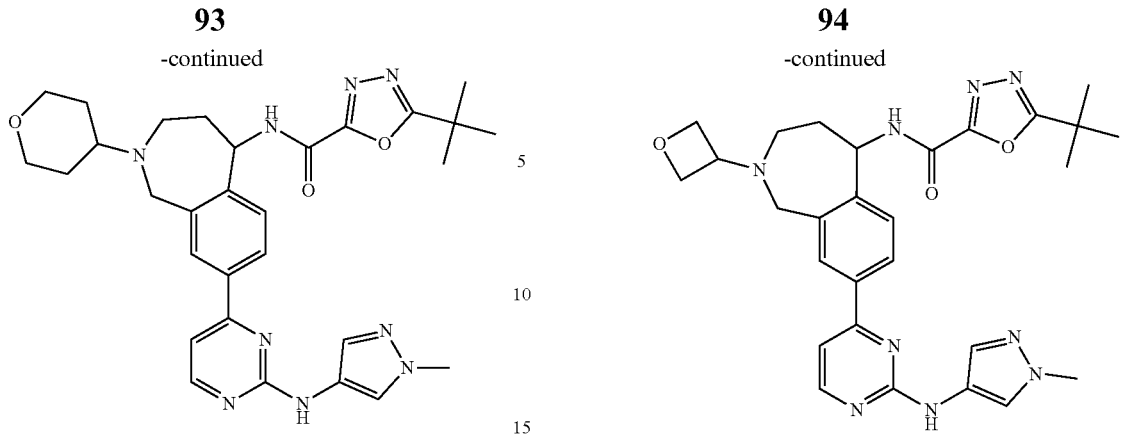

To a solution of 5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide (170 mg, 0.35 mmol) and dihydro-pyran-4-one (175 mg, 1.75 mmol) in MeOH (30 mL) were added NaBH$_3$CN (112 mg, 1.75 mmol) and CH$_3$COOH (cat). The mixture was stirred at 50° C. for 4 h. After cooling to rt, the mixture was adjusted to pH=8 with conc. NH$_4$OH. After concentration, the crude product was purified by prep-HPLC (CH$_3$CN/H$_2$O with 0.05% NH$_4$HCO$_3$ as mobile phase) to give 5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,3,4-oxadiazole-2-carboxamide as a yellow solid (24 mg, yield: 9%). ESI-MS (M+H)$^+$: 572.3. $^1$H NMR (400 MHz, CD$_3$OD) δ: 8.29 (d, J=5.2 Hz, 1H), 7.91-7.85 (m, 3H), 7.53 (s, 1H), 7.36 (d, J=8.0 Hz, 1H), 7.10 (d, J=5.6 Hz, 1H), 5.44 (d, J=9.2 Hz, 1H), 4.08-3.86 (m, 4H), 3.78 (s, 3H), 3.28-3.20 (m, 3H), 3.08-3.01 (m, 1H), 2.63-2.57 (m, 1H), 2.14-2.09 (m, 1H), 1.94-1.76 (m, 3H), 1.63-1.49 (m, 2H), 1.38 (s, 9H).

Example 13. 5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide (Compound 13)

Synthesis of 5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide was similar to that of 5-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1,2,4-oxadiazole-3-carboxamide in Example 8. The crude product was purified by prep-HPLC (CH$_3$CN/H$_2$O with 0.05% NH$_4$HCO$_3$ as mobile phase) to give 5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide as a yellow solid (59 mg, yield: 33%). ESI-MS (M+H)$^+$: 544.2. $^1$H NMR (400 MHz, CD$_3$OD) δ: 8.29 (d, J=5.2 Hz, 1H), 7.91 (d, J=8.0 Hz, 1H), 7.86 (s, 1H), 7.83 (s, 1H), 7.51 (s, 1H), 7.36 (d, J=8.4 Hz, 1H), 7.09 (d, J=5.2 Hz, 1H), 5.46 (d, J=10.0 Hz, 1H), 4.65-5.55 (m, 4H), 3.83-3.67 (m, 3H), 3.77 (s, 3H), 2.96-2.93 (m, 1H), 2.79-2.73 (m, 1H), 2.13-2.10 (m, 1H), 1.93-1.90 (m, 1H), 1.38 (s, 9H).

Example 14. (R)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide (Compound 14a) and (S)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide (Compound 14b)

Method 1

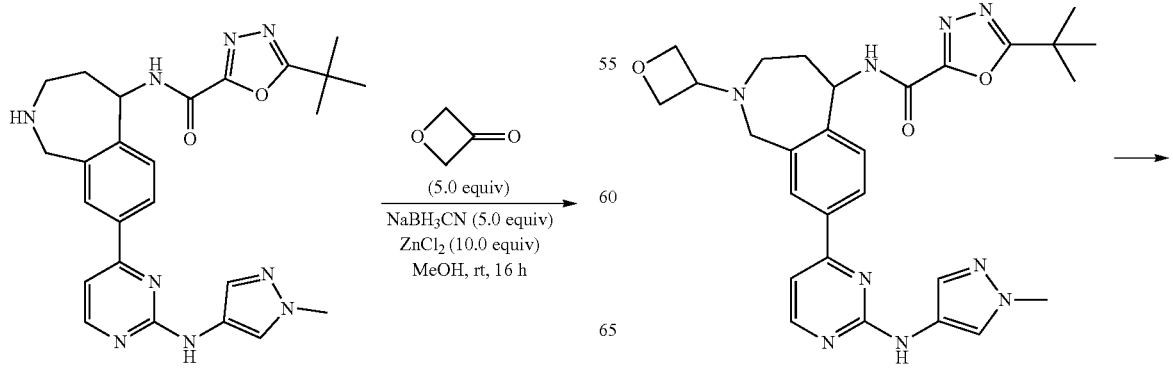

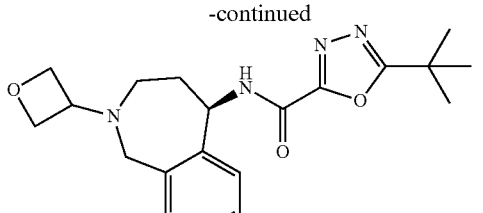

14a

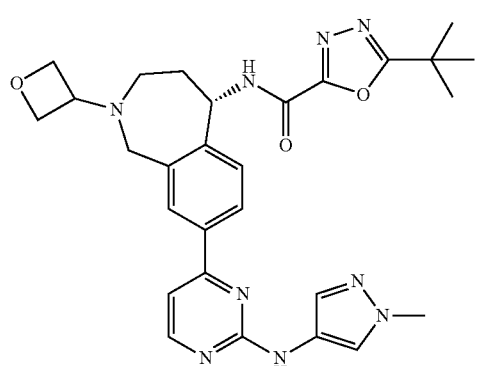

14b 5-tert-Butyl-1,3,4-oxadiazole-2-carboxylic acid {8-[2-(1-methyl-1H-pyrazol-4-ylamino)-pyrimidin-4-yl]-2-oxetan-3-yl-2,3,4,5-tetrahydro-1H-2-benzazepin-5-yl}-amide (264 mg) was subjected to SFC separation (OD-H (2×25 cm), 30% methanol (0.1% DEA)/CO₂, 100 bar, 65 mL/min, 220 nm, inj vol.: 0.5 mL, 4 mg/mL, methanol) and yielded 93 mg of peak-1 (chemical purity >99%, ee>99%) and 97 mg of peak-2 (chemical purity >99%, ee>99%).

Peak 1 was assigned as 5-tert-butyl-1,3,4-oxadiazole-2-carboxylic acid {(R)-8-[2-(1-methyl-1H-pyrazol-4-ylamino)-pyrimidin-4-yl]-2-oxetan-3-yl-2,3,4,5-tetrahydro-1H-2-benzazepin-5-yl}-amide: LCMS: Rt 0.84 min, m/z 544.2. ¹H NMR (400 MHz, METHANOL-d₄) δ 8.41 (br. s., 1H), 7.84-8.14 (m, 3H), 7.63 (br. s., 1H), 7.47 (t, J=7.56 Hz, 1H), 7.21 (d, J=10.04 Hz, 1H), 5.57 (d, J=9.29 Hz, 1H), 4.61-4.80 (m, 4H), 3.66-4.07 (m, 6H), 3.05 (br. s., 1H), 2.88 (d, J=9.04 Hz, 1H), 2.23 (br. s., 1H), 2.05 (br. s., 1H), 1.50 (d, J=2.89 Hz, 9H).

Peak 2 was assigned as 5-tert-butyl-1,3,4-oxadiazole-2-carboxylic acid {(S)-8-[2-(1-methyl-1H-pyrazol-4-ylamino)-pyrimidin-4-yl]-2-oxetan-3-yl-2,3,4,5-tetrahydro-1H-2-benzazepin-5-yl}-amide: LCMS: Rt 0.84 min, m/z 544.2. ¹H NMR (400 MHz, METHANOL-d₄) δ 8.42 (d, J=5.02 Hz, 1H), 7.86-8.14 (m, 3H), 7.63 (s, 1H), 7.48 (d, J=8.09 Hz, 1H), 7.22 (d, J=5.27 Hz, 1H), 5.58 (d, J=9.73 Hz, 1H), 4.59-4.81 (m, 4H), 3.73-4.05 (m, 6H), 3.05 (br. s., 1H), 2.89 (br. s., 1H), 2.23 (br. s., 1H), 2.06 (d, J=5.52 Hz, 1H), 1.50 (s, 9H).

Method 2

I. Synthesis of tert-butyl (R)-8-bromo-5-(5-(tert-butyl)-1,3,4-oxadiazole-2-carboxamido)-1,3,4,5-tetrahydro-2H-benzo[c]azepine-2-carboxylate

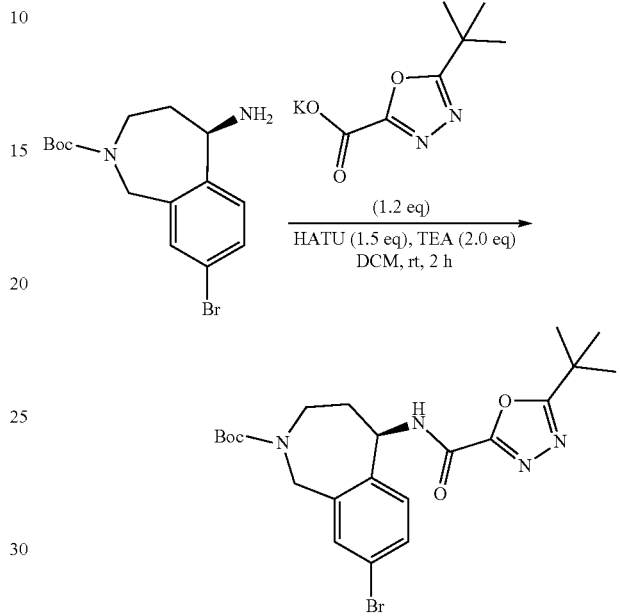

To a solution of tert-butyl (R)-5-amino-8-bromo-1,3,4,5-tetrahydro-2H-benzo[c]azepine-2-carboxylate (3.1 g, 4.5 mmol) and triethylamine (910 mg, 9.0 mmol) in DCM (100 mL) were added HATU (2.6 g, 6.8 mmol) and potassium 5-(tert-butyl)-1,3,4-oxadiazole-2-carboxylate (1.12 g, 5.4 mmol). The mixture was stirred at rt for 2 h. Then water (100 mL) was added and the mixture was extracted with DCM (2×100 mL). The combined organics were dried and concentrated. The crude product was purified by silica gel column chromatography (petroleum ether/EtOAc=4:1) to give tert-butyl (R)-8-bromo-5-(5-(tert-butyl)-1,3,4-oxadiazole-2-carboxamido)-1,3,4,5-tetrahydro-2H-benzo[c]azepine-2-carboxylate as white solid (1.8 g, yield: 82%). ESI-MS (M+H)⁺: 493.1.

2. Synthesis of tert-butyl (R)-5-(5-(tert-butyl)-1,3,4-oxadiazole-2-carboxamido)-8-(4,4,5,5-tetramethyl-1,3,2-dioxaborolan-2-yl)-1,3,4,5-tetrahydro-2H-benzo[c]azepine-2-carboxylate

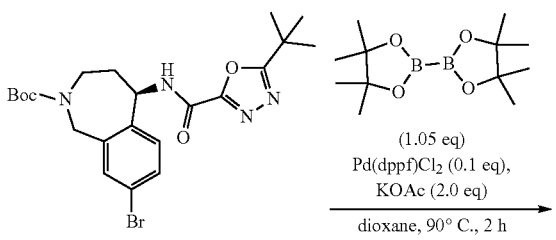

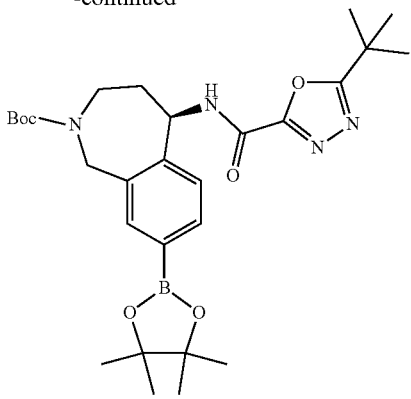

A mixture of tert-butyl (R)-8-bromo-5-(5-(tert-butyl)-1,3,4-oxadiazole-2-carboxamido)-1,3,4,5-tetrahydro-2H-benzo[c]azepine-2-carboxylate (1.8 g, 3.65 mmol), bis(pinocolato)diboron (975 mg, 3.84 mmol), KOAc (715 mg, 7.30 mmol) and Pd(dppf)Cl$_2$·DCM (293 mg, 0.36 mmol) in 30 mL 1,4-dioxane was stirred at 90° C. for 2 h under nitrogen. After cooling to rt, the mixture was diluted with EtOAc (200 mL), washed with water (2×50 mL), dried with Na$_2$SO$_4$ and concentrated. The crude product tert-butyl (R)-5-(5-(tert-butyl)-1,3,4-oxadiazole-2-carboxamido)-8-(4,4,5,5-tetramethyl-1,3,2-dioxaborolan-2-yl)-1,3,4,5-tetrahydro-2H-benzo[c]azepine-2-carboxylate was used for next step without purification. ESI-MS (M+H)$^+$: 541.3.

3. Synthesis of tert-butyl (R)-5-(5-(tert-butyl)-1,3,4-oxadiazole-2-carboxamido)-8-(2-((1-methyl-1H-pyrazol-4-yl)amino)pyrimidin-4-yl)-1,3,4,5-tetrahydro-2H-benzo[c]azepine-2-carboxylate

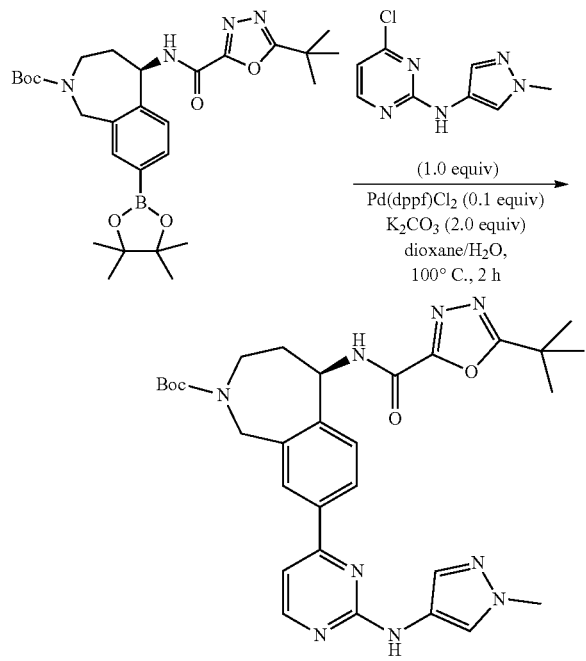

A mixture of tert-butyl (R)-5-(5-(tert-butyl)-1,3,4-oxadiazole-2-carboxamido)-8-(4,4,5,5-tetramethyl-1,3,2-dioxaborolan-2-yl)-1,3,4,5-tetrahydro-2H-benzo[c]azepine-2-carboxylate (4.85 g, 8.98 mmol), 4-chloro-N-(1-methyl-1H-pyrazol-4-yl)pyrimidin-2-amine (1.88 g, 8.98 mmol), Pd(dppf)Cl$_2$ (734 mg, 0.9 mmol) and K$_2$CO$_3$ (2.48 g, 18 mmol) in dioxane/H$_2$O (4:1, 20 mL) was degassed and stirred at 100° C. for 2 h under a N$_2$ atmosphere. After concentration of the reaction mixture, the residue was purified by silica-gel chromatography (EtOAc:PE=2:1) to give tert-butyl (R)-5-(5-(tert-butyl)-1,3,4-oxadiazole-2-carboxamido)-8-(2-((1-methyl-1H-pyrazol-4-yl)amino)pyrimidin-4-yl)-1,3,4,5-tetrahydro-2H-benzo[c]azepine-2-carboxylate as a yellow solid (3.4 g, yield: 51%). ESI-MS (M+H)$^+$: 588.3.

4. Synthesis of (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide

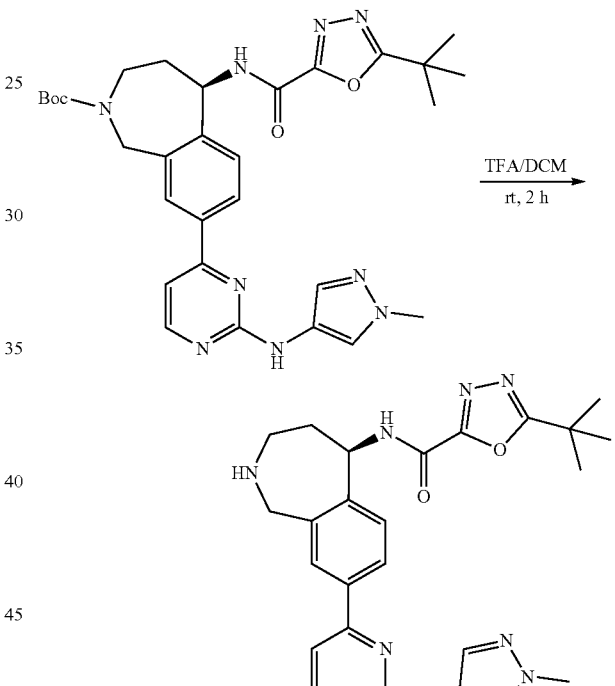

To a solution of tert-butyl (R)-5-(5-(tert-butyl)-1,3,4-oxadiazole-2-carboxamido)-8-(2-((1-methyl-1H-pyrazol-4-yl)amino)pyrimidin-4-yl)-1,3,4,5-tetrahydro-2H-benzo[c]azepine-2-carboxylate (3.4 g, 5.79 mmol) in DCM (10 mL) was added TFA (4 mL). The resulting solution was stirred at room temperature for 2 h. After concentration of the reaction mixture, the residue was dissolved in MeOH (10 mL) and adjusted to pH=8 with aqueous ammonia. Then water (20 mL) was added and the mixture was extracted with DCM/MeOH solutions (20:1, 30 mL×3). The organic phase was dried and concentrated to give crude (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide as a yellow solid (2.47 g, yield: 88%), which was used to next step without further purification. ESI-MS (M+H)$^+$: 488.2.

5. Synthesis of (R)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide (I-RP38)

Example 15. 5-(tert-butyl)-N-(8-(2-((1-methyl-1H-pyrazol-4-yl)amino)pyrimidin-4-yl)-2-(methylsulfonyl)-2,3,4,5-tetrahydro-1H-benzo[c]azepin-5-yl)-1,3,4-oxadiazole-2-carboxamide (Compound 15)

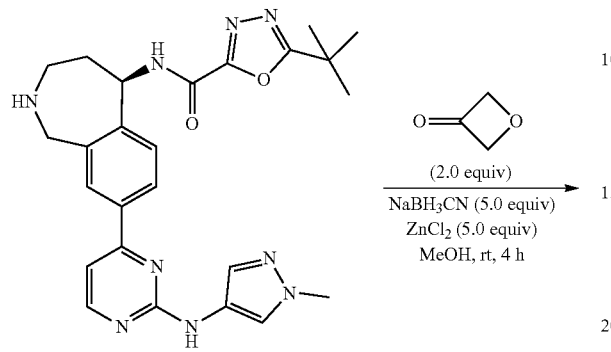

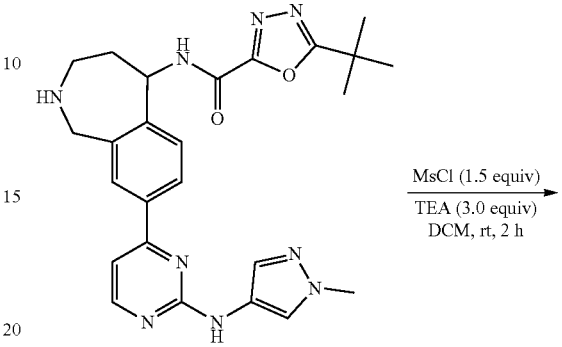

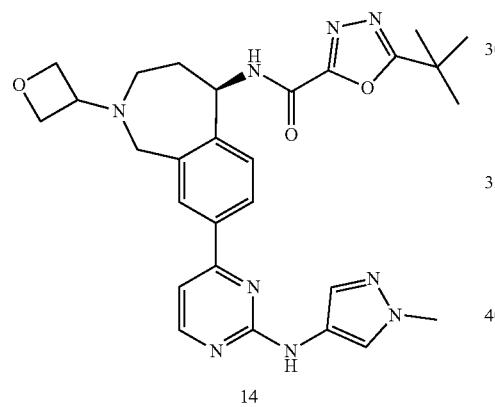

14

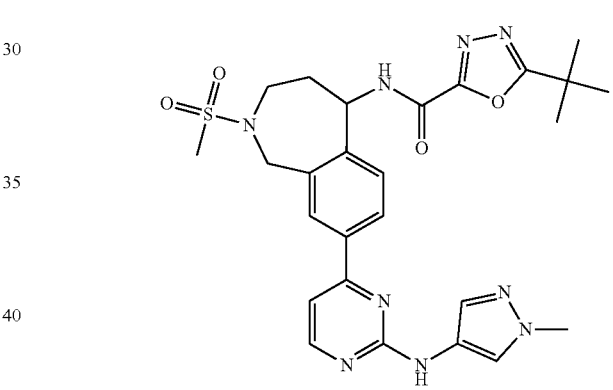

To a solution of (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide (1.5 g, 3.08 mmol) and oxetan-3-one (1.1 g, 15.4 mmol) in MeOH (30 mL) was added NaBH$_3$CN (970 mg, 15.4 mmol) and ZnCl$_2$ (4.2 g, 30.8 mmol). The resulting mixture was stirred at room temperature for 4 h. After diluting with H$_2$O (20 mL), the mixture was extracted with DCM/MeOH solutions (20:1, 20 mL×3). The combined organic layers were dried and concentrated. The residue was purified by silica-gel chromatography (DCM:MeOH=50:1 to 20:1) to give (R)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide as a yellow solid (1.1 g, yield: 58%). ESI-MS (M+H)$^+$: 544.3. $^1$H NMR (400 MHz, CDCl$_3$) δ: 8.42 (d, J=5.2 Hz, 1H), 8.32 (br, 1H), 7.86-7.78 (m, 3H), 7.53-7.26 (m, 2H), 7.15 (s, 1H), 7.05-7.03 (m, 1H), 5.62 (t, J=8.4 Hz, 1H), 4.75-4.67 (m, 4H), 3.94-3.85 (m, 6H), 3.02-2.96 (m, 1H), 2.75-2.70 (m, 1H), 2.35-2.31 (m, 1H), 2.14-2.07 (m, 1H), 1.47 (s, 9H).

To a solution of 5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide (100 mg, 0.20 mmol) in CH$_2$Cl$_2$ (20 mL) were added MsCl (34 mg, 0.3 mmol) and triethylamine (61 mg, 0.60 mmol). The mixture was stirred at rt for 2 h. The mixture was diluted with CH$_2$Cl$_2$ (100 mL), washed with brine (60 mL), and concentrated. The crude product was purified by prep-HPLC (CH$_3$CN/H$_2$O with 0.05% NH$_4$HCO$_3$ as mobile phase) to give 5-(tert-butyl)-N-(8-(2-((1-methyl-1H-pyrazol-4-yl)amino)pyrimidin-4-yl)-2-(methylsulfonyl)-2,3,4,5-tetrahydro-1H-benzo[c]azepin-5-yl)-1,3,4-oxadiazole-2-carboxamide as a yellow solid (130 mg, yield: 87%). ESI-MS (M+H)$^+$: 566.3. $^1$H NMR (400 MHz, DMSO-d$_6$) δ: 10.01 (d, J=7.6 Hz, 1H), 9.57 (s, 1H), 8.49 (d, J=5.2 Hz, 1H), 8.07 (s, 1H), 8.04 (d, J=8.4 Hz, 1H), 7.99 (br, 1H), 7.50 (s, 1H), 7.47 (d, J=8.4 Hz, 1H), 7.27 (d, J=5.2 Hz, 1H), 5.56-5.51 (m, 1H), 4.75-4.70 (m, 1H), 4.60-4.56 (m, 1H), 3.86-3.84 (m, 1H), 3.83 (s, 3H), 3.61-3.58 (m, 1H), 2.80 (s, 3H), 2.15-2.09 (m, 2H), 1.43 (s, 9H).

Example 16. (R)-5-(tert-butyl)-N-(2-(2-hydroxy-ethyl)-8-(2-((1-isopropyl-1H-pyrazol-4-yl)amino)pyrimidin-4-yl)-2,3,4,5-tetrahydro-1H-benzo[c]azepin-5-yl)-1,3,4-oxadiazole-2-carboxamide (Compound 16)

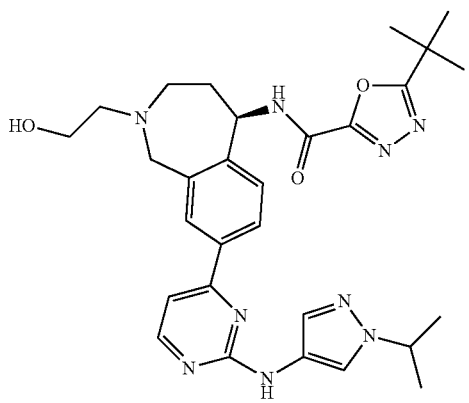 [SMILES: CC(C)n1cc(Nc2nccc(-c3ccc4c(c3)CN(CCO)CC[C@H]4NC(=O)c3nnc(C(C)(C)C)o3)n2)cn1]

I. Synthesis of tert-butyl (R)-8-bromo-5-(5-(tert-butyl)-1,3,4-oxadiazole-2-carboxamido)-1,3,4,5-tetrahydro-2H-benzo[c]azepine-2-carboxylate

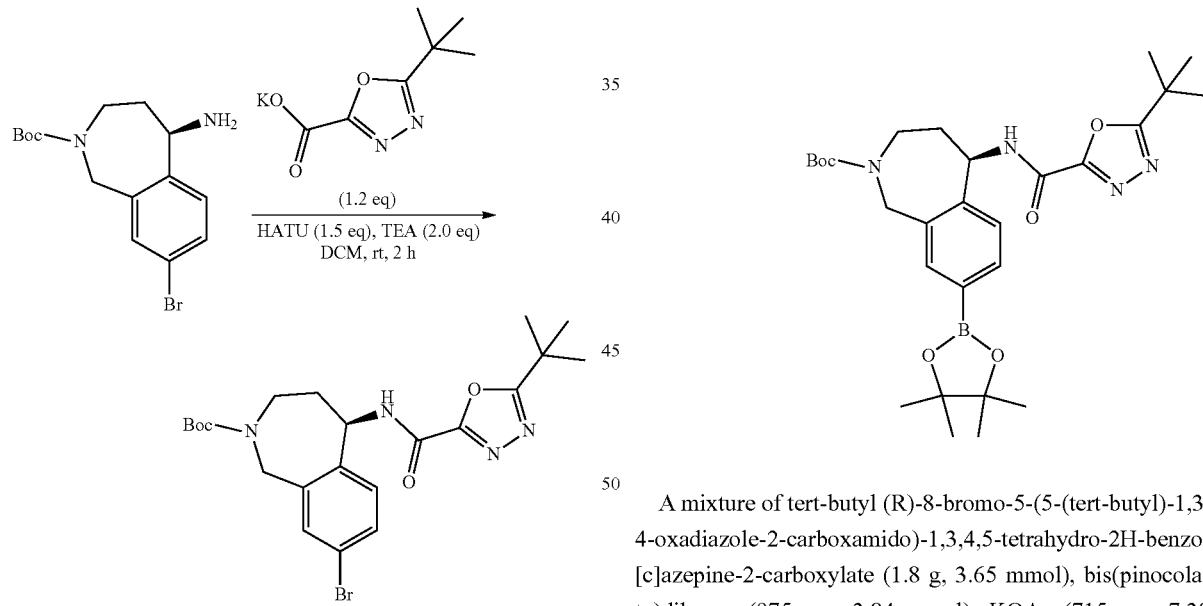

To a solution of tert-butyl (R)-5-amino-8-bromo-1,3,4,5-tetrahydro-2H-benzo[c]azepine-2-carboxylate (3.1 g, 4.5 mmol) and triethylamine (910 mg, 9.0 mmol) in DCM (100 mL) were added HATU (2.6 g, 6.8 mmol) and potassium 5-(tert-butyl)-1,3,4-oxadiazole-2-carboxylate (1.12 g, 5.4 mmol). The mixture was stirred at rt for 2 h. Then water (100 mL) was added and the mixture was extracted with DCM (2×100 mL). The combined organics were dried and concentrated. The crude product was purified by silica gel column chromatography (petroleum ether/EtOAc=4:1) to give tert-butyl (R)-8-bromo-5-(5-(tert-butyl)-1,3,4-oxadiazole-2-carboxamido)-1,3,4,5-tetrahydro-2H-benzo[c]azepine-2-carboxylate as white solid (1.8 g, yield: 82%). ESI-MS (M+H)$^+$: 493.1.

2. Synthesis of tert-butyl (R)-5-(5-(tert-butyl)-1,3,4-oxadiazole-2-carboxamido)-8-(4,4,5,5-tetramethyl-1,3,2-dioxaborolan-2-yl)-1,3,4,5-tetrahydro-2H-benzo[c]azepine-2-carboxylate

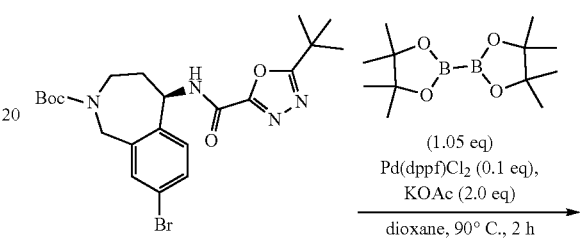

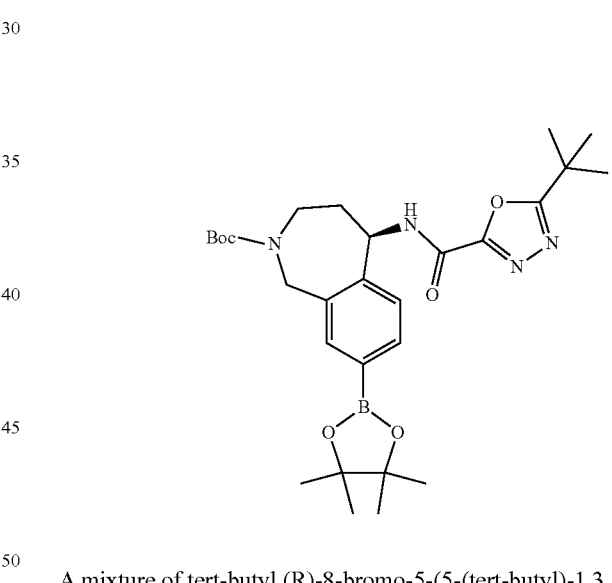

A mixture of tert-butyl (R)-8-bromo-5-(5-(tert-butyl)-1,3,4-oxadiazole-2-carboxamido)-1,3,4,5-tetrahydro-2H-benzo[c]azepine-2-carboxylate (1.8 g, 3.65 mmol), bis(pinocolato)diboron (975 mg, 3.84 mmol), KOAc (715 mg, 7.30 mmol) and Pd(dppf)Cl$_2$.DCM (293 mg, 0.36 mmol) in 30 mL 1,4-dioxane was stirred at 90° C. for 2 h under nitrogen. After cooling to rt, the mixture was diluted with EtOAc (200 mL), washed with water (2×50 mL), dried with Na$_2$SO$_4$ and concentrated. The crude product tert-butyl (R)-5-(5-(tert-butyl)-1,3,4-oxadiazole-2-carboxamido)-8-(4,4,5,5-tetramethyl-1,3,2-dioxaborolan-2-yl)-1,3,4,5-tetrahydro-2H-benzo[c]azepine-2-carboxylate was used for next step without purification. ESI-MS (M+H)$^+$: 541.3.

3. Synthesis of tert-butyl (R)-5-(5-(tert-butyl)-1,3,4-oxadiazole-2-carboxamido)-8-(2-chloropyrimidin-4-yl)-1,3,4,5-tetrahydro-2H-benzo[c]azepine-2-carboxylate

4. Synthesis of tert-butyl (R)-5-(5-(tert-butyl)-1,3,4-oxadiazole-2-carboxamido)-8-(2-((1-isopropyl-1H-pyrazol-4-yl)amino)pyrimidin-4-yl)-1,3,4,5-tetrahydro-2H-benzo[e]azepine-2-carboxylate

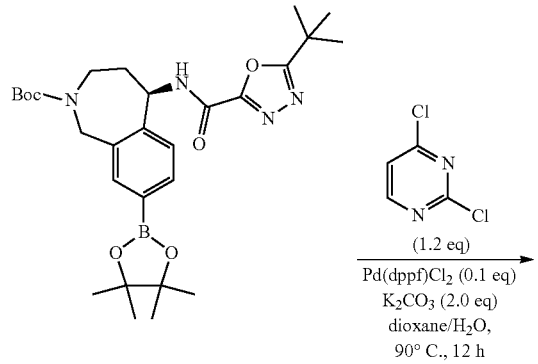

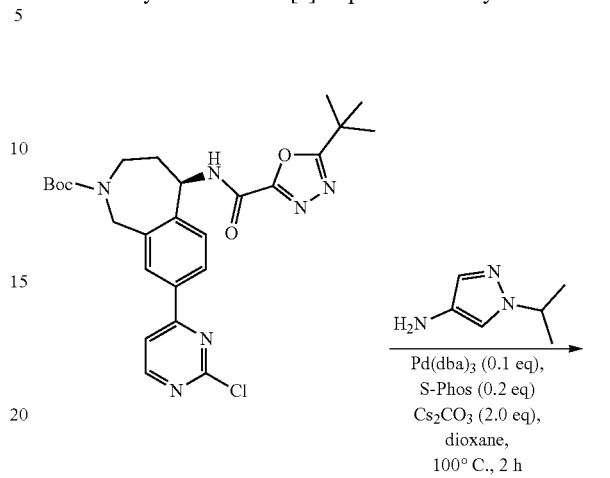

A mixture of tert-butyl (R)-5-(5-(tert-butyl)-1,3,4-oxadiazole-2-carboxamido)-8-(4,4,5,5-tetramethyl-1,3,2-dioxaborolan-2-yl)-1,3,4,5-tetrahydro-2H-benzo[c]azepine-2-carboxylate, 2,4-dichloropyrimidine (648 mg, 4.38 mmol), $K_2CO_3$ (1.0 g, 7.30 mmol) and Pd(dppf)Cl$_2$·DCM (293 mg, 0.36 mmol) in 30 mL 1,4-dioxane and 6 mL water was stirred at 90° C. for 12 h under nitrogen. The mixture was dilute with EtOAc (200 mL) and washed with water (2×60 mL). The organic phase was dried with $Na_2SO_4$ and concentrated. The crude product was purified by silica gel column chromatography (DCM/MeOH=20:1) to give tert-butyl (R)-5-(5-(tert-butyl)-1,3,4-oxadiazole-2-carboxamido)-8-(2-chloropyrimidin-4-yl)-1,3,4,5-tetrahydro-2H-benzo[c]azepine-2-carboxylate as a yellow solid (1.3 g, yield: 67% for two steps). ESI-MS (M+H)$^+$: 527.2.

Synthesis of tert-butyl (R)-5-(5-(tert-butyl)-1,3,4-oxadiazole-2-carboxamido)-8-(2-((1-isopropyl-1H-pyrazol-4-yl)amino)pyrimidin-4-yl)-1,3,4,5-tetrahydro-2H-benzo[c]azepine-2-carboxylate was similar to that of tert-butyl (R)-5-(5-(tert-butyl)-1,2,4-oxadiazole-3-carboxamido)-8-(2-((1,5-dimethyl-1H-pyrazol-4-yl)amino)pyrimidin-4-yl)-1,3,4,5-tetrahydro-2H-benzo[c]azepine-2-carboxylate (Example 9, Step 3). The crude product was purified by silica gel column chromatography (EtOAc/petroleum ether=3:1) to give tert-butyl (R)-5-(5-(tert-butyl)-1,3,4-oxadiazole-2-carboxamido)-8-(2-((1-isopropyl-1H-pyrazol-4-yl)amino)pyrimidin-4-yl)-1,3,4,5-tetrahydro-2H-benzo[c]azepine-2-carboxylate as a yellow solid (280 mg, yield: 78%). ESI-MS (M+H)$^+$: 616.3.

5. Synthesis of (R)-5-(tert-butyl)-N-(8-(2-((1-isopropyl-1H-pyrazol-4-yl)amino)pyrimidin-4-yl)-2,3,4,5-tetrahydro-1H-benzo[c]azepin-5-yl)-1,3,4-oxadiazole-2-carboxamide

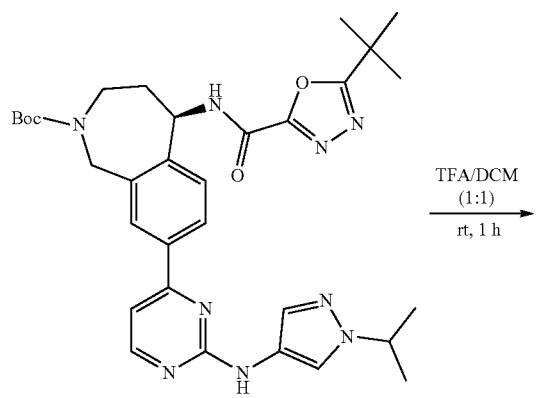

Synthesis of (R)-5-(tert-butyl)-N-(8-(2-((1-isopropyl-1H-pyrazol-4-yl)amino)pyrimidin-4-yl)-2,3,4,5-tetrahydro-1H-benzo[c]azepin-5-yl)-1,3,4-oxadiazole-2-carboxamide was similar to that of (R)-5-(tert-butyl)-N-(8-(2-((1,5-dimethyl-1H-pyrazol-4-yl)amino)pyrimidin-4-yl)-2,3,4,5-tetrahydro-1H-benzo[c]azepin-5-yl)-1,2,4-oxadiazole-3-carboxamide (Example 9, Step 4). Crude (R)-5-(tert-butyl)-N-(8-(2-((1-isopropyl-1H-pyrazol-4-yl)amino)pyrimidin-4-yl)-2,3,4,5-tetrahydro-1H-benzo[c]azepin-5-yl)-1,3,4-oxadiazole-2-carboxamide as yellow solid (240 mg) was used to next step without further purification. ESI-MS (M+H)$^+$: 516.3.

6. Synthesis of (R)-5-(tert-butyl)-N-(2-(2-hydroxyethyl)-8-(2-((1-isopropyl-1H-pyrazol-4-yl)amino)pyrimidin-4-yl)-2,3,4,5-tetrahydro-1H-benzo[c]azepin-5-yl)-1,3,4-oxadiazole-2-carboxamide

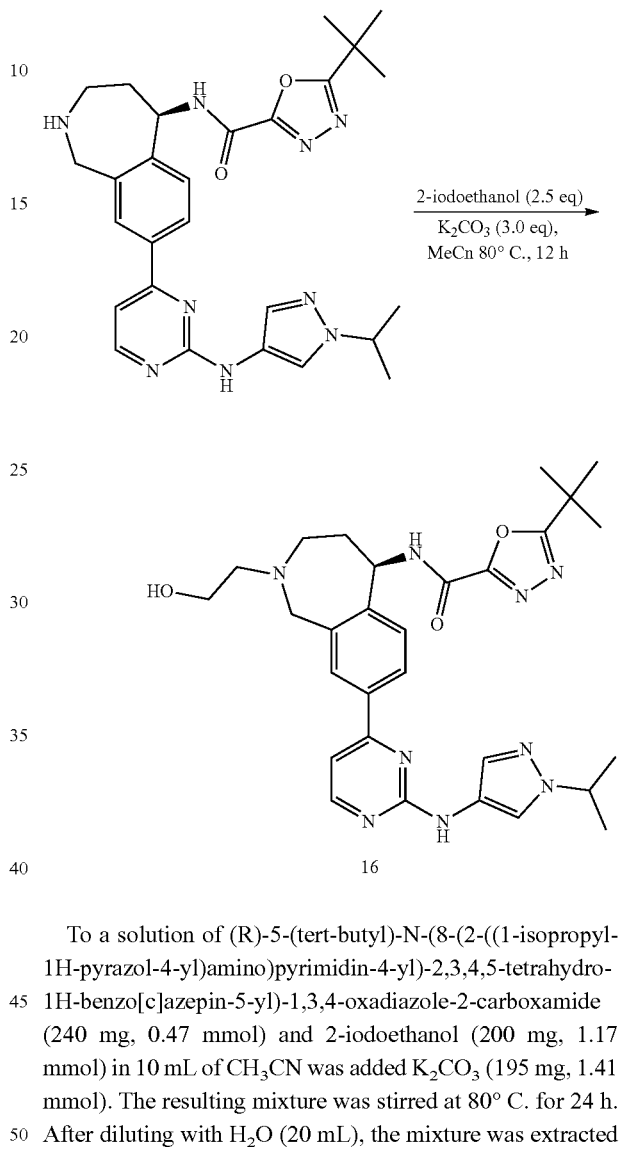

To a solution of (R)-5-(tert-butyl)-N-(8-(2-((1-isopropyl-1H-pyrazol-4-yl)amino)pyrimidin-4-yl)-2,3,4,5-tetrahydro-1H-benzo[c]azepin-5-yl)-1,3,4-oxadiazole-2-carboxamide (240 mg, 0.47 mmol) and 2-iodoethanol (200 mg, 1.17 mmol) in 10 mL of CH$_3$CN was added K$_2$CO$_3$ (195 mg, 1.41 mmol). The resulting mixture was stirred at 80° C. for 24 h. After diluting with H$_2$O (20 mL), the mixture was extracted with DCM/MeOH solutions (20:1, 3×40 mL). The combined organic layers were dried (Na$_2$SO$_4$) and concentrated. The residue was purified by prep-TLC (DCM/MeOH=10:1) to give (R)-5-(tert-butyl)-N-(2-(2-hydroxyethyl)-8-(2-((1-isopropyl-1H-pyrazol-4-yl)amino)pyrimidin-4-yl)-2,3,4,5-tetrahydro-1H-benzo[c]azepin-5-yl)-1,3,4-oxadiazole-2-carboxamide as a yellow solid (108 mg, yield: 42%). ESI-MS (M+H)$^+$: 560.3. $^1$H NMR (400 MHz, CD$_3$OD) δ: 8.37 (d, J=5.2 Hz, 1H), 8.03 (s, 1H), 7.98-7.95 (m, 2H), 7.66 (s, 1H), 7.44 (d, J=8.4 Hz, 1H), 7.17 (d, J=5.2 Hz, 1H), 5.55 (d, J=9.6 Hz, 1H), 4.54-4.37 (m, 1H), 4.17-4.04 (m, 2H), 3.71 (t, J=6.0 Hz, 2H), 3.30-3.17 (m, 2H), 2.29-2.25 (m, 2H), 2.29-2.25 (m, 1H), 1.99-1.95 (m, 1H), 1.52 (d, J=6.4 Hz, 6H), 1.49 (s, 9H).

Example 17. (R)-5-(tert-butyl)-N-(8-(2-((1-isopropyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide (Compound 17)

Example 18. (R)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,3,4-oxadiazole-2-carboxamide (Compound 18)

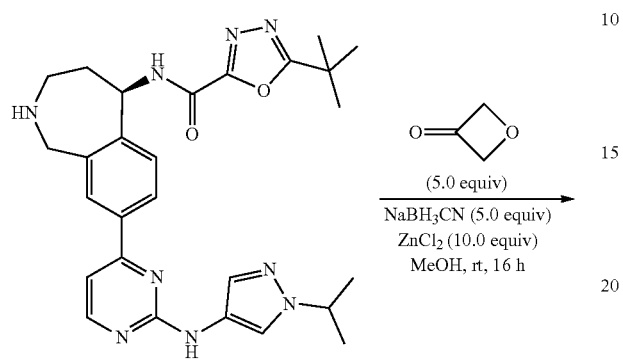

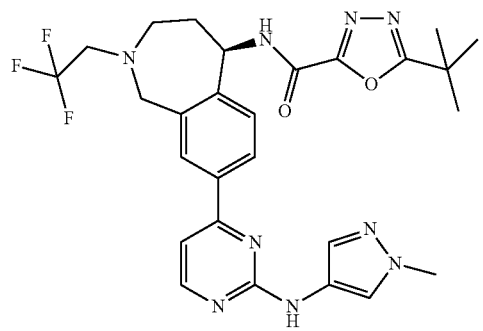 [SMILES: Cn1cc(Nc2nccc(-c3ccc4c(c3)CN(CC(F)(F)F)CC[C@H]4NC(=O)c3nnc(C(C)(C)C)o3)n2)cn1]

I. Synthesis of tert-butyl (R)-5-(5-(tert-butyl)-1,3,4-oxadiazole-2-carboxamido)-8-(2-((1-methyl-1H-pyrazol-4-yl)amino)pyrimidin-4-yl)-1,3,4,5-tetrahydro-2H-benzo[c]azepine-2-carboxylate

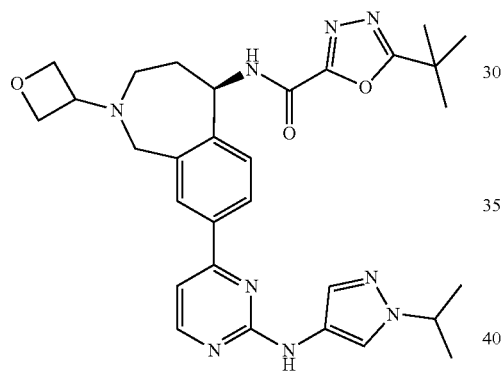

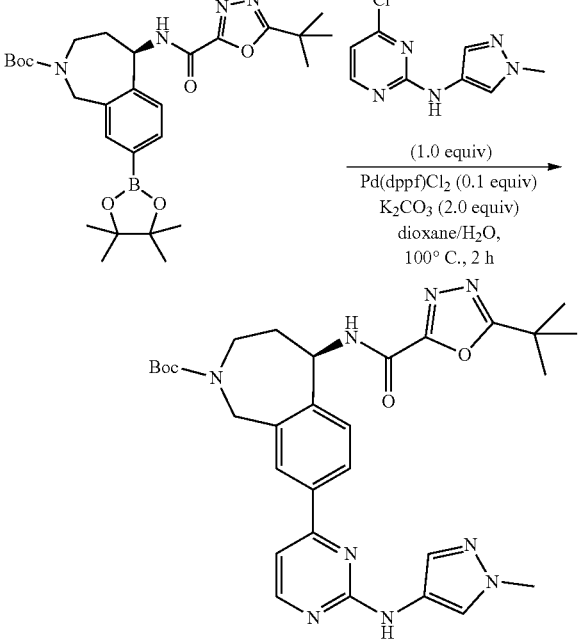

A mixture of (R)-5-(tert-butyl)-N-(8-(2-((1-isopropyl-1H-pyrazol-4-yl)amino)pyrimidin-4-yl)-2,3,4,5-tetrahydro-1H-benzo[c]azepin-5-yl)-1,3,4-oxadiazole-2-carboxamide (220 mg, 0.43 mmol), oxetan-3-one (157 mg, 2.15 mmol), NaBH$_3$CN (135 mg, 2.15 mmol) and ZnCl$_2$ (585 mg, 4.30 mmol) in 10 mL MeOH was stirred at rt for 16 h. The mixture was dilute with EtOAc (150 mL) and washed with water (50 mL×2). The organic phase was dried with Na$_2$SO$_4$ and concentrated. The crude product was purified by silica gel chromatography (DCM:MeOH=15:1) to give (R)-5-(tert-butyl)-N-(8-(2-((1-isopropyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide as a yellow solid (146 mg, yield: 60%). ESI-MS (M+H)$^+$: 572.3. $^1$H NMR (400 MHz, CDCl$_3$) δ: 8.42 (d, J=5.2 Hz, 1H), 8.05-7.97 (m, 3H), 7.67 (s, 1H), 7.48 (d, J=8.0 Hz, 1H), 7.22 (d, J=8.4 Hz, 1H), 5.59-5.57 (m, 1H), 4.87-4.66 (m, 4H), 4.53-4.50 (m, 1H), 3.98-3.81 (m, 3H), 3.09-3.03 (m, 1H), 2.92-2.86 (m, 1H), 2.29-2.20 (m, 1H), 2.07-2.03 (m, 1H), 1.54-1.51 (m, 15H)

A mixture of tert-butyl (R)-5-(5-(tert-butyl)-1,3,4-oxadiazole-2-carboxamido)-8-(4,4,5,5-tetramethyl-1,3,2-dioxaborolan-2-yl)-1,3,4,5-tetrahydro-2H-benzo[c]azepine-2-carboxylate (4.85 g, 8.98 mmol), 4-chloro-N-(1-methyl-1H-pyrazol-4-yl)pyrimidin-2-amine (1.88 g, 8.98 mmol), Pd(dppf)Cl$_2$ (734 mg, 0.9 mmol) and K$_2$CO$_3$ (2.48 g, 18 mmol) in dioxane/H$_2$O (4:1, 20 mL) was degassed and stirred at 100° C. for 2 h under a N$_2$ atmosphere. After concentration of the reaction mixture, the residue was purified by silica-gel chromatography (EtOAc:PE=2:1) to give tert-butyl (R)-5-(5-(tert-butyl)-1,3,4-oxadiazole-2-carboxamido)-8-(2-((1-methyl-1H-pyrazol-4-yl)amino)pyrimidin-4-yl)-1,3,4,5-tetrahydro-2H-benzo[c]azepine-2-carboxylate as a yellow solid (3.4 g, yield: 51%). ESI-MS (M+H)⁺: 588.3.

2. Synthesis of (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide 3. Synthesis of (R)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,3,4-oxadiazole-2-carboxamide

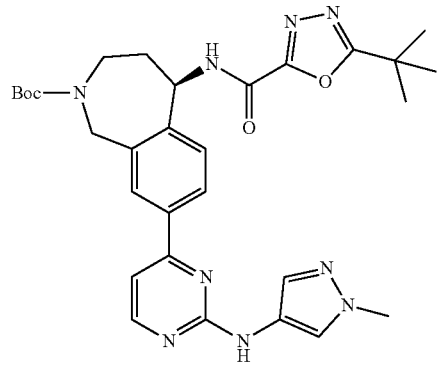

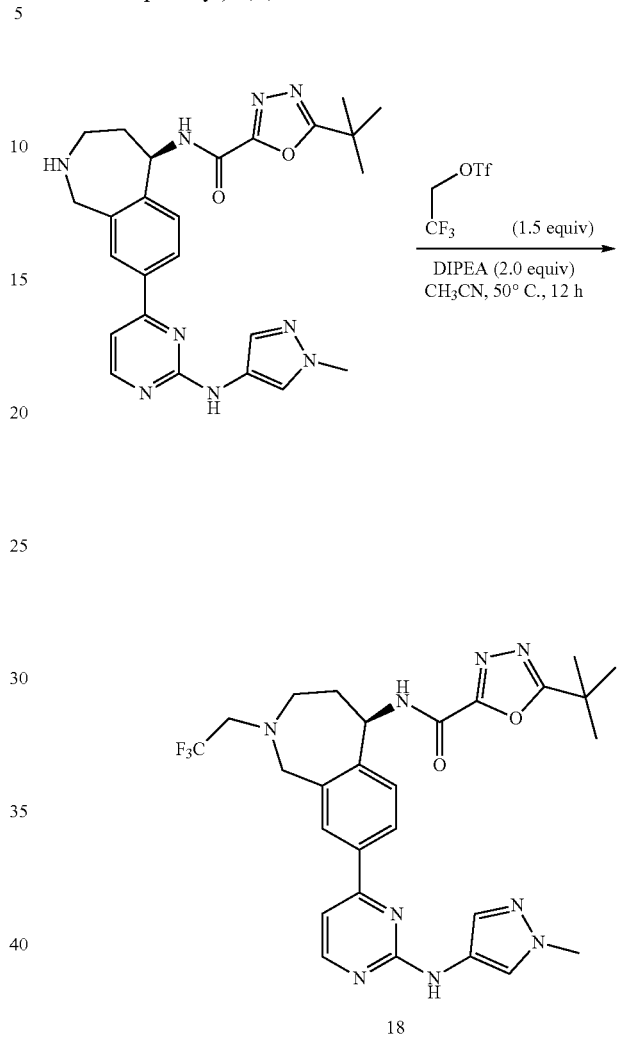

To a solution of tert-butyl (R)-5-(5-(tert-butyl)-1,3,4-oxadiazole-2-carboxamido)-8-(2-((1-methyl-1H-pyrazol-4-yl)amino)pyrimidin-4-yl)-1,3,4,5-tetrahydro-2H-benzo[c]azepine-2-carboxylate (3.4 g, 5.79 mmol) in DCM (10 mL) was added TFA (4 mL). The resulting solution was stirred at room temperature for 2 h. After concentration of the reaction mixture, the residue was dissolved in MeOH (10 mL) and adjusted to pH=8 with aqueous ammonia. Then water (20 mL) was added and the mixture was extracted with DCM/MeOH solutions (20:1, 30 mL×3). The organic phase was dried and concentrated to give crude (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide as a yellow solid (2.47 g, yield: 88%), which was used to next step without further purification. ESI-MS (M+H)⁺: 488.2.

To a solution of (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide (1.5 g, 3.1 mmol) and DIPEA (800 mg, 6.2 mmol) in CH₃CN (30 mL) was added 2,2,2-trifluoroethyl trifluoromethanesulfonate (1.1 g, 4.7 mmol). The mixture was stirred at 50° C. for 12 h. After diluting with water (100 mL), the mixture was extracted with DCM (100 mL×3). The combined organic layers were washed with brine (100 mL), dried (Na₂SO₄), filtered and concentrated. The crude product was purified by silica gel chromatography (DCM:MeOH=10:1) to give (R)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,3,4-oxadiazole-2-carboxamide as a yellow solid (1.2 g, yield: 68%). ESI-MS (M+H)⁺: 570.2. ¹H NMR (400 MHz, CD₃OD) δ: 8.31 (d, J=5.2 Hz, 1H), 7.94-7.88 (m, 3H), 7.51 (s, 1H), 7.38 (d, J=8.0 Hz, 1H), 7.12 (d, J=5.2 Hz, 1H), 5.49-5.47 (m, 1H), 4.27-4.23 (m, 1H), 4.04-4.00 (m, 1H), 3.78 (s, 3H), 3.33-3.24 (m, 2H), 3.04-2.98 (m, 2H), 2.14-2.05 (m, 1H), 1.87-1.84 (m, 1H), 1.40 (s, 9H).

Example 19. 5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide (Compound 19)

Example 20. 5-(tert-butyl)-N—((R)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1,3,4-oxadiazole-2-carboxamide (Compound 20)

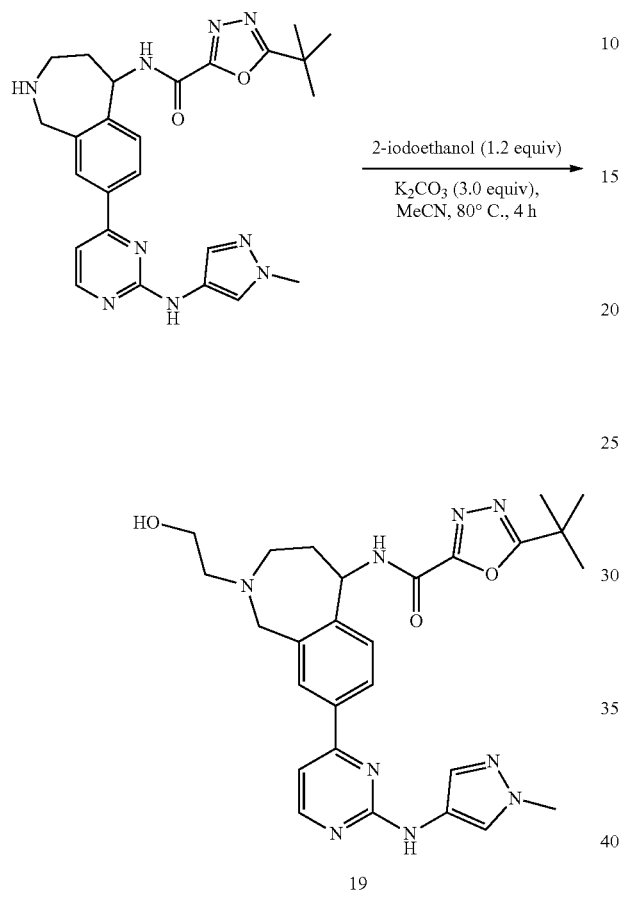

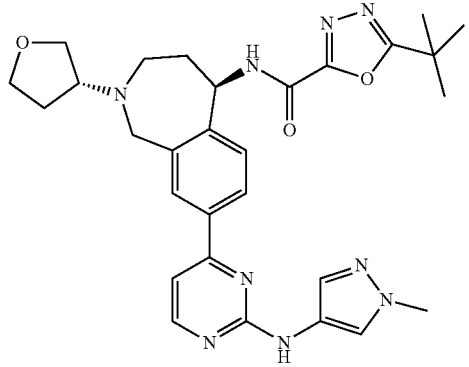 [SMILES: Cn1cc(Nc2nccc(-c3ccc4c(c3)CN([C@@H]3CCOC3)CC[C@H]4NC(=O)c3nnc(C(C)(C)C)o3)n2)cn1]

I. Synthesis of (S)-tetrahydrofuran-3-yl Trifluoromethanesulfonate

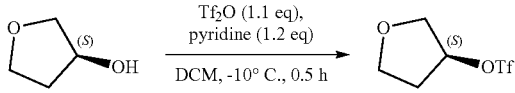

To a solution of (S)-tetrahydrofuran-3-ol (500 mg, 5.7 mmol) and pyridine (538 mg, 6.8 mmol) in DCM (15 mL) at 10° C. was added Tf$_2$O (1.8 g, 6.3 mmol). The mixture was stirred at 10° C. for 0.5 h. The mixture was quenched with 2N HCl solution. The organic layer were separated, dried over Na$_2$SO$_4$ and filtered. The resulting DCM solution of (S)-tetrahydrofuran-3-yl trifluoromethanesulfonate was used for next step. ESI-MS (M+H)$^+$: 221.0.

Synthesis of 5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide was similar to that of 5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide in Example 3. The crude product was purified by prep-HPLC (CH$_3$CN/H$_2$O with 0.05% NH$_4$HCO$_3$ as mobile phase) to give 5-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide as a yellow solid (165 mg, yield: 84%). ESI-MS (M+H)$^+$: 532.2. $^1$H NMR (400 MHz, CD$_3$OD) δ: 8.42 (d, J=5.2 Hz, 1H), 8.03-8.00 (m, 3H), 7.64 (s, 1H), 7.48 (d, J=8.0 Hz, 1H), 7.23-7.22 (m, 1H), 5.58 (d, J=9.6 Hz, 1H), 4.21-4.09 (m, 2H), 3.90 (s, 3H), 3.74 (t, J=5.6 Hz, 2H), 3.20-3.18 (m, 2H), 2.70-2.62 (m, 2H), 2.30-2.28 (m, 1H), 2.00-1.98 (m, 1H), 1.52 (s, 9H).

2. Synthesis of 5-(tert-butyl)-N—((R)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1,3,4-oxadiazole-2-carboxamide

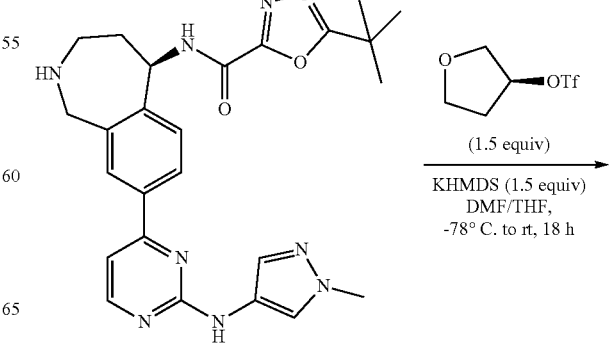

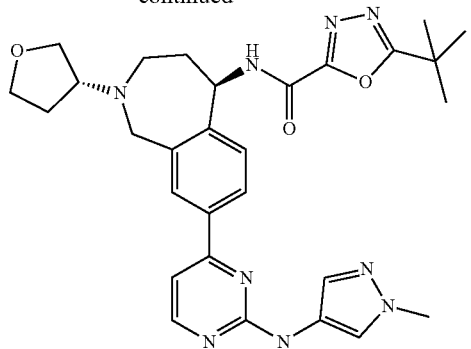
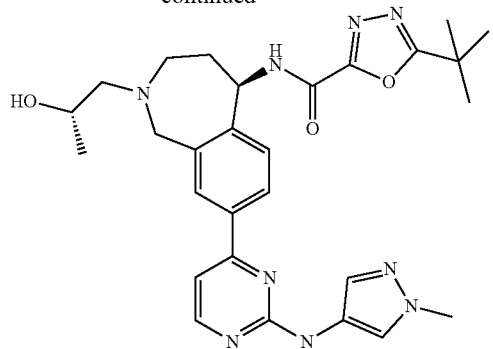

To a solution of (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide (1.7 g, 3.5 mmol) in THF (24 mL) and DMF (3 mL) was added KHMDS (5.2 mL, 5.2 mmol, 1M solution) dropwise at 78° C. The solution was stirred under nitrogen at 78° C. for 0.5 h. Then, the solution of (S)-tetrahydrofuran-3-yl trifluoromethanesulfonate (from previous step) was added dropwise. The mixture was stirred at room temperature for 16 h. After diluting with water (40 mL), the mixture was extracted with DCM (40 mL×3). The combined organic layers were washed with brine (60 mL), dried (Na$_2$SO$_4$), filtered and concentrated. The crude product was purified by silica gel chromatography (DCM:MeOH=10:1) to give 5-(tert-butyl)-N—((R)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1,3,4-oxadiazole-2-carboxamide as a yellow solid (448 mg, yield: 23%). ESI-MS (M+H)$^+$: 558.3. $^1$H NMR (400 MHz, DMSO-d$_6$) δ: 9.82-9.80 (m, 1H), 9.51 (s, 1H), 8.47 (d, J=4.8 Hz, 1H), 7.99-7.95 (m, 3H), 7.55 (s, 1H), 7.40 (d, J=8.0 Hz, 1H), 7.28 (d, J=5.2 Hz, 1H), 5.43-5.38 (m, 1H), 4.06-3.99 (m, 2H), 3.83-380 (m, 5H), 3.63-3.50 (m, 2H), 3.10-3.05 (m, 3H), 2.22-2.02 (m, 2H), 1.85-1.82 (m, 2H), 1.42 (s, 9H).

Example 21. 5-(tert-butyl)-N—((R)-2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide (Compound 21)

To a solution of (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide (101 mg, 0.21 mmol) in MeOH (7 mL) was added (S)-2-methyloxirane (29 μL, 0.42 mmol) and cesium carbonate (135 mg, 0.42 mmol). The mixture was stirred at 60° C. for 16 h. The reaction mixture was cooled to room temperature and filtered. The filtrate was concentrated and the crude product was purified by silica gel chromatography (DCM:MeOH=10:1) to give 5-(tert-butyl)-N—((R)-2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide as a yellow solid (50 mg, yield: 44%). ESI-MS (M+H)$^+$: 546.0. $^1$H NMR (400 MHz, METHANOL-d$_4$) δ: 8.41 (d, J=5.3 Hz, 1H), 8.07-8.02 (m, 2H), 7.97 (s, 1H), 7.63 (s, 1H), 7.48 (d, J=8.5 Hz, 1H), 7.22 (d, J=5.3 Hz, 1H), 5.62-5.53 (m, 1H), 4.33-4.10 (m, 2H), 4.04-3.95 (m, 1H), 3.89 (s, 3H), 3.33-3.27 (m, 2H), 2.58-2.46 (m, 2H), 2.38-2.23 (m, 1H), 2.07-1.95 (m, 1H), 1.48 (s, 9H), 1.15 (d, J=6.3 Hz, 3H).

Example 22. 5-(tert-butyl)-N—((R)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1,3,4-oxadiazole-2-carboxamide (Compound 22)

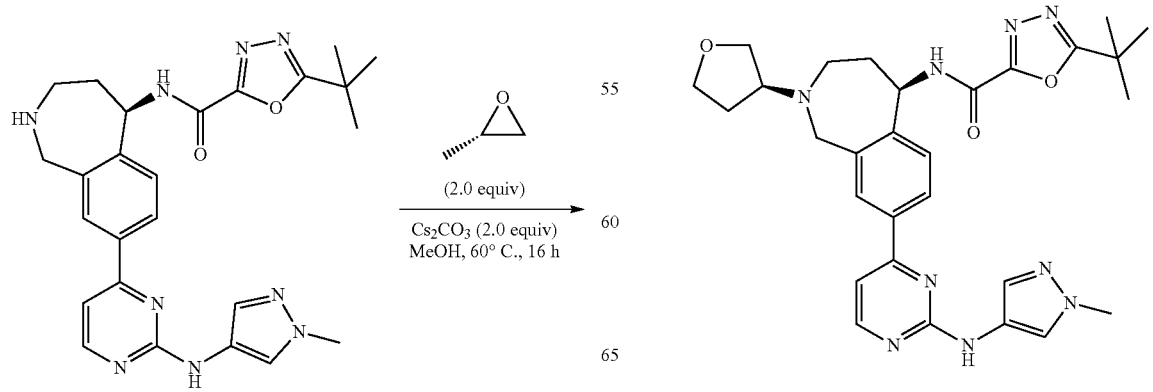

I. Synthesis of (R)-tetrahydrofuran-3-yl Trifluoromethanesulfonate

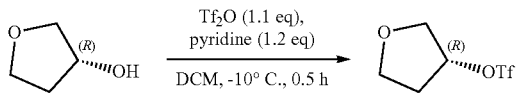

Synthesis of (R)-tetrahydrofuran-3-yl trifluoromethanesulfonate) was similar to that of (S)-tetrahydrofuran-3-yl trifluoromethanesulfonate) in Example 20, Step 1. The resulting DCM solution was used for the next step. ESI-MS (M+H)+: 221.0.

2. Synthesis of 5-(tert-butyl)-N—((R)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1,3,4-oxadiazole-2-carboxamide (I-RP58)

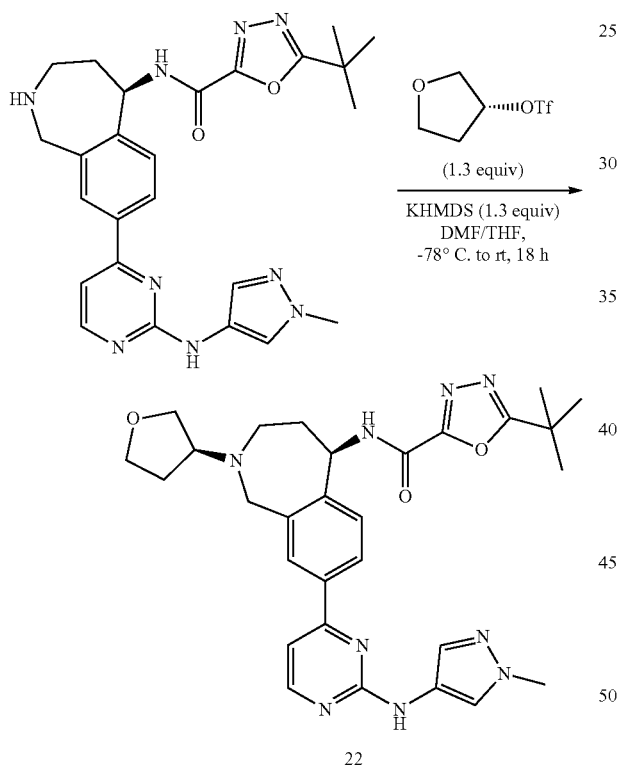

Synthesis of 5-(tert-butyl)-N—((R)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1,3,4-oxadiazole-2-carboxamide was similar to that of 5-(tert-butyl)-N—((R)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1,3,4-oxadiazole-2-carboxamide in Example 20, Step 2. The crude product was purified by silica gel chromatography (DCM:MeOH=10:1) to give 5-(tert-butyl)-N—((R)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1,3,4-oxadiazole-2-carboxamide as a yellow solid (50 mg, yield: 38%).

ESI-MS (M+H)+: 558.1. $^1$H NMR (400 MHz, METHANOL-$d_4$) δ: 8.38 (d, J=5.3 Hz, 1H), 8.03-7.95 (m, 3H), 7.60 (s, 1H), 7.45 (d, J=8.5 Hz, 1H), 7.19 (d, J=5.3 Hz, 1H), 5.56 (br d, J=9.3 Hz, 1H), 4.12-4.01 (m, 2H), 4.01-3.90 (m, 2H), 3.88 (s, 3H), 3.79-3.68 (m, 2H), 3.29-3.21 (m, 1H), 3.20-3.09 (m, 1H), 2.33-2.11 (m, 2H), 2.09-1.90 (m, 2H), 1.48 (s, 9H).

Example 23. 1-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide (Compound 23)

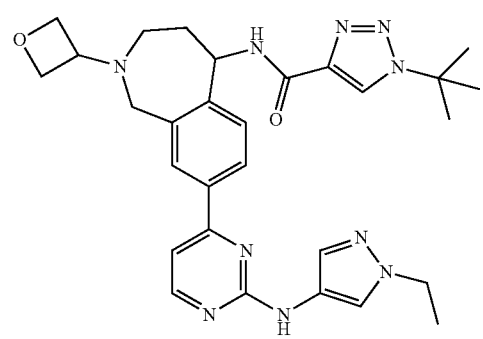 [SMILES: CCn1cc(Nc2nccc(-c3ccc4c(c3)CN(C3COC3)CCC4NC(=O)c3cn(C(C)(C)C)nn3)n2)cn1]

I. The Preparation of tert-butyl 8-bromo-5-(1-(tert-butyl)-1H-1,2,3-triazole-4-carboxamido)-1,3,4,5-tetrahydro-2H-benzo[c]azepine-2-carboxylate

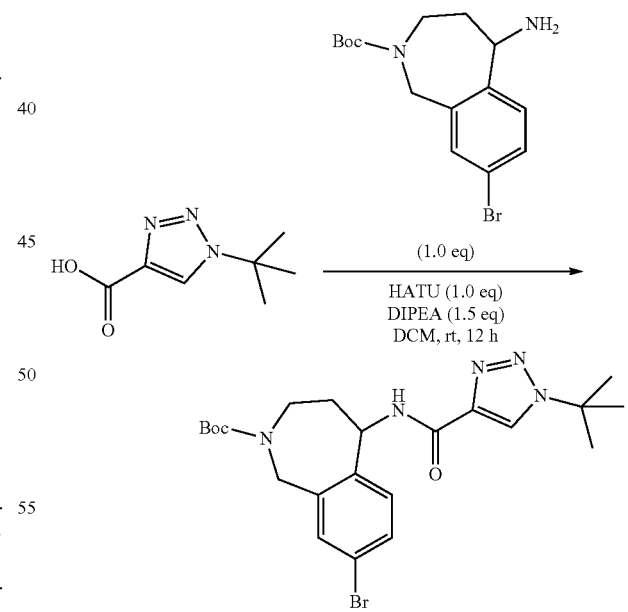

To a solution of tert-butyl 8-bromo-5-(1-(tert-butyl)-1H-1,2,3-triazole-4-carboxamido)-1,3,4,5-tetrahydro-2H-benzo[c]azepine-2-carboxylate (556 mg, 3.06 mmol) in $CH_2Cl_2$ (10 mL) were added HATU (1.16 g, 3.06 mmol) and DIPEA (592 mg, 4.6 mmol). The mixture was stirred at rt for 1 h before 1-(tert-butyl)-1H-1,2,3-triazole-4-carboxylic acid (1.04 g, 3.06 mmol) was added. The mixture was stirred at rt for 12 h. The mixture was diluted with CH₂Cl₂ (200 mL), washed with water (100 mL), brine (100 mL), dried and concentrated. The crude product was purified by silica gel column (PE:EtOAc=1:1) to give tert-butyl 8-bromo-5-(1-(tert-butyl)-1H-1,2,3-triazole-4-carboxamido)-1,3,4,5-tetrahydro-2H-benzo[c]azepine-2-carboxylate (1.1 g, yield: 73%) as a yellow solid. ESI-MS (M+H)⁺: 492.1. ¹H NMR (400 MHz, CDCl₃) δ: 8.17 (s, 1H), 7.35-7.33 (m, 2H), 7.21 (d, J=8.0 Hz, 1H), 5.52-5.42 (m, 1H), 4.54-4.34 (m, 2H), 4.04-3.86 (m, 1H), 3.65-3.55 (m, 1H), 2.80 (s, 9H), 2.10-2.07 (m, 2H), 1.41 (s, 9H).

2. The Preparation of tert-butyl 5-(1-(tert-butyl)-1H-1,2,3-triazole-4-carboxamido)-8-(2-((1-ethyl-1H-pyrazol-4-yl)amino)pyrimidin-4-yl)-1,3,4,5-tetrahydro-2H-benzo[c]azepine-2-carboxylate

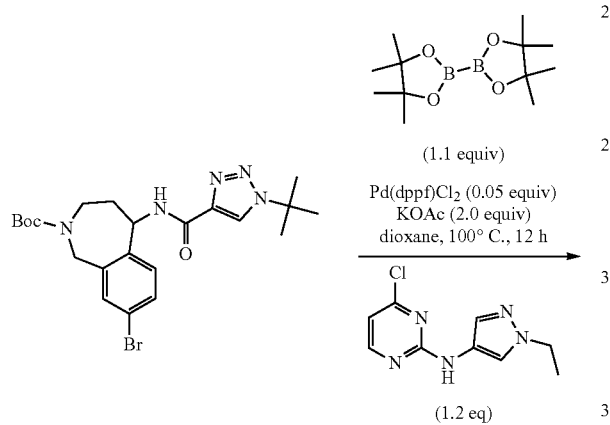

Synthesis of tert-butyl 5-(1-(tert-butyl)-1H-1,2,3-triazole-4-carboxamido)-8-(2-((1-ethyl-1H-pyrazol-4-yl)amino)pyrimidin-4-yl)-1,3,4,5-tetrahydro-2H-benzo[c]azepine-2-carboxylate was similar to that of tert-butyl 5-(5-(tert-butyl)-1,2,4-oxadiazole-3-carboxamido)-8-(2-((1-ethyl-1H-pyrazol-4-yl)amino)pyrimidin-4-yl)-1,3,4,5-tetrahydro-2H-benzo[c]azepine-2-carboxylate in Example 7. The crude product was purified by silica gel column chromatography (CH₂Cl₂:MeOH=20:1) to give tert-butyl 5-(1-(tert-butyl)-1H-1,2,3-triazole-4-carboxamido)-8-(2-((1-ethyl-1H-pyrazol-4-yl)amino)pyrimidin-4-yl)-1,3,4,5-tetrahydro-2H-benzo[c]azepine-2-carboxylate as a yellow solid (170 mg, Y: 35%). ESI-MS (M+H)⁺: 601.2.

3. The Preparation of 1-(tert-butyl)-N-(8-(2-((1-ethyl-1H-pyrazol-4-yl)amino)pyrimidin-4-yl)-2,3,4,5-tetrahydro-1H-benzo[c]azepin-5-yl)-1H-1,2,3-triazole-4-carboxamide

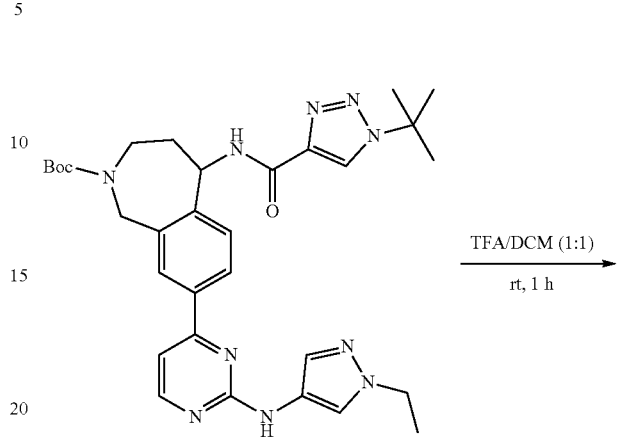

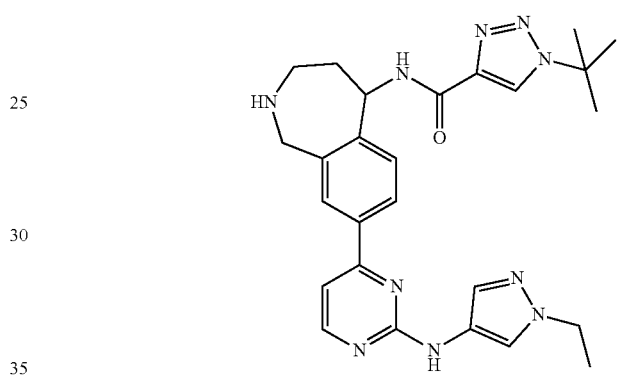

Synthesis of 1-(tert-butyl)-N-(8-(2-((1-ethyl-1H-pyrazol-4-yl)amino)pyrimidin-4-yl)-2,3,4,5-tetrahydro-1H-benzo[c]azepin-5-yl)-1H-1,2,3-triazole-4-carboxamide was similar to that of 5-(tert-butyl)-N-(8-(2-((1-ethyl-1H-pyrazol-4-yl)amino)pyrimidin-4-yl)-2,3,4,5-tetrahydro-1H-benzo[c]azepin-5-yl)-1,2,4-oxadiazole-3-carboxamide in Example 7. The crude product (135 mg, yield: 95%) was used in the next step without further purification. ESI-MS (M+H)⁺: 501.2.

4. The Preparation of 1-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide

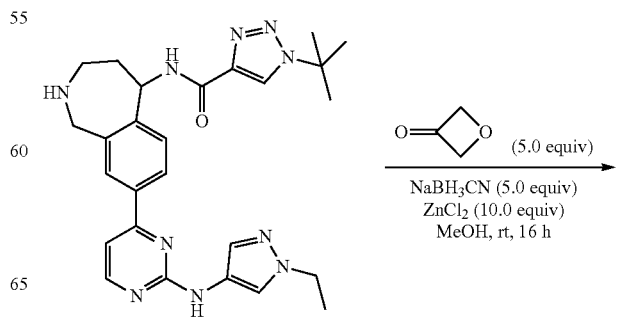

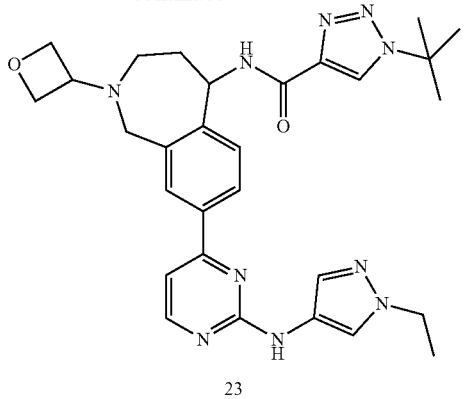

23

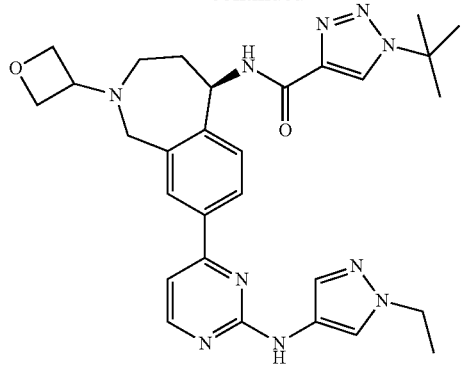

24a

Synthesis of 1-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide was similar to that of 5-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide in Example 7. The crude product was purified by silica gel column chromatography (EtOAc: MeOH=10:1) to give 1-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide as a yellow solid (67 mg, yield: 45%). ESI-MS (M+H)$^+$: 556.7. $^1$H NMR (400 MHz, DMSO-$d_6$) δ: 9.48 (s, 1H), 9.02 (d, J=8.8 Hz, 1H), 8.76 (s, 1H), 8.46 (d, J=5.2 Hz, 1H), 7.97-7.91 (m, 3H), 7.56 (s, 1H), 7.37 (d, J=8.0 Hz, 1H), 7.25 (d, J=5.2 Hz, 1H), 5.47-5.43 (m, 1H), 4.61-1.47 (m, 4H), 4.13-4.08 (m, 2H), 3.88-3.65 (m, 3H), 2.90-2.78 (m, 2H), 2.15-2.06 (m, 1H), 1.88-1.82 (m, 1H), 1.65 (s, 9H), 1.36 (t, J=7.2 Hz, 3H).

Example 24. (R)-1-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide (compound 24a) and (S)-1-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide (compound 24b)

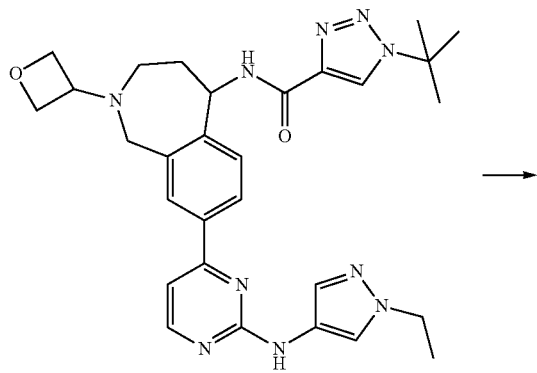

24b 1-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide (50 mg) was subjected to SFC separation (2.1×25.0 cm (S,S) Whelk0-1, 58% methanol with 0.5% isopropylamine/CO$_2$, 120 bar, 85 mL/min, 230 nm, methanol) and yielded 23 mg of peak-1 (chemical purity 99%, ee>99%) and 24 mg of peak-2 (chemical purity 99%, ee=99%).

Peak 1 is assigned as (R)-1-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide: LCMS: Rt 4.0 min, m/z 557.20. $^1$H NMR (400 MHz, METHANOL-$d_4$) δ ppm 8.51 (s, 1H), 8.40 (d, J=5.27 Hz, 1H), 8.05-7.92 (m, 3H), 7.64 (s, 1H), 7.47 (d, J=8.28 Hz, 1H), 7.21 (d, J=5.27 Hz, 1H), 5.57 (br d, J=9.04 Hz, 1H), 4.78-4.71 (m, 1H), 4.71-4.65 (m, 3H), 4.17 (q, J=7.28 Hz, 2H), 4.01-3.91 (m, 1H), 3.91-3.78 (m, 2H), 3.15-2.98 (m, 1H), 2.88 (ddd, J=12.99 Hz, 9.60 Hz, 3.51 Hz, 1H), 2.36-2.14 (m, 1H), 2.11-1.87 (m, 1H), 1.73 (s, 9H), 1.46 (t, J=7.28 Hz, 3H).

Peak 2 is assigned as (S)-1-(tert-butyl)-N-(8-(2-((1-ethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide: LCMS: Rt 5.3 min, m/z 557.00. $^1$H NMR (400 MHz, METHANOL-$d_4$) δ ppm 8.51 (s, 1H), 8.40 (d, J=5.27 Hz, 1H), 8.06-7.92 (m, 3H), 7.64 (s, 1H), 7.47 (d, J=8.03 Hz, 1H), 7.21 (d, J=5.27 Hz, 1H), 5.57 (br d, J=9.29 Hz, 1H), 4.77-4.70 (m, 1H), 4.70-4.63 (m, 2H), 4.17 (q, J=7.28 Hz, 2H), 4.05-3.91 (m, 1H), 3.91-3.76 (m, 2H), 3.15-2.98 (m, 1H), 2.89 (ddd, J=12.8 Hz, 9.7 Hz, 3.6 Hz, 1H), 2.40-2.13 (m, 1H), 2.12-1.87 (m, 1H), 1.74 (s, 9H), 1.47 (t, J=7.28 Hz, 3H).

Example 25. (R)-1-(tert-butyl)-N-(8-(2-((1-isopropyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide (compound 25)

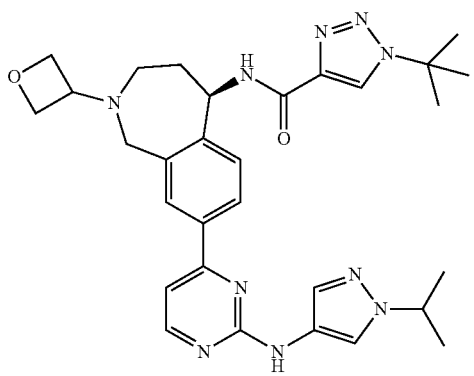

I. Synthesis of tert-butyl (R)-5-(1-(tert-butyl)-1H-1,2,3-triazole-4-carboxamido)-8-(2-((1-isopropyl-1H-pyrazol-4-yl)amino)pyrimidin-4-yl)-1,3,4,5-tetrahydro-2H-benzo[c]azepine-2-carboxylate

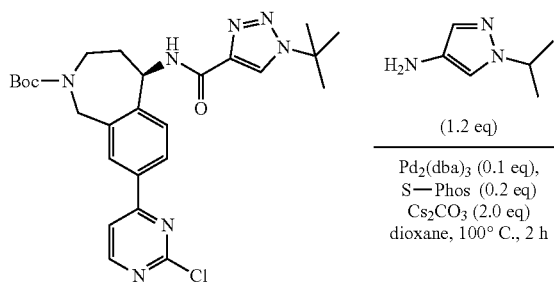

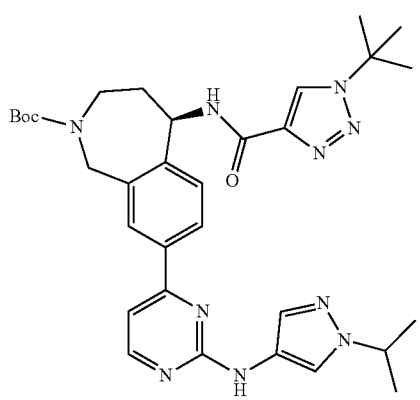

Synthesis of tert-butyl (R)-5-(1-(tert-butyl)-1H-1,2,3-triazole-4-carboxamido)-8-(2-((1-isopropyl-1H-pyrazol-4-yl)amino)pyrimidin-4-yl)-1,3,4,5-tetrahydro-2H-benzo[c]azepine-2-carboxylate was similar to that of tert-butyl (R)-5-(5-(tert-butyl)-1,2,4-oxadiazole-3-carboxamido)-8-(2-((1,5-dimethyl-1H-pyrazol-4-yl)amino)pyrimidin-4-yl)-1,3,4,5-tetrahydro-2H-benzo[c]azepine-2-carboxylate (Example 9, Step 3). The crude material was purified by silica gel chromatography (EtOAc:PE=4:1) to give tert-butyl (R)-5-(1-(tert-butyl)-1H-1,2,3-triazole-4-carboxamido)-8-(2-((1-isopropyl-1H-pyrazol-4-yl)amino)pyrimidin-4-yl)-1,3,4,5-tetrahydro-2H-benzo[c]azepine-2-carboxylate as a yellow solid (520 mg, yield: 56%). ESI-MS (M+H)+: 615.3.

2. Synthesis of (R)-1-(tert-butyl)-N-(8-(2-((1-isopropyl-1H-pyrazol-4-yl)amino)pyrimidin-4-yl)-2,3,4,5-tetrahydro-1H-benzo[c]azepin-5-yl)-1H-1,2,3-triazole-4-carboxamide

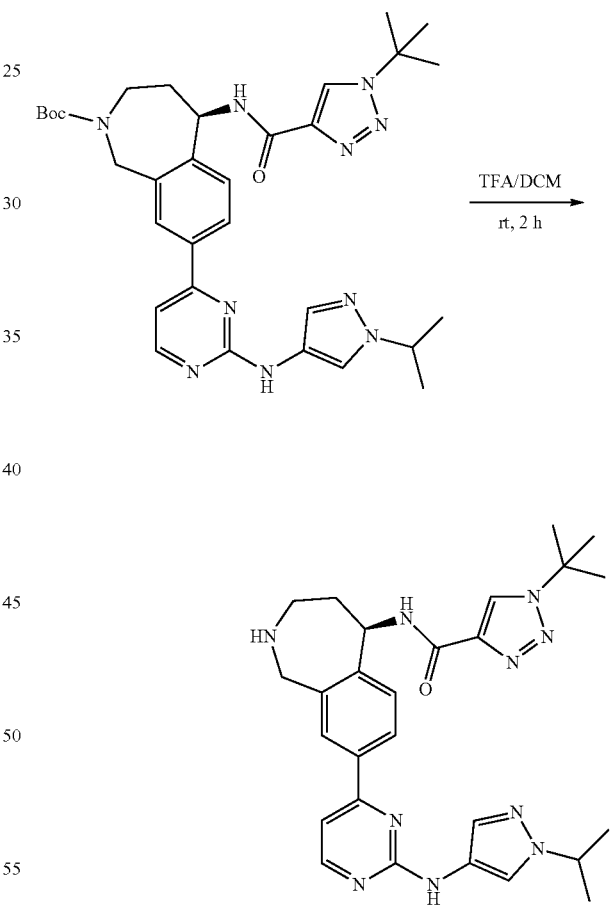

Synthesis of (R)-1-(tert-butyl)-N-(8-(2-((1-isopropyl-1H-pyrazol-4-yl)amino)pyrimidin-4-yl)-2,3,4,5-tetrahydro-1H-benzo[c]azepin-5-yl)-1H-1,2,3-triazole-4-carboxamide was similar to that of (R)-5-(tert-butyl)-N-(8-(2-((1,5-dimethyl-1H-pyrazol-4-yl)amino)pyrimidin-4-yl)-2,3,4,5-tetrahydro-1H-benzo[c]azepin-5-yl)-1,2,4-oxadiazole-3-carboxamide in Example 9, Step 4. The crude product was isolated as a yellow solid and was used for the next step without further purification (420 mg, yield: 96%). ESI-MS (M+H)+: 515.3.

3. Synthesis of (R)-1-(tert-butyl)-N-(8-(2-((1-isopropyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide (I-RP35)

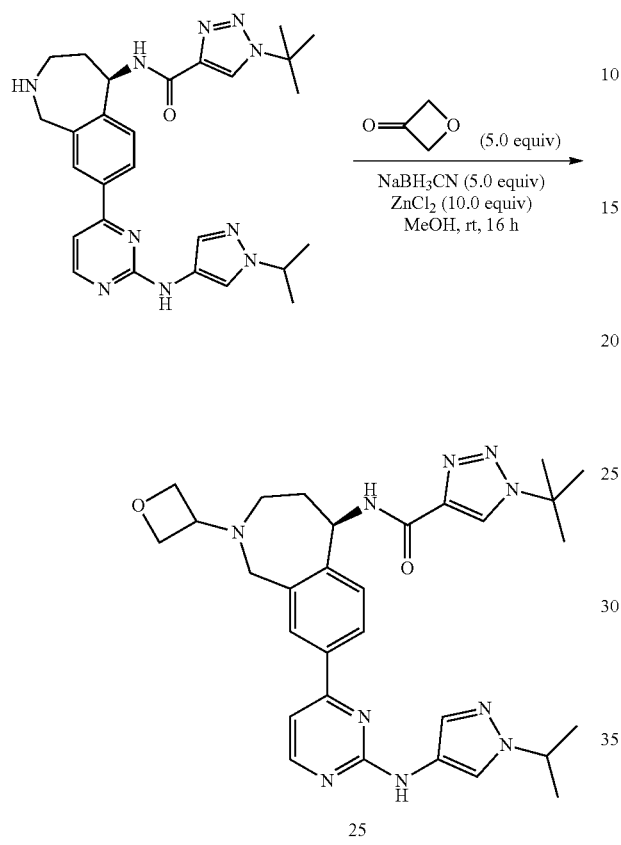

Synthesis of (R)-1-(tert-butyl)-N-(8-(2-((1-isopropyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide was similar to that of (R)-5-(tert-butyl)-N-(8-(2-((1-isopropyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide in Example 17. The crude material was purified by silica gel chromatography (DCM:MeOH=20:1) to give (R)-1-(tert-butyl)-N-(8-(2-((1-isopropyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide as a yellow solid (116 mg, yield: 51%). ESI-MS (M+H)$^+$: 571.2. $^1$H NMR (400 MHz, CDCl$_3$) δ: 8.42 (d, J=4.8 Hz, 1H), 8.17 (s, 1H), 8.07 (d, J=8.8 Hz, 1H), 7.94 (s, 1H), 7.85 (d, J=8.0 Hz, 1H), 7.77 (s, 1H), 7.57 (s, 1H), 7.48 (d, J=8.0 Hz, 1H), 7.11 (s, 1H), 7.03 (d, J=5.2 Hz, 1H), 5.64 (t, J=8.0 Hz, 1H), 4.78-4.68 (m, 4H), 4.53-4.45 (m, 1H), 3.91-3.80 (m, 3H), 3.04-2.99 (m, 1H), 2.82-2.79 (m, 1H), 2.27-2.23 (m, 1H), 2.10-2.05 (m, 1H), 1.70 (s, 9H), 1.55 (s, 3H), 1.52 (s, 3H).

Example 26. 1-(tert-butyl)-N—((R)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1H-1,2,3-triazole-4-carboxamide (compound 26a) & 1-(tert-butyl)-N—((R)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1H-1,2,3-triazole-4-carboxamide (Compound 26b)

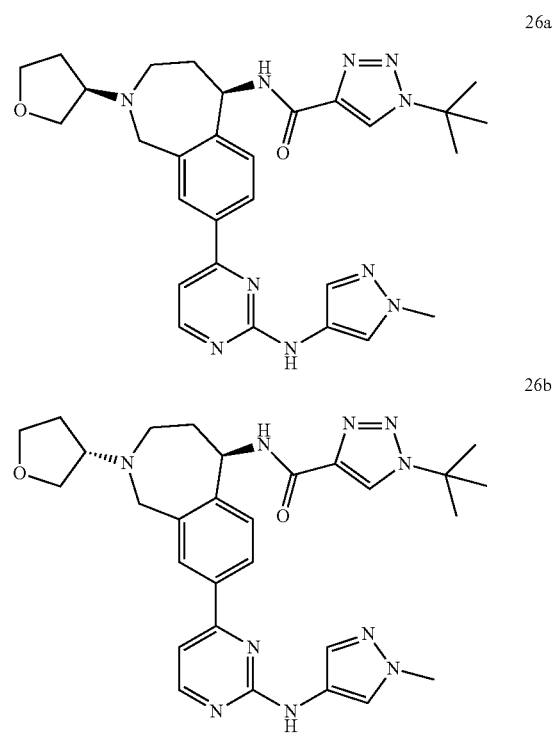

I. Synthesis of tert-butyl (R)-8-bromo-5-(1-(tert-butyl)-1H-1,2,3-triazole-4-carboxamido)-1,3,4,5-tetrahydro-2H-benzo[c]azepine-2-carboxylate

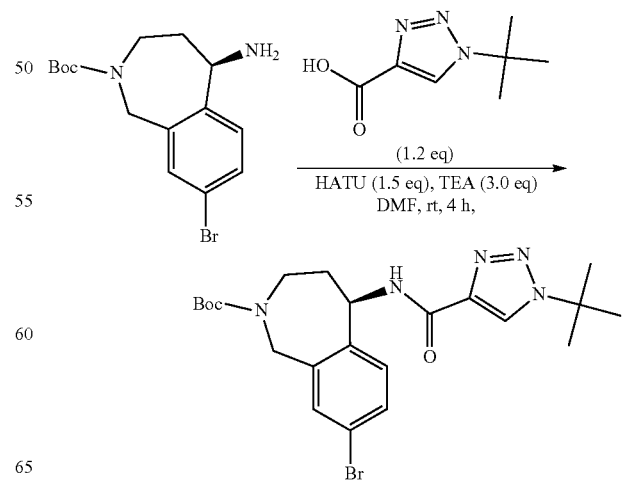

Synthesis of tert-butyl (R)-8-bromo-5-(1-(tert-butyl)-1H-1,2,3-triazole-4-carboxamido)-1,3,4,5-tetrahydro-2H-benzo[c]azepine-2-carboxylate was similar to that of tert-butyl 8-bromo-5-(5-(tert-butyl)-1,3,4-oxadiazole-2-carboxamido)-4,5-dihydro-1H-benzo[c]azepine-2(3H)-carboxylate in Example 12, Step 1. The crude product was purified by silica gel column chromatography (EtOAc/petroleum ether=1:2) to give tert-butyl (R)-8-bromo-5-(1-(tert-butyl)-1H-1,2,3-triazole-4-carboxamido)-1,3,4,5-tetrahydro-2H-benzo[c]azepine-2-carboxylate as yellow solid (2.3 g, yield: 95%). ESI-MS (M+H)$^+$: 492.2.

2. Synthesis of tert-butyl (R)-5-(1-(tert-butyl)-1H-1,2,3-triazole-4-carboxamido)-8-(4,4,5,5-tetramethyl-1,3,2-dioxaborolan-2-yl)-1,3,4,5-tetrahydro-2H-benzo[c]azepine-2-carboxylate Synthesis of tert-butyl (R)-5-(1-(tert-butyl)-1H-1,2,3-triazole-4-carboxamido)-8-(4,4,5,5-tetramethyl-1,3,2-dioxaborolan-2-yl)-1,3,4,5-tetrahydro-2H-benzo[c]azepine-2-carboxylate was similar to the synthesis of tert-butyl (R)-5-(5-(tert-butyl)-1,2,4-oxadiazole-3-carboxamido)-8-(4,4,5,5-tetramethyl-1,3,2-dioxaborolan-2-yl)-1,3,4,5-tetrahydro-2H-benzo[c]azepine-2-carboxylate described in Example 9, Step 1. The crude product was used for next step without purification. ESI-MS (M+H)$^+$: 540.3.

3. Synthesis of tert-butyl (R)-5-(1-(tert-butyl)-1H-1,2,3-triazole-4-carboxamido)-8-(2-((1-methyl-1H-pyrazol-4-yl)amino)pyrimidin-4-yl)-1,3,4,5-tetrahydro-2H-benzo[c]azepine-2-carboxylate

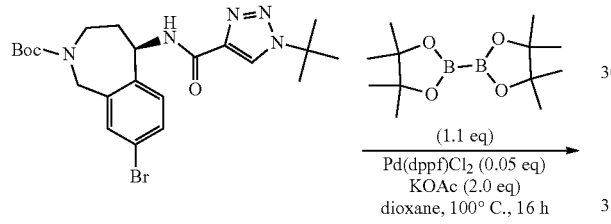

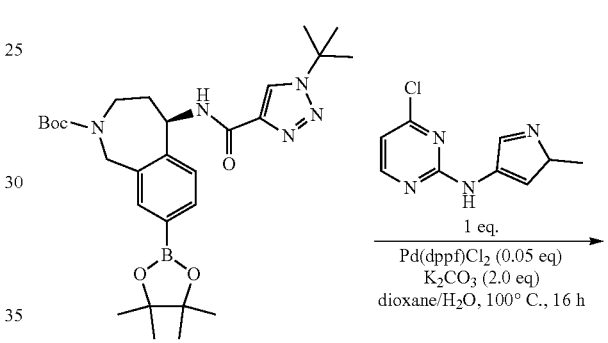

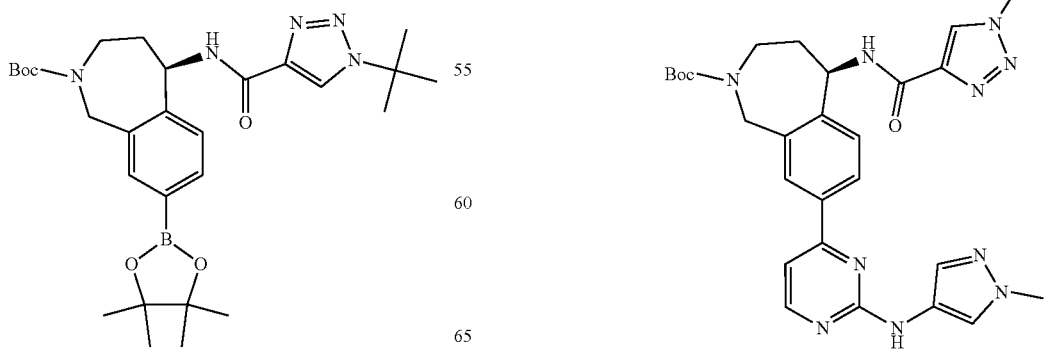

To a solution of tert-butyl (R)-5-(1-(tert-butyl)-1H-1,2,3-triazole-4-carboxamido)-8-(4,4,5,5-tetramethyl-1,3,2-dioxaborolan-2-yl)-1,3,4,5-tetrahydro-2H-benzo[c]azepine-2-carboxylate (5.4 g, 10.0 mmol) in dioxane/H$_2$O (100 mL) was added 4-chloro-N-(1-methyl-1H-pyrazol-4-yl)pyrimidin-2-amine (2.1 g, 10.0 mmol), K$_2$CO$_3$ (2.8 g, 20.0 mmol) and Pd(dppf)Cl$_2$ (0.4 g, 0.5 mmol) were added. The mixture was stirred at 100° C. for 16 h under nitrogen. After cooling to rt, the mixture was concentrated and purified by silica gel column chromatography (petroleum ether/EtOAc=1:3) to give tert-butyl (R)-5-(1-(tert-butyl)-1H-1,2,3-triazole-4-carboxamido)-8-(2-((1-methyl-1H-pyrazol-4-yl)amino)pyrimidin-4-yl)-1,3,4,5-tetrahydro-2H-benzo[c]azepine-2-carboxylate as a yellow solid (3.2 g, yield: 55%). ESI-MS (M+H)$^+$: 586.7. $^1$H NMR (400 MHz, CDCl$_3$) δ: 8.42 (s, 1H), 8.19 (s, 1H), 8.02-7.87 (m, 3H), 7.68 (s, 1H), 7.54-7.49 (m, 2H), 7.06 (d, J=5.2 Hz, 1H), 5.63-5.58 (m, 1H), 4.83-4.67 (m, 1H), 4.51-4.47 (m, 1H), 4.02-4.00 (m, 1H), 3.93 (s, 3H), 3.65-3.62 (m, 1H), 2.14-2.12 (m, 2H), 1.72 (s, 9H), 1.41-1.38 (m, 9H).

4. Synthesis of (R)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide

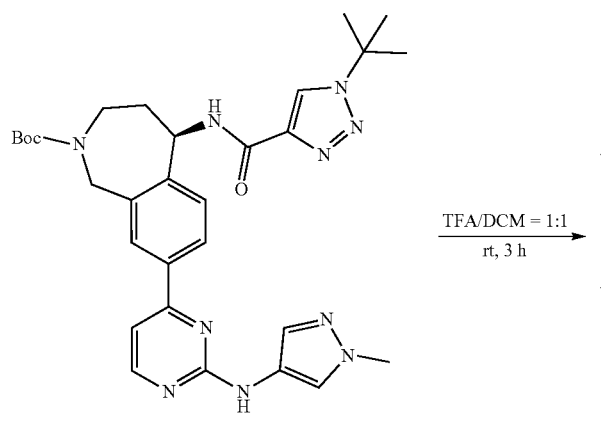

TFA/DCM = 1:1
rt, 3 h

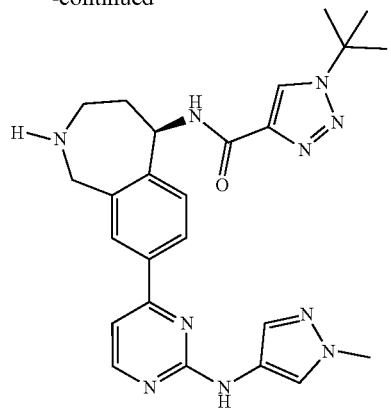

To a solution of tert-butyl (R)-5-(1-(tert-butyl)-1H-1,2,3-triazole-4-carboxamido)-8-(2-((1-methyl-1H-pyrazol-4-yl)amino)pyrimidin-4-yl)-1,3,4,5-tetrahydro-2H-benzo[c]azepine-2-carboxylate (3.2 g, 5.5 mmol) in DCM (30 mL) was added TFA (30 mL). The mixture was stirred at rt for 3 h. The solvent was removed. The crude was dissolved in MeOH (30 mL)/water (20 mL). The mixture was basified with NH$_4$OH to pH=8-9 and extracted with DCM (3×50 mL). The combined organic layers were washed with brine, dried over Na$_2$SO$_4$, filtered and concentrated to give (R)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide as a gray solid (2.6 g, yield: 98%). ESI-MS (M+H)$^+$: 486.7.

5. Synthesis of 1-(tert-butyl)-N—((R)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1H-1,2,3-triazole-4-carboxamide & 1-(tert-butyl)-N—((R)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1H-1,2,3-triazole-4-carboxamide

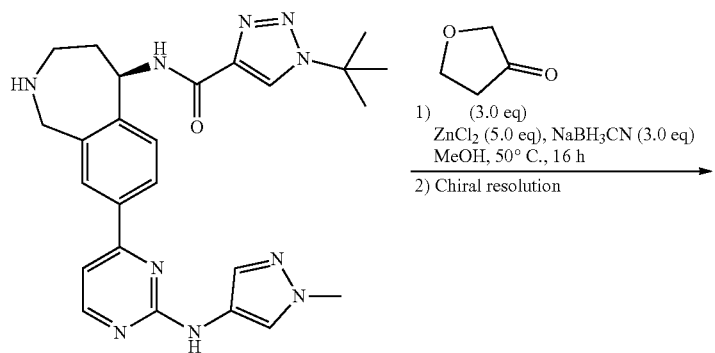

1) (3.0 eq)
ZnCl$_2$ (5.0 eq), NaBH$_3$CN (3.0 eq)
MeOH, 50° C., 16 h
2) Chiral resolution To a solution of (R)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (500 mg, 1.0 mmol) in MeOH (30 mL) were added dihydrofuran-3(2H)-one (258 mg, 3.0 mmol), ZnCl$_2$ (682 mg, 5.0 mmol) and NaBH$_3$CN (189 mg, 3.0 mmol). The mixture was stirred at 50° C. for 16 h. The mixture was concentrated and purified by silica gel column chromatography (DCM/MeOH=20/1 to 15/1) to give the racemic product as a yellow solid (542 mg, yield: 79%).

1-(tert-butyl)-N—((R)-8-(2-((1-methyl-1H-pyrazol-4-yl)amino)pyrimidin-4-yl)-2-((S)-tetrahydrofuran-3-yl)-2,3,4,5-tetrahydro-1H-benzo[c]azepin-5-yl)-1H-1,2,3-triazole-4-carboxamide (154 mg) and 1-(tert-butyl)-N—((R)-8-(2-((1-methyl-1H-pyrazol-4-yl)amino)pyrimidin-4-yl)-2-((R)-tetrahydrofuran-3-yl)-2,3,4,5-tetrahydro-1H-benzo[c]azepin-5-yl)-1H-1,2,3-triazole-4-carboxamide (167 mg) were separated by chiral resolution. ESI-MS (M+H)$^+$: 557.3.

Isomer 1: $^1$H NMR (400 MHz, CD$_3$OD) δ: 8.53 (s, 1H), 8.42 (d, J=5.2 Hz, 1H), 8.05-7.99 (m, 3H), 7.64 (s, 1H), 7.48 (d, J=8.4 Hz, 1H), 7.23 (d, J=5.2 Hz, 1H), 5.58 (d, J=10.4 Hz, 1H), 4.16-4.09 (m, 2H), 4.02-3.96 (m, 2H), 3.90 (s, 3H), 3.79-3.71 (m, 2H), 3.31-3.24 (m, 2H), 3.15-3.10 (m, 1H), 2.31-2.17 (m, 2H), 2.07-1.97 (m, 2H), 1.74 (s, 9H).

Isomer 2: $^1$H NMR (400 MHz, CD$_3$OD) δ: 8.43 (s, 1H), 8.30 (d, J=5.2 Hz, 1H), 7.95-7.86 (m, 3H), 7.67 (s, 1H), 7.37 (d, J=8.0 Hz, 1H), 7.13 (d, J=5.2 Hz, 1H), 5.47 (d, J=9.6 Hz, 1H), 4.00 (br, 2H), 3.93-3.85 (m, 2H), 3.85 (s, 3H), 3.69-3.58 (m, 2H), 3.28-3.22 (m, 1H), 3.17-2.97 (m, 2H), 2.21-2.01 (m, 2H), 1.99-1.80 (m, 2H), 1.63 (s, 9H).

Example 27a. (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide (Compound 27)

To a solution of (R)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (500 mg, 1.0 mmol) in MeOH (30 mL) were added oxetan-3-one (216 mg, 3.0 mmol), ZnCl$_2$ (682 mg, 5.0 mmol) and NaBH$_3$CN (189 mg, 3.0 mmol). The mixture was stirred at 50° C. for 3 h. The mixture was concentrated and the crude material was purified by silica gel chromatography (CH$_2$Cl$_2$:MeOH grading from 20:1 to 15:1) to give (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide as a yellow solid (307 mg, yield: 55%). ESI-MS (M+H)$^+$: 542.7. $^1$H NMR (400 MHz, CD$_3$OD) δ: 8.54 (s, 1H), 8.42 (d, J=5.6 Hz, 1H), 8.04-7.98 (m, 3H), 7.71 (s, 1H), 7.49 (d, J=8.0 Hz, 1H), 7.24 (d, J=5.2 Hz, 1H), 5.59 (d, J=9.2 Hz, 1H), 4.79-4.75 (m, 1H), 4.71-4.69 (m, 3H), 4.00-3.83 (m, 6H), 3.09-3.05 (m, 1H), 3.94-2.88 (m, 1H), 2.29-2.21 (m, 1H), 2.07-2.04 (m, 1H), 1.75 (s, 9H).

Example 27b. (R)-1-(tert-butyl)-N-(8-(2-((1-(methyl-d3)-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide 1. Synthesis of 1-(methyl-d3)-1H-pyrazol-4-amine -continued

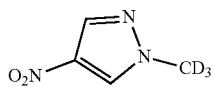

A mixture of 4-nitro-1-pyrazole (5.0 g, 44 mmol) and d6-dimethyl sulfate (10.0 g, 75.7 mmol) in 1 M solution of NaOH in water (50.0 mL) was heated at 35° C. overnight. The solid formed was filtered, washed with water, and dried (Na$_2$SO$_4$) to give 1-d3-methyl-4-nitro-1-pyrazole as a white crystal (3.9 g, yield: 68%). LCMS: RT 0.36 min.; MH+ 131.1; 1H NMR (400 MHz, DMSO-d6) δ: 8.84 (s, 1H), 8.23 (s, 1H).

2. Synthesis of 1-(methyl-d3)-4-nitro-1H-pyrazole

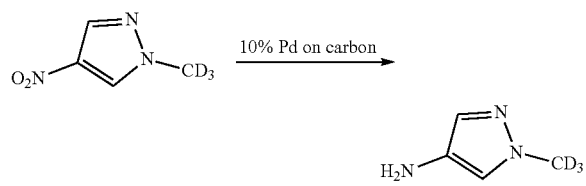

A solution of 1-d3-methyl-4-nitro-1-pyrazole (3.9 g, 30 mmol) in EtOH (50.0 mL) was degassed with nitrogen, followed by the addition of 10% palladium on carbon (0.32 g, 0.30 mmol). The mixture was placed under an atmosphere of hydrogen and stirred at rt for 2 h. The mixture was filtered and the filtrate was concentrated in vacuo to give 1-(d3-methyl-1H-pyrazol-4-amine as an oil (2.9 g, yield: 96%) which was used in the next step without further purification.

3. Synthesis of 4-methoxy-N-(1-(methyl-d3)-1H-pyrazol-4-yl)pyrimidin-2-amine

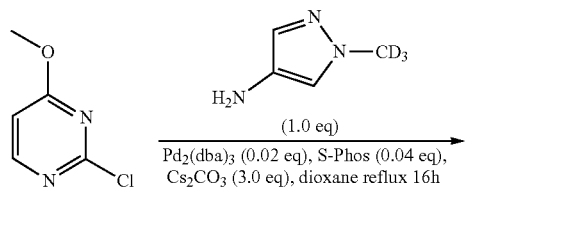

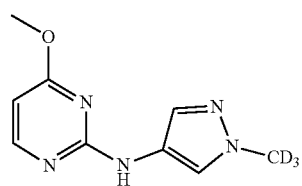

To a solution of 2-chloro-4-methoxypyrimidine (9.4 g, 65.1 mmol) in 1,4-dioxane (0.3 L) was added 1-methyl-d3-1H-pyrazol-4-amine (8.5 g, 85 mmol), Cs$_2$CO$_3$ (63.6 g, 195 mmol), S-Phos (13.3 g, 0.03 mol) and Pd$_2$(dba)$_3$ (16.7 g, 0.02 mol). The reaction mixture was stirred at reflux under N$_2$ for 16 h. The reaction mixture was cooled to room temperature and the mixture was filtered through a silica gel pad, and washed with EtOAc (500 mL). The combined filtrates were concentrated in vacuo. The crude material was purified by silica gel chromatography (heptane:EtOAc=100:0 to 0:100) to give 4-methoxy-N-(1-(methyl-d3)-1H-pyrazol-4-yl)pyrimidin-2-amine (9.2 g, yield: 68%) as a light yellow solid. ESI-MS (M+H)$^+$: 209.1. $^1$H NMR (400 MHz, CDCl$_3$) δ: 8.10 (d, J=5.7 Hz, 1H), 7.77 (s, 1H), 7.51 (s, 1H), 6.13 (d, J=5.7 Hz, 1H), 3.94 (s, 3H).

4. Synthesis of 4-chloro-N-(1-(methyl-d3)-1H-pyrazol-4-yl)pyrimidin-2-amine

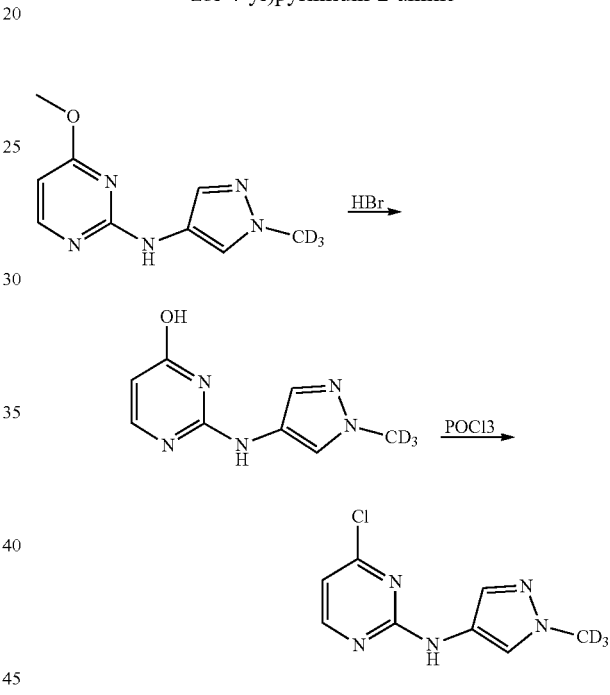

To 4-methoxy-N-(1-(methyl-d3)-1H-pyrazol-4-yl)pyrimidin-2-amine (9.1 g, 43.7 mmol) was added HBr (90 mL, 38% aqueous). The reaction mixture was heated to 100° C. and stirred at that temperature for 3 h. The reaction mixture was cooled to room temperature and concentrated in vacuo, azetroped with toluene (3×100 mL) and dried at 50° C. overnight to afford the HBr salt (16 g) as a yellow/brown solid. The salt was then dissolved in POCl$_3$ (250 mL) and heated to 100° C. for 36 hrs. The reaction mixture was cooled to room temperature and concentrated in vacuo and azetroped with Toluene (3×100 mL). the resulting residue was diluted with EtOAc (500 mL) and water (100 mL) and the layer were separated. The aqueous layer was extracted with EtOAc (3×100 mL) and the combined organic layers were washed with brine (200 mL), dried (Na$_2$SO$_4$), filtered and concentrated in vacuo to afford a residue which was triturated with EtOAc/heptanes (1:1) to afford added to 4-chloro-N-(1-(methyl-d3)-1H-pyrazol-4-yl)pyrimidin-2-amine as a white solid (7.4 g, yield: 80%). ESI-MS (M+H)$^+$: 213.0.

5. Synthesis of tert-butyl (R)-5-(1-(tert-butyl)-1H-1,2,3-triazole-4-carboxamido)-8-(2-((1-(methyl-d3)-1H-pyrazol-4-yl)amino)pyrimidin-4-yl)-1,3,4,5-tetrahydro-2H-benzo[c]azepine-2-carboxylate

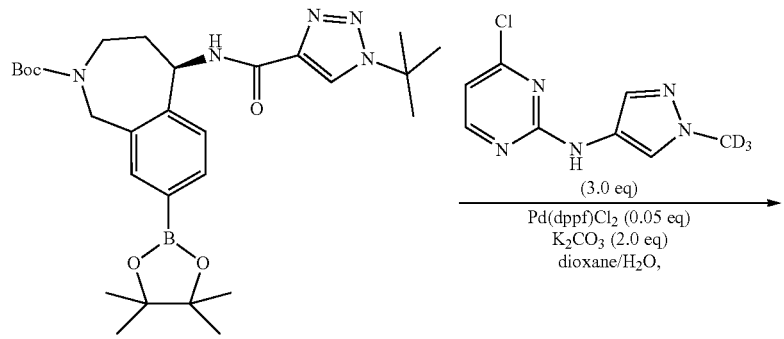

To a solution of tert-butyl (R)-5-(1-(tert-butyl)-1H-1,2,3-triazole-4-carboxamido)-8-(4,4,5,5-tetramethyl-1,3,2-dioxaborolan-2-yl)-1,3,4,5-tetrahydro-2H-benzo[c]azepine-2-carboxylate (4.6 g, 8.5 mmol) in 1,4-dioxane (100 mL) and water (20 mL) was added 4-chloro-N-(1-(methyl-d3)-1H-pyrazol-4-yl)pyrimidin-2-amine (1.8 g, 8.5 mmol), $K_2CO_3$ (2.4 g, 17 mmol) and Pd(dppf)$Cl_2$ (0.7 g, 0.85 mmol) were added. The mixture was stirred at 100° C. for 16 h under nitrogen. After cooling to rt, the mixture was diluted with EtOAc (300 mL) and washed with saturated brine (100 mL). The aqueous layer was extracted with EtOAc (3×100 mL) and the organics were combined, dried ($Na_2SO_4$), filtered, concentrated in vacuo to afford a residue. The crude material was purified by silica gel column chromatography (gradient heptanes/EtOAc=100:0-0:100) to give tert-butyl (R)-5-(1-(tert-butyl)-1H-1,2,3-triazole-4-carboxamido)-8-(2-((1-(methyl-d3)-1H-pyrazol-4-yl)amino)pyrimidin-4-yl)-1,3,4,5-tetrahydro-2H-benzo[c]azepine-2-carboxylate as a yellow solid (3.2 g, yield: 55%). ESI-MS (M+H)$^+$: 590.4.

6. Synthesis of (R)-1-(tert-butyl)-N-(8-(2-((1-(methyl-d3)-1H-pyrazol-4-yl)amino)pyrimidin-4-yl)-2,3,4,5-tetrahydro-1H-benzo[c]azepin-5-yl)-1H-1,2,3-triazole-4-carboxamide

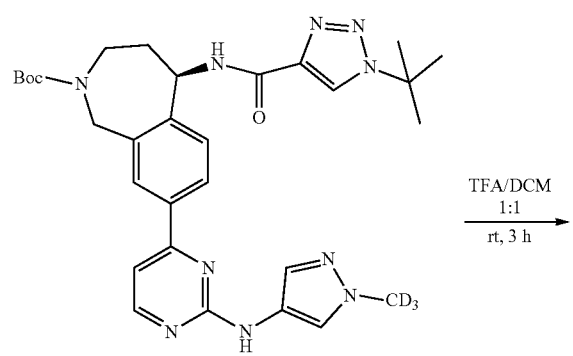

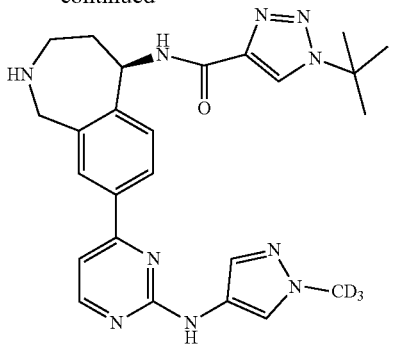

To a solution of tert-butyl (R)-5-(1-(tert-butyl)-1H-1,2,3-triazole-4-carboxamido)-8-(2-((1-(methyl-d3)-1H-pyrazol-4-yl)amino)pyrimidin-4-yl)-1,3,4,5-tetrahydro-2H-benzo[c]azepine-2-carboxylate (3.2 g, 5.5 mmol) in $CH_2Cl_2$ (40 mL) was added TFA (40 mL). The mixture was stirred at rt for 3 h. The solvent was removed and the crude material was re-dissolved in MeOH (30 mL)/water (20 mL). The mixture was basified with $NH_4OH$ to pH=8-9 and extracted with $CH_2Cl_2$ (3×100 mL). The combined organic layers were washed with brine (100 mL), dried over $Na_2SO_4$, filtered and concentrated in vacuo to give (R)-1-(tert-butyl)-N-(8-(2-((1-(methyl-d3)-1H-pyrazol-4-yl)amino)pyrimidin-4-yl)-2,3,4,5-tetrahydro-1H-benzo[c]azepin-5-yl)-1H-1,2,3-triazole-4-carboxamide as a yellow solid (3.0 g, yield: 86%). ESI-MS $(M+H)^+$: 490.2.

7. (R)-1-(tert-butyl)-N-(8-(2-((1-(methyl-d3)-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide

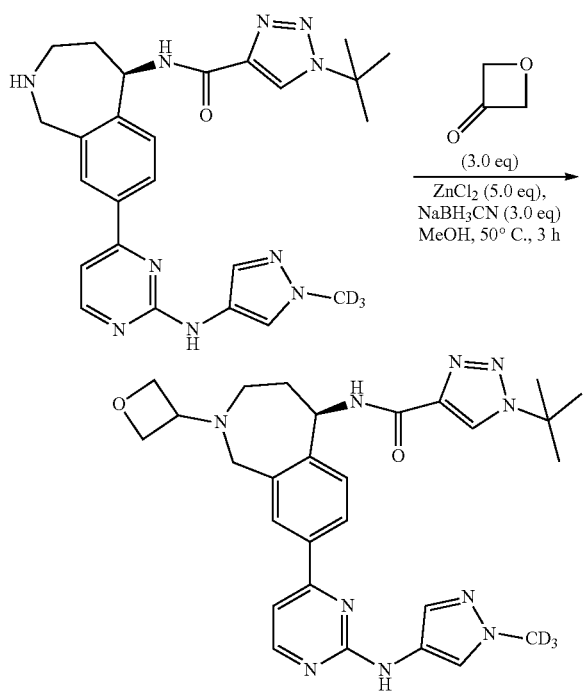

(R)-1-(tert-butyl)-N-(8-(2-((1-methyl-d3)-1H-pyrazol-4-yl)amino)pyrimidin-4-yl)-2,3,4,5-tetrahydro-1H-benzo[c]azepin-5-yl)-1H-1,2,3-triazole-4-carboxamide (2.6 g, 15.9 mmol) was dissolved in MeOH (160 mL) and treated with oxetan-3-one (1.15 g, 16.0 mmol), $ZnCl_2$ (3.6 g, 26.5 mmol) and $NaBH_3CN$ (1.0 mg, 15.9 mmol). The mixture was stirred at 50° C. for 16 h, concentrated in vacuo and the crude material was purified by silica gel chromatography (gradient $CH_2Cl_2$:MeOH 100:10) to give a yellow solid which was further washed purified by dissolving in MeOH (100 mL) and $CH_2Cl_2$ (500 mL) and washed with water (100 mL) and saturated brine (100 mL), the organic layer was separated, dried ($Na_2SO_4$), filtered and concentrated in vacuo to afford (R)-1-(tert-butyl)-N-(8-(2-((1-methyl-d3)-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide as a yellow solid (2.32 g, 67% yield: 55%). ESI-MS $(M+H)^+$: 546.3.

$^1$H NMR (400 MHz, DMSO-$d_6$) δ: 9.46 (s, 1H), 8.98 (d, J=8.3 Hz, 1H), 8.74 (s, 1H), 8.46 (d, J=5.6 Hz, 1H), 7.95 (m, 3H), 7.54 (s, 1H), 7.38 (d, J=8.1 Hz, 1H), 7.25 (d, J=5.2 Hz, 1H), 5.45 (m, 1H), 4.61-4.47 (m, 4H), 3.86 (m, 1H), 3.78 (m, 1H), 3.67 (m, 1H), 2.93 (m, 1H), 2.77 (m, 1H), 2.12 (m, 1H), 1.86 (m, 1H), 1.66 (s, 9H).

Example 27c. Preparation of Crystalline Form a and Crystalline Form G of Compound 27

Compound (R)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (1200 g, 2.47 mol) was added to a 20 L reactor at room temperature (25° C.), followed by addition of 24 L of 1,2-dichloroethane at 25° C. To the solution was added oxetan-3-one (534 g, 24.7 mol), NaBH(OAc)$_3$ (523 g, 2.47 mol), and AcOH (24 mL, 0.17 eq). An additional amount of NaBH(OAc)$_3$ (1046 g, 4.94 mol) was added in portion to the reactor at room temperature. The mixture was stirred at 25° C. for 16 h. Ice water (12 kg) was added slowly to reactor at room temperature. The organic layer was separated and the aqueous layer was extracted with dichloromethane three time (3×12 L). The combined organic layer was washed with brine (20 L), dried over $Na_2SO_4$, filtered and concentrated. The crude material was purified by silica gel chromatography ($CH_2Cl_2$:MeOH=20:1) to afford (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide (compound 27).

The purified compound 27 (950 g) and EtOH (5 L) were vigorously stirred for 4 h and the slurry was filtered and washed with 1 L EtOH. The resulting wet cake was dried under vacuum at 45° C. for 24 h until reaching a constant weight to afford crystalline Form A (960 g, yield 85.7%, purity 99%).

300.2 mg of crystalline Form A was weighed into a 20 mL glass vial followed by addition of 6 mL of isopropyl acetate (IPAc) for suspension. The sample was magnetically stirred at 50° C. with a rate of ~1000 rpm for three days. Solids were isolated by filtration after three days and then dried at room temperature under vacuum for about 5 h to yield crystalline Form G.

Alternatively, to 2.1 g of crystalline Form A was charged 15 volumes of dichloromethane (mL/g). Distill the resulting mixture under atmospheric conditions using a Dean-Stark trap under the conditions of $T_j-T_r=20$ K and $T_{jmax}=110°$ C., wherein $T_j$=jacket temperature, $T_r$=reaction/reactor temperature and $T_{jmax}$=max jacket temperature. 5 mL or 2 volumes of dichloromethane was removed, followed by addition of 2 volumes of isopropyl acetate (IPAc). Continue to distill under the conditions of $T_j-T_r=40K$ and $T_{jmax}=110°$ C. until 10 mL or 5 volumes of the solvent(s) was removed. 5 volumes of IPAc was then added, followed by continued distillation to remove another 10 mL or 5 volumes of the solvent(s). 5 volumes of IPAc was added followed by an additional 30 mL of IPAc. The resulting mixture was stirred and temperature was cycled over the weekend between 20° C. to 60° C. to form a slurry and Form G was isolated from the slurry.

Powder X-Ray Diffraction

Crystallinity of the compound was studied using a XRD-D8 X-ray powder diffractometer using Cu Kα radiation (Bruker, Madison, Wis.). The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a Lynxeye detector. A θ-2θ continuous scan at 1.6°/min from 3 to 42° 2θ was used. The sample was prepared for analysis by placing it on a zero background plate.

The powder X-ray diffraction (PXRD) pattern of crystalline Form A is shown in FIG. 1 and the main peaks are listed in Table 1. The PXRD pattern of crystalline Form G is shown in FIG. 4 and the main peaks are listed in Table 2.

TABLE 1

PXRD peak list for crystalline Form A

| 2θ angle | Net Intensity | Relative Intensity |
|---|---|---|
| 4.31 | 53.6 | 0.08 |
| 5.68 | 700.9 | 1.00 |
| 7.94 | 247.9 | 0.35 |
| 8.73 | 136.1 | 0.19 |
| 9.65 | 176.0 | 0.25 |
| 11.89 | 168.3 | 0.24 |
| 13.05 | 91.4 | 0.13 |
| 14.79 | 118.9 | 0.17 |
| 15.17 | 61.7 | 0.09 |
| 16.08 | 171.5 | 0.24 |
| 4.31 | 53.6 | 0.08 |
| 5.68 | 700.9 | 1.00 |
| 7.94 | 247.9 | 0.35 |
| 8.73 | 136.1 | 0.19 |
| 9.65 | 176.0 | 0.25 |
| 16.96 | 164.8 | 0.24 |
| 17.82 | 132.6 | 0.19 |
| 18.21 | 488.1 | 0.70 |
| 19.02 | 208.4 | 0.30 |
| 20.45 | 143.8 | 0.21 |
| 21.23 | 116.4 | 0.17 |
| 16.96 | 164.8 | 0.24 |
| 22.42 | 248.8 | 0.35 |
| 22.80 | 79.2 | 0.11 |
| 23.79 | 136.4 | 0.19 |
| 25.61 | 103.5 | 0.15 |

TABLE 2

PXRD peak list for crystalline Form G

| 2θ angle | Net Intensity | Relative Intensity |
|---|---|---|
| 3.62 | 1071.5 | 0.58 |
| 8.92 | 96.8 | 0.05 |
| 10.96 | 184.5 | 0.10 |
| 12.59 | 206.5 | 0.11 |
| 14.53 | 81.6 | 0.04 |
| 15.41 | 252.1 | 0.14 |
| 16.33 | 133.3 | 0.07 |
| 18.44 | 294.9 | 0.16 |
| 20.18 | 701.1 | 0.38 |
| 21.79 | 1860.2 | 1.00 |
| 23.36 | 205.8 | 0.11 |
| 25.40 | 502.9 | 0.27 |
| 26.78 | 34.5 | 0.02 |
| 34.18 | 28.8 | 0.02 |

Differential Scanning calorimetry (DSC) and Thermogravimetric Analysis (TGA)

Thermal properties of the compound were examined using a Discovery Differential Scanning calorimeter (DSC) (TA Instruments) and a Discovery Thermogravimetric Analyzer (TGA) (TA Instruments). Sample was enclosed in a closed aluminum DSC pan for DSC analysis and in an open aluminum pan for TGA analysis. The thermal analysis was performed with a linear gradient from 25° C. to 300° C. at 10° C. per minute for both DSC and TGA studies. The differential scanning calorimetry (DSC) analysis for crystalline Form A shows that Form A has an onset temperature at 175.6° C. and a melting temperature at 186° C. (FIG. 2).

The DSC analysis for crystalline Form G shows that Form G has an onset temperature at 215.4° C. and a melting temperature at 217.3° C. (FIG. 5).

The TGA analysis for Form A of compound 27 shows a 3.16% weight loss, indicating Form A is a hydrate (FIG. 3).

The TGA analysis of Form G of compound 27 shows no weight loss until the melt, indicating that Form G is anhydrous (FIG. 5).

Solid State NMR

The $^{13}$C CP/MAS (Cross polarization/magic angle spinning) solid-state NMR spectra were acquired on a 363 MHz Tecmag Redstone spectrometer by Spectral Data Services of Champaign, Ill. Each sample was packed into a 7 mm (OD) zirconia rotor closed with kel-F end caps for subsequent data acquisition. All three samples were about half full in the rotor. The $^{13}$C CP/MAS NMR spectra were acquired on the Doty XC 7 mm CP/MAS probe at an observing frequency of 91 MHz (spin 7 kHz, 1H pulse width 5.0 μs, spectral width 29.8 kHz, acquisition time 0.0344 sec, CP pulse width 2 ms, relaxation delay 5.0 sec, number of scans 1296). Spectra were referenced to the chemical shift of external sample of glycine carbonyl carbon at 176 ppm and processed using Nuts (line broadening of 10 Hz). The peak listing and overlay of spectra are processed using MNOVA.

$^{13}$C CP/MAS solid state NMR for Form A and Form G are shown in FIG. 3B and FIG. 6B, respectively. Diagnostic chemical shifts are listed in Table 3.

TABLE 3

Diagnostic $^{13}$C CP/MAS NMR chemical shifts for solid forms of compound 27

| Peak assignment* | Form A (ppm) | Form G (ppm) |
|---|---|---|
| carbonyl | 163.2 | 163.6 |
|  |  | 163.2 |
| aromatic carbons | 159.5 | 159.4 |
|  | 157.9 |  |
|  | 156.2 (shoulder) | 147.0 |
|  | 143.7 | 146.0 |
|  | 142.5 (shoulder) | 141.5 |
|  | 135.8 | 140.6 |
|  | 134.4 | 137.1 |
|  | 132.3 | 136.0 |

TABLE 3-continued

Diagnostic $^{13}$C CP/MAS NMR chemical shifts for solid forms of compound 27

| Peak assignment* | Form A (ppm) | Form G (ppm) |
|---|---|---|
|  | 130.5 | 130.2 |
|  | 129.6 | 125.9 |
|  | 126.9 | 125.0 |
|  | 124.7 | 120.7 |
|  | 123.6 | 105.9 |
|  | 106.1 | 104.4 |
|  | 105.1 |  |
| aliphatic carbons | 77.4 | 77.7 |
|  | 75.9 | 76.8 |
|  | 60.7 | 75.5 |
|  | 59.5 | 61.4 |
|  | 55.9 | 60.9 |
|  | 51.6 | 58.2 |
|  | 50.3 | 54.4 |
|  | 39.5 | 51.7 |
|  | 37.9 | 49.9 |
|  | 35.2 | 40.0 |
|  | 30.1 | 37.3 |
|  | 29.1 | 30.0 |

*This is a tentative assignment based on the chemical structure and ChemDraw chemical shift prediction and solution $^{13}$C NMR spectra in DMSO Example 28. (R)-1-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1H-1,2,3-triazole-4-carboxamide (Compound 28)

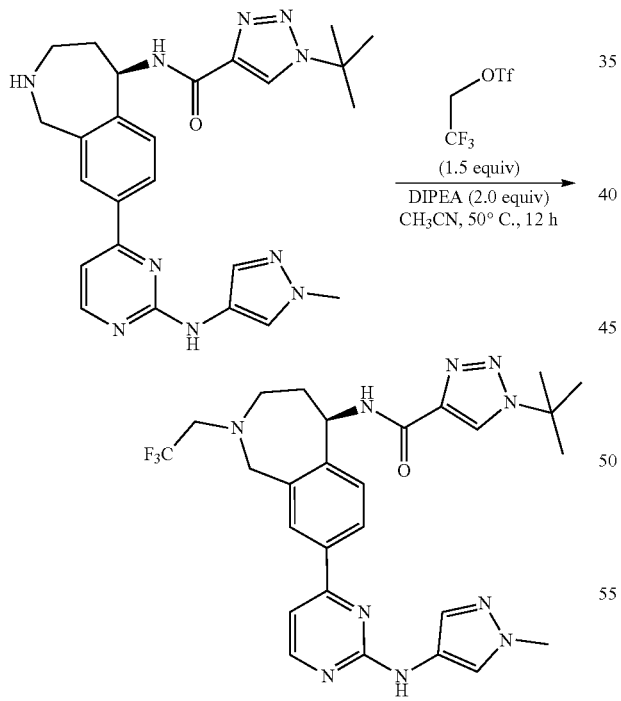

To a solution of (R)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (200 mg, 0.4 mmol) in CH$_3$CN (5 mL) was added 2,2,2-trifluoroethyl trifluoromethanesulfonate (190 mg, 0.6 mmol). The mixture was stirred at 50° C. for 12 h. After concentration of the reaction mixture, the residue was purified by silica gel chromatography (PE:EtOAc=1:1) to give (R)-1-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1H-1,2,3-triazole-4-carboxamide as a yellow solid (85 mg, yield: 36%). ESI-MS (M+H)$^+$: 569.3. $^1$H NMR (400 MHz, CD$_3$OD) δ: 8.54 (s, 1H), 8.42 (d, J=5.2 Hz, 1H), 8.03-7.99 (m, 3H), 7.61 (s, 1H), 7.49 (d, J=7.6 Hz, 1H), 7.22 (d, J=5.2 Hz, 1H), 5.60-5.57 (m, 1H), 4.39-4.35 (m, 1H), 4.17-4.12 (m, 1H), 3.89 (s, 3H) 3.43-3.32 (m, 2H), 3.16-3.09 (m, 2H), 2.24-2.20 (m, 1H), 1.98-1.94 (m, 1H), 1.74 (s, 9H).

Example 29. 1-(tert-butyl)-N—((R)-2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (Compound 29)

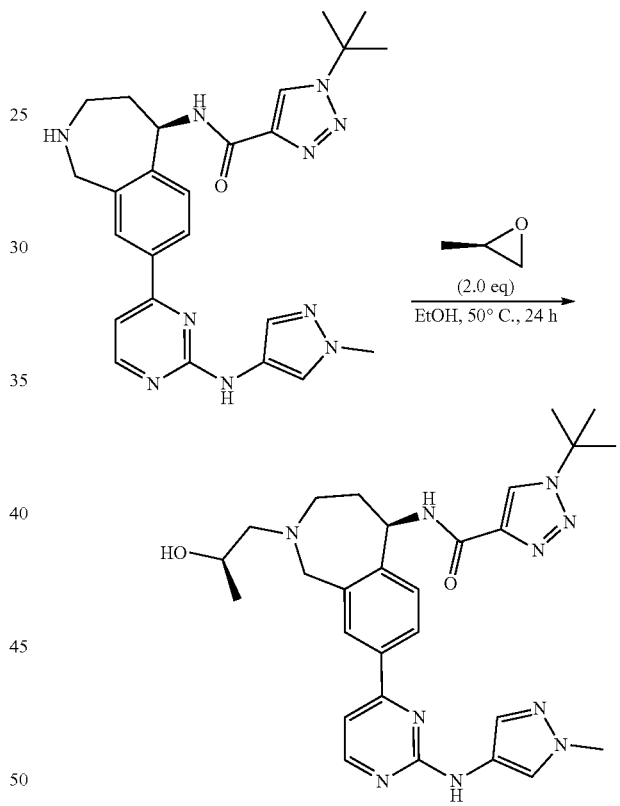

To a solution of (R)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (250 mg, 0.51 mmol) in EtOH (5 mL) were added (R)-2-methyloxirane (58 mg, 1.0 mmol). The mixture was stirred at 50° C. for 24 h. After concentration, the residue purified by silica gel column (petroleum ether/EtOAc=1:2) to give 1-(tert-butyl)-N—((R)-2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide as a white solid (110 mg, yield: 40%). ESI-MS (M+H)$^+$: 545.3. $^1$H NMR (400 MHz, CD$_3$OD) δ: 8.42 (s, 1H), 8.28 (d, J=5.2 Hz, 1H), 7.93-7.84 (m, 3H), 7.52 (s, 1H), 7.35 (d, J=8.8 Hz, 1H), 7.09 (d, J=5.2 Hz, 1H), 5.46 (d, J=10 Hz, 1H), 4.13-4.00 (m, 2H), 3.92-3.87 (m, 1H), 3.78 (s, 3H)

3.21-3.12 (m, 2H), 2.40-2.32 (m, 2H), 2.17-2.13 (m, 1H), 1.89-1.84 (m, 1H), 1.62 (s, 9H), 1.02 (d, J=6.0 Hz, 3H).

Example 30. 1-(tert-butyl)-N—((R)-2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (Compound 30)

Example 31. (R)-1-(tert-butyl)-N-(2-(2-methoxyethyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (Compound 31)

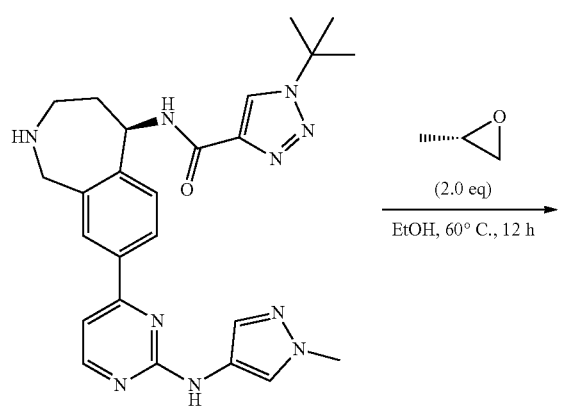

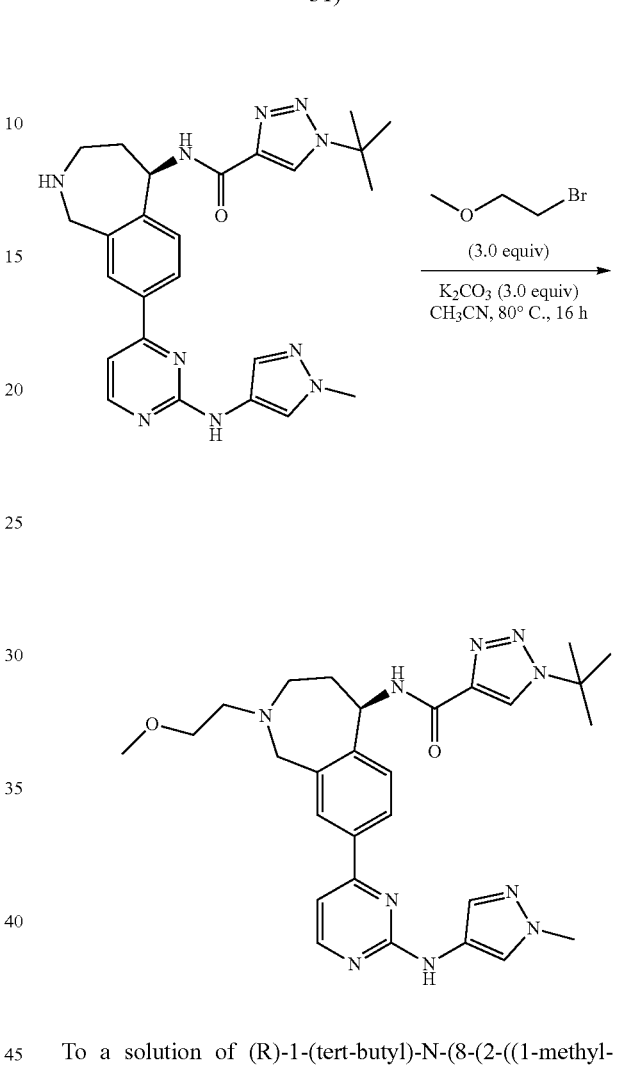

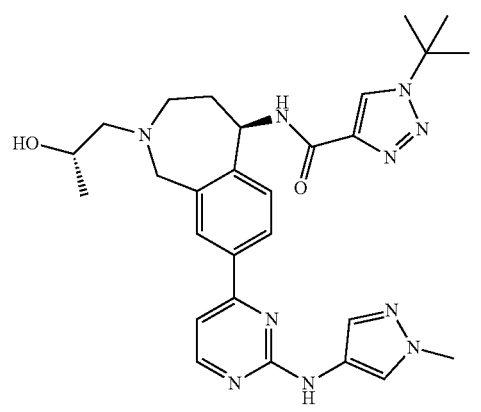

Synthesis of 1-(tert-butyl)-N—((R)-2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide was similar to that of 1-(tert-butyl)-N—((R)-2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (Example 29). The crude was purified by prep-TLC (DCM/MeOH=10:1) to give 1-(tert-butyl)-N—((R)-2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide as a yellow solid (97 mg, yield: 44%). ESI-MS (M+H)$^+$: 545.3. $^1$H NMR (400 MHz, CD$_3$OD) δ: 8.54 (s, 1H), 8.41 (d, J=5.2 Hz, 1H), 8.01-7.97 (m, 3H), 7.63 (s, 1H), 7.46 (d, J=8.0 Hz, 1H), 7.22 (d, J=5.6 Hz, 1H), 5.57 (d, J=9.6 Hz, 1H), 4.23-4.20 (m, 1H), 4.12-4.07 (m, 1H), 4.02-3.97 (m, 1H), 3.90 (s, 3H), 3.30-3.28 (m, 1H), 3.26-3.19 (m, 1H), 2.47-2.45 (m, 2H), 2.31-2.22 (m, 1H), 2.01-1.97 (m, 1H), 1.74 (s, 9H), 1.16 (d, J=6.4 Hz, 3H).

To a solution of (R)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (140 mg, 0.29 mmol) in MeOH (10 mL) were added 1-bromo-2-methoxyethane (121 mg, 0.87 mmol) and K$_2$CO$_3$ (120 mg, 0.87 mmol). The mixture was stirred at 80° C. for 16 h. After diluting with water (20 mL), the mixture was extracted with CH$_2$Cl$_2$ (30 mL×2). The combined organic layers were washed with H$_2$O (20 mL×2), dried (Na$_2$SO$_4$), filtered and concentrated. The crude material was purified by prep-TLC (DCM:MeOH=20:1) to give (R)-1-(tert-butyl)-N-(2-(2-methoxyethyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide as a yellow solid (66 mg, yield: 42%). ESI-MS (M+H)$^+$: 545.1. $^1$H NMR (400 MHz, CDCl$_3$) δ: 8.41 (d, J=5.2 Hz, 1H), 8.18 (s, 1H), 7.98 (d, J=8.4 Hz, 1H), 7.90 (s, 1H), 7.84 (d, J=8.0 Hz, 1H), 7.80 (s, 1H), 7.53 (s, 1H), 7.46 (d, J=8.0 Hz, 1H), 7.04 (d, J=5.2 Hz, 1H), 6.97 (s, 1H), 5.60 (t, J=8.8 Hz, 1H), 4.19-4.07 (m, 2H), 3.91 (s, 3H), 3.57 (t, J=5.6 Hz, 2H), 3.37 (s, 3H), 3.32-3.26 (m, 1H), 3.19-3.15 (m, 1H), 2.78-2.69 (m, 2H), 2.24-2.20 (m, 1H), 2.02-1.99 (m, 1H), 1.70 (s, 9H).

Example 32. (R)-5-(tert-butyl)-N-(2-(2,2-difluoro-ethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide (Compound 32)

Example 33. 5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,2,4-oxadiazole-3-carboxamide (Compound 33)

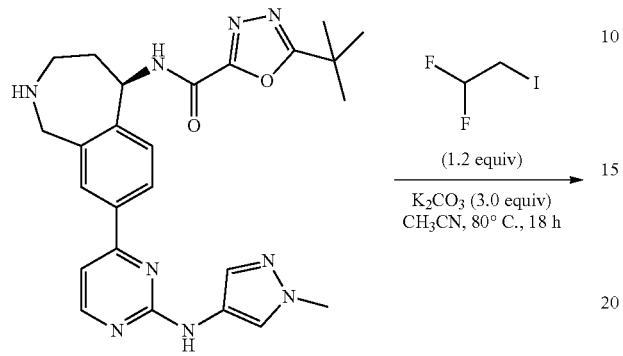

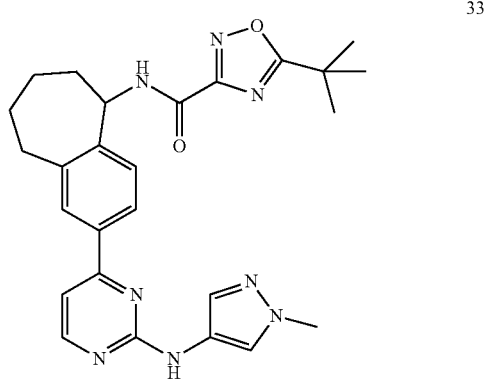 [SMILES: Cn1cc(Nc2nccc(-c3ccc4c(c3)CCCCC4NC(=O)c3noc(C(C)(C)C)n3)n2)cn1]

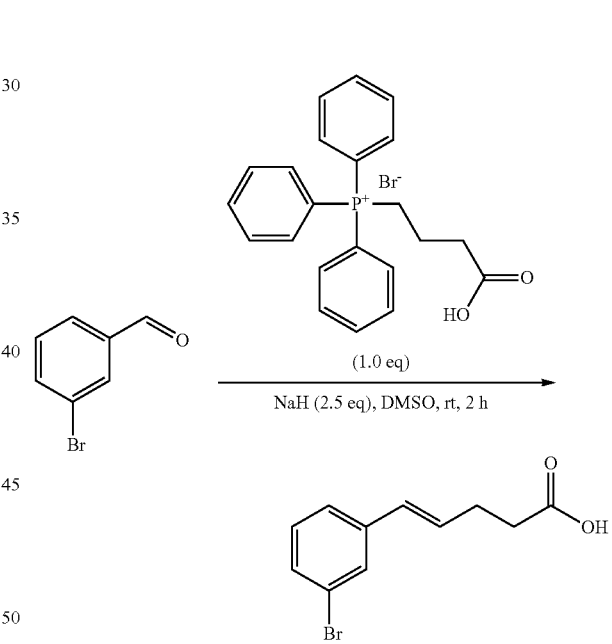

I. Synthesis of (E)-5-(3-bromophenyl)pent-4-enoic Acid

To a solution of (R)-5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide (105 mg, 0.21 mmol) in CH$_3$CN (8 mL) was added 1,1-difluoro-2-iodoethane (23 μL, 0.26 mmol) and potassium carbonate (89 mg, 0.64 mmol). The mixture was stirred at 80° C. for 18 h. The reaction mixture was cooled to room temperature and filtered. The filtrate was concentrated and the crude product was purified by prep-HPLC (CH$_3$CN/H$_2$O with 0.05% TFA as mobile phase) to give (R)-5-(tert-butyl)-N-(2-(2,2-difluoroethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide as a yellow solid (30 mg, yield: 25%). ESI-MS (M+H)$^+$: 552.0. $^1$H NMR (400 MHz, METHANOL-d$_4$) δ: 8.42 (d, J=5.3 Hz, 1H), 8.23 (d, J=8.4 Hz, 1H), 8.19 (s, 1H), 7.95 (s, 1H), 7.68-7.65 (m, 1H), 7.62 (d, J=7.8 Hz, 1H), 7.30 (d, J=5.5 Hz, 1H), 6.40 (tt, J=53.5 Hz, 3.6 Hz, 1H), 5.70 (dd, J=9.8 Hz, 2.5 Hz, 1H), 4.83 (br d, J=14.3 Hz, 1H), 4.67 (br d, J=14.3 Hz, 1H), 3.90 (s, 3H), 3.83-3.67 (m, 2H), 3.59 (dt, J=15.0 Hz, 3.4 Hz, 2H), 2.52-2.31 (m, 2H), 1.49 (s, 9H)

To a solution of (3-carboxypropyl)triphenylphosphonium bromide (12.87 g, 30 mmol, 1.0 equiv) in dry DMSO (50 mL) was added NaH (3 g, 75 mmol, 2.5 equiv) by portions at 0° C. The reaction was stirred at room temperature for 30 min before 3-bromobenzaldehyde (5.5 g, 30 mmol, 1.0 equiv) was dropwise added. The mixture was stirred at room temperature for another 2 h and then poured into water (200 mL) and extracted with EtOAc (100 mL). The aqueous solution was acidified with concentrated HCl and extracted with EtOAc (200 mL×3). The combined organic layer was washed with brine (100 mL×3). The organic layer was dried over sodium sulfate and concentrated under reduced pressure. The residue was purified by silica gel column (petroleum ether/EtOAc=2:1) to give (E)-5-(3-bromophenyl)pent-4-enoic acid (4.4 g, yield: 58%) as a yellow oil. ESI-MS (M+1)+: 254.9. ¹H NMR (400 MHz, CDCl₃) δ: 7.48 (s, 1H), 7.33 (d, J=7.6 Hz, 1H), 7.23 (d, J=8.0 Hz, 1H), 7.15 (t, J=8.0 Hz, 1H), 6.39-6.35 (m, 1H), 6.23-6.19 (m, 1H), 2.55-2.53 (m, 4H).

2. Synthesis of 5-(3-bromophenyl)pentanoic Acid

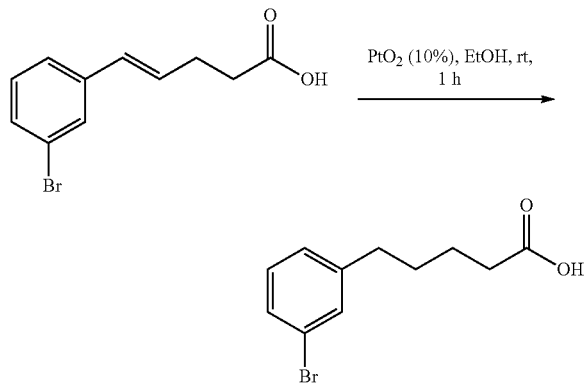

To a solution of (E)-5-(3-bromophenyl)pent-4-enoic acid (2.4 g, 9.4 mmol, 1.0 equiv) in ethanol (20 mL) was added PtO₂ (200 mg, 10%). The mixture was stirred for 1 h under hydrogen atmosphere. The catalyst was filtered out and the resulting filtrate was concentrated to give target compound 5-(3-bromophenyl)pentanoic acid (2.1 g, yield: 87%) as a yellow solid, which was used to next step without further purification. ESI-MS (M+1)+: 256.9. ¹H NMR (400 MHz, CD₃OD) δ: 7.24 (s, 1H), 7.21-7.18 (m, 1H), 7.06-7.03 (m, 2H), 2.50 (t, J=6.8 Hz, 2H), 2.20 (t, J=6.8 Hz, 2H), 1.53-1.51 (m, 4H).

3. Synthesis of 2-bromo-6,7,8,9-tetrahydro-5H-benzo[7]annulen-5-one

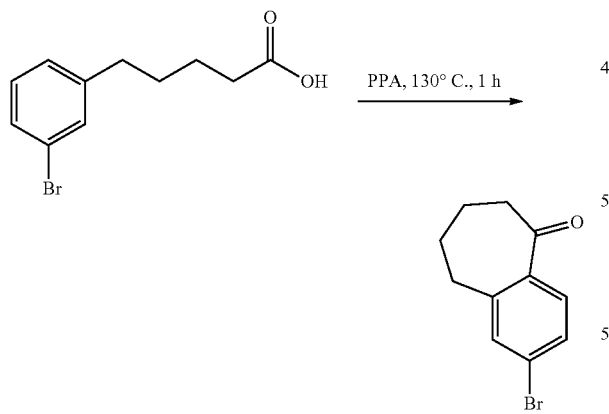

A mixture of 5-(3-bromophenyl)pentanoic acid (2.1 g, 8.2 mmol, 1.0 equiv) in PPA (5 ml) was stirred at 130° C. for 1 h. After cooling down, the mixture was basified to pH=7-8 with NaOH (1 N). The mixture was extracted with EtOAc (200 mL×2). The combined organic layers was concentrated and purified by prep-HPLC (Gradient: 5% B increase to 95% B, A: 0.5% NH₃ in water, B: CH₃CN) to give 2-bromo-6,7,8,9-tetrahydro-5H-benzo[7]annulen-5-one (1.1 g, yield: 56%) as a colorless oil. ESI-MS (M+H)+: 239.0. ¹H NMR (400 MHz, CDCl₃) δ: 7.59 (d, J=8.4 Hz, 1H), 7.43 (dd, J=8.4, 2.0 Hz, 1H), 7.38 (s, 1H), 2.89 (t, J=6.8 Hz, 2H), 2.72 (t, J=6.0 Hz, 2H), 1.90-1.79 (m, 4H).

4. Synthesis of 2-bromo-6,7,8,9-tetrahydro-5H-benzo[7]annulen-5-ol

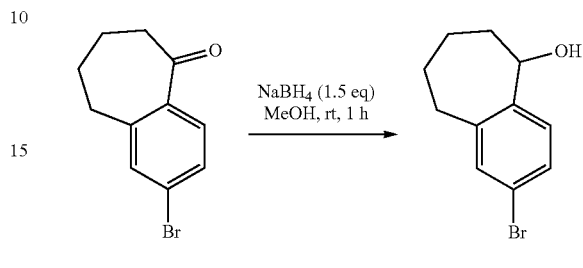

To a solution of 2-bromo-6,7,8,9-tetrahydro-5H-benzo[7]annulen-5-one (600 mg, 2.5 mmol, 1.0 equiv) in MeOH (10 mL) was added NaBH₄ (144 mg, 3.8 mmol, 1.5 equiv) and then stirred at room temperature for 1 h. After evaporation of the solvent, the residue was purified by silica gel column (EtOAc/hexane=1:5) to give 2-bromo-6,7,8,9-tetrahydro-5H-benzo[7]annulen-5-ol (600 mg, yield: 99%) as a white solid. ESI-MS (M+H−17)+: 222.9. ¹H NMR (400 MHz, CDCl₃) δ: 7.34-7.30 (m, 2H), 7.24 (s, 1H), 4.88-4.86 (m, 1H), 2.88-8.82 (m, 1H), 2.70-2.63 (m, 1H), 2.08-2.00 (m, 2H), 1.81-1.72 (m, 4H).

5. Synthesis of 5-azido-2-bromo-6,7,8,9-tetrahydro-5H-benzo[7]annulene

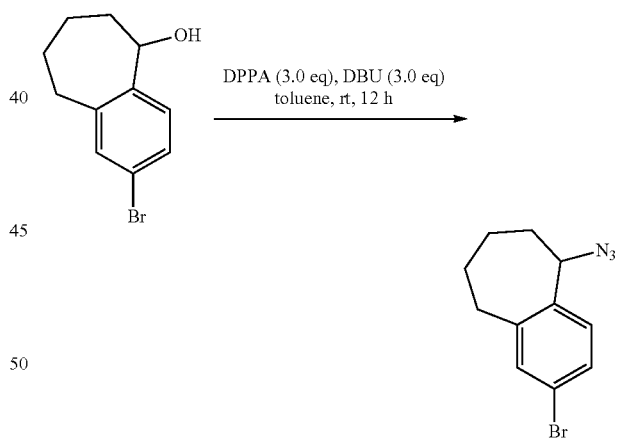

A solution of 2-bromo-6,7,8,9-tetrahydro-5H-benzo[7]annulen-5-ol (600 mg, 2.5 mmol, 1.0 equiv) in toluene (10 mL) was cooled in an ice bath under N₂ and treated with DPPA (2.06 g, 7.5 mmol, 3.0 equiv) in one portion followed by DBU (1.14 g, 7.5 mmol, 3.0 equiv). The reaction temperature was kept at 0° C. for 1 h and then was warmed to room temperature for 12 h. The mixture was diluted with EtOAc (100 mL), washed with 2N HCl (2×50 mL), brine and the organic layer was dried over Na₂SO₄, filtered then concentrated. The crude product was purified by silica gel column (eluted with PE) to give 5-azido-2-bromo-6,7,8,9-tetrahydro-5H-benzo[7]annulene (350 mg, yield: 45%) as a yellow oil. ESI-MS (M+H-N₃)+: 223.0. ¹H NMR (400 MHz, CDCl₃) δ: 7.31-7.29 (m, 2H), 7.15 (d, J=8.0 Hz, 1H), 4.72 (t, J=5.2 Hz, 1H), 2.99-2.92 (m, 1H), 2.70-2.64 (m, 1H), 2.08-2.00 (m, 1H), 1.90-1.59 (m, 5H).

6. Synthesis of 2-bromo-6,7,8,9-tetrahydro-5H-benzo[7]annulen-5-amine

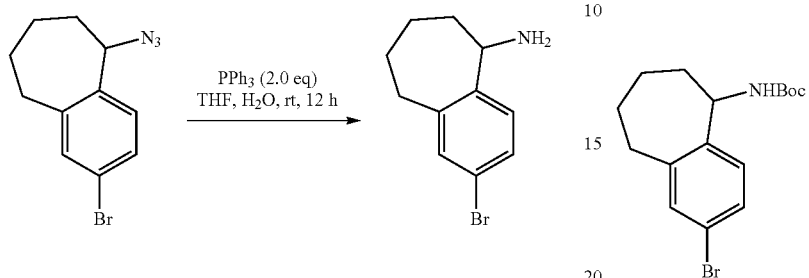

To a mixture of 5-azido-2-bromo-6,7,8,9-tetrahydro-5H-benzo[7]annulene (375 mg, 1.4 mmol, 1.0 equiv) in THF (5 mL) and H₂O (0.5 mL) was added PPh₃ (741 mg, 2.8 mmol, 2.0 equiv). The mixture was stirred at room temperature for 12 h. The mixture was acidified to pH=1 with HCl (1 N) and extracted with EtOAc (100 mL). The separated aqueous layer was basified to pH=10 with NaOH (1 N). The resulting precipitate was collected and dried to give 2-bromo-6,7,8,9-tetrahydro-5H-benzo[7]annulen-5-amine (360 mg, yield: 100%) as a white solid. ESI-MS (M+H−17)⁺: 222.9.

7. Synthesis of tert-butyl (2-bromo-6,7,8,9-tetrahydro-5H-benzo[7]annulen-5-yl)carbamate

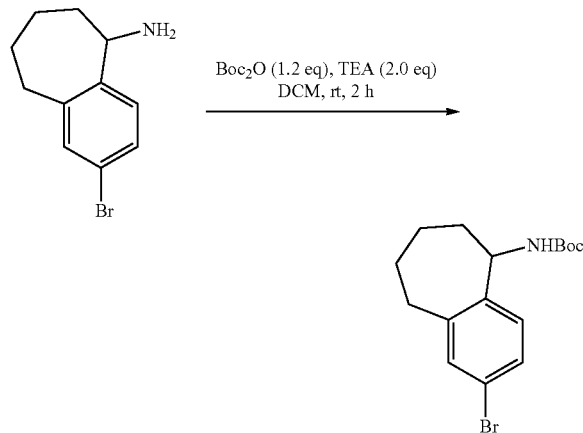

To a mixture of tert-butyl (2-bromo-6,7,8,9-tetrahydro-5H-benzo[7]annulen-5-yl)carbamate (360 mg, 1.5 mmol, 1.0 equiv) in CH₂Cl₂ (5 mL) and triethylamine (303 mg, 3.0 mmol, 2.0 equiv) was added Boc₂O (394 mg, 1.8 mmol, 1.2 equiv). The mixture was stirred at room temperature for 2 h. After diluted with EtOAc (100 mL), the mixture was washed with water (100 mL×2). The organic layer was concentrated and purified by silica gel column (PE:EtOAc=30:1) to give tert-butyl (2-bromo-6,7,8,9-tetrahydro-5H-benzo[7]annulen-5-yl)carbamate (310 mg, yield: 61%) as a white solid. ESI-MS (M−55): 284.0. ¹H NMR (400 MHz, CDCl₃) δ: 7.29-7.23 (m, 2H), 7.10 (d, J=8.0 Hz, 1H), 4.92-4.82 (m, 2H), 2.84-2.75 (m, 2H), 1.88-1.83 (m, 5H), 1.44 (s, 9H).

8. Synthesis of tert-butyl (2-(2-chloropyrimidin-4-yl)-6,7,8,9-tetrahydro-5H-benzo[7]annulen-5-yl)carbamate

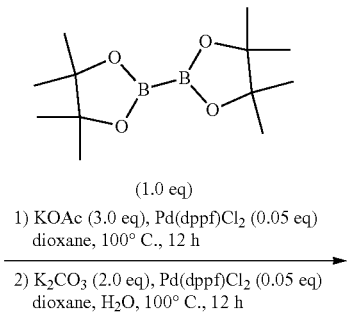

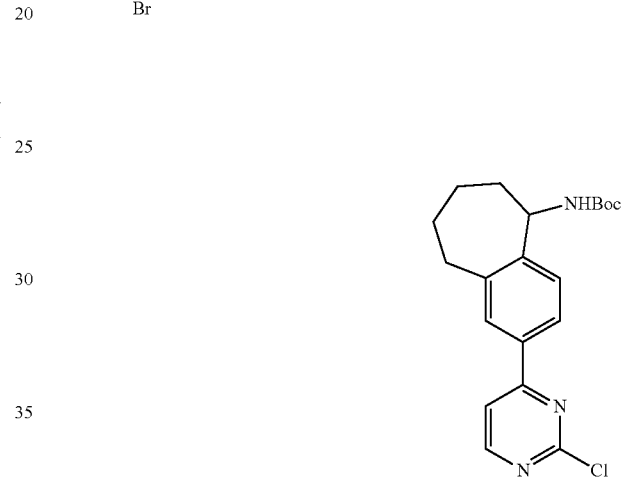

Synthesis of tert-butyl (2-(2-chloropyrimidin-4-yl)-6,7,8,9-tetrahydro-5H-benzo[7]annulen-5-yl)carbamate was similar to that of tert-butyl 4-(2-chloropyrimidin-4-yl)-2-methylbenzylcarbamate. The mixture was concentrated and purified by silica gel column (PE:EtOAc=4:1) to give tert-butyl (2-(2-chloropyrimidin-4-yl)-6,7,8,9-tetrahydro-5H-benzo[7]annulen-5-yl)carbamate (200 mg, yield: 66%) as a white solid. ESI-MS (M+H)⁺: 374.1.

9. Synthesis of tert-butyl (2-(2-((1-methyl-1H-pyrazol-4-yl)amino)pyrimidin-4-yl)-6,7,8,9-tetrahydro-5H-benzo[7]annulen-5-yl)carbamate

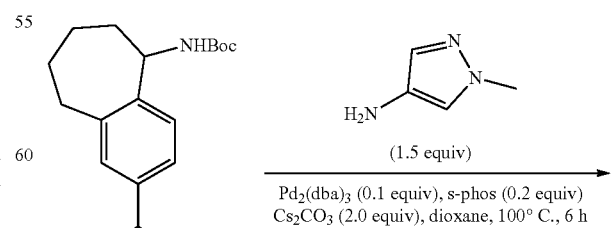

-continued

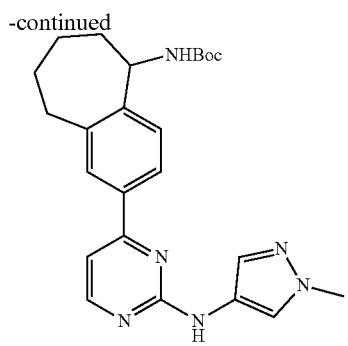

A mixture of tert-butyl (2-(2-chloropyrimidin-4-yl)-6,7,8,9-tetrahydro-5H-benzo[7]annulen-5-yl)carbamate (500 mg, 1.34 mmol), 1-methyl-1H-pyrazol-4-amine (195 mg, 2.01 mmol), Pd$_2$(dba)$_3$ (120 mg, 0.13 mmol), S-phos (111 mg, 0.27 mmol) and Cs$_2$CO$_3$ (870 mg, 2.68 mmol) in 1,4-dioxane (12 ml) was stirred at 100° C. for 6 h under N$_2$. The mixture was filtrated through a Celite pad and the filtrate was concentrated. The residue was purified by silica-gel-column (EtOAc) to give tert-butyl (2-(2-((1-methyl-1H-pyrazol-4-yl)amino)pyrimidin-4-yl)-6,7,8,9-tetrahydro-5H-benzo[7]annulen-5-yl)carbamate as a white solid (480 mg, yield: 83%). ESI-MS (M+H)$^+$: 435.3. $^1$H NMR (400 MHz, CDCl$_3$) δ: 8.46 (d, J=5.2 Hz, 1H), 7.88-7.80 (m, 3H), 7.38-6.85 (m, 4H), 4.97-4.94 (m, 2H), 3.85 (s, 3H), 2.96-2.94 (m, 2H), 1.93-1.64 (m, 6H), 1.47 (s, 9H).

10. Synthesis of 4-(5-amino-6,7,8,9-tetrahydro-5H-benzo[7]annulen-2-yl)-N-(1-methyl-1H-pyrazol-4-yl)pyrimidin-2-amine

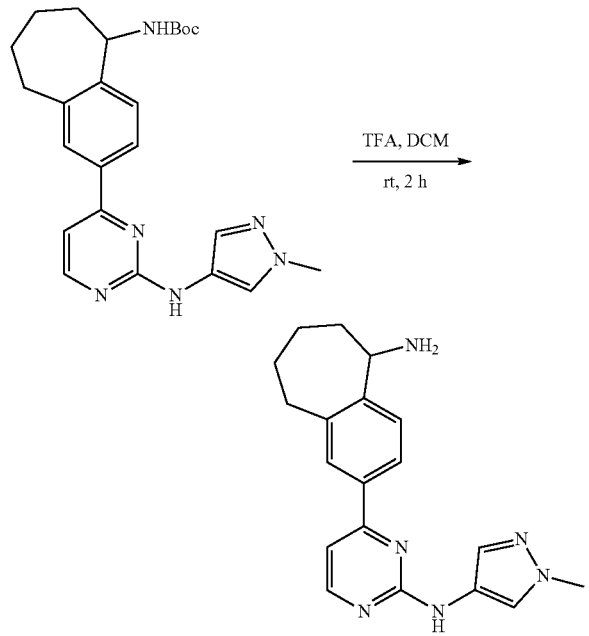

A mixture of tert-butyl (2-(2-((1-methyl-1H-pyrazol-4-yl)amino)pyrimidin-4-yl)-6,7,8,9-tetrahydro-5H-benzo[7]annulen-5-yl)carbamate (240 mg, 0.55 mmol) in TFA (4.0 mL) and CH$_2$Cl$_2$ (4.0 mL) was stirred at rt for 2 h. Then the reaction mixture was concentrated to give compound 4-(5-amino-6,7,8,9-tetrahydro-5H-benzo[7]annulen-2-yl)-N-(1-methyl-1H-pyrazol-4-yl)pyrimidin-2-amine (250 mg, crude) as a yellow oil, which was used in the next step without further purification. ESI-MS (M+H)$^+$: 335.3.

11. Synthesis of 5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,2,4-oxadiazole-3-carboxamide

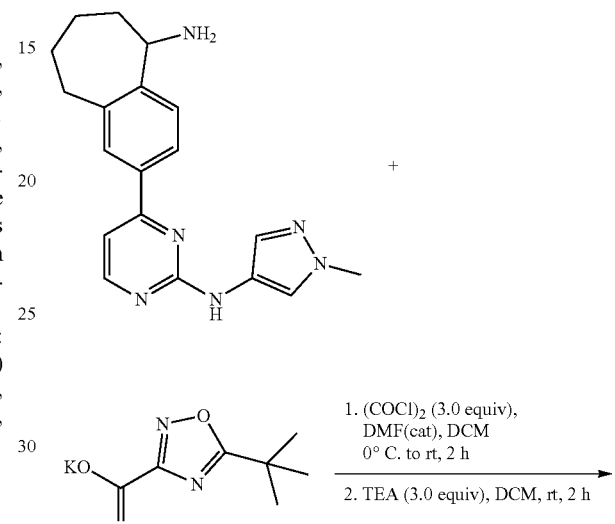

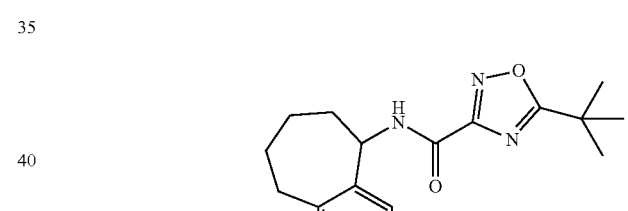

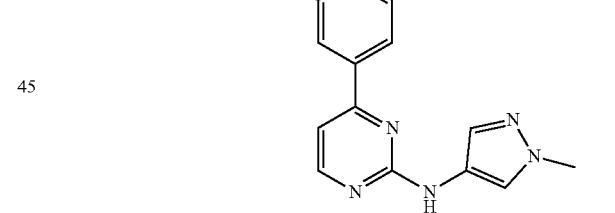

Synthesis of 5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,2,4-oxadiazole-3-carboxamide was similar to that of tert-butyl 8-bromo-5-(5-(tert-butyl)-1,2,4-oxadiazole-3-carboxamido)-4,5-dihydro-1H-benzo[c]azepine-2(3H)-carboxylate in Example 2. The residue was purified by prep-HPLC (CH$_3$CN/H$_2$O with 0.05% NH$_4$HCO$_3$ as mobile phase) to give 5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,2,4-oxadiazole-3-carboxamide as a yellow solid (120 mg, yield: 42%). ESI-MS (M+H)$^+$: 487.3. $^1$H NMR (400 MHz, CD$_3$OD) δ: 8.43 (d, J=5.2 Hz, 1H), 7.98-7.96 (m, 2H), 7.51-7.30 (m, 3H), 6.74 (d, J=2.4 Hz, 1H), 5.44 (d, J=10.0 Hz, 1H), 3.83 (s, 3H), 3.09-3.03 (m, 2H), 2.10-1.43 (m, 6H), 1.54 (s, 9H).

Example 34. (R)—N-(2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide (Compound 34)

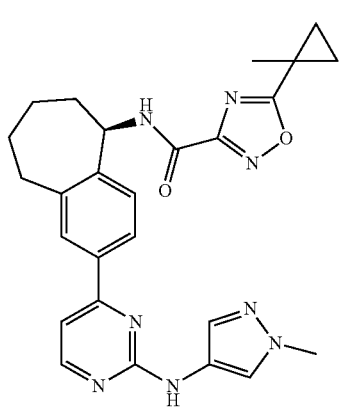

I. Synthesis of (R,Z)-5-((1-phenylethyl)imino)-6,7,8,9-tetrahydro-5H-benzo[7]annulen-2-ol

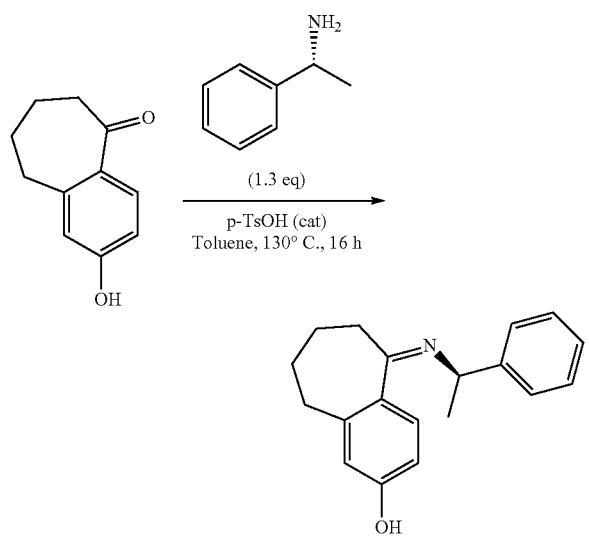

A slurry mixture of 2-hydroxy-6,7,8,9-tetrahydro-5H-benzo[7]annulen-5-one (Herdman C. A. et al., Structural interrogation of benzosuberen-based inhibitors of tubulin polymerization, *Bioorganic & Medical Chemistry*, 23(24), 7497-7520, 2015) (10 g, 57 mmol), (R)-(+)-α-methylbenzylamine (9.0 g, 74 mmol), and p-toluenesulfonic acid (0.48 g, 2.84 mmol) in 150 mL toluene was heated at reflux with a Dean Stark apparatus. After 16 hr, the Dean Stark apparatus was removed and reflux was continued until ~80 mL toluene was distilled, during which solid crystallized. The mixture was cooled to 0° C., kept at 0° C. for 2 hr, and then filtered to give (R,Z)-5-((1-phenylethyl)imino)-6,7,8,9-tetrahydro-5H-benzo[7]annulen-2-ol as a tan solid (after drying—13.5 g, yield: 85%). The crude product was used for next step without further purification.

2. Synthesis of (R)-5-amino-6,7,8,9-tetrahydro-5H-benzo[7]annulen-2-ol Acetate

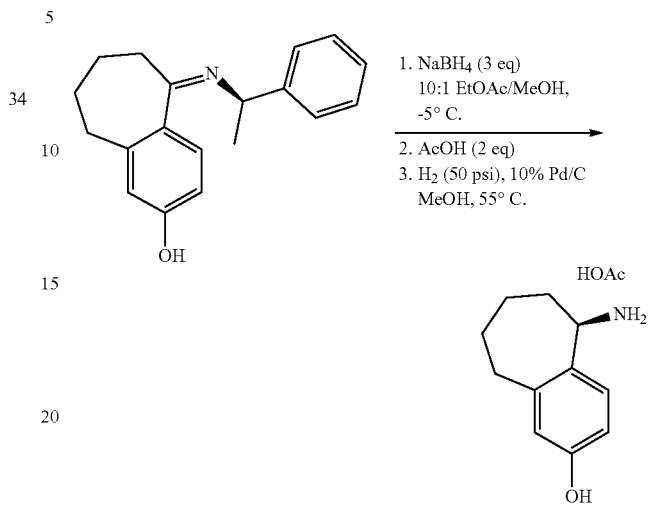

A slurry of (R,Z)-5-((1-phenylethyl)imino)-6,7,8,9-tetrahydro-5H-benzo[7]annulen-2-ol (13.5 g, 48 mmol) in 10:1 EtOAc/MeOH (148 mL) was cooled to 5° C. Solid NaBH$_4$ (5.45 g, 144 mmol) was added in portions, while maintaining the temperature under 5° C. The mixture was stirred at 5° C. for 40 min. After 1 hr, water (135 mL) was added, followed by 5N HCl until pH 6. The layers were separated, and the aqueous layer was extracted with 135 mL EtOAc. The combined organics were washed with brine (100 mL) and dried (Na$_2$SO$_4$) and filtered to give a solution of (R)-5-(((R)-1-phenylethyl)amino)-6,7,8,9-tetrahydro-5H-benzo[7]annulen-2-ol which was carried forward.

To the solution of (R)-5-(((R)-1-phenylethyl)amino)-6,7,8,9-tetrahydro-5H-benzo[7]annulen-2-ol (48 mmol) in EtOAc (~185 mL) was added acetic acid (5.8 g, 96 mmol). The solution was then concentrated and carried forward.

MeOH (200 mL) was added, followed by 10% Pd/C (1.4 g, 10% wt %). The mixture was stirred under an atmosphere of H$_2$ (50 psi) at 55° C. for 16 hr. The mixture was filtered and the filtrate was concentrated. Methyl tert-butyl ether (100 mL) was added, followed by petroleum ether (100 mL). The mixture was stirred at 25° C. for 2 hr, and filtered. After drying at 50° C., (R)-5-amino-6,7,8,9-tetrahydro-5H-benzo[7]annulen-2-ol acetate was isolated (9.9 g, yield: 87% for three steps.

3. Synthesis of tert-butyl (R)-(2-hydroxy-6,7,8,9-tetrahydro-5H-benzo[7]annulen-5-yl)carbamate

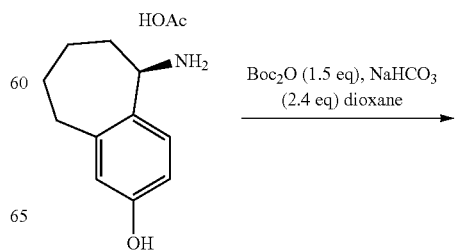

-continued

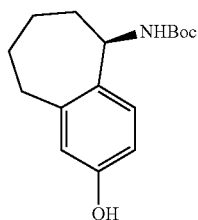

To a solution of (R)-5-amino-6,7,8,9-tetrahydro-5H-benzo[7]annulen-2-ol acetate (9.9 g, 42 mmol) in dioxane (50 mL) was added aqueous NaHCO$_3$ (1N, 100 mL, 100 mmol) followed by Boc$_2$O (13.7 g, 63 mmol. The mixture was stirred at rt overnight. EtOAc (150 mL) was added and the layers were separated. The aqueous layer was extracted with EtOAc (150 mL). The combined organic layers were dried (Na$_2$SO$_4$), filtered, and concentrated. MTBE (150 mL) was added, followed by petroleum ether (150 mL). After stirring for 2 hr, the mixture was filtered and the filtrate was concentrated to give an oil. The crude material was purified by silica gel chromatography to give tert-butyl (R)-(2-hydroxy-6,7,8,9-tetrahydro-5H-benzo[7]annulen-5-yl)carbamate as a white solid (7.8 g, yield: 67%, ee: 98.5%). $^1$H NMR (400 MHz, DMSO-d$_6$) δ: 9.06 (s, 1H), 7.29-7.27 (m, 1H), 6.94 (d, J=8.8 Hz, 1H), 6.49 (s, 2H), 4.48 (m, 1H), 2.65 (br s, 2H), 1.99-1.64 (m, 4H), 1.48-1.25 (m, 11H).

4. Synthesis of (R)-5-((tert-butoxycarbonyl)amino)-6,7,8,9-tetrahydro-5H-benzo[7]annulen-2-yl Trifluoromethanesulfonate

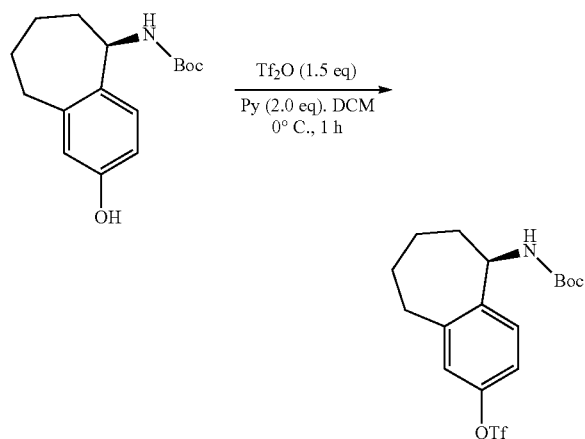

To a solution of tert-butyl (R)-(2-hydroxy-6,7,8,9-tetrahydro-5H-benzo[7]annulen-5-yl)carbamate (1.0 g, 3.6 mmol) and pyridine (570 mg, 7.2 mmol) in DCM (30 mL) was added Tf$_2$O (1.5 g, 5.4 mmol) at 0° C. The mixture was stirred at 0° C. for 1 h. After diluting with water (20 mL), the mixture was extracted with DCM (3×40 mL). The combined organic layers were washed by aq. NaHSO4 (0.5 N, 20 mL) to adjust water layer to pH=5-6, dried (Na$_2$SO$_4$), filtered and concentrated. The crude product was used for next step without further purification. ESI-MS (M+H)$^+$: 410.1. $^1$H NMR (400 MHz, CDCl$_3$) δ: 7.31 (d, J=8.8 Hz, 1H), 7.07-7.00 (m, 2H), 4.93-4.88 (m, 2H), 2.89-2.82 (m, 2H), 1.91-1.68 (m, 6H), 1.45 (s, 9H).

5. Synthesis of tert-butyl (R)-(2-(2-((1-methyl-1H-pyrazol-4-yl)amino)pyrimidin-4-yl)-6,7,8,9-tetrahydro-5H-benzo[7]annulen-5-yl)carbamate

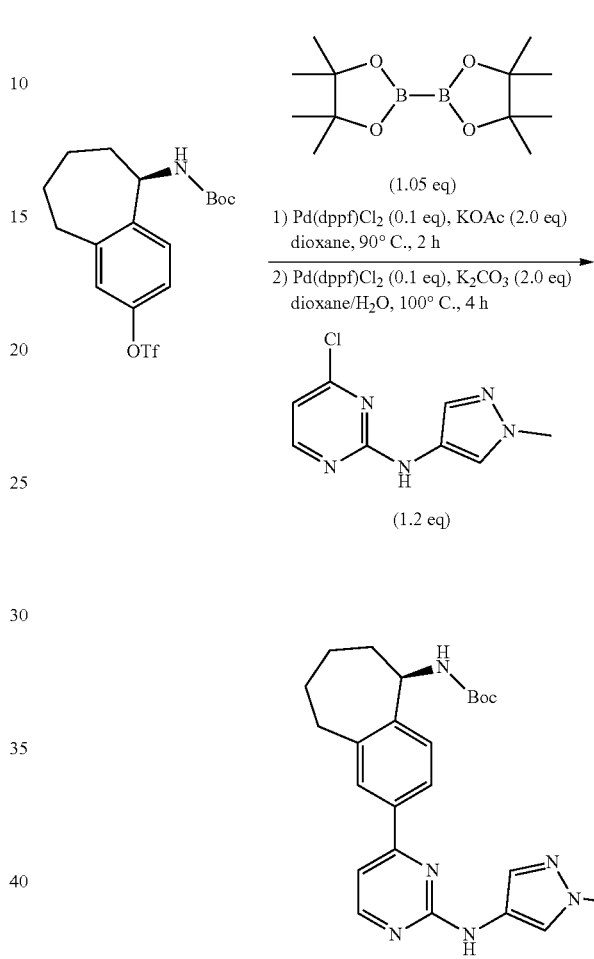

Synthesis of tert-butyl (R)-(2-(2-((1-methyl-1H-pyrazol-4-yl)amino)pyrimidin-4-yl)-6,7,8,9-tetrahydro-5H-benzo[7]annulen-5-yl)carbamate was similar to that of tert-butyl 5-(5-(tert-butyl)-1,2,4-oxadiazole-3-carboxamido)-8-(2-((1-methyl-1H-pyrazol-4-yl)amino)pyrimidin-4-yl)-4,5-dihydro-1H-benzo[c]azepine-2(3H)-carboxylate (Example 2, Step 11). The crude product was purified by silica gel column chromatograph (DCM/MeOH=20:1) to give tert-butyl (R)-(2-(2-((1-methyl-1H-pyrazol-4-yl)amino)pyrimidin-4-yl)-6,7,8,9-tetrahydro-5H-benzo[7]annulen-5-yl)carbamate as a yellow solid (420 mg, yield: 68%). ESI-MS (M+H)$^+$: 435.2. $^1$H NMR (400 MHz, CDCl$_3$) δ: 8.41-8.37 (m, 1H), 7.88-7.77 (m, 3H), 7.55-7.36 (m, 4H), 7.05 (d, J=5.2 Hz, 1H), 5.09-5.01 (m, 1H), 3.90 (s, 3H), 2.93-2.91 (m, 2H), 2.18-2.17 (m, 1H), 1.91-1.82 (m, 5H), 1.28-1.24 (m, 9H).

6. Synthesis of (R)-4-(5-amino-6,7,8,9-tetrahydro-5H-benzo[7]annulen-2-yl)-N-(1-methyl-1H-pyrazol-4-yl)pyrimidin-2-amine

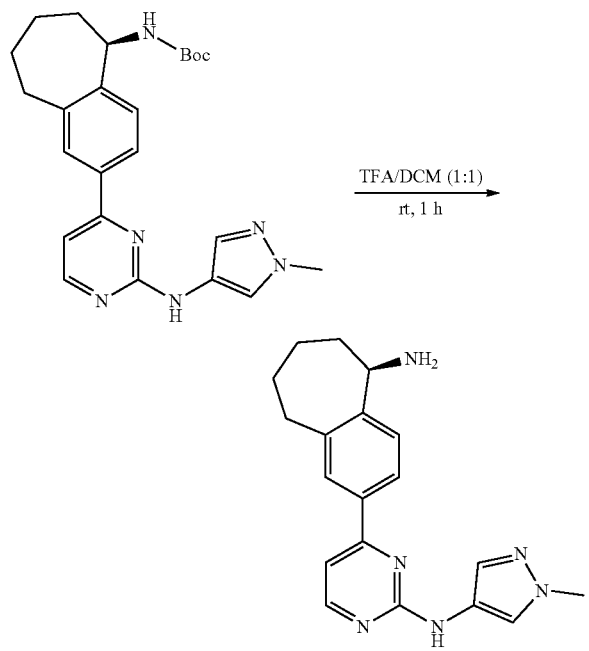

Synthesis of (R)-4-(5-amino-6,7,8,9-tetrahydro-5H-benzo[7]annulen-2-yl)-N-(1-methyl-1H-pyrazol-4-yl)pyrimidin-2-amine was similar to 5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide described in Example 2, Step 12. The crude product was used for next step without further purification. ESI-MS (M+H)$^+$: 335.2.

7. Synthesis of ethyl (Z)-2-amino-2-(((1-methylcyclopropane-1-carbonyl)oxy)imino)acetate

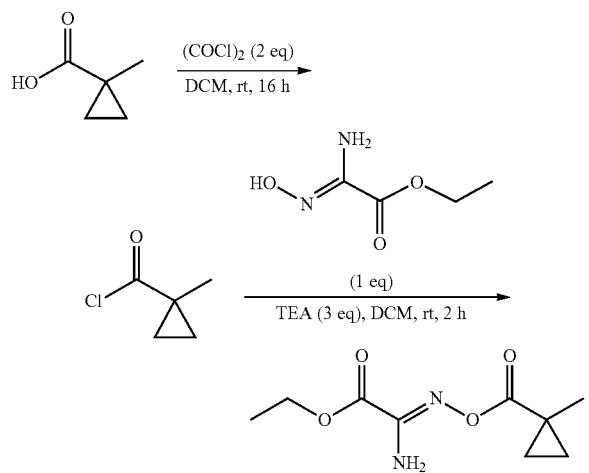

To a solution of 1-methylcyclopropane-1-carboxylic acid (2 g, 20 mmol) in DCM (50 mL) was added (COCl)$_2$ (5 g, 40 mmol). The mixture was stirred at rt for 16 h and then concentrated to give the intermediate acyl chloride. To a solution of ethyl (Z)-2-amino-2-(hydroxyimino)acetate (2.6 g, 20 mmol) and triethylamine (6 g, 60 mmol) in DCM (20 mL) was added a solution of the intermediate acyl chloride in DCM (20 mL). The reaction was stirred at rt for 2 h, washed by water, dried by Na$_2$SO$_4$, concentrated to give ethyl (Z)-2-amino-2-(((1-methylcyclopropane-1-carbonyl)oxy)imino)acetate as a white solid (3.0 g, yield: 63%). ESI-MS (M+H)$^+$: 215.1.

8. Synthesis of ethyl 5-(1-methylcyclopropyl)-1,2,4-oxadiazole-3-carboxylate

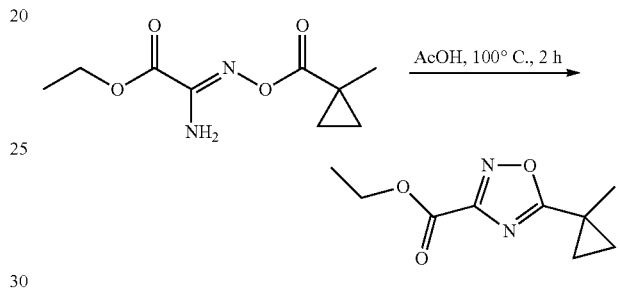

A solution of ethyl (Z)-2-amino-2-(((1-methylcyclopropane-1-carbonyl)oxy)imino)acetate (3.0 g, 14 mmol) in AcOH (20 mL) was stirred at 100° C. for 2 h and then concentrated. The residue was diluted with DCM (20 mL), washed by saturated NaHCO$_3$ solution (3×10 mL), dried over Na$_2$SO$_4$, and concentrated. The residue was purified by silica gel column (petroleum ether:EtOAc=10:1) to give ethyl 5-(1-methylcyclopropyl)-1,2,4-oxadiazole-3-carboxylate as a yellow solid (1.1 g, yield: 52%). ESI-MS (M+H)$^+$: 197.1.

9. Synthesis of potassium 5-(1-methylcyclopropyl)-1,2,4-oxadiazole-3-carboxylate

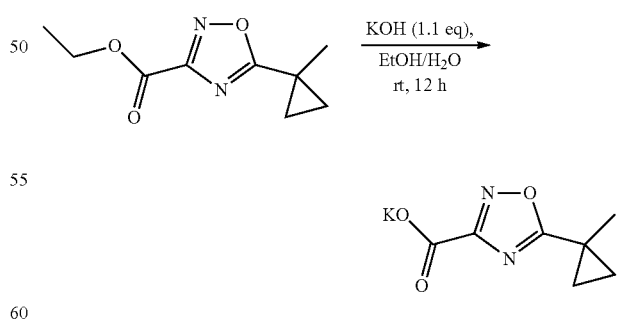

Ethyl 5-(1-methylcyclopropyl)-1,2,4-oxadiazole-3-carboxylate (1.0 g, 5.0 mmol) and KOH (308 mg, 5.5 mmol) was dissolved in EtOH/H$_2$O (4:1, 20 mL). The reaction was stirred at rt for 12 h and then concentrated to give potassium 5-(1-methylcyclopropyl)-1,2,4-oxadiazole-3-carboxylate as a yellow solid (1.1 g, yield: 95%). ESI-MS (M+H)$^+$: 169.1.

10. Synthesis of N-(2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide (I-IM_6)

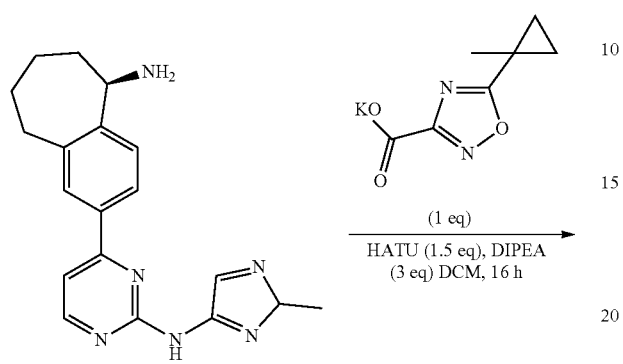

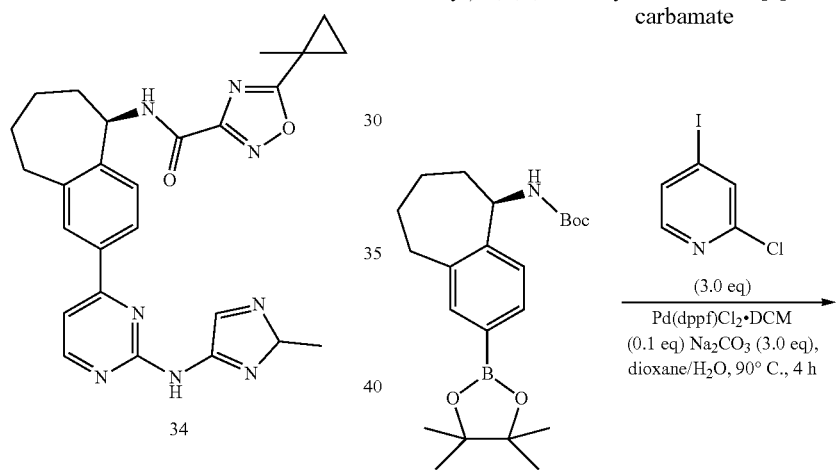

34

To a solution of potassium 5-(1-methylcyclopropyl)-1,2,4-oxadiazole-3-carboxylate (123 mg, 0.6 mmol), DIPEA (232 mg, 0.75 mmol) and HATU (342 mg, 0.9 mmol) in DCM (5 mL) was added (R)-4-(5-amino-6,7,8,9-tetrahydro-5H-benzo[7]annulen-2-yl)-N-(1-methyl-1H-pyrazol-4-yl)pyrimidin-2-amine (150 mg, 0.50 mmol). The mixture was stirred at rt for 1 h. After diluted with water (60 mL), the mixture was extracted with DCM (80 mL×2). The combined organic layers were dried and concentrated. The crude product was purified by prep-HPLC to give (R)—N-(2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide as a white solid (60 mg, yield: 30%). ESI-MS (M+H)$^+$: 485.2. $^1$H NMR (400 MHz, CD$_3$OD) δ: 8.40 (d, J=5.2 Hz, 1H), 7.97 (s, 1H), 7.98-7.93 (m, 2H), 7.66 (s, 1H), 7.39 (d, J=8.4 Hz, 1H), 7.21 (d, J=5.2 Hz, 1H), 5.43 (d, J=10 Hz, 1H), 3.90 (s, 3H), 3.09-3.02 (m, 2H), 2.09-1.86 (m, 5H), 1.64 (s, 3H), 1.54-1.45 (m, 3H), 1.21-1.18 (m, 2H).

Example 35. (R)-5-(tert-butyl)-N-(2-(2-((1-methyl-1H-pyrazol-4-yl)amino)pyridin-4-yl)-6,7,8,9-tetrahydro-5H-benzo[7]annulen-5-yl)-1,2,4-oxadiazole-3-carboxamide (Compound 35)

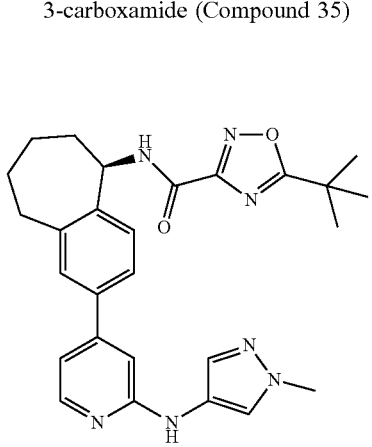

35

I. Synthesis of tert-butyl (R)-(2-(2-chloropyridin-4-yl)-6,7,8,9-tetrahydro-5H-benzo[7]annulen-5-yl)carbamate

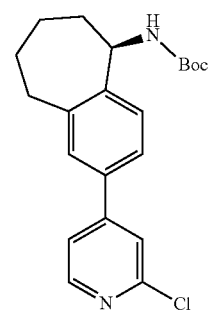

Synthesis of tert-butyl (R)-(2-(2-chloropyridin-4-yl)-6,7,8,9-tetrahydro-5H-benzo[7]annulen-5-yl)carbamate was similar to that of tert-butyl 1-(5-(tert-butyl)-1,2,4-oxadiazole-3-carboxamido)-7-(2-((1-methyl-1H-pyrazol-4-yl)amino)pyrimidin-4-yl)-4,5-dihydro-1H-benzo[d]azepine-3(2H)-carboxylate (Example 1, Step 12). The crude was purified by silica gel column chromatography (MeOH/EtOAc=1/50) to give tert-butyl (R)-(2-(2-chloropyridin-4-yl)-6,7,8,9-tetrahydro-5H-benzo[7]annulen-5-yl)carbamate as a yellow solid (350 mg, yield: 44%). ESI-MS (M+H)$^+$: 373.2.

2. Synthesis of tert-butyl (R)-(2-(2-((1-methyl-1H-pyrazol-4-yl)amino)pyridin-4-yl)-6,7,8,9-tetrahydro-5H-benzo[7]annulen-5-yl)carbamate

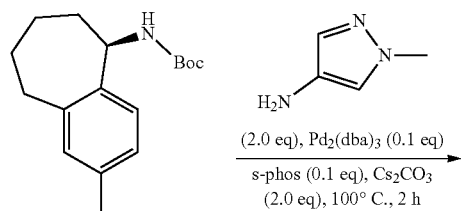

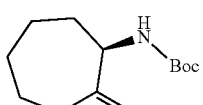

To a solution of tert-butyl (R)-(2-(2-chloropyridin-4-yl)-6,7,8,9-tetrahydro-5H-benzo[7]annulen-5-yl)carbamate (400 mg, 1.1 mmol) in dioxane (20 mL) were added 1-methyl-1H-pyrazol-4-amine (210 mg, 2.1 mmol), Pd$_2$(dba)$_3$ (100 mg, 0.11 mmol), SPhos (45 mg, 0.11 mmol) and Cs$_2$CO$_3$ (680 mg, 2.1 mmol). The mixture was heated to 100° C. for 2 h and concentrated. The crude was purified by silica gel column chromatography (MeOH/EtOAc=1/50) to give tert-butyl (R)-(2-(2-((1-methyl-1H-pyrazol-4-yl)amino)pyridin-4-yl)-6,7,8,9-tetrahydro-5H-benzo[7]annulen-5-yl)carbamate (330 mg, yield: 71%) as a yellow solid. ESI-MS (M+H)$^+$: 434.2.

3. Synthesis of (R)-4-(5-amino-6,7,8,9-tetrahydro-5H-benzo[7]annulen-2-yl)-N-(1-methyl-1H-pyrazol-4-yl)pyridin-2-amine

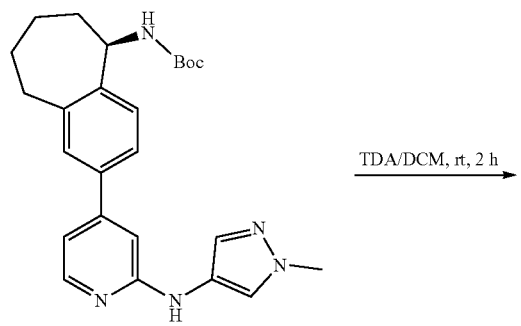

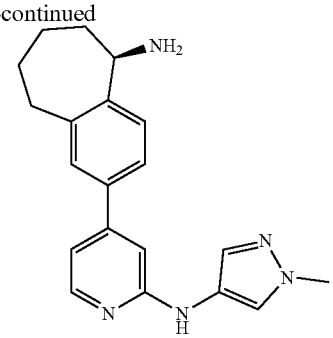

Synthesis of (R)-4-(5-amino-6,7,8,9-tetrahydro-5H-benzo[7]annulen-2-yl)-N-(1-methyl-1H-pyrazol-4-yl)pyridin-2-amine was similar to that of 5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,2,4-oxadiazole-3-carboxamide (Example 1, Step 13). The crude product (R)-4-(5-amino-6,7,8,9-tetrahydro-5H-benzo[7]annulen-2-yl)-N-(1-methyl-1H-pyrazol-4-yl)pyridin-2-amine was obtained as yellow solid (200 mg, yield: 79%). ESI-MS (M+H)$^+$: 334.2.

4. Synthesis of (R)-5-(tert-butyl)-N-(2-(2-((1-methyl-1H-pyrazol-4-yl)amino)pyridin-4-yl)-6,7,8,9-tetrahydro-5H-benzo[7]annulen-5-yl)-1,2,4-oxadiazole-3-carboxamide (I-IM_65)

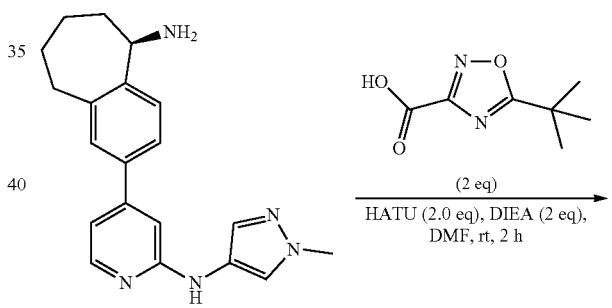

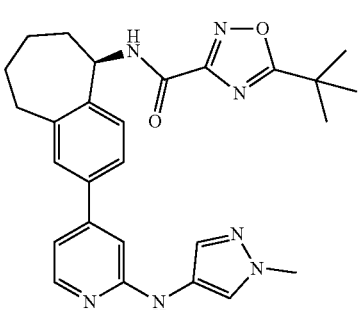

Synthesis of (R)-5-(tert-butyl)-N-(2-(2-((1-methyl-1H-pyrazol-4-yl)amino)pyridin-4-yl)-6,7,8,9-tetrahydro-5H-benzo[7]annulen-5-yl)-1,2,4-oxadiazole-3-carboxamide was similar to N-(2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide described in Example 34, Step 10. The mixture was purified by prep-HPLC (CH$_3$CN/H$_2$O with 0.05% NH$_3$H$_2$O as mobile phase) to give (R)-5-(tert-butyl)-N-(2-(2-((1-methyl-1H-pyrazol-4-yl)amino)pyridin-4-yl)-6,7,8,9-tetrahydro-5H-benzo[7]annulen-5-yl)-1,2,4-oxadiazole-3-carboxamide as yellow solid (100 mg, yield: 88%). ESI-MS (M+H)+: 486.3. 1H NMR (400 MHz, CDCl3) δ: 8.17-8.16 (m, 1H), 7.61 (s, 1H), 7.48 (s, 1H), 7.43-7.41 (m, 1H), 7.36-7.30 (m, 3H), 6.87-6.86 (m, 1H), 6.71 (s, 1H), 6.22-6.18 (m, 1H), 5.44-5.40 (m, 1H), 3.91 (s, 3H), 3.01-2.89 (m, 2H), 2.05-1.93 (m, 4H), 1.82-1.78 (m, 2H), 1.49 (s, 9H).

Example 36. (R)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide (Compound 36a)

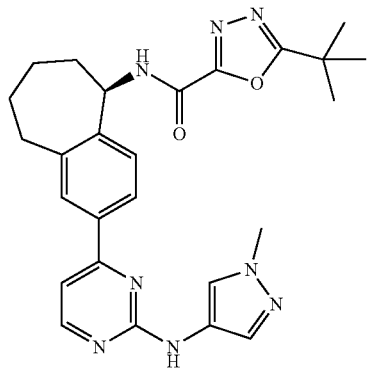 [SMILES: Cn1cc(Nc2nccc(-c3ccc4c(c3)CCCC[C@H]4NC(=O)c3nnc(C(C)(C)C)o3)n2)cn1]

I. Synthesis of (R)-1-(tert-butyl)-N-(8-(2-chloropyrimidin-4-yl)-2,3,4,5-tetrahydro-1H-benzo[c]azepin-5-yl)-1H-1,2,3-triazole-4-carboxamide

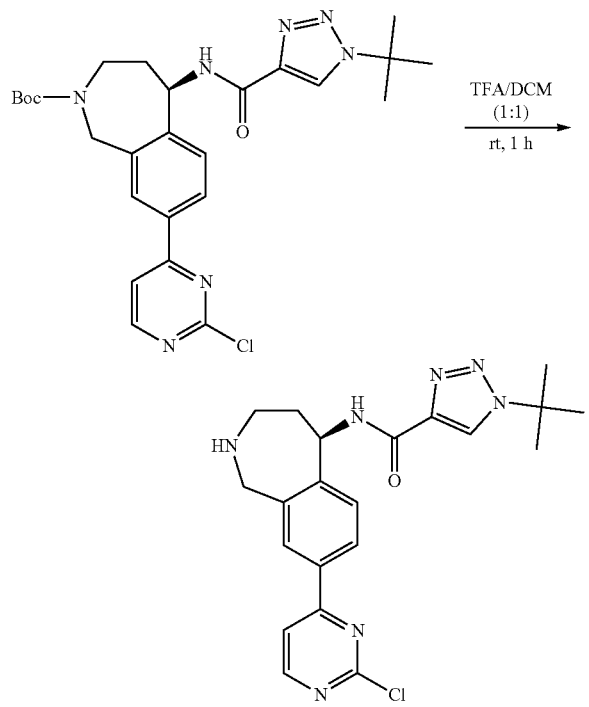

Synthesis of (R)-1-(tert-butyl)-N-(8-(2-chloropyrimidin-4-yl)-2,3,4,5-tetrahydro-1H-benzo[c]azepin-5-yl)-1H-1,2,3-triazole-4-carboxamide was similar to that of (R)-5-(tert-butyl)-N-(8-(2-((1,5-dimethyl-1H-pyrazol-4-yl)amino) pyrimidin-4-yl)-2,3,4,5-tetrahydro-1H-benzo[c]azepin-5-yl)-1,2,4-oxadiazole-3-carboxamide (Example 9, Step 4). The crude product was used for next step without purification. ESI-MS (M+H)+: 427.2.

2. Synthesis of (R)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide (Compound 36a) and (S)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide (Compound 36b)

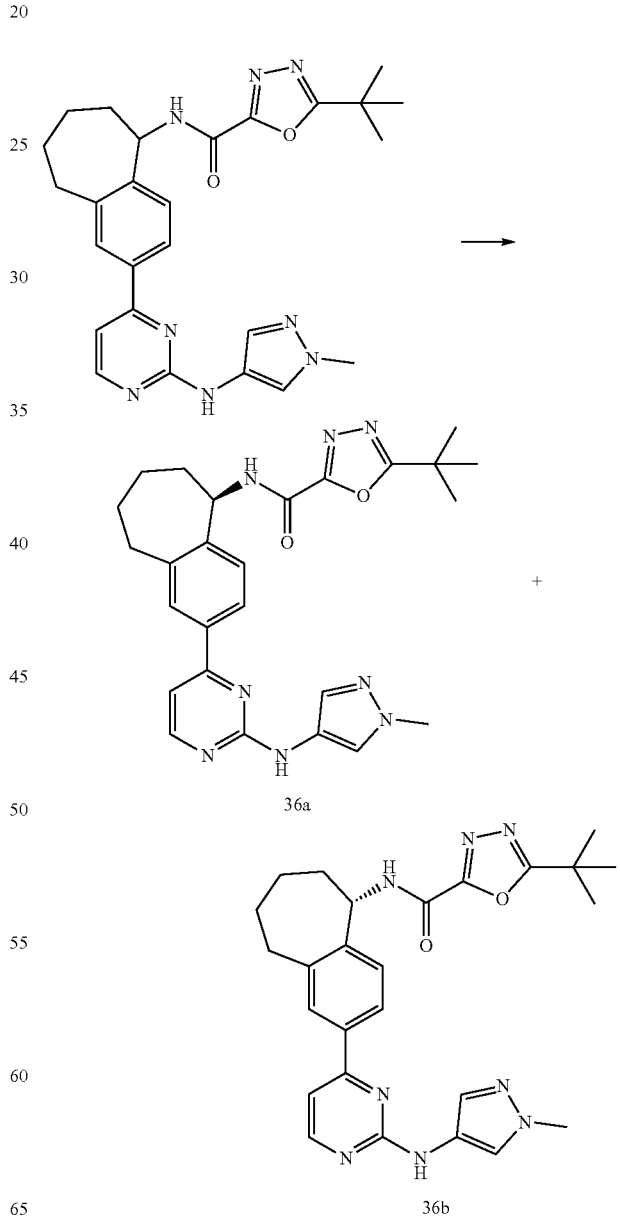

3-tert-Butyl-1,2,4-oxadiazole-5-carboxylic acid {2-[2-(1-methyl-1H-pyrazol-4-ylamino)-pyrimidin-4-yl]-6,7,8,9-tetrahydro-5H-benzocyclohepten-5-yl}-amide (76 mg) was subjected to SFC separation (IA 2×(2×15 cm), 30% ethanol/ $CO_2$, 100 bar, 70 mL/min, 220 nm, inj vol.: 1 mL, 5 mg/mL, ethanol) and yielded 43 mg of peak-1 (chemical purity 99%, ee>99%) and 36 mg of peak-2 (chemical purity 99%, ee>99%).

Peak 1 is assigned as (R)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide: LCMS: Rt 1.23 min, m/z 487.00. $^1$H NMR (400 MHz, METHANOL-d4) δ 8.41 (d, J=5.27 Hz, 1H), 7.96 (d, J=11.80 Hz, 3H), 7.66 (s, 1H), 7.43 (d, J=8.53 Hz, 1H), 7.22 (d, J=5.27 Hz, 1H), 5.43 (d, J=9.29 Hz, 1H), 3.90 (s, 3H), 2.96-3.24 (m, 2H), 1.74-2.25 (m, 5H), 1.51 (s, 9H), 1.28-1.43 (m, 1H).

Peak 2 is assigned as (S)-5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide: LCMS: Rt 1.23 min, m/z 487.00. $^1$H NMR (400 MHz, METHANOL-d4) δ 8.40 (d, J=5.27 Hz, 1H), 7.96 (d, J=12.05 Hz, 3H), 7.66 (s, 1H), 7.43 (d, J=8.53 Hz, 1H), 7.22 (d, J=5.27 Hz, 1H), 5.44 (s, 1H), 3.90 (s, 3H), 2.93-3.21 (m, 2H), 1.78-2.23 (m, 5H), 1.51 (s, 9H), 1.31 (s, 1H).

Example 37. 3-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,2,4-oxadiazole-5-carboxamide (Compound 37)

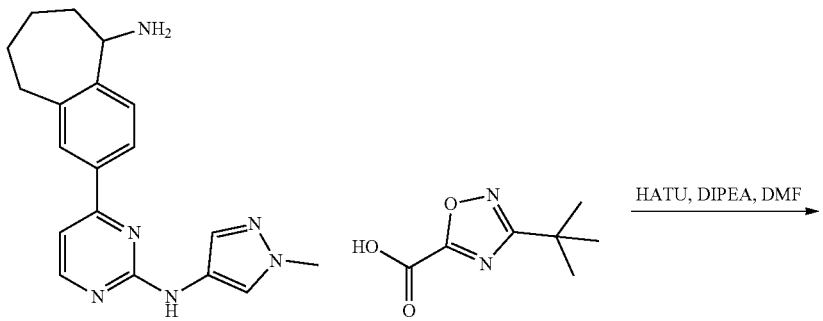

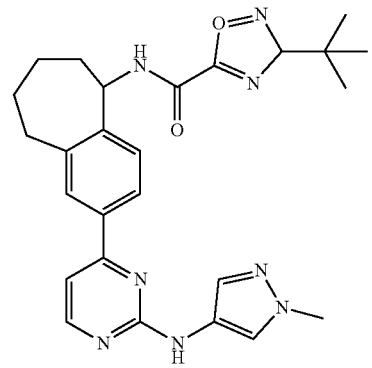

37

To a solution of 3-tert-butyl-1,2,4-oxadiazole-5-carboxylic acid (1.00 mg, 0.60 mmol) and N,N,N',N'-tetramethyl-O-(7-azabenzotriazol-1-yl)uronium hexafluorophosphate (273 mg, 0.72 mmol) and 4-(5-amino-6,7,8,9-tetrahydro-5H-benzo[7]annulen-2-yl)-N-(1-methyl-1H-pyrazol-4-yl)pyrimidin-2-amine (200 mg, 0.6 mmol) in N,N-dimethylformamide (2.3 mL) was added N,N-diisopropylethylamine (0.42 mL, 2.4 mmol). The reaction was stirred at rt overnight and was quenched with MeOH. After workup, prep HPLC gave 3-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,2,4-oxadiazole-5-carboxamide as a solid (186 mg; yield: 64%). LCMS: Rt 1.38 min.; m/z 487.1; $^1$H NMR (400 MHz, METHANOL-d4) δ: 8.29 (br. s., 1H), 7.97-8.09 (m, 2H), 7.94 (s, 1H), 7.68 (br. s., 1H), 7.43 (d, J=8.78 Hz, 2H), 5.41 (d, J=9.79 Hz, 1H), 3.92 (s, 3H), 2.87-3.18 (m, 2H), 1.70-2.29 (m, 5H), 1.45 (s, 10H).

Example 38: 5-(tert-butyl)-N-(8-(2-((1-methyl-1H-pyrazol-4-yl)amino)pyrimidin-4-yl)-2,3,4,5-tetrahydrobenzo[b]oxepin-5-yl)-1,3,4-oxadiazole-2-carboxamide (Compound 38)

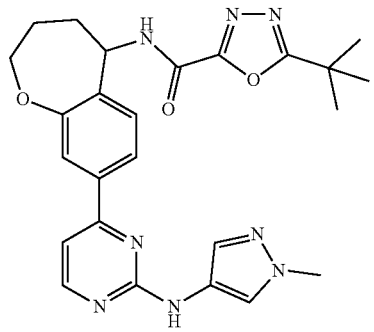 [SMILES: Cn1cc(Nc2nccc(-c3ccc4c(c3)OCCCC4NC(=O)c3noc(C(C)(C)C)n3)n2)cn1]

I. Synthesis of methyl 4-(3-bromophenoxy)butanoate

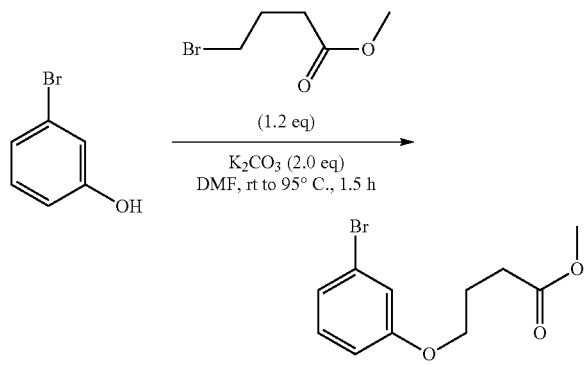

To a solution of 3-bromophenol (3.44 g, 20.0 mmol) and methyl 4-bromobutanoate (4.32 g, 24.0 mmol) in DMF (20 mL) was added K$_2$CO$_3$ (5.52 g, 40.0 mmol). The mixture was stirred at rt for 0.5 h and then heated with stirring at 90° C. for 1 h. After diluting with EtOAc (200 mL), the mixture was washed with water (3×50 mL), dried and concentrated. The crude product was purified by silica gel column chromatograph (petroleum/EtOAc=10:1) to give methyl 4-(3-bromophenoxy)butanoate as a white liquid (5.2 g, yield: 96%). ESI-MS (M+H)$^+$: 273.1.

2. Synthesis of 4-(3-bromophenoxy)butanoic Acid

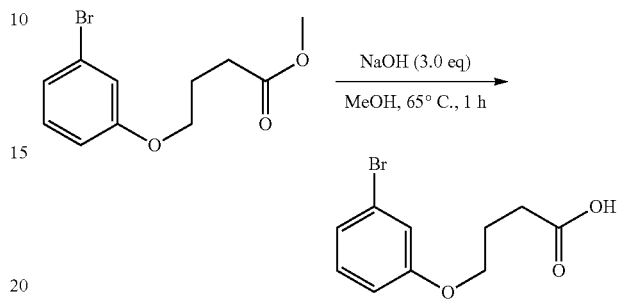

To a solution of methyl 4-(3-bromophenoxy)butanoate (4.9 g, 19 mmol) in MeOH (40 mL) and H$_2$O (40 mL) was added NaOH (2.3 g, 57 mmol). The reaction mixture was stirred at 65° C. for 1 h. Then the solvent was concentrated under reduced pressure. The residue was adjusted to pH=3 with HCl (1 N). The mixture was extracted with EtOAc (3×100 mL×3). The organic layers were dried over sodium sulfate and concentrated under reduced pressure to give 4-(3-bromophenoxy)butanoic acid (4.8 g, yield: 98%). The crude product was used in next step without further purification. ESI-MS (M+H)$^+$: 259.1. $^1$H NMR (400 MHz, CDCl$_3$) δ: 7.24-7.20 (m, 1H), 7.10-7.08 (m, 2H), 6.93 (d, J=9.6 Hz, 1H), 3.97 (t, J=6.4 Hz, 2H), 2.35 (t, J=7.2 Hz, 2H), 1.92-1.88 (m, 2H).

3. Synthesis of 8-bromo-3,4-dihydrobenzo[b]oxepin-5(2H)-one

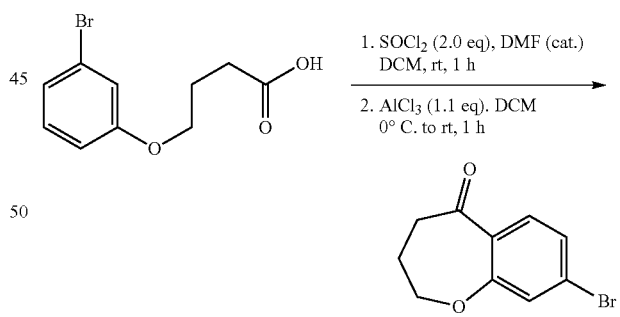

To a solution of 4-(3-bromophenoxy)butanoic acid (1.82 g, 7.04 mmol) in DCM (35 mL) was added SOCl$_2$ (1.67 g, 14 mmol) and DMF (cat.). The reaction mixture was stirred at 40° C. for 1 h. Then the solvent was removed under reduced pressure, dried in vacuo for 2 h. The residue was dissolved in DCM (35 mL) and cooling down with an ice bath. AlCl$_3$ (1.02 g, 80 mmol) was added and the mixture was stirred at 0° C.—rt for 12 h. The mixture was poured into con. HCl (10 mL) and extracted with EtOAc (2×50 mL). The organic layers were washed with water (50 mL), brine (50 mL) and dried over sodium sulfate. After concentration under reduced pressure, the crude product was purified by silica gel column chromatograph (petroleum ether/EtOAc=4:1) to give 8-bromo-3,4-dihydrobenzo[b]oxepin-5(2H)-one as a white solid (1.2 g, yield: 71%). ESI-MS (M+H)⁺: 241.1. ¹H NMR (400 MHz, CDCl₃) δ: 7.64 (d, J=8.8 Hz, 1H), 7.27-7.23 (m, 2H), 4.25 (t, J=6.8 Hz, 2H), 2.89 (t, J=7.2 Hz, 2H), 2.25-2.18 (m, 2H).

4. Synthesis of 8-bromo-2,3,4,5-tetrahydrobenzo[b]oxepin-5-amine

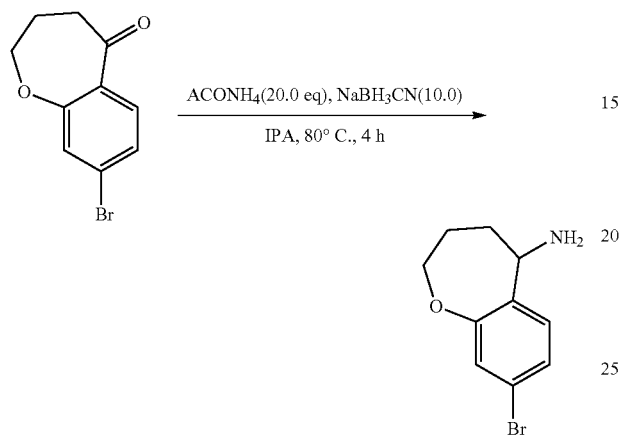

To a mixture of 8-bromo-3,4-dihydrobenzo[b]oxepin-5(2H)-one (1.2 g, 5.0 mmol) in i-PrOH (50 mL), NH₄OAc (7.63 g, 100 mmol) and NaBH₃CN (3.15 g, 50 mol) was added. The mixture was stirred at 80° C. for 4 h. After cooling down, the mixture was basified to pH>12 with NaOH (1 N). The mixture was extracted with DCM (250 mL×2). The combined organic layers were dried and concentrated. The resulting residue was purified by silica gel column (DCM:MeOH=20:1) to give 8-bromo-2,3,4,5-tetrahydrobenzo[b]oxepin-5-amine as a white solid (900 mg, yield: 75%) was obtained. ESI-MS (M+H—NH₃)⁺: 225.1.

5. Synthesis of N-(8-bromo-2,3,4,5-tetrahydrobenzo[b]oxepin-5-yl)-5-(tert-butyl)-1,3,4-oxadiazole-2-carboxamide

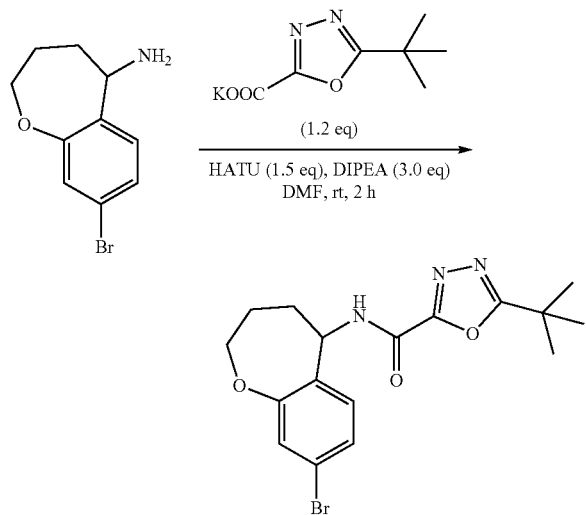

To a solution of 8-bromo-2,3,4,5-tetrahydrobenzo[b]oxepin-5-amine (500 mg, 2.23 mmol, 1.0 eq) in DMF (20 mL), potassium 5-tert-butyl-1,3,4-oxadiazole-2-carboxylate (557 mg, 2.68 mmol, 1.2 eq), HATU (1.3 g, 3.35 mmol, 1.5 eq) and triethylamine (863 mg, 6.69 mmol, 3.0 eq) were added. The mixture was stirred at rt for 2 h. The solution was diluted with EtOAc (150 mL) and washed with water (50 mL), brine (2×50 mL). The organic layer was dried (Na₂SO₄), filtered, and concentrated via rotary evaporator. The residue was purified by reverse phase chromatography (CH₃CN/H₂O with 0.05% NH₃.H₂O as mobile phase) to give N-(8-bromo-2,3,4,5-tetrahydrobenzo[b]oxepin-5-yl)-5-(tert-butyl)-1,3,4-oxadiazole-2-carboxamide (210 mg, yield: 30%) as a slight yellow solid. ESI-MS (M+H)⁺: 394.1.

6. The Preparation of 5-(tert-butyl)-N-(8-(2-((1-methyl-1H-pyrazol-4-yl)amino)pyrimidin-4-yl)-2,3,4,5-tetrahydrobenzo[b]oxepin-5-yl)-1,3,4-oxadiazole-2-carboxamide

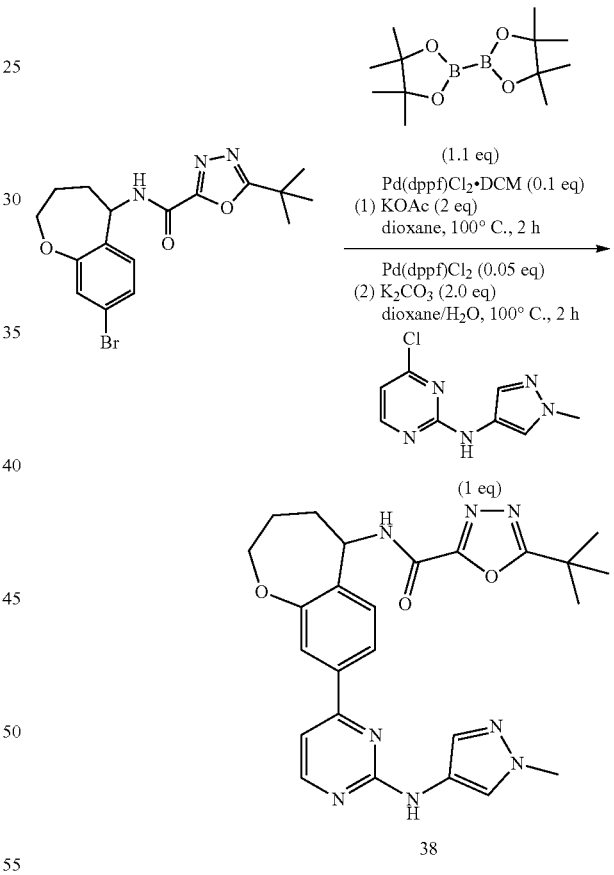

38

To a mixture of N-(8-bromo-2,3,4,5-tetrahydrobenzo[b]oxepin-5-yl)-5-(tert-butyl)-1,3,4-oxadiazole-2-carboxamide (393 mg, 1.00 mmol) and PinB-BPin (263 mg, 1.1 mmol) in dry 1,4-dioxane (10 mL), KOAc (196 mg, 2.0 mmol), Pd(dppf)Cl₂.DCM (81 mg, 0.1 mmol) was added under N₂. The mixture was stirred at 100° C. for 2 h under N₂. After cooling down, 4-chloro-N-(1-methyl-1H-pyrazol-4-yl)pyrimidin-2-amine (209 mg, 1.0 mmol), K₂CO₃ (276 mg, 2.0 mmol) and H₂O (2.5 mL) was added. The mixture was stirred at 100° C. for 2 h under N₂. After cooling down, the mixture was concentrated and purified silica gel column chromatograph (DCM/MeOH=20:1) to give 5-(tert-butyl)-N-(8-(2-((1-methyl-1H-pyrazol-4-yl)amino)pyrimidin-4-yl)-2,3,4,5-tetrahydrobenzo[b]oxepin-5-yl)-1,3,4-oxadiazole-2-carboxamide as yellow solid (50 mg, yield: 21%). ESI-MS (M+H)⁺: 489.2. ¹H NMR (400 MHz, CD₃OD) δ: 8.26 (d, J=5.2 Hz, 1H), 7.82 (s, 1H), 7.69-7.64 (m, 2H), 7.51 (s, 1H), 7.29 (d, J=8.0 Hz, 1H), 7.02 (d, J=5.2 Hz, 1H), 5.35-5.32 (m, 1H), 4.14-4.10 (m, 1H), 3.83-3.80 (m, 1H), 3.76 (s, 3H), 2.00-1.98 (m, 4H), 1.36 (s, 9H).

Example 39. Synthesis of 5-(tert-butyl)-N-(8-(2-((1-methyl-1H-pyrazol-4-yl)amino)pyrimidin-4-yl)-2,3,4,5-tetrahydrobenzo[b]oxepin-5-yl)-1,2,4-oxadiazole-2-carboxamide (Compound 39)

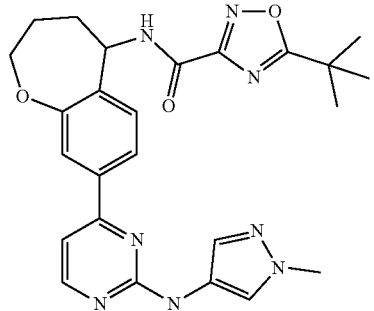

I. Synthesis of N-(8-bromo-2,3,4,5-tetrahydrobenzo[b]oxepin-5-yl)-5-(tert-butyl)-1,2,4-oxadiazole-2-carboxamide

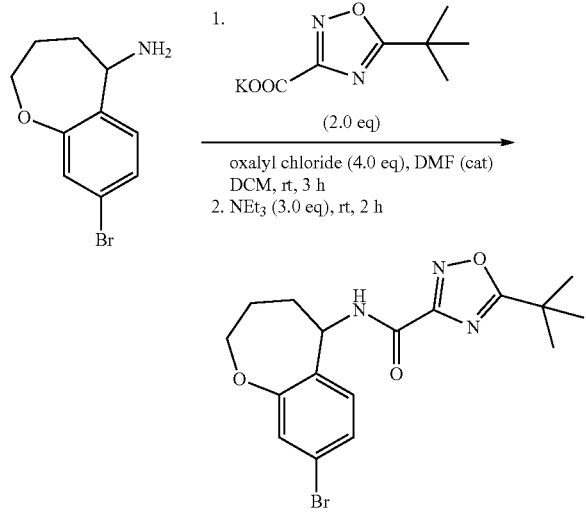

Synthesis of N-(8-bromo-2,3,4,5-tetrahydrobenzo[b]oxepin-5-yl)-5-(tert-butyl)-1,2,4-oxadiazole-3-carboxamide was similar to that of tert-butyl (R)-8-bromo-5-(5-(tert-butyl)-1,2,4-oxadiazole-3-carboxamido)-1,3,4,5-tetrahydro-2H-benzo[c]azepine-2-carboxylate in Example 2, Method 2, Step 2. The crude material was purified by silica gel chromatography (PE:EtOAc=3:1) to give N-(8-bromo-2,3,4,5-tetrahydrobenzo[b]oxepin-5-yl)-5-(tert-butyl)-1,2,4-oxadiazole-2-carboxamide (610 mg, yield: 85%) as a slight yellow solid. ESI-MS (M+H)⁺: 394.1.

2. The Preparation of 5-(tert-butyl)-N-(8-(2-((1-methyl-1H-pyrazol-4-yl)amino)pyrimidin-4-yl)-2,3,4,5-tetrahydrobenzo[b]oxepin-5-yl)-1,2,4-oxadiazole-2-carboxamide

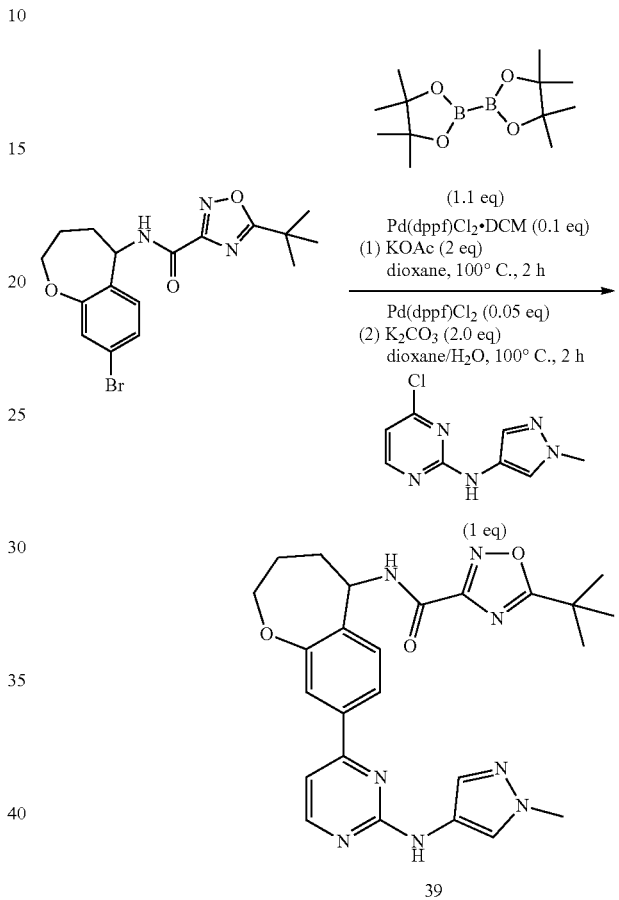

To a mixture of N-(8-bromo-2,3,4,5-tetrahydrobenzo[b]oxepin-5-yl)-5-(tert-butyl)-1,2,4-oxadiazole-2-carboxamide (135 mg, 0.34 mmol) and PinB-BPin (96 mg, 0.38 mmol) in dry 1,4-dioxane (3 mL), KOAc (68 mg, 0.69 mmol), Pd(dppf)Cl₂.DCM (24 mg, 0.03 mmol) was added under N₂. The mixture was stirred at 100° C. for 2 h under N₂. After cooling down, 4-chloro-N-(1-methyl-1H-pyrazol-4-yl)pyrimidin-2-amine (71 mg, 0.34 mmol), K₂CO₃ (95 mg, 0.69 mmol) and H₂O (0.8 mL) was added. The mixture was stirred at 100° C. for 2 h under N₂. After cooling down, the mixture was concentrated and purified by silica gel chromatography (DCM:MeOH=20:1) to give 5-(tert-butyl)-N-(8-(2-((1-methyl-1H-pyrazol-4-yl)amino)pyrimidin-4-yl)-2,3,4,5-tetrahydrobenzo[b]oxepin-5-yl)-1,2,4-oxadiazole-2-carboxamide as yellow solid (77 mg, yield: 46%). ESI-MS (M+H)⁺: 489.2. ¹H NMR (400 MHz, CD₃OD) δ: 8.35 (d, J=5.2 Hz, 1H), 7.91 (s, 1H), 7.78-7.73 (m, 2H), 7.62 (s, 1H), 7.38 (d, J=8.4 Hz, 1H), 7.10 (d, J=5.6 Hz, 1H), 5.46-5.44 (m, 1H), 4.18-4.15 (m, 1H), 3.98-3.95 (m, 1H), 3.86 (s, 3H), 2.10-2.02 (m, 4H), 1.48 (s, 9H).

Example 40. 5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,3,4-oxadiazole-2-carboxamide (Compound 40)

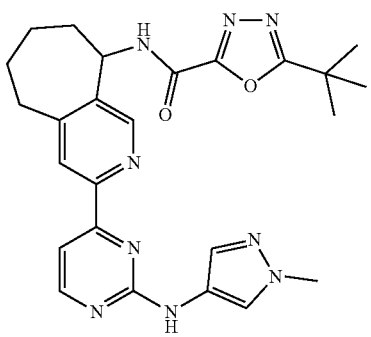

I. Synthesis of 3-chlorocyclohept-2-en-1-one

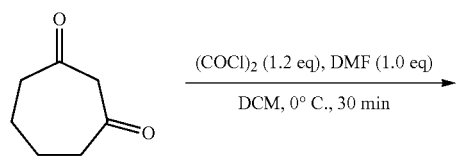

To a solution of cycloheptane-1,3-dione (20.0 g, 0.16 mol) and DMF (11.6 g, 0.16 mol) in DCM (500 mL) was added oxalyl chloride (24.4 g, 0.19 mol) dropwise at 0° C. After stirring at 0° C. for 30 min, the reaction mixture was washed with water (3×500 mL). The aqueous phase was then extracted with diethyl ether (4×300 mL). The combined DCM and diethyl ether phases were dried over MgSO$_4$ and concentrated to yield 3-chlorocyclohept-2-en-1-one (crude 22.8 g, used for next step) as a brown oil. ESI-MS (M+H)$^+$: 145.1.

2. Synthesis of 2-cyano-2-(3-oxocyclohept-1-en-1-yl)acetamide

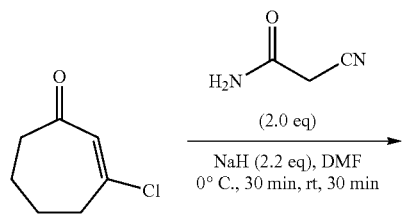

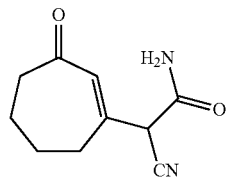

To a solution of 2-cyanoacetamide (26.9 g, 0.32 mol) in DMF (300 mL) was added NaH (60 percent in mineral oil, 14.1 g, 0.35 mol) in one portion at 0° C. After stirring at 0° C. for 30 min, a solution of 3-chlorocyclohept-2-en-1-one (22.8 g, 0.16 mol) in DMF (100 mL) was added dropwise. The reaction mixture was stirred at room temperature for 30 min and DMF was removed under reduced pressure. The residue was dissolved in water (350 mL). The solution was washed with ethyl acetate (4×150 mL), adjusted with 3.0 N aqueous HCl to pH 2-3 and extracted with 10% MeOH/DCM (6×300 mL). The latter combined extracts were dried over MgSO$_4$ and concentrated. The crude product was purified by silica gel column chromatography (EtOAc/petroleum ether=4:1) to give 2-cyano-2-(3-oxocyclohept-1-en-1-yl)acetamide as yellow oil (22.0 g, yield: 73% for two steps). ESI-MS (M+H)$^+$: 193.1.

3. Synthesis of 3,9-dioxo-3,5,6,7,8,9-hexahydro-2H-cyclohepta[c]pyridine-4-carbonitrile

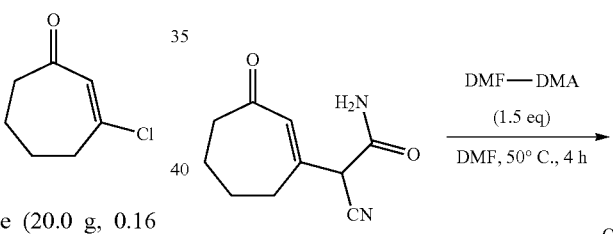

To a solution of 2-cyano-2-(3-oxocyclohept-1-en-1-yl)acetamide (22.0 g, 0.11 mol) in DMF (150 mL) was added DMF-DMA (22.8 mL, 0.17 mol) dropwise over 0.5 h. The reaction mixture was stirred at 50° C. for 4 h and concentrated under reduced pressure. The resulting brown oil was dissolved in aqueous NaOH (1.0 N, 200 mL), washed with chloroform (5×150 mL) and acidified with HCl (6.0 N) slowly at 0° C. to pH 2-3. The brown solid, 3,9-dioxo-3,5,6,7,8,9-hexahydro-2H-cyclohepta[c]pyridine-4-carbonitrile (17.0 g, yield: 74%), was collected by filtration and dried in vacuo. ESI-MS (M+H)$^+$: 203.1. $^1$H NMR (400 MHz, CDCl$_3$) δ: 8.16 (s, 1H), 3.17-3.14 (m, 2H), 2.77-2.74 (m, 2H), 2.04-2.00 (m, 2H), 1.90-1.87 (m, 2H).

4. Synthesis of 5,6,7,8-tetrahydro-2H-cyclohepta[e]pyridine-3,9-dione

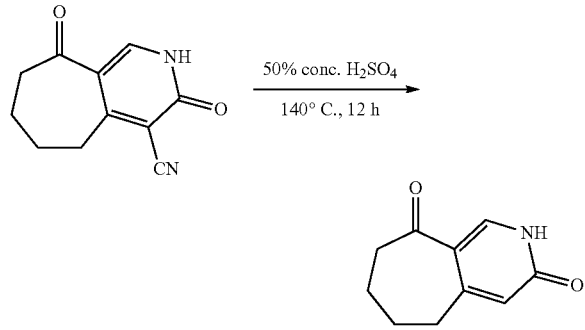

A solution of 3,9-dioxo-3,5,6,7,8,9-hexahydro-2H-cyclohepta[c]pyridine-4-carbonitrile (17.0 g, 0.084 mol) in 50 percent conc. sulfuric acid (100 mL) was stirred at 140° C. for 12 h. The reaction mixture was neutralized with 50 percent sodium hydroxide slowly at 0° C. to pH 7-8. The water was removed under reduced pressure. The residue was dissolved into warm chloroform and an insoluble solid was removed by filtration. The filtrate was concentrated and purified by silica gel column chromatograph (DCM/MeOH=20:1) to give 5,6,7,8-tetrahydro-2H-cyclohepta[c]pyridine-3,9-dione as a yellow solid (9.5 g, yield: 63%). ESI-MS (M+H)$^+$: 178.1.

5. Synthesis of 9-amino-2,5,6,7,8,9-hexahydro-3H-cyclohepta[e]pyridin-3-one

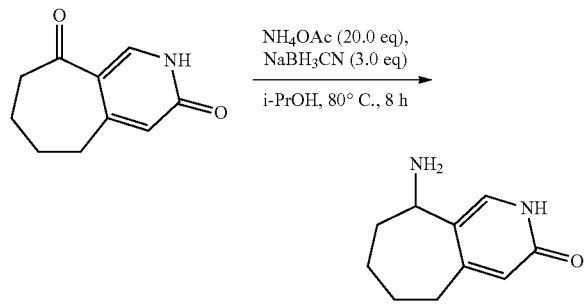

A mixture of 5,6,7,8-tetrahydro-2H-cyclohepta[c]pyridine-3,9-dione (7.0 g, 39.5 mmol), NH$_4$OAc (60.8 g, 790.0 mmol), and NaBH$_3$CN (7.4 g, 118.5 mmol) in i-PrOH (150 mL) was heated to 80° C. for 8 h and cooled to rt. The solution was used for next step without purification. ESI-MS (M+H)$^+$: 179.2.

6. Synthesis of tert-butyl (3-oxo-3,5,6,7,8,9-hexahydro-2H-cyclohepta[e]pyridin-9-yl)carbamate

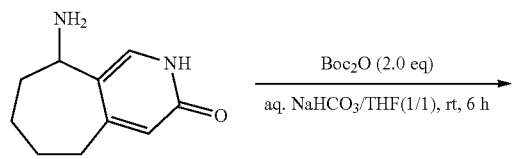

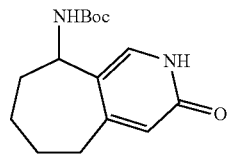

To the previous solution was added NaHCO$_3$ (aq, 50 mL), THF (50 mL) and Boc$_2$O (17.2 g, 79.0 mmol). The mixture was stirred at rt for 6 h. After concentration and diluting with water (100 mL), the mixture was extracted with DCM (3×200 mL). The combined organic layers were washed with brine (200 mL), dried (Na$_2$SO$_4$), filtered and concentrated. The crude product was purified by silica gel column chromatograph (DCM/MeOH=20:1) to give tert-butyl (3-oxo-3,5,6,7,8,9-hexahydro-2H-cyclohepta[c]pyridin-9-yl)carbamate as yellow solid (6.2 g, yield: 56% for two steps). ESI-MS (M+H)$^+$: 279.2. $^1$H NMR (400 MHz, CDCl$_3$) δ: 7.25 (s, 1H), 6.35 (s, 1H), 5.30 (brs, 1H), 2.65-2.63 (m, 2H), 1.86-1.76 (m, 4H), 1.45 (s, 9H), 1.39-1.35 (m, 2H).

7. Synthesis of 9-((tert-butoxycarbonyl)amino)-6,7,8,9-tetrahydro-5H-cyclohepta[c]pyridin-3-yl trifluoromethanesulfonate To a solution of tert-butyl (3-oxo-3,5,6,7,8,9-hexahydro-2H-cyclohepta[c]pyridin-9-yl)carbamate (6.2 g, 22.3 mmol) and triethylamine (6.8 g, 66.9 mmol) in DCM (150 mL) at 0° C. was added Tf$_2$O (9.4 g, 33.5 mmol) dropwise. The mixture was stirred for 1 h. The solution was diluted with water (150 mL), extracted with DCM (2×200 mL). The combined organic layers were washed with brine, dried over Na$_2$SO$_4$, filtered, and concentrated. The crude product was purified by silica gel column chromatograph (petroleum ether/EtOAc=4:1) to give 9-((tert-butoxycarbonyl)amino)-6,7,8,9-tetrahydro-5H-cyclohepta[c]pyridin-3-yl trifluoromethanesulfonate as a yellow solid (5.7 g, Y: 63%). ESI-MS (M+H)$^+$: 411.1.

8. Synthesis of tert-butyl (3-(1-ethoxyvinyl)-6,7,8,9-tetrahydro-5H-cyclohepta[c]pyridin-9-yl)carbamate

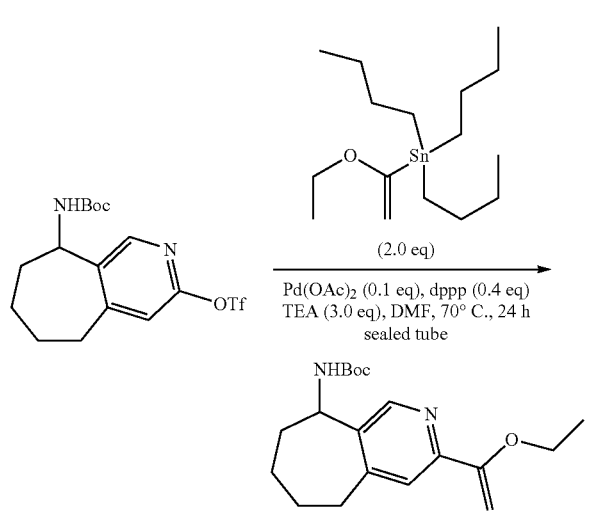

A mixture of 9-((tert-butoxycarbonyl)amino)-6,7,8,9-tetrahydro-5H-cyclohepta[c]pyridin-3-yl trifluoromethanesulfonate (2.4 g, 5.85 mmol), tributyl(1-ethoxyvinyl)stannane (4.3 g, 11.7 mmol), triethylamine (1.8 g, 17.6 mmol), Pd(OAc)$_2$ (131 mg, 0.58 mmol) and dppp (903 mg, 2.34 mmol) in 50 mL DMF was stirred at 70° C. for 2 h under nitrogen in sealed tube. The mixture was diluted with EtOAc (200 mL) and washed with water (3×100 mL). The organic phase was dried with Na$_2$SO$_4$ and concentrated. The crude product was purified by silica gel column chromatograph (petroleum ether/EtOAc=4:1) to give tert-butyl (3-(1-ethoxyvinyl)-6,7,8,9-tetrahydro-5H-cyclohepta[c]pyridin-9-yl)carbamate as a yellow solid (1.0 g, yield: 51%). ESI-MS (M+H)$^+$: 333.2.

9. Synthesis of 1-(9-amino-6,7,8,9-tetrahydro-5H-cyclohepta[c]pyridin-3-yl)ethan-1-one

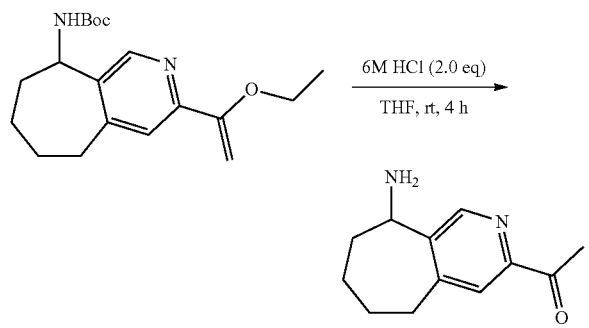

To a solution of tert-butyl (3-(1-ethoxyvinyl)-6,7,8,9-tetrahydro-5H-cyclohepta[c]pyridin-9-yl)carbamate (1.0 g, 3.0 mmol) in THF (30 mL) was added HCl (1 mL, 6.0 mmol) dropwise. The mixture was stirred at rt for 1 h. The solution was used for next step without purification. ESI-MS (M+H)$^+$: 205.1.

10. Synthesis of tert-butyl (3-acetyl-6,7,8,9-tetrahydro-5H-cyclohepta[c]pyridin-9-yl)carbamate

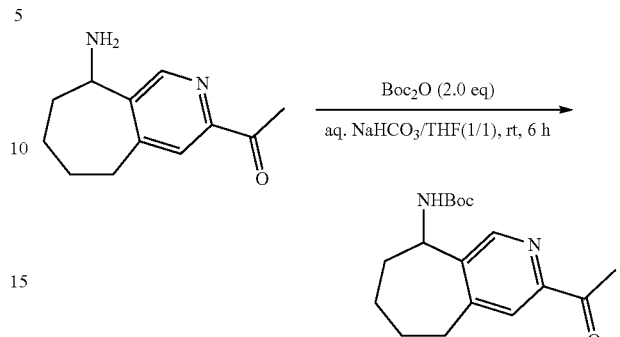

Synthesis of tert-butyl (3-acetyl-6,7,8,9-tetrahydro-5H-cyclohepta[c]pyridin-9-yl)carbamate was similar to that of tert-butyl (3-oxo-3,5,6,7,8,9-hexahydro-2H-cyclohepta[c]pyridin-9-yl)carbamate (Example 40, Step 6). The crude product was purified by silica gel column chromatograph (petroleum ether/EtOAc=4:1) to give tert-butyl (3-acetyl-6,7,8,9-tetrahydro-5H-cyclohepta[c]pyridin-9-yl)carbamate as a yellow solid (550 mg, yield: 60% for two steps). ESI-MS (M+H)$^+$: 305.2. $^1$H NMR (400 MHz, CDCl$_3$) δ: 8.54 (s, 1H), 7.78 (s, 1H), 4.99-4.97 (m, 2H), 2.91-2.90 (m, 2H), 2.70 (s, 3H), 1.94-1.74 (m, 4H), 1.62-1.60 (m, 2H), 1.45 (s, 9H).

11. Synthesis of tert-butyl (3-(3-(dimethylamino)acryloyl)-6,7,8,9-tetrahydro-5H-cyclohepta[c]pyridin-9-yl)carbamate

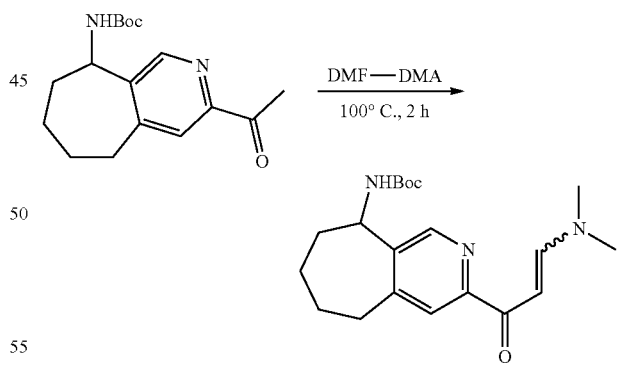

A solution of tert-butyl (3-acetyl-6,7,8,9-tetrahydro-5H-cyclohepta[c]pyridin-9-yl)carbamate (550 mg, 1.8 mmol) in DMF-DMA (10 mL) was stirred at 100° C. for 2 h. After concentration, the crude product was purified by reversed phase HPLC (CH$_3$CN/0.05% NH$_3$.H$_2$O in water) to give tert-butyl (3-(3-(dimethylamino)acryloyl)-6,7,8,9-tetrahydro-5H-cyclohepta[c]pyridin-9-yl)carbamate (380 mg, yield: 61%). ESI-MS (M+H)$^+$: 360.2.

12. Synthesis of 1-(1-methyl-1H-pyrazol-4-yl)guanidine Hydrochloride

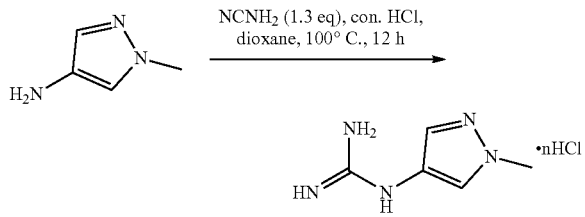

To a solution of 1-methyl-1H-pyrazol-4-amine (500 mg, 5 mmol, 1.0 eq) in dioxane (10 mL) was added cyanamide (273 g, 6.5 mmol, 1.3 eq) and conc. HCl (1 mL). The reaction was stirred at 100° C. for 12 h. The solvent was removed under reduced pressure. The residue was recrystallized from the co-solvent of MeOH and Et$_2$O. 1-(1-methyl-1H-pyrazol-4-yl)guanidine hydrochloride (600 mg, yield: 55%) was obtained as a yellow solid. ESI-MS (M+H)$^+$: 140.1. $^1$H NMR (400 MHz, CD$_3$OD) δ: 7.78 (s, 1H), 7.48 (s, 1H), 3.91 (s, 3H).

13. Synthesis of tert-butyl (3-(2-((1-methyl-1H-pyrazol-4-yl)amino)pyrimidin-4-yl)-6,7,8,9-tetrahydro-5H-cyclohepta[c]pyridin-9-yl)carbamate

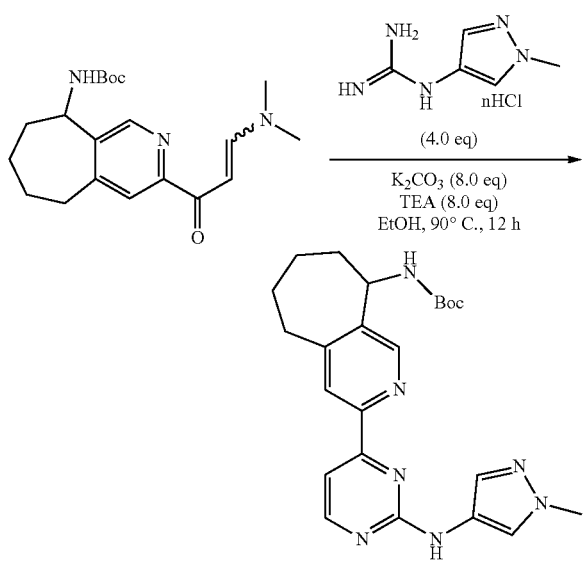

A mixture of 1-(1-methyl-1H-pyrazol-4-yl)guanidine hydrochloride (588 mg, 4.23 mmol), K$_2$CO$_3$ (1.2 g, 8.46 mmol), and triethylamine (855 mg, 8.46 mmol) in EtOH (10 mL) was stirred at rt for 1 h, then tert-butyl (3-(3-(dimethylamino)acryloyl)-6,7,8,9-tetrahydro-5H-cyclohepta[c]pyridin-9-yl)carbamate (380 mg, 1.06 mmol) was added and the mixture was heated to 90° C. for 12 h. After concentration, the crude product was purified by reversed phase HPLC (CH$_3$CN/0.05% NH$_3$.H$_2$O in water) to give tert-butyl (3-(2-((1-methyl-1H-pyrazol-4-yl)amino)pyrimidin-4-yl)-6,7,8,9-tetrahydro-5H-cyclohepta[c]pyridin-9-yl)carbamate (240 mg, yield: 52%). ESI-MS (M+H)$^+$: 436.2. $^1$H NMR (400 MHz, CDCl$_3$) δ: 8.57 (s, 1H), 8.50 (d, J=5.2 Hz, 1H), 8.08 (s, 1H), 7.85 (s, 1H), 7.66 (d, J=5.6 Hz, 1H), 7.60 (s, 1H), 6.92 (s, 1H), 5.00 (br, 2H), 3.92 (s, 3H), 2.97-2.90 (m, 2H), 2.01-1.82 (m, 5H), 1.51-1.46 (m, 10H).

14. Synthesis of 3-(2-((1-methyl-1H-pyrazol-4-yl)amino)pyrimidin-4-yl)-6,7,8,9-tetrahydro-5H-cyclohepta[c]pyridin-9-amine

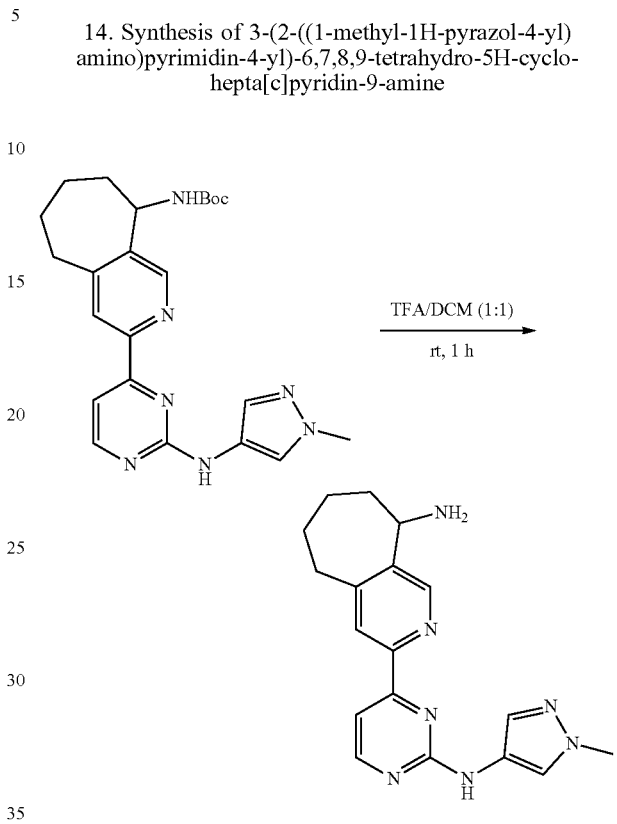

To a solution of tert-butyl (3-(2-((1-methyl-1H-pyrazol-4-yl)amino)pyrimidin-4-yl)-6,7,8,9-tetrahydro-5H-cyclohepta[c]pyridin-9-yl)carbamate (240 mg, 0.55 mmol) in DCM (5 mL) was added TFA (5 mL). The mixture was stirred at rt for 1 h. After concentration, the residue was basified with NaHCO$_3$ (aq) and extracted with DCM (3×30 mL), dried and concentrated to afford 3-(2-((1-methyl-1H-pyrazol-4-yl)amino)pyrimidin-4-yl)-6,7,8,9-tetrahydro-5H-cyclohepta[c]pyridin-9-amine as yellow solid (170 mg, Y: 92%, used for next step without further purification). ESI-MS (M+H)$^+$: 336.2.

15. Synthesis of 5-(tert-butyl)-N-(3-(2-((1-methyl-1H-pyrazol-4-yl)amino)pyrimidin-4-yl)-6,7,8,9-tetrahydro-5H-cyclohepta[e]pyridin-9-yl)-1,3,4-oxadiazole-2-carboxamide (I-IM_29)

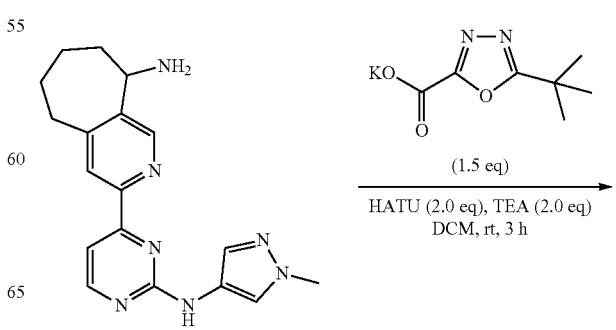

179

-continued

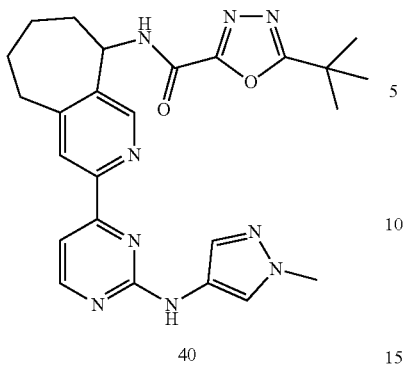

40

To a solution of 3-(2-((1-methyl-1H-pyrazol-4-yl)amino) pyrimidin-4-yl)-6,7,8,9-tetrahydro-5H-cyclohepta[c]pyridin-9-amine (80 mg, 0.24 mmol) and triethylamine (49 mg, 0.48 mmol) in DCM (5 mL) were added HATU (182 mg, 0.48 mmol) and potassium 5-(tert-butyl)-1,3,4-oxadiazole-2-carboxylate (75 mg, 0.36 mmol). The mixture was stirred at rt for 3 h. Then water (30 mL) was added and the mixture was extracted with DCM (2×50 mL). The combined organics were dried and concentrated. The crude product was purified by silica gel column chromatograph (DCM/MeOH=10:1) to give 5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,3,4-oxadiazole-2-carboxamide as a yellow solid (60 mg, yield: 51%). ESI-MS (M+H)+: 487.9. ¹H NMR (400 MHz, CD₃OD) δ: 8.52 (s, 1H), 8.49 (d, J=5.2 Hz, 1H), 8.22 (s, 1H), 7.97 (s, 1H), 7.66 (s, 1H), 7.54 (d, J=5.2 Hz, 1H), 5.47-5.45 (m, 1H), 3.90 (s, 3H), 3.08-3.06 (m, 2H), 2.13-1.98 (m, 5H), 1.51-1.49 (m, 10H).

Example 41: (R)-5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,3,4-oxadiazole-2-carboxamide (Compound 41)

180

-continued

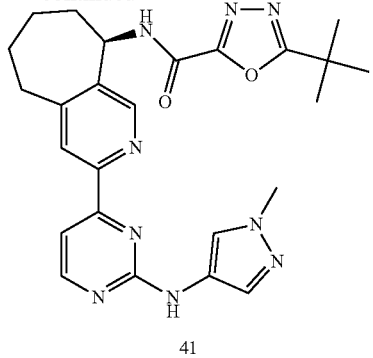

41

5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,3,4-oxadiazole-2-carboxamide (216 mg, 0.44 mmol) was subjected to chiral SFC separation (CHIRALPAK AS-H 30×250 mm, 5 um; Co-solvent: 20% Methanol+0.1% DEA in CO₂ (flow rate: 100 g/min); System backpressure: 120 bar) to afford (R)-5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,3,4-oxadiazole-2-carboxamide (93 mg, yield: 43%) as a white solid. ESI-MS (M+H)+: 488.1. ¹H NMR (400 MHz, CD₃OD) δ: ppm 8.52 (s, 1H), 8.49 (d, J=5.1 Hz, 1H), 8.22 (s, 1H), 7.97 (s, 1H), 7.65 (s, 1H), 7.55 (d, J=5.0 Hz, 1H), 5.46 (br d, J=9.5 Hz, 1H), 3.90 (s, 3H), 3.07 (br t, J=4.4 Hz, 2H), 2.12 (br d, J=8.8 Hz, 2H), 1.91-2.05 (m, 3H), 1.44-1.57 (m, 10H).

Example 42: (R)-5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,2,4-oxadiazole-3-carboxamide (Compound 42a) & (S)-5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,2,4-oxadiazole-3-carboxamide (Compound 42b)

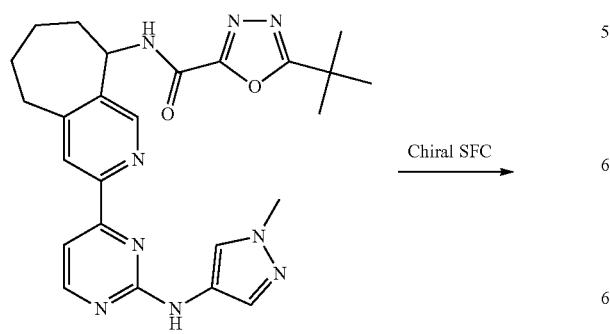

Chiral SFC →

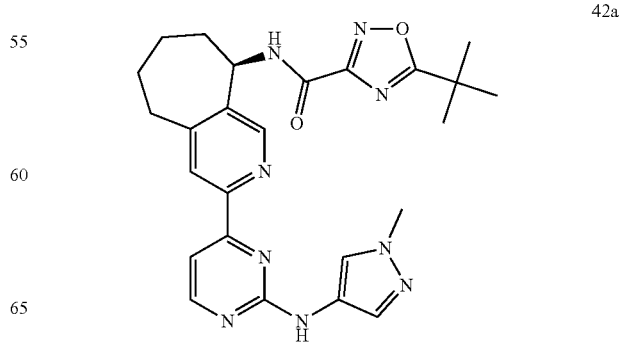

42a

-continued

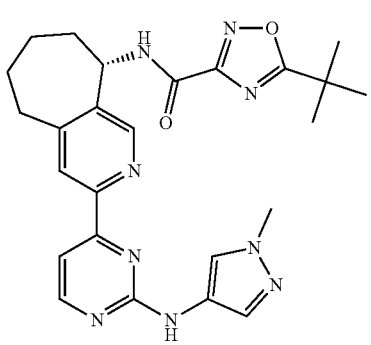
42b

I. Synthesis of 5-(tert-butyl)-N-(3-(2-((1-methyl-1H-pyrazol-4-yl)amino)pyrimidin-4-yl)-6,7,8,9-tetrahydro-5H-cyclohepta[e]pyridin-9-yl)-1,2,4-oxadiazole-3-carboxamide

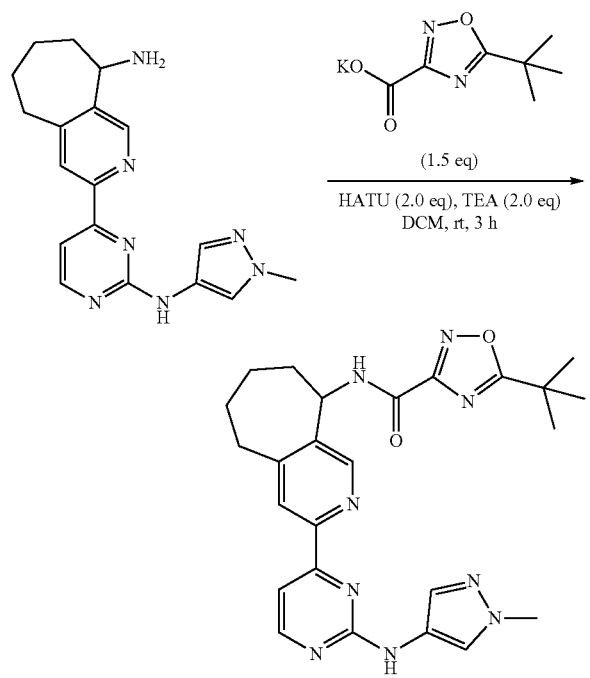

Synthesis of 5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,2,4-oxadiazole-3-carboxamide was similar to that of 5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,3,4-oxadiazole-2-carboxamide (Example 40, Step 15). The filtrate was purified by silica gel column chromatograph (DCM/MeOH=10:1) to give 5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,2,4-oxadiazole-3-carboxamide as a yellow solid (55 mg, yield: 47%). ESI-MS (M+H)$^+$: 487.9. $^1$H NMR (400 MHz, CD$_3$OD) δ: 8.50 (s, 1H), 8.49 (d, J=5.6 Hz, 1H), 8.21 (s, 1H), 7.97 (s, 1H), 7.66 (s, 1H), 7.54 (d, J=5.2 Hz, 1H), 5.49-5.47 (m, 1H), 3.90 (s, 3H), 3.08-3.06 (m, 2H), 2.12-1.97 (m, 5H), 1.52-1.50 (m, 10H).

2. Synthesis of (R)-5-(tert-butyl)-N-(3-(2-((1-methyl-1H-pyrazol-4-yl)amino)pyrimidin-4-yl)-6,7,8,9-tetrahydro-5H-cyclohepta[e]pyridin-9-yl)-1,2,4-oxadiazole-3-carboxamide (I-IM_31) & (S)-5-(tert-butyl)-N-(3-(2-((1-methyl-1H-pyrazol-4-yl)amino)pyrimidin-4-yl)-6,7,8,9-tetrahydro-5H-cyclohepta[e]pyridin-9-yl)-1,2,4-oxadiazole-3-carboxamide (Compound 42)

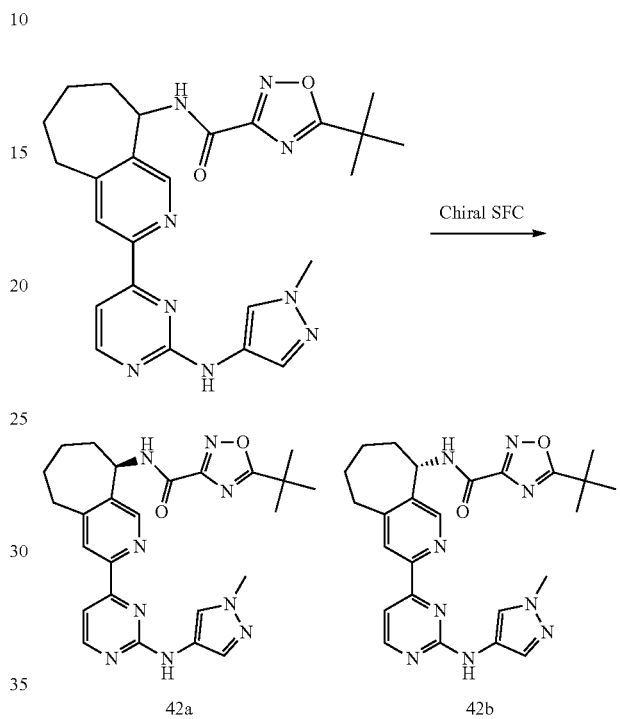

5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,2,4-oxadiazole-3-carboxamide (40 mg, 0.08 mmol) was subjected to chiral SFC separation (CHIRALPAK AS-H 30×250 mm, 5um; Co-solvent: 30% Methanol+0.1% DEA in CO2 (flow rate: 100 g/min); System backpressure: 120 bar) to afford (R)-5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,2,4-oxadiazole-3-carboxamide (11 mg, yield: 27%) & (S)-5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,2,4-oxadiazole-3-carboxamide (10 mg, 26%) as white solids.

(R): ESI-MS (M+H)$^+$: 488.1. $^1$H NMR (400 MHz, CD$_3$OD) δ: 8.51 (s, 1H), 8.49 (s, 1H), 8.22 (s, 1H), 7.97 (s, 1H), 7.65 (s, 1H), 7.55 (d, J=5.1 Hz, 1H), 5.48 (br d, J=9.3 Hz, 1H), 3.90 (s, 3H), 3.01-3.11 (m, 2H), 1.90-2.14 (m, 5H), 1.50-1.53 (m, 9H).

(S): ESI-MS (M+H)$^+$: 488.1. $^1$H NMR (400 MHz, CD$_3$OD) δ: 8.50-8.51 (m, 1H), 8.48 (s, 1H), 8.21 (s, 1H), 7.96 (s, 1H), 7.65 (s, 1H), 7.53-7.56 (m, 1H), 5.47 (br d, J=9.5 Hz, 1H), 3.89 (s, 3H), 3.02-3.13 (m, 2H), 1.91-2.16 (m, 5H), 1.50-1.52 (m, 10H).

Example 43. 1-(tert-butyl)-N-(3-(2-((1-methyl-1H-pyrazol-4-yl)amino)pyridin-4-yl)-6,7,8,9-tetrahydro-5H-cyclohepta[c]pyridin-9-yl)-1H-1,2,3-triazole-4-carboxamide (Compound 43)

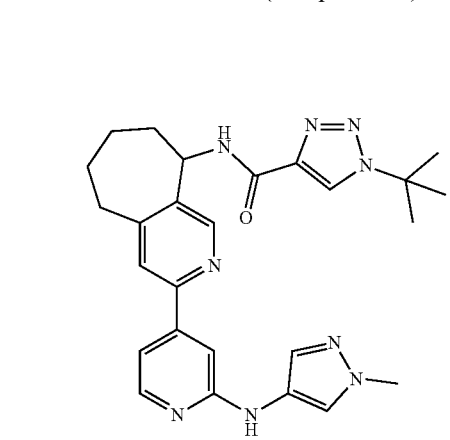

I. Synthesis of tert-butyl (3-(2-chloropyridin-4-yl)-6,7,8,9-tetrahydro-5H-cyclohepta[c]pyridin-9-yl)carbamate

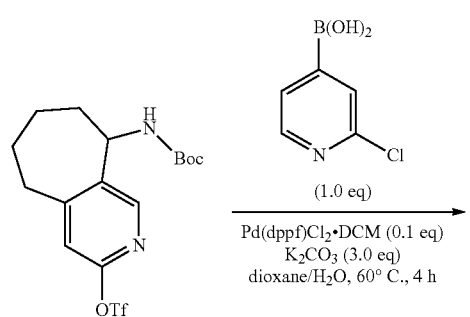

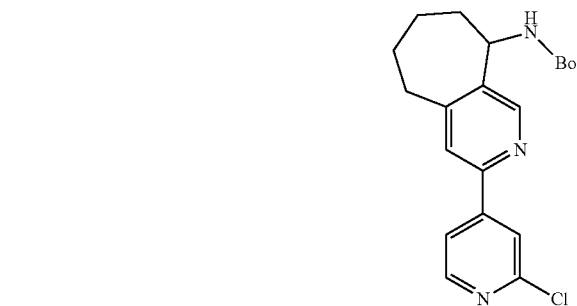

Synthesis of tert-butyl (3-(2-chloropyridin-4-yl)-6,7,8,9-tetrahydro-5H-cyclohepta[c]pyridin-9-yl)carbamate was similar to that of tert-butyl 1-(5-(tert-butyl)-1,2,4-oxadiazole-3-carboxamido)-7-(2-((1-methyl-1H-pyrazol-4-yl)amino)pyrimidin-4-yl)-4,5-dihydro-1H-benzo[d]azepine-3(2H)-carboxylate (Example 1, Step 12). The crude product was purified by silica gel chromatography (petroleum ether/EtOAc=3:1) to give tert-butyl (3-(2-chloropyridin-4-yl)-6,7,8,9-tetrahydro-5H-cyclohepta[c]pyridin-9-yl)carbamate as a yellow solid (170 mg, yield: 42%). ESI-MS (M+H)$^+$: 374.2.

2. Synthesis of tert-butyl (3-(2-((1-methyl-1H-pyrazol-4-yl)amino)pyridin-4-yl)-6,7,8,9-tetrahydro-5H-cyclohepta[c]pyridin-9-yl)carbamate

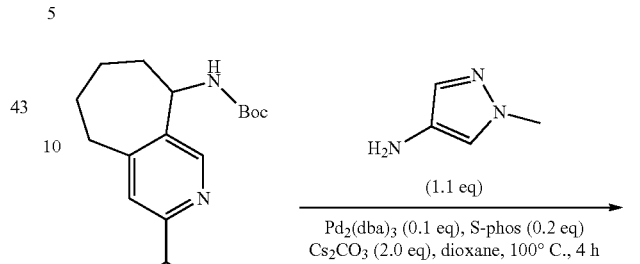

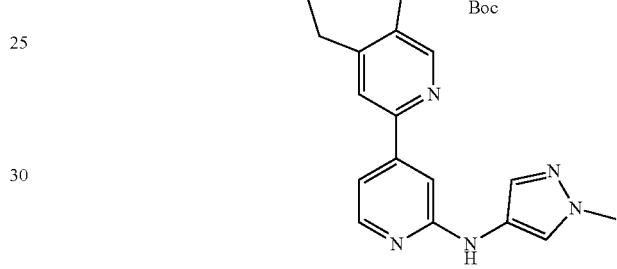

Synthesis of tert-butyl (3-(2-((1-methyl-1H-pyrazol-4-yl)amino)pyridin-4-yl)-6,7,8,9-tetrahydro-5H-cyclohepta[c]pyridin-9-yl)carbamate was similar to that of tert-butyl (R)-(2-(2-((1-methyl-1H-pyrazol-4-yl)amino)pyridin-4-yl)-6,7,8,9-tetrahydro-5H-benzo[7]annulen-5-yl)carbamate (Example 35, Step 2). The crude product was purified by silica gel column chromatograph (PE/EtOAc=1:1) to give tert-butyl (3-(2-((1-methyl-1H-pyrazol-4-yl)amino)pyridin-4-yl)-6,7,8,9-tetrahydro-5H-cyclohepta[c]pyridin-9-yl)carbamate as a yellow solid (140 mg, Y: 71%). ESI-MS (M+H)$^+$: 435.2.

3. Synthesis of 3-(2-((1-methyl-1H-pyrazol-4-yl)amino)pyridin-4-yl)-6,7,8,9-tetrahydro-5H-cyclohepta[c]pyridin-9-amine

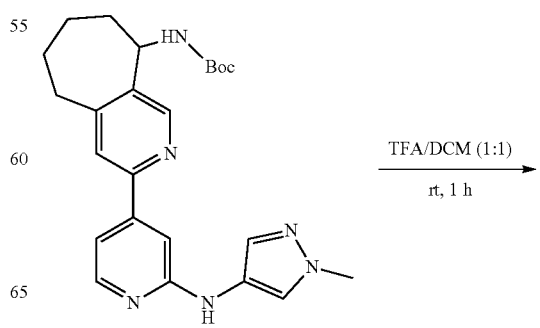

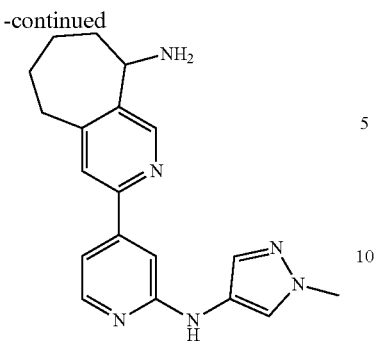

Synthesis of 3-(2-((1-methyl-1H-pyrazol-4-yl)amino)pyridin-4-yl)-6,7,8,9-tetrahydro-5H-cyclohepta[c]pyridin-9-amine was similar to that of 5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,2,4-oxadiazole-3-carboxamide (Example 1, Step 13). The crude product 3-(2-((1-methyl-1H-pyrazol-4-yl)amino)pyridin-4-yl)-6,7,8,9-tetrahydro-5H-cyclohepta[c]pyridin-9-amine was obtained as yellow solid (100 mg, yield: 94%). ESI-MS (M+H)+: 335.2.

4. Synthesis of 1-(tert-butyl)-N-(3-(2-((1-methyl-1H-pyrazol-4-yl)amino)pyridin-4-yl)-6,7,8,9-tetrahydro-5H-cyclohepta[c]pyridin-9-yl)-1H-1,2,3-triazole-4-carboxamide

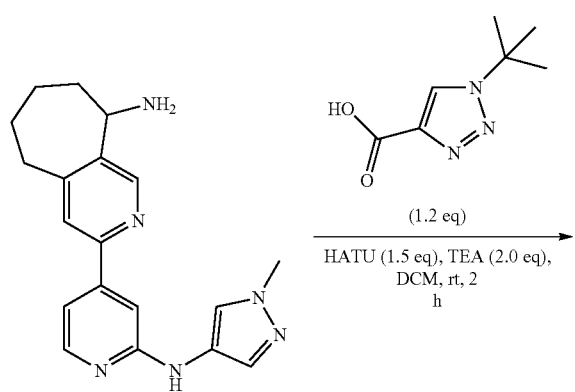

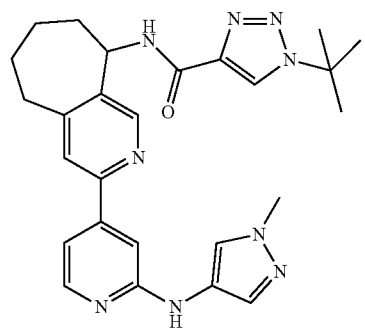

Synthesis of 1-(tert-butyl)-N-(3-(2-((1-methyl-1H-pyrazol-4-yl)amino)pyridin-4-yl)-6,7,8,9-tetrahydro-5H-cyclohepta[c]pyridin-9-yl)-1H-1,2,3-triazole-4-carboxamide was similar to that of 5-(tert-butyl)-N-(3-(2-((1-methyl-1H-pyrazol-4-yl)amino)pyrimidin-4-yl)-6,7,8,9-tetrahydro-5H-cyclohepta[c]pyridin-9-yl)-1,3,4-oxadiazole-2-carboxamide in Example 40, Step 15. The crude product was purified by silica gel chromatography (DCM/MeOH=15:1) to give 1-(tert-butyl)-N-(3-(2-((1-methyl-1H-pyrazol-4-yl)amino)pyridin-4-yl)-6,7,8,9-tetrahydro-5H-cyclohepta[c]pyridin-9-yl)-1H-1,2,3-triazole-4-carboxamide as a yellow solid (46 mg, yield: 32%). ESI-MS (M+H)+: 486.3. $^1$H NMR (400 MHz, CD$_3$OD) δ: 8.53-8.49 (m, 2H), 8.16 (d, J=5.2 Hz, 1H), 7.92 (s, 1H), 7.69 (s, 1H), 7.51 (s, 1H), 7.20-7.17 (m, 2H), 5.45-5.43 (m, 1H), 3.89 (s, 3H), 3.08-3.06 (m, 2H), 2.14-2.00 (m, 5H), 1.74 (s, 9H), 1.59-1.50 (m, 1H).

Examples 44-154

The following compounds were synthesized according to procedures similar to those described in Examples 1-43.

| Compd No. | Chemical Name | Structure | $^1$H-NMR and MS |
|---|---|---|---|
| 44 | (S)-5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,2,4-oxadiazole-3-carboxamide | 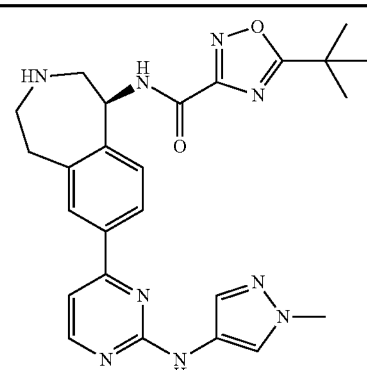 | LCMS: Rt 0.89 min, m/z 488.00. $^1$H NMR (400 MHz, METHANOL-d$_4$) δ: 8.38 (d, J = 5.27 Hz, 1H), 7.83-8.04 (m, 3H), 7.64 (s, 1H), 7.47 (d, J = 7.97 Hz, 1H), 7.19 (s, 1H), 5.34 (d, J = 6.46 Hz, 1H), 3.89 (s, 3H), 2.81-3.28 (m, 6H), 1.43-1.54 (m, 9H). |

| Compd No. | Chemical Name | Structure | ¹H-NMR and MS |
|---|---|---|---|
| 45 | (R)-5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,2,4-oxadiazole-3-carboxamide | 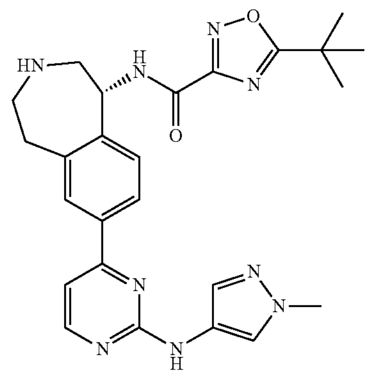 [SMILES: Cn1cc(Nc2nccc(-c3ccc4c(c3)CCNC[C@@H]4NC(=O)c3noc(C(C)(C)C)n3)n2)cn1] | LCMS: Rt = 0.89 min, m/z 488.00. ¹H NMR (400 MHz, METHANOL-$d_4$) δ: 8.32-8.46 (m, 1H), 7.89-8.05 (m, 3H), 7.64 (s, 1H), 7.48 (d, J = 7.97 Hz, 1H), 7.19 (d, J = 5.33 Hz, 1H), 5.34 (d, J = 6.46 Hz, 1H), 3.89 (s, 3H), 2.91-3.28 (m, 6H), 1.45-1.55 (m, 9H). |
| 46 | 5-(tert-butyl)-N-(3-(2-hydroxyethyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide | 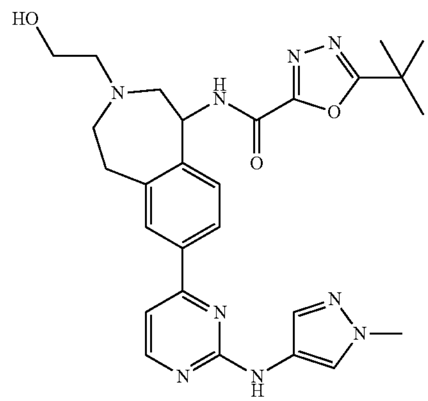 [SMILES: Cn1cc(Nc2nccc(-c3ccc4c(c3)CCN(CCO)CC4NC(=O)c3nnc(C(C)(C)C)o3)n2)cn1] | ¹H NMR (400 MHz, CD₃OD) δ: 8.28-8.26 (m, 1H), 7.85-7.76 (m, 3H), 7.52 (s, 1H), 7.40-7.37 (m, 1H), 7.08-7.05 (m, 1H), 5.15-5.12 (m, 1H), 3.77 (s, 3H), 3.65-3.62 (m, 2H), 3.14-3.12 (m, 2H), 2.94-2.91 (m, 2H), 2.74-2.65 (m, 3H), 2.61-2.57 (m, 1H), 1.34 (s, 9H). ESI-MS (M + H)⁺: 532.3. |
| 47 | 5-(tert-butyl)-N-(7-(2-((1-methyl-1H-pyrazol-4-yl)amino)pyrimidin-4-yl)-3-(methylsulfonyl)-2,3,4,5-tetrahydro-1H-benzo[d]azepin-1-yl)-1,3,4-oxadiazole-2-carboxamide | 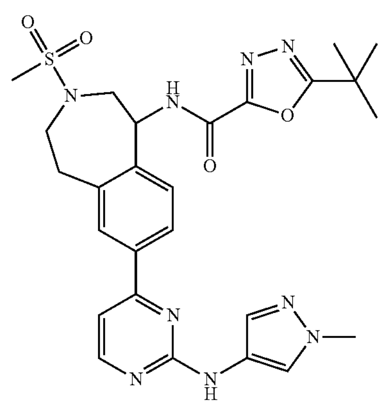 [SMILES: Cn1cc(Nc2nccc(-c3ccc4c(c3)CCN(S(C)(=O)=O)CC4NC(=O)c3nnc(C(C)(C)C)o3)n2)cn1] | ¹H NMR (400 MHz, CD3OD) δ: 8.41 (d, J = 5.6 Hz, 1H), 7.99-7.93 (m, 3H), 7.65 (s, 1H), 7.56 (d, J = 7.6 Hz, 1H), 7.16 (d, J = 5.2 Hz, 1H), 5.47-5.45 (m, 1H), 4.00-3.95 (m, 1H), 3.90 (s, 3H), 3.82-3.78 (m, 1H), 3.65-3.61 (m, 1H), 3.44-3.37 (m, 2H), 3.22-3.17 (m, 1H), 2.90 (s, 3H), 1.47 (s, 9H). ESI-MS (M + H)+: 566.2. |
| 48 | 5-(tert-butyl)-N-(7-(2-((1-methyl-1H-pyrazol-4-yl)amino)pyrimidin-4-yl)-3-(oxetan-3-yl)-2,3,4,5-tetrahydro-1H-benzo[d]azepin-1-yl)-1,3,4-oxadiazole-2-carboxamide | 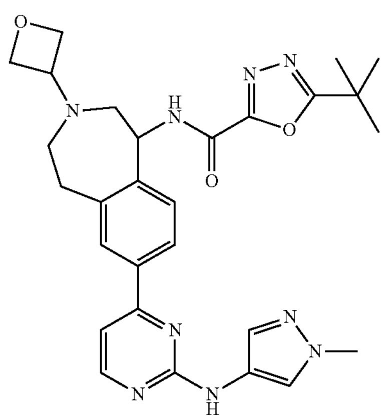 [SMILES: Cn1cc(Nc2nccc(-c3ccc4c(c3)CCN(C3COC3)CC4NC(=O)c3nnc(C(C)(C)C)o3)n2)cn1] | ¹H NMR (400 MHz, CD₃OD) δ: 8.29 (d, J = 5.2 Hz, 1H), 7.85-7.80 (m, 3H), 7.52 (s, 1H), 7.41 (d, J = 8.0 Hz, 1H), 7.08 (d, J = 4.8 Hz, 1H), 5.16-5.15 (m, 1H), 4.62-4.58 (m, 3H), 4.55-4.51 (m, 1H), 3.78 (s, 3H), 3.70-3.66 (m, 1H), 3.20-3.15 (m, 1H), 2.98-2.93 (m, 1H), 2.88-2.83 (m, 1H), 2.70-2.66 (m, 1H), 2.47-2.44 (m, 1H), 2.35-2.29 (m, 1H), 1.35 (s, 9H). ESI-MS (M + H)⁺: 544.3. |

| Compd No. | Chemical Name | Structure | ¹H-NMR and MS |
|---|---|---|---|
| 49 | 5-(tert-butyl)-N-(7-(2-((1-methyl-1H-pyrazol-4-yl)amino)pyrimidin-4-yl)-3-(tetrahydrofuran-3-yl)-2,3,4,5-tetrahydro-1H-benzo[d]azepin-1-yl)-1,3,4-oxadiazole-2-carboxamide | 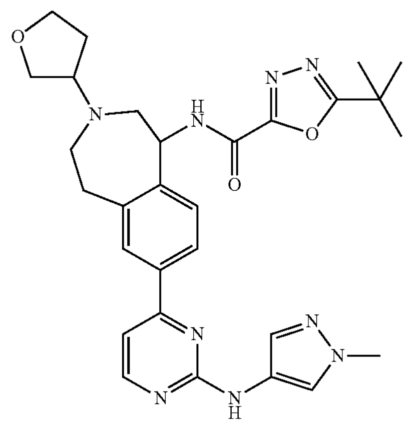 [SMILES: Cn1cc(Nc2nccc(-c3ccc4c(c3)CCN(C3CCOC3)CC4NC(=O)c3nnc(C(C)(C)C)o3)n2)cn1] | ¹H NMR (400 MHz, CD₃OD) δ: 8.39 (d, J = 5.6 Hz, 1H), 7.96 (s, 1H), 7.94 (dd, J = 8.0, 2.0 Hz, 1H), 7.89 (s, 1H), 7.64 (s, 1H), 7.51 (d, J = 8.0 Hz, 1H), 7.18 (d, J = 5.2 Hz, 1H), 5.24-5.22 (m, 1H), 4.01-3.96 (m, 1H), 3.89 (s, 3H), 3.87-3.83 (m, 1H), 3.80-3.70 (m, 2H), 3.53-3.49 (m, 1H), 3.29-3.20 (m, 2H), 3.15-2.97 (m, 2H), 2.82-2.62 (m, 2H), 2.15-2.10 (m, 1H), 1.98-1.91 (m, 1H), 1.46 (s, 9H). ESI-MS (M + H)⁺: 558.3. |
| 50 | 5-(tert-butyl)-N-(3-(2-hydroxy-2-methylpropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide | 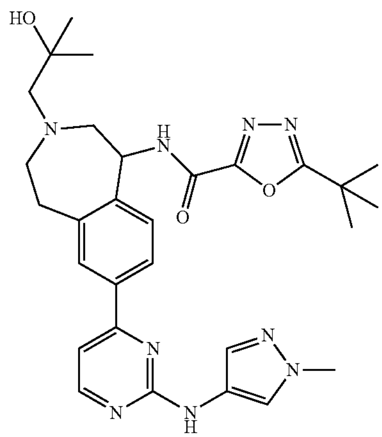 [SMILES: Cn1cc(Nc2nccc(-c3ccc4c(c3)CCN(CC(C)(C)O)CC4NC(=O)c3nnc(C(C)(C)C)o3)n2)cn1] | ¹H NMR (400 MHz, CD₃OD) δ: 8.40 (d, J = 4.8 Hz, 1H), 7.97-7.89 (m, 3H), 7.64 (s, 1H), 7.51 (d, J = 8.0, 2.0 Hz, 1H), 7.20-7.19 (m, 1H), 5.22-5.20 (m, 1H), 3.89 (s, 3H), 3.29-3.21 (m, 3H), 3.05-3.00 (m, 1H), 2.93-2.90 (m, 1H), 2.77-2.72 (m, 1H), 2.60 (s, 2H), 1.46 (s, 9H), 1.32-1.31 (m, 6H). ESI-MS (M + H)⁺: 560.3. |
| 51 | 1-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1H-1,2,3-triazole-4-carboxamide | 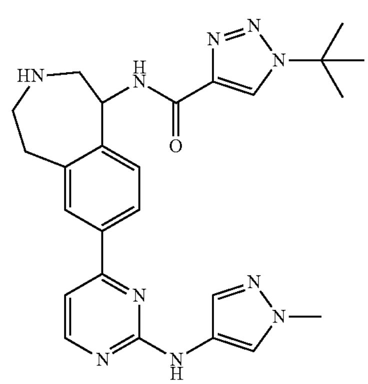 [SMILES: Cn1cc(Nc2nccc(-c3ccc4c(c3)CCNCC4NC(=O)c3cn(C(C)(C)C)nn3)n2)cn1] | ¹H NMR (400 MHz, CD₃OD) δ: 8.48 (s, 1H), 8.40 (d, J = 5.6 Hz, 1H), 7.98-7.93 (m, 3H), 7.65 (br, 1H), 7.50 (d, J = 7.6 Hz, 1H), 7.21 (d, J = 5.2 Hz, 1H), 5.35-5.34 (m, 1H), 3.90 (s, 3H), 3.28-2.99 (m, 6H), 1.73 (s, 9H). ESI-MS (M + H)⁺: 487.2. |

-continued

| Compd No. | Chemical Name | Structure | ¹H-NMR and MS |
|---|---|---|---|
| 52 | 1-(tert-butyl)-N-(3-methyl-7-(2-((1-methyl-1H-pyrazol-4-yl)amino)pyrimidin-4-yl)-2,3,4,5-tetrahydro-1H-benzo[d]azepin-1-yl)-1H-1,2,3-triazole-4-carboxamide | 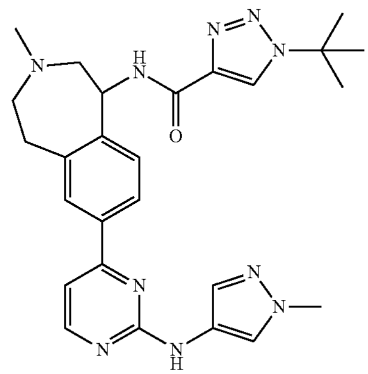 [SMILES: CN1CCc2cc(-c3ccnc(Nc4cnn(C)c4)n3)ccc2C(NC(=O)c2cn(C(C)(C)C)nn2)C1] | ¹H NMR (400 MHz, CD₃OD) δ: 8.45 (s, 1H), 8.41 (d, J = 5.2 Hz, 1H), 7.98-7.92 (m, 3H), 7.65 (s, 1H), 7.52 (d, J = 8.0 Hz, 1H), 7.21 (d, J = 5.2 Hz, 1H), 5.33-5.31 (m, 1H), 3.90 (s, 3H), 3.31-3.26 (m, 1H), 3.11-3.05 (m, 2H), 2.92-2.59 (m, 3H), 2.51 (s, 3H), 1.72 (s, 9H). ESI-MS (M + H)⁺: 501.3. |
| 53 | 1-(tert-butyl)-N-(3-(2-hydroxyethyl)-7-(2-((1-methyl-1H-pyrazol-4-yl)amino)pyrimidin-4-yl)-2,3,4,5-tetrahydro-1H-benzo[d]azepin-1-yl)-1H-1,2,3-triazole-4-carboxamide | 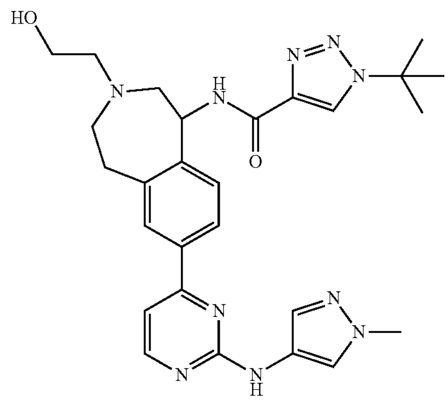 [SMILES: Cn1cc(Nc2nccc(-c3ccc4c(c3)CCN(CCO)CC4NC(=O)c3cn(C(C)(C)C)nn3)n2)cn1] | ¹H NMR (400 MHz, CD₃OD) δ: 8.44 (s, 1H), 8.41 (d, J = 5.2 Hz, 1H), 7.98-7.91 (m, 3H), 7.65 (s, 1H), 7.54 (d, J = 7.6 Hz, 1H), 7.21 (d, J = 5.2 Hz, 1H), 5.21-5.25 (m, 1H), 3.90 (s, 3H), 3.79-3.76 (m, 2H), 3.19-3.02 (m, 4H), 2.86-2.64 (m, 4H), 1.71 (s, 9H). ESI-MS (M + H)⁺: 531.3. |
| 54 | 5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,2,4-oxadiazole-3-carboxamide | 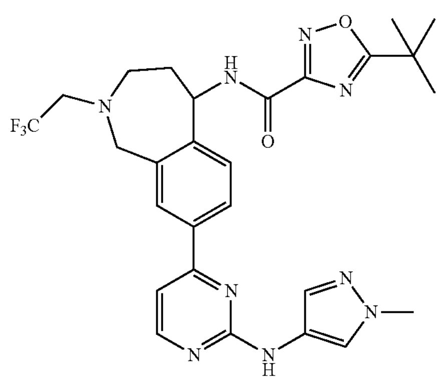 [SMILES: Cn1cc(Nc2nccc(-c3ccc4c(c3)CN(CC(F)(F)F)CCC4NC(=O)c3noc(C(C)(C)C)n3)n2)cn1] | ESI-MS (M + H)⁺: 570.2. ¹H NMR (400 MHz, CD₃OD) δ: 8.31 (d, J = 4.8 Hz, 1H), 7.93-7.88 (m, 3H), 7.50 (s, 1H), 7.37 (d, J = 8.4 Hz, 1H), 7.12 (d, J = 4.8 Hz, 1H), 5.51 (d, J = 10.0 Hz, 1H), 4.26-4.22 (m, 1H), 4.02-3.98 (m, 1H), 3.48 (s, 3H), 3.30-3.27 (m, 2H), 3.05-2.98 (m, 2H), 2.13-2.08 (m, 1H), 1.85-1.82 (m, 1H), 1.41 (s, 9H). |
| 55 | 5-(tert-butyl)-N-(2-(2-(dimethylamino)acetyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide | 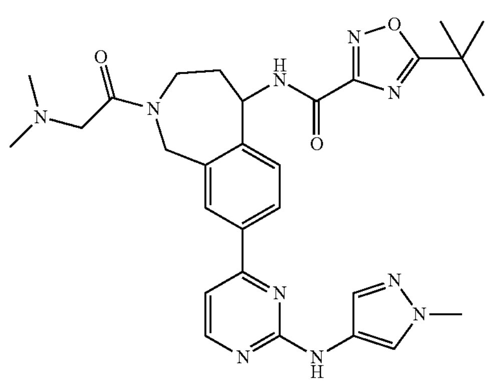 [SMILES: CN(C)CC(=O)N1CCC(NC(=O)c2noc(C(C)(C)C)n2)c2ccc(-c3ccnc(Nc4cnn(C)c4)n3)cc2C1] | ESI-MS (M + H)⁺: 573.3. ¹H NMR (400 MHz, CD₃OD) δ: 8.33-8.29 (m, 1H), 8.10 (s, 1H), 8.02-7.86 (m, 2H), 7.56-7.34 (m, 2H), 7.15-7.12 (m, 1H), 5.61-5.50 (m, 1H), 5.03-4.94 (m, 2H), 4.77-4.36 (m, 1H), 4.16-4.13 (m, 1H), 4.04-3.99 (m, 3H), 3.83-3.35 (m, 2H), 3.10-3.05 (m, 2H), 2.17-2.12 (m, 6H), 1.42 (s, 9H). |

| Compd No. | Chemical Name | Structure | ¹H-NMR and MS |
|---|---|---|---|
| 56 | N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-5-(1,1,1-trifluoro-2-methylpropan-2-yl)-1,3,4-oxadiazole-2-carboxamide | 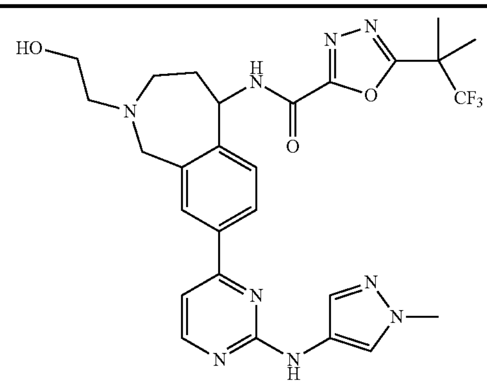 | ESI-MS (M + H)⁺: 586.3. ¹H NMR (400 MHz, CD₃OD) δ: 8.43 (d, J = 5.2 Hz, 1H), 8.05 (s, 1H), 8.03-8.00 (m, 2H), 7.65 (s, 1H), 7.49 (d, J = 7.6 Hz, 1H), 7.24 (d, J = 5.2 Hz, 1H), 5.59-5.57 (m, 1H), 4.64 (br, 1H), 4.17-4.15 (m, 2H), 3.91 (s, 3H), 3.75 (t, J = 6.0 Hz, 2H), 3.26-3.16 (m, 1H), 2.72-2.61 (m, 2H), 2.34-2.25 (m, 1H), 2.02-1.97 (m, 1H), 1.76 (s, 6H). |
| 57 | N-(2-methyl-8-(2-((1-methyl-1H-pyrazol-4-yl)amino)pyrimidin-4-yl)-2,3,4,5-tetrahydro-1H-benzo[c]azepin-5-yl)-5-(1,1,1-trifluoro-2-methylpropan-2-yl)-1,3,4-oxadiazole-2-carboxamide | 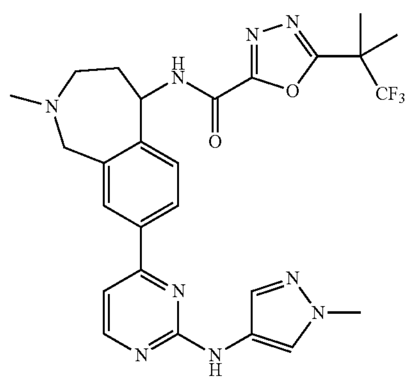 [SMILES: CN1CCC(NC(=O)c2nnc(C(C)(C)C(F)(F)F)o2)c2ccc(-c3ccnc(Nc4cnn(C)c4)n3)cc2C1] | ESI-MS (M + H)⁺: 556.2. ¹H NMR (400 MHz, CDCl₃) δ: 8.52 (br, 1H), 8.42 (d, J = 5.2 Hz, 1H), 7.87 (s, 1H), 7.85-7.81 (m, 2H), 7.55 (s, 1H), 7.47 (d, J = 8.0 Hz, 1H), 7.05 (d, J = 5.2 Hz, 1H), 6.91 (s, 1H), 5.61-5.56 (m, 1H), 3.94-3.92 (m, 5H), 3.14-3.07 (m, 1H), 2.85-2.80 (m, 1H), 2.52 (s, 3H), 2.36-2.28 (m, 1H), 2.11-2.03 (m, 1H), 1.71 (s, 6H). |
| 58 | (R)-5-(1,1-difluoro-2-methylpropan-2-yl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide | 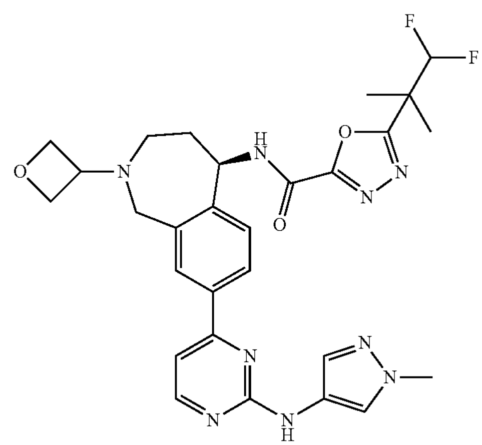 [SMILES: Cn1cc(Nc2nccc(-c3ccc4c(c3)CN(C3COC3)CC[C@H]4NC(=O)c3nnc(C(C)(C)C(F)F)o3)n2)cn1] | ESI-MS (M + H)⁺: 580.2. ¹H NMR (400 MHz, CD₃OD) δ: 8.42 (d, J = 5.2 Hz, 1H), 8.04 (d, J = 8.0 Hz, 1H), 7.99-7.98 (m, 2H), 7.64 (s, 1H), 7.48 (d, J = 8.0 Hz, 1H), 7.23 (d, J = 5.2 Hz, 1H), 6.15 (t, J = 55.6 Hz, 1H), 5.60-5.56 (m, 1H), 4.78-4.75 (m, 1H), 4.70-4.66 (m, 3H), 3.98-3.94 (m, 1H), 3.90 (s, 3H), 3.88-3.79 (m, 2H), 3.09-3.06 (m, 1H), 2.93-2.87 (m, 1H), 2.30-2.20 (m, 1H), 2.07-2.04 (m, 1H), 1.60 (s, 6H). |
| 59 | 5-(1,1-difluoro-2-methylpropan-2-yl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 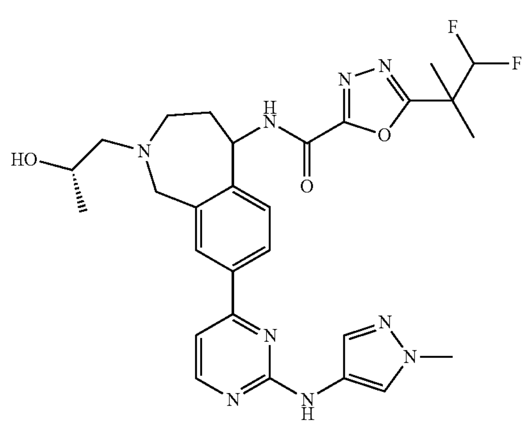 [SMILES: C[C@H](O)CN1CCC(NC(=O)c2nnc(C(C)(C)C(F)F)o2)c2ccc(-c3ccnc(Nc4cnn(C)c4)n3)cc2C1] | ESI-MS (M + H)⁺: 582.3. ¹H NMR (400 MHz, CD₃OD) δ: 8.42 (d, J = 5.2 Hz, 1H), 8.03-8.00 (m, 3H), 7.64 (s, 1H), 7.48-7.46 (m, 1H), 7.23 (d, J = 5.2 Hz, 1H), 6.15 (t, J = 55.6 Hz, 1H), 5.57 (d, J = 9.6 Hz, 1H), 4.23-4.19 (m, 1H), 4.13-4.06 (m, 1H), 4.00-3.96 (m, 1H), 3.91 (s, 3H), 3.26-3.20 (m, 2H), 2.44 (d, J = 6.0 Hz, 2H), 2.31-225 (m, 1H), 1.99-1.95 (m, 1H), 1.60 (s, 6H), 1.16 (d, J = 6.0 Hz, 3H). |

| Compd No. | Chemical Name | Structure | ¹H-NMR and MS |
|---|---|---|---|
| 60 | 5-(1-fluoro-2-methylpropan-2-yl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-oxadiazole-2-carboxamide | 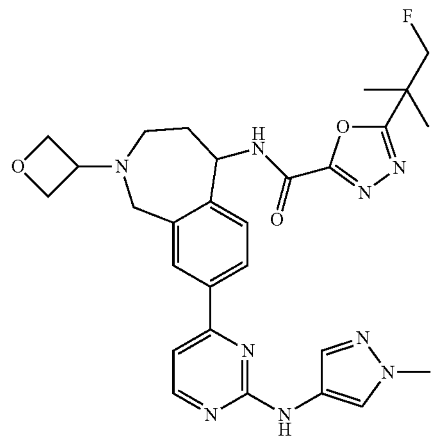 [SMILES: Cn1cc(Nc2nccc(-c3ccc4c(c3)CN(C3COC3)CCC4NC(=O)c3nnc(C(C)(C)CF)o3)n2)cn1] | ESI-MS (M + H)⁺: 562.3. ¹H NMR (400 MHz, CD₃OD) δ: 8.29 (d, J = 5.6 Hz, 1H), 8.21 (s, 1H), 7.91-7.89 (m, 1H), 7.86-7.83 (m, 2H), 7.35 (d, J = 8.0 Hz, 1H), 7.09 (d, J = 5.6 Hz, 1H), 5.46 (d, J = 9.6 Hz, 1H), 4.75-4.57 (m, 1H), 4.56-4.55 (m, 4H), 4.43 (s, 1H), 3.85-3.66 (m, 6H), 2.96-2.92 (m, 1H), 1.94-1.91 (m, 1H), 1.41 (d, J = 2.0 Hz, 6H), 1.19 (m, 2H). |
| 61 | 5-(1-fluoro-2-methylpropan-2-yl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 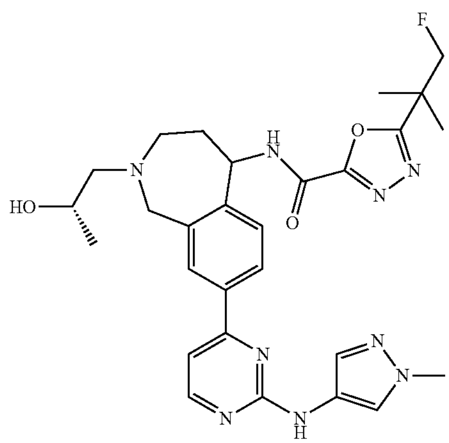 [SMILES: C[C@H](O)CN1CCC(NC(=O)c2nnc(C(C)(C)CF)o2)c2ccc(-c3ccnc(Nc4cnn(C)c4)n3)cc2C1] | ESI-MS (M + H)⁺: 564.3. ¹H NMR (400 MHz, MeOD) δ: 8.31-8.29 (m, 1H), 7.89-7.88 (m, 3H), 7.55 (s, 1H), 7.38-7.36 (m, 1H), 7.11-7.10 (m, 1H), 5.48-5.46 (m, 1H), 4.53 (d, J = 47.2 Hz, 2H), 4.11-3.86 (m, 3H), 3.81 (s, 3H), 3.21-3.14 (m, 2H), 2.35-2.17 (m, 3H), 1.89-1.87 (m, 1H), 1.44 (s, 6H), 1.07-1.03 (m, 3H). |
| 62 | 5-cyclobutyl-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 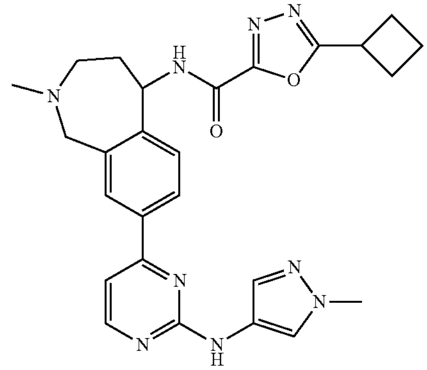 [SMILES: CN1CCC(NC(=O)c2nnc(C3CCC3)o2)c2ccc(-c3ccnc(Nc4cnn(C)c4)n3)cc2C1] | ESI-MS (M + H)⁺: 500.3. ¹H NMR (400 MHz, CD₃OD) δ: 8.31-8.28 (m, 1H), 7.92-7.86 (m, 3H), 7.52 (s, 1H), 7.35-7.33 (m, 1H), 7.12-7.08 (m, 1H), 5.43 (d, J = 10.0 Hz, 1H), 4.00-3.98 (m, 1H), 3.82-3.79 (m, 2H), 3.77 (s, 3H), 3.08-2.95 (m, 2H), 2.45-2.38 (m, 4H), 2.28 (s, 3H), 2.15-1.89 (m, 4H). |

| Compd No. | Chemical Name | Structure | ¹H-NMR and MS |
|---|---|---|---|
| 63 | 5-(2-cyanopropan-2-yl)-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 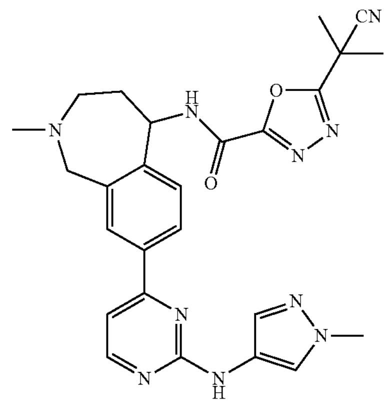 [SMILES: CN1CCC(NC(=O)c2nnc(C(C)(C)C#N)o2)c2ccc(-c3ccnc(Nc4cnn(C)c4)n3)cc2C1] | ESI-MS (M + H)⁺: 513.6. ¹H NMR (400 MHz, CDCl₃) δ: 8.59-8.58 (m, 1H), 8.41 (d, J = 5.2 Hz, 1H), 7.85-7.81 (m, 3H), 7.53 (s, 1H), 7.45 (d, J = 7.6 Hz, 1H), 7.04 (d, J = 5.2 Hz, 1H), 5.58 (t, J = 8.0 Hz, 1H), 3.93-3.92 (m, 1H), 3.90 (s, 3H), 3.13-3.06 (m, 1H), 2.86-2.80 (m, 1H), 2.51 (s, 3H), 2.35-2.28 (m, 1H), 2.10-2.03 (m, 2H), 1.91 (s, 6H). |
| 64 | 5-(2-cyanopropan-2-yl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 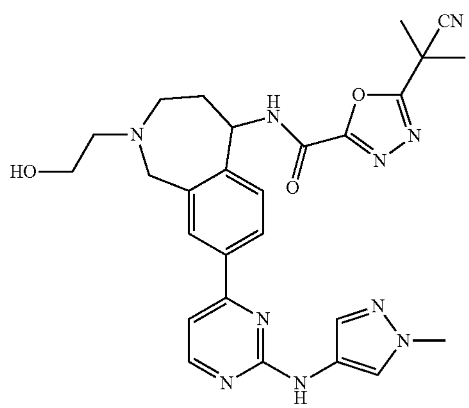 [SMILES: Cn1cc(Nc2nccc(-c3ccc4c(c3)CN(CCO)CCC4NC(=O)c3nnc(C(C)(C)C#N)o3)n2)cn1] | ESI-MS (M + H)⁺: 543.6. ¹H NMR (400 MHz, CD₃OD) δ: 8.40 (d, J = 5.2 Hz, 1H), 8.01-7.98 (m, 3H), 7.64 (s, 1H), 7.47 (d, J = 8.0 Hz, 1H), 7.20 (d, J = 5.2 Hz, 1H), 5.57 (d, J = 9.6 Hz, 1H), 4.20-4.11 (m, 2H), 3.90 (s, 3H), 3.75-3.72 (m, 2H), 3.28-3.20 (m, 2H), 2.68-2.63 (m, 2H), 2.31-2.27 (m, 1H), 2.01-1.97 (m, 1H), 1.94 (s, 6H). |
| 65 | 1-isopropyl-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide | 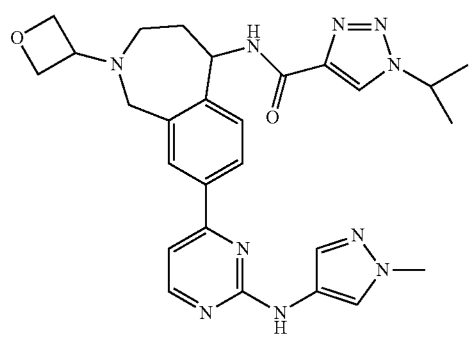 [SMILES: CC(C)n1cc(C(=O)NC2CCN(C3COC3)Cc3cc(-c4ccnc(Nc5cnn(C)c5)n4)ccc32)nn1] | ESI-MS (M + H)⁺: 529.2. ¹H NMR (400 MHz, DMSO-d₆) δ: 9.49 (s, 1H), 9.05 (d, J = 8.0 Hz, 1H), 8.74 (s, 1H), 8.46 (d, J = 5.2 Hz, 1H), 8.03-7.81 (m, 3H), 7.54 (s, 1H), 7.37 (d, J = 8.0 Hz, 1H), 7.25 (d, J = 5.2 Hz, 1H), 5.44 (t, J = 9.6 Hz, 1H), 5.00-4.80 (m, 1H), 4.59 (t, J = 6.4 Hz, 1H), 4.56-4.41 (m, 3H), 3.93-3.59 (m, 6H), 2.98-2.70 (m, 2H), 2.19-2.03 (m, 1H), 1.90-1.77 (m, 1H), 1.54 (d, J = 6.8 Hz, 6H). |
| 66 | 1-cyclobutyl-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide | 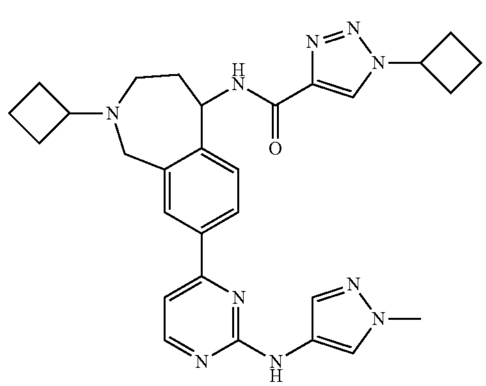 [SMILES: Cn1cc(Nc2nccc(-c3ccc4c(c3)CN(C3CCC3)CCC4NC(=O)c3cn(C4CCC4)nn3)n2)cn1] | ESI-MS (M + H)⁺: 540.7. ¹H NMR (400 MHz, DMSO-d₆) δ: 9.49 (s, 1H), 9.07 (d, J = 8.4 Hz, 1H), 8.81 (s, 1H), 8.47 (d, J = 5.2 Hz, 1H), 7.97-7.94 (m, 2H), 7.90 (s, 1H), 7.53 (s, 1H), 7.37 (d, J = 8.0 Hz, 1H), 7.26 (d, J = 5.2 Hz, 1H), 5.44 (t, J = 9.6 Hz, 1H), 5.25-5.16 (m, 1H), 4.59 (t, J = 6.4 Hz, 1H), 4.54-4.47 (m, 3H), 3.88-3.62 (m, 2H), 3.68 (s, 3H), 2.93-2.90 (m, 1H), 2.81-2.76 (m, 1H), 2.74-2.72 (m, 1H), 2.60-2.48 (m, 4H), 2.14-2.06 (m, 1H), 1.92-1.83 (m, 3H). |

| Compd No. | Chemical Name | Structure | ¹H-NMR and MS |
|---|---|---|---|
| 67 | 5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,3,4-thiadiazole-2-carboxamide | 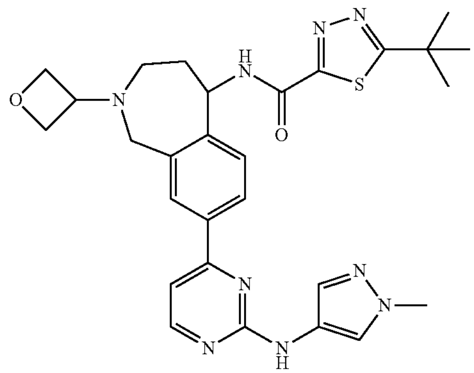 [SMILES: Cn1cc(Nc2nccc(-c3ccc4c(c3)CN(C3COC3)CCC4NC(=O)c3nnc(C(C)(C)C)s3)n2)cn1] | ESI-MS (M + H)⁺: 560.0. ¹H NMR (400 MHz, CDCl₃) δ: 8.42 (d, J = 5.2 Hz, 1H), 8.33 (d, J = 8.4 Hz, 1H), 7.87 (s, 1H), 7.86 (dd, J = 8.0 Hz, 1.6 Hz, 1H), 7.77 (d, J = 1.6 Hz, 1H), 7.53 (s, 1H), 7.49 (d, J = 8.0 Hz, 1H), 7.04 (d, J = 5.2 Hz, 1H), 6.95 (s, 1H), 5.62-5.58 (m, 1H), 4.77-4.68 (m, 4H), 3.92-3.86 (m, 6H), 3.04-2.97 (m, 1H), 2.81-2.75 (m, 1H), 2.32-2.26 (m, 1H), 2.13-2.06 (m, 1H), 1.51 (s, 9H). |
| 68 | 3-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-5-carboxamide | 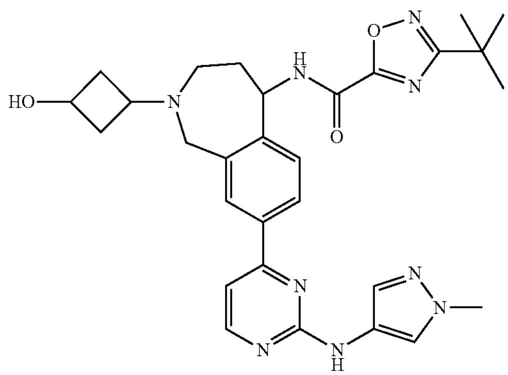 [SMILES: Cn1cc(Nc2nccc(-c3ccc4c(c3)CN(C3CC(O)C3)CCC4NC(=O)c3nc(C(C)(C)C)no3)n2)cn1] | ESI-MS (M + H)⁺: 558.3. ¹H NMR (400 MHz, CDCl₃) δ: 8.61 (br, 1H), 8.43 (d, J = 4.8 Hz, 1H), 7.85-7.82 (m, 3H), 7.55 (s, 1H), 7.49 (d, J = 7.6 Hz, 1H), 7.05 (d, J = 4.2 Hz, 1H), 7.02 (s, 1H), 5.61 (t, J = 8.0 Hz, 1H), 4.07-3.73 (m, 6H), 3.15-3.06 (m, 1H), 2.73-2.49 (m, 3H), 2.37-2.30 (m, 1H), 2.12-1.85 (m, 4H), 1.39 (s, 9H). |
| 69 | 1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide | 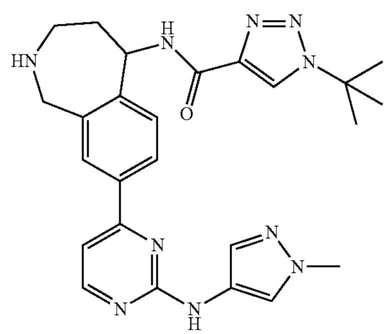 [SMILES: Cn1cc(Nc2nccc(-c3ccc4c(c3)CNCCC4NC(=O)c3cn(C(C)(C)C)nn3)n2)cn1] | ESI-MS (M + H)⁺: 487.2. ¹H NMR (400 MHz, CDCl₃) δ: 8.40 (d, J = 5.2 Hz, 1H), 8.19 (s, 1H), 7.98 (d, J = 8.8 Hz, 1H), 7.89 (s, 1H), 7.84-7.81 (m, 2H), 7.51-7.47 (m, 2H), 7.03 (d, J = 5.2 Hz, 1H), 5.63 (t, J = 9.2 Hz, 1H), 4.16-4.14 (m, 2H), 3.90 (s, 3H), 3.42-3.32 (m, 2H), 2.10-2.08 (m, 2H), 1.71 (s, 9H). |
| 70 | 1-(tert-butyl)-N-(2-ethyl-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide | 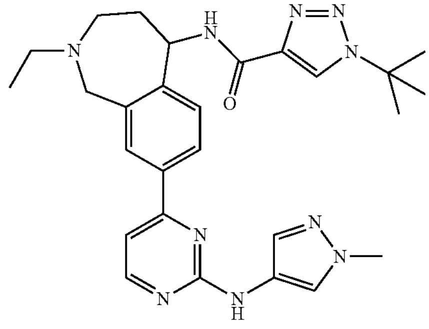 [SMILES: CCN1CCC(NC(=O)c2cn(C(C)(C)C)nn2)c2ccc(-c3ccnc(Nc4cnn(C)c4)n3)cc2C1] | ESI-MS (M + H)⁺: 514.8. ¹H NMR (400 MHz, CDCl₃) δ: 8.41 (d, J = 5.2 Hz, 1H), 8.17 (s, 1H), 7.91 (s, 1H), 7.84-7.24 (m, 2H), 7.53 (s, 1H), 7.48 (d, J = 8.8 Hz, 1H), 7.04 (d, J = 5.2 Hz, 2H), 6.95 (s, 1H), 5.61 (t, J = 9.2 Hz, 1H), 4.02 (s, 2H), 3.91 (s, 3H), 3.31-3.22 (m, 1H), 3.02-2.98 (m, 1H), 2.66-2.60 (m, 2H), 2.28-2.21 (m, 1H), 2.06-2.02 (m, 1H), 1.67 (s, 9H), 1.20 (t, J = 7.2 Hz, 3H). |

| Compd No. | Chemical Name | Structure | ¹H-NMR and MS |
|---|---|---|---|
| 71 | 1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide | 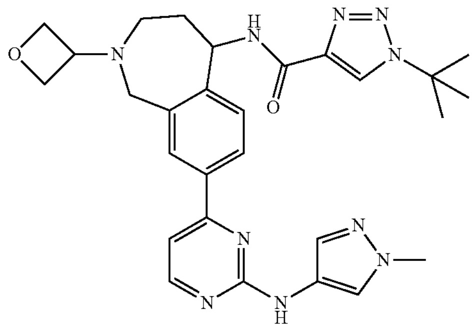 [SMILES: Cn1cc(Nc2nccc(-c3ccc4c(c3)CN(C3COC3)CCC4NC(=O)c3cn(C(C)(C)C)nn3)n2)cn1] | ESI-MS (M + H)⁺: 542.7. ¹H NMR (400 MHz, CD₃OD) δ: 8.52 (s, 1H), 8.42 (d, J = 5.6 Hz, 1H), 8.02 (d, J = 7.6 Hz, 1H), 7.98-7.97 (m, 2H), 7.64 (s, 1H), 7.48 (d, J = 8.0 Hz, 1H), 7.22 (d, J = 4.4 Hz, 1H), 5.60-5.57 (m, 1H), 4.76 (t, J = 6.4 Hz, 1H), 4.71-4.69 (m, 3H), 3.99-3.82 (m, 6H), 3.10-3.05 (m, 1H), 2.92-2.86 (m, 1H), 2.27-2.18 (m, 1H), 2.07-2.02 (m, 1H), 1.74 (s, 9H). |
| 72 | 1-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide | 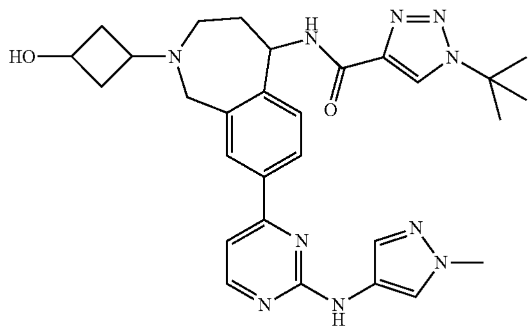 [SMILES: Cn1cc(Nc2nccc(-c3ccc4c(c3)CN(C3CC(O)C3)CCC4NC(=O)c3cn(C(C)(C)C)nn3)n2)cn1] | ESI-MS (M + H)⁺: 556.7. ¹H NMR (400 MHz, CDCl₃) δ: 8.41 (d, J = 5.2 Hz, 1H), 8.17 (s, 1H), 7.88 (s, 1H), 7.81-7.78 (m, 2H), 7.54 (s, 1H), 7.48 (d, J = 8.4 Hz, 1H), 7.04-7.02 (s, 2H), 5.59 (t, J = 8.4 Hz, 1H), 4.03-3.79 (m, 6H), 3.19-3.13 (m, 1H), 2.76-2.63 (m, 4H), 2.31-2.25 (m, 1H), 2.15-1.93 (m, 3H), 1.68 (s, 9H). |
| 73 | 1-(tert-butyl)-N-(8-(2-((1-methyl-1H-pyrazol-4-yl)amino)pyrimidin-4-yl)-2-(tetrahydrofuran-3-yl)-2,3,4,5-tetrahydro-1H-benzo[c]azepin-5-yl)-1H-1,2,3-triazole-4-carboxamide | 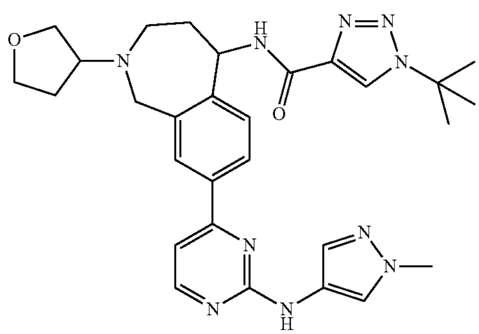 [SMILES: Cn1cc(Nc2nccc(-c3ccc4c(c3)CN(C3CCOC3)CCC4NC(=O)c3cn(C(C)(C)C)nn3)n2)cn1] | ESI-MS (M + H)⁺: 556.7. ¹H NMR (400 MHz, CD₃OD) δ: 8.47 (s, 1H), 8.38 (d, J = 5.2 Hz, 1H), 7.98-7.95 (m, 3H), 7.62 (d, J = 5.2 Hz, 1H), 7.47 (d, J = 7.6 Hz, 1H), 7.17 (d, J = 5.2 Hz, 1H), 5.57-5.55 (m, 1H), 4.09-3.94 (m, 4H), 3.89 (s, 3H), 3.78-3.70 (m, 2H), 3.28-3.06 (m, 3H), 2.32-1.94 (m, 4H), 1.74 (s, 9H). |
| 74 | 1-(tert-butyl)-N-(8-(2-((1-methyl-1H-pyrazol-4-yl)amino)pyrimidin-4-yl)-2-(tetrahydro-2H-pyran-4-yl)-2,3,4,5-tetrahydro-1H-benzo[c]azepin-5-yl)-1H-1,2,3-triazole-4-carboxamide | 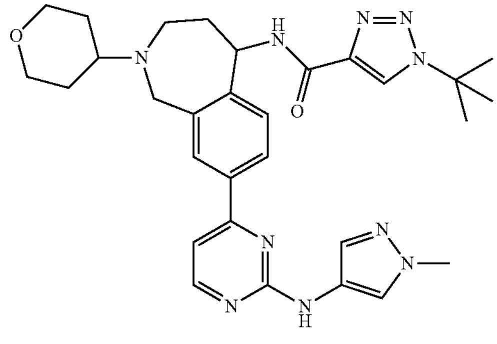 [SMILES: Cn1cc(Nc2nccc(-c3ccc4c(c3)CN(C3CCOCC3)CCC4NC(=O)c3cn(C(C)(C)C)nn3)n2)cn1] | ESI-MS (M + H)⁺: 570.7. ¹H NMR (400 MHz, CDCl₃) δ: 8.41 (d, J = 4.8 Hz, 1H), 8.22 (d, J = 10.0 Hz, 1H), 8.16 (s, 1H), 7.88 (s, 1H), 7.83-7.80 (m, 2H), 7.50 (s, 1H), 7.48 (d, J = 7.6 Hz, 1H), 7.04 (d, J = 5.2 Hz, 1H), 6.93 (s, 1H), 5.65 (t, J = 8.4 Hz, 1H), 4.10-4.05 (m, 4H), 3.91 (s, 3H), 3.44-3.37 (m, 2H), 3.19-3.16 (m, 1H), 3.10-3.05 (m, 1H), 2.86-2.81 (m, 1H), 2.31-2.26 (m, 1H), 2.10-2.04 (m, 1H), 1.95-1.70 (m, 4H), 1.69 (s, 9H). |

| Compd No. | Chemical Name | Structure | ¹H-NMR and MS |
|---|---|---|---|
| 75 | 1-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1H-1,2,3-triazole-4-carboxamide | 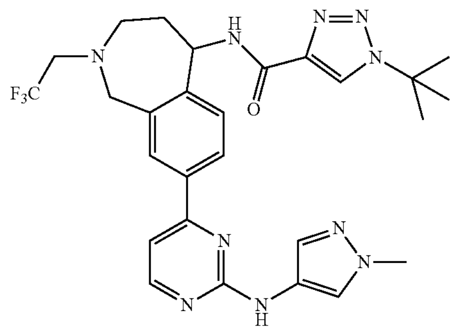 [SMILES: Cn1cc(Nc2nccc(-c3ccc4c(c3)CN(CC(F)(F)F)CCC4NC(=O)c3cn(C(C)(C)C)nn3)n2)cn1] | ESI-MS (M + H)⁺: 568.7. ¹H NMR (400 MHz, CDCl₃) δ: 8.42 (d, J = 5.2 Hz, 1H), 8.18 (s, 1H), 7.91 (s, 1H), 7.87 (d, J = 7.6 Hz, 1H), 7.83 (s, 1H), 7.78 (d, J = 8.8 Hz, 1H), 7.51 (s, 1H), 7.48 (d, J = 8.0 Hz, 1H), 7.05 (d, J = 5.2 Hz, 1H), 7.02 (s, 1H), 5.61 (t, J = 8.4 Hz, 1H), 4.33-4.12 (m, 2H), 3.91 (s, 3H), 3.41-3.35 (m, 2H), 3.10-3.03 (m, 2H), 2.22-2.14 (m, 1H), 2.03-1.97 (m, 1H), 1.71 (s, 9H). |
| 76 | 1-(tert-butyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide | 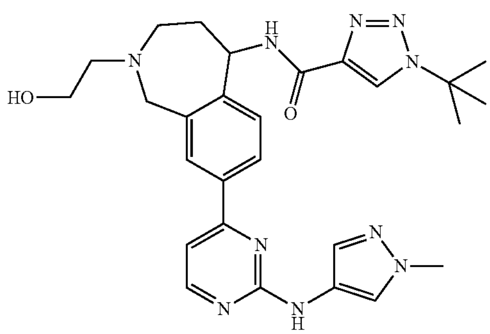 [SMILES: Cn1cc(Nc2nccc(-c3ccc4c(c3)CN(CCO)CCC4NC(=O)c3cn(C(C)(C)C)nn3)n2)cn1] | ESI-MS (M + H)⁺: 531.3. ¹H NMR (400 MHz, CDCl₃) δ: 8.50 (br, 1H), 8.41 (d, J = 5.2 Hz, 1H), 8.16 (s, 1H), 7.88 (s, 1H), 7.83-7.80 (m, 2H), 7.54 (s, 1H), 7.49 (d, J = 7.6 Hz, 1H), 7.03 (d, J = 5.2 Hz, 1H), 6.91 (s, 1H), 5.61 (t, J = 8.8 Hz, 1H), 4.14-4.03 (m, 2H), 3.92 (s, 3H), 3.80-3.79 (m, 2H), 3.29-3.26 (m, 1H), 3.99-3.96 (m, 1H), 2.80-2.77 (m, 2H), 2.30-2.27 (m, 1H), 2.08-2.01 (m, 1H), 1.70 (s, 9H). |
| 77 | 1-(tert-butyl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide | 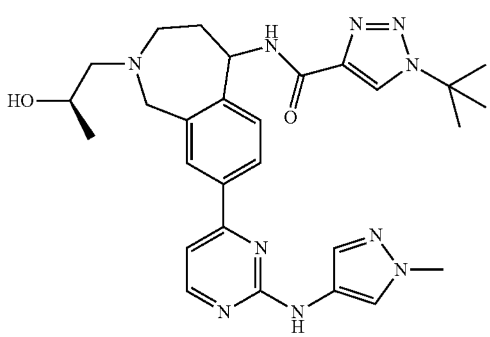 [SMILES: C[C@@H](O)CN1CCC(NC(=O)c2cn(C(C)(C)C)nn2)c2ccc(-c3ccnc(Nc4cnn(C)c4)n3)cc2C1] | ESI-MS (M + H)⁺: 544.3. ¹H NMR (400 MHz, DMSO-d₆) δ: 9.50 (s, 1H), 9.00 (d, J = 7.2 Hz, 1H), 8.75 (s, 1H), 8.45 (d, J = 5.2 Hz, 1H), 7.95 (s, 3H), 7.53 (s, 1H), 7.36 (d, J = 8.0 Hz, 1H), 7.25 (d, J = 5.2 Hz, 1H), 5.46-5.42 (m, 1H), 4.35-3.94 (m, 3H), 3.82-3.76 (m, 4H), 3.31-3.13 (m, 2H), 2.36-2.11 (m, 3H), 1.79-1.73 (m, 1H), 1.65 (s, 9H), 1.03 (t, J = 5.2 Hz, 3H). |
| 78 | 5-(tert-butyl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide | 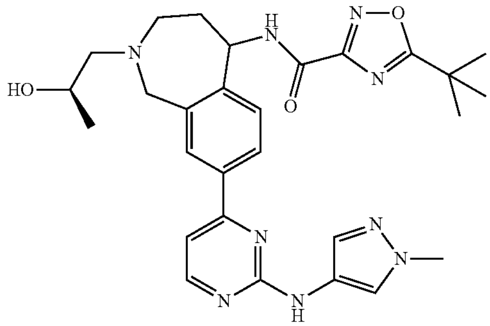 [SMILES: C[C@@H](O)CN1CCC(NC(=O)c2noc(C(C)(C)C)n2)c2ccc(-c3ccnc(Nc4cnn(C)c4)n3)cc2C1] | ESI-MS (M + H)⁺: 546.3. ¹H NMR (400 MHz, CD₃OD) δ: 8.42 (d, J = 5.2 Hz, 1H), 8.03-7.99 (m, 3H), 7.64 (s, 1H), 7.46 (d, J = 7.2 Hz, 1H), 7.24-7.22 (m, 1H), 5.61-5.58 (m, 1H), 4.22-3.98 (m, 3H), 3.91 (s, 3H), 3.28-3.21 (m, 2H), 2.47-2.26 (m, 3H), 1.97-1.94 (m, 1H), 1.52 (s, 9H), 1.16-1.28 (m, 3H). |

| Compd No. | Chemical Name | Structure | ¹H-NMR and MS |
|---|---|---|---|
| 79 | 5-(tert-butyl)-N-(2-(2-methoxyethyl)-8-(2-((1-methyl-1H-pyrazol-4-yl)amino)pyrimidin-4-yl)-2,3,4,5-tetrahydro-1H-benzo[c]azepin-5-yl)-1,2,4-oxadiazole-3-carboxamide | 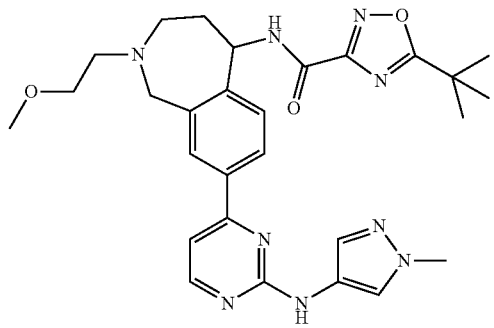 [SMILES: COCCN1CCC(NC(=O)c2noc(C(C)(C)C)n2)c2ccc(-c3ccnc(Nc4cnn(C)c4)n3)cc2C1] | ESI-MS (M + H)⁺: 545.7. ¹H NMR (400 MHz, CD₃OD) δ: 8.43 (d, J = 5.2 Hz, 1H), 8.05-8.03 (m, 2H), 7.99 (s, 1H), 7.65 (s, 1H), 7.46 (d, J = 8.8 Hz, 1H), 7.24 (d, J = 5.6 Hz, 1H), 5.59 (d, J = 10.0 Hz, 1H), 4.22-4.11 (m, 2H), 3.90 (s, 3H), 3.61 (t, J = 5.6 Hz, 2H), 3.36 (s, 3H), 3.27-3.15 (m, 2H), 2.77-2.69 (m, 2H), 2.31-2.25 (m, 1H), 2.00-1.97 (m, 1H), 1.53 (s, 9H). |
| 80 | 5-(tert-butyl)-N-(8-(2-((1-methyl-1H-pyrazol-4-yl)amino)pyrimidin-4-yl)-2-(tetrahydrofuran-3-yl)-2,3,4,5-tetrahydro-1H-benzo[c]azepin-5-yl)-1,3,4-oxadiazole-2-carboxamide | 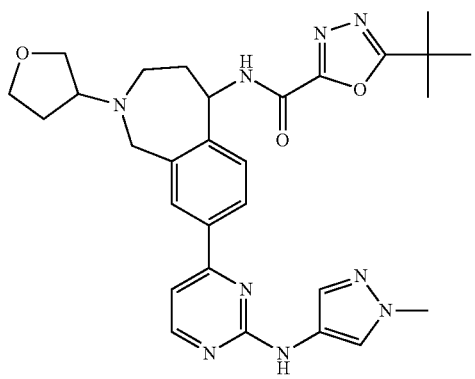 [SMILES: Cn1cc(Nc2nccc(-c3ccc4c(c3)CN(C3CCOC3)CCC4NC(=O)c3nnc(C(C)(C)C)o3)n2)cn1] | ESI-MS (M + H)⁺: 558.3. ¹H NMR (400 MHz, CD₃OD) δ: 8.42 (d, J = 5.2 Hz, 1H), 8.04-7.99 (m, 3H), 7.64-7.63 (m, 1H), 7.50 (d, J = 8.0 Hz, 1H), 7.24 (d, J = 5.2 Hz, 1H), 5.59 (d, J = 10.0 Hz, 1H), 4.10-3.91 (m, 4H), 3.90 (s, 3H), 3.79-3.70 (m, 2H), 3.32-3.12 (m, 3H), 2.30-2.18 (m, 2H), 2.05-1.97 (m, 2H), 1.51 (s, 9H). |
| 81 | 5-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 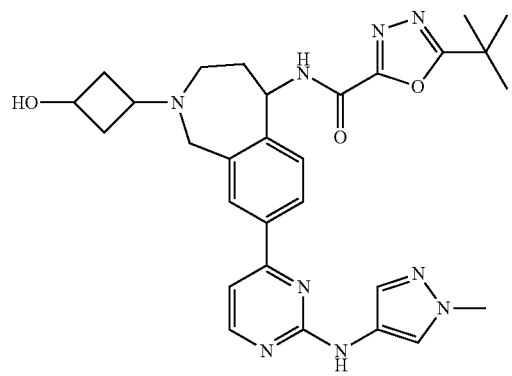 [SMILES: Cn1cc(Nc2nccc(-c3ccc4c(c3)CN(C3CC(O)C3)CCC4NC(=O)c3nnc(C(C)(C)C)o3)n2)cn1] | ESI-MS (M + H)⁺: 558.2. ¹H NMR (400 MHz, CD₃OD) δ: 8.42 (d, J = 5.2 Hz, 1H), 8.03-8.01 (m, 3H), 7.63 (s, 1H), 7.47 (d, J = 8.4 Hz, 1H), 7.23 (d, J = 5.2 Hz, 1H), 5.56-5.54 (m, 1H), 3.98-3.87 (m, 6H), 3.25-3.21 (m, 1H), 2.96-2.91 (m, 1H), 2.64-2.18 (m, 4H), 2.02-1.83 (m, 3H), 1.51 (s, 9H). |
| 82 | (R)-5-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 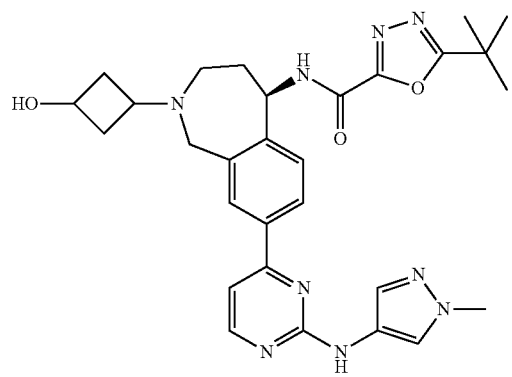 [SMILES: Cn1cc(Nc2nccc(-c3ccc4c(c3)CN(C3CC(O)C3)CC[C@H]4NC(=O)c3nnc(C(C)(C)C)o3)n2)cn1] | LCMS: Rt 2.9 min, m/z 558.00. ¹H NMR (400 MHz, METHANOL-d₄) δ: 8.41 (d, J = 5.3 Hz, 1H), 8.07-7.94 (m, 3H), 7.65-7.59 (m, 1H), 7.50-7.43 (m, 1H), 7.22 (d, J = 5.3 Hz, 1H), 5.54 (br d, J = 9.5 Hz, 1H), 4.58 (s, 1H), 4.07-3.94 (m, 2H), 3.92-3.82 (m, 4H), 3.29-3.18 (m, 1H), 3.04-2.78 (m, 1H), 2.66-2.50 (m, 2H), 2.37-2.10 (m, 1H), 2.10-1.94 (m, 1H), 1.88-1.79 (m, 2H), 1.49 (s, 9H), 0.98-0.79 (m, 1H). |

| Compd No. | Chemical Name | Structure | ¹H-NMR and MS |
|---|---|---|---|
| 83 | 5-(tert-butyl)-N-(2-ethyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 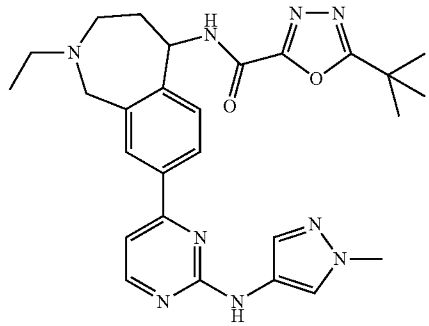 [SMILES: CCN1CCC(NC(=O)c2nnc(C(C)(C)C)o2)c2ccc(-c3ccnc(Nc4cnn(C)c4)n3)cc2C1] | ESI-MS (M + H)⁺: 516.2. ¹H NMR (400 MHz, CD₃OD) δ: 8.41 (d, J = 5.2 Hz, 1H), 8.04-7.98 (m, 3H), 7.64 (s, 1H), 7.47 (d, J = 7.6 Hz, 1H), 7.21 (d, J = 5.2 Hz, 1H), 5.56-5.54 (m, 1H), 4.07 (s, 2H), 3.90 (s, 3H), 3.30-3.07 (m, 2H), 2.61-2.55 (m, 2H), 2.28-2.00 (m, 2H), 1.51 (s, 9H), 1.19 (t, J = 7.2 Hz, 3H). |
| 84 | (R)-5-(tert-butyl)-N-(2-ethyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 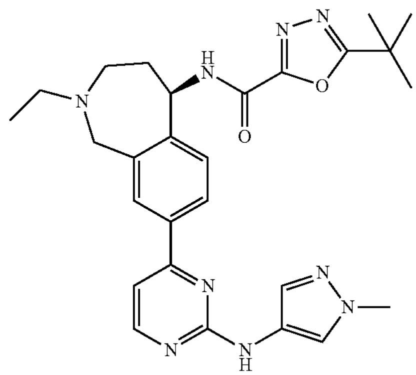 [SMILES: CCN1CC[C@@H](NC(=O)c2nnc(C(C)(C)C)o2)c2ccc(-c3ccnc(Nc4cnn(C)c4)n3)cc2C1] | LCMS: Rt 2.7 min, m/z 516.10. ¹H NMR (400 MHz, METHANOL-d₄) δ: 8.38 (d, J = 5.3 Hz, 1H), 8.02-7.98 (m, 2H), 7.96 (s, 1H), 7.62 (s, 1H), 7.44 (d, J = 7.8 Hz, 1H), 7.19 (d, J = 5.3 Hz, 1H), 5.53 (br d, J = 9.3 Hz, 1H), 4.05 (s, 2H), 3.87 (s, 3H), 3.29-3.22 (m, 1H), 3.09 (ddd, J = 13.3 Hz, 10.4 Hz, 2.9 Hz, 1H), 2.64-2.50 (m, 2H), 2.31-2.17 (m, 1H), 2.09-1.91 (m, 1H), 1.49 (s, 9H), 1.17 (t, J = 7.2 Hz, 3H). |
| 85 | (S)-5-(tert-butyl)-N-(2-ethyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 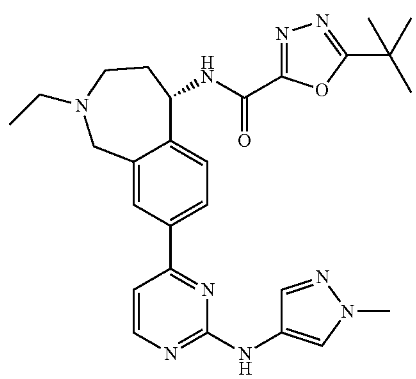 [SMILES: CCN1CC[C@H](NC(=O)c2nnc(C(C)(C)C)o2)c2ccc(-c3ccnc(Nc4cnn(C)c4)n3)cc2C1] | LCMS: Rt 3.9 min, m/z 516.10. ¹H NMR (400 MHz, METHANOL-d₄) δ: 8.39 (d, J = 5.3 Hz, 1H), 8.04-7.98 (m, 2H), 7.96 (s, 1H), 7.62 (s, 1H), 7.45 (d, J = 8.0 Hz, 1H), 7.20 (d, J = 5.3 Hz, 1H), 5.54 (d, J = 9.3 Hz, 1H), 4.07 (s, 2H), 3.88 (s, 3H), 3.29-3.20 (m, 1H), 3.10 (ddd, J = 13.2 Hz, 10.5 Hz, 2.6 Hz, 1H), 2.66-2.50 (m, 2H), 2.25 (dtd, J = 14.0 Hz, 10.4 Hz, 3.4 Hz, 1H), 2.01 (dt, J = 14.4 Hz, 2.3 Hz, 1H), 1.49 (s, 9 H), 1.18 (t, J = 7.2 Hz, 3H). |
| 86 | 5-(tert-butyl)-N-(2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 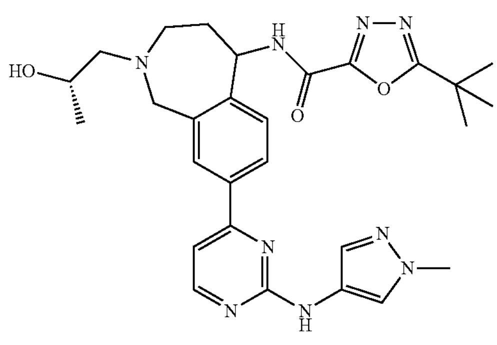 [SMILES: C[C@H](O)CN1CCC(NC(=O)c2nnc(C(C)(C)C)o2)c2ccc(-c3ccnc(Nc4cnn(C)c4)n3)cc2C1] | ESI-MS (M + H)⁺: 546.3. ¹H NMR (400 MHz, CD₃OD) δ: 8.33 (d, J = 5.2 Hz, 1H), 7.94-7.90 (m, 3H), 7.61 (d, J = 2.0 Hz, 1H), 7.42 (d, J = 8.4 Hz, 1H), 7.11 (dd, J = 5.2, 1.6 Hz, 1H), 5.55-5.52 (m, 1H), 4.12-3.93 (m, 3H), 3.87 (s, 3H), 3.23-3.18 (m, 2H), 2.42-2.37 (m, 2H), 2.24-2.22 (m, 1H), 1.93-1.91 (m, 1H), 1.48 (s, 9H), 1.13-1.09 (m, 3H). |

| Compd No. | Chemical Name | Structure | ¹H-NMR and MS |
|---|---|---|---|
| 87 | 5-(tert-butyl)-N-(2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 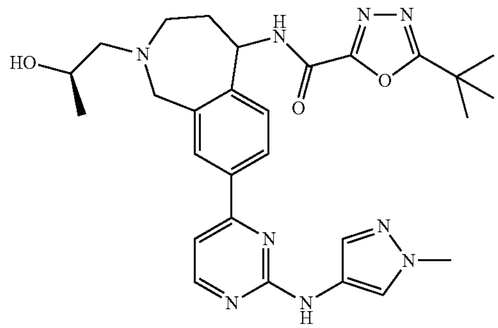 [SMILES: C[C@@H](O)CN1CCC(NC(=O)c2nnc(C(C)(C)C)o2)c2ccc(-c3ccnc(Nc4cnn(C)c4)n3)cc2C1] | ESI-MS (M + H)+: 545.7. ¹H NMR (400 MHz, CD₃OD) δ: 8.30-8.28 (m, 1H), 7.91-7.69 (m, 3H), 7.52 (s, 1H), 7.36 (d, J = 8.4 Hz, 1H), 7.11 (s, 1H), 5.46 (d, J = 10.0 Hz, 1H), 4.11-3.85 (m, 3H), 3.79 (s, 3H), 3.10-3.06 (m, 2H), 2.33-2.14 (m, 3H), 1.86-1.83 (m, 1H), 1.39 (s, 9H), 1.05-1.00 (m, 3H). |
| 88 | 5-(tert-butyl)-N-(2-(2-hydroxy-2-methylpropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 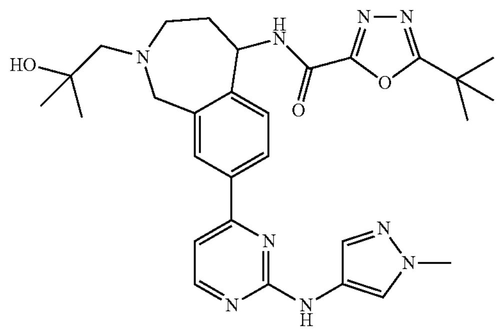 [SMILES: Cn1cc(Nc2nccc(-c3ccc4c(c3)CN(CC(C)(C)O)CCC4NC(=O)c3nnc(C(C)(C)C)o3)n2)cn1] | ESI-MS (M + H)+: 559.7. ¹H NMR (400 MHz, CD₃OD) δ: 8.27-8.25 (m, 1H), 7.84-7.81 (m, 3H), 7.52 (s, 1H), 7.34-7.33 (m, 1H), 7.07-7.05 (m, 1H), 5.46 (d, J = 10.0 Hz, 1H), 4.11-3.97 (m, 2H), 3.77 (s, 3H), 3.21-3.17 (m, 2H), 2.37-2.27 (m, 2H), 2.13-2.12 (m, 1H), 1.84-1.80 (m, 1H), 1.38 (s, 9H), 1.09 (s, 6H). |
| 89a | 5-tert-butyl-1,3,4-oxadiazole-2-carboxylic acid {(R)-2-(2-hydroxy-2-methyl-propyl)-8-[2-(1-methyl-1H-pyrazol-4-ylaimno)-pyrimidin-4-yl]-2,3,4,5-tetrahydro-1H-2-benzazepin-5-yl}-amide | 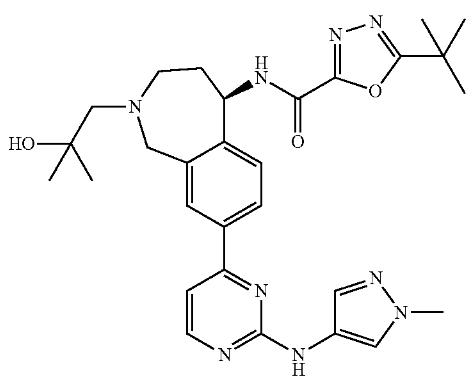 [SMILES: Cn1cc(Nc2nccc(-c3ccc4c(c3)CN(CC(C)(C)O)CC[C@H]4NC(=O)c3nnc(C(C)(C)C)o3)n2)cn1] | LCMS: Rt 0.87 min, m/z 560.3. ¹H NMR (400 MHz, METHANOL-d₄) δ: 8.42 (br. s., 1H), 7.90-8.13 (m, 3H), 7.64 (s, 1H), 7.47 (d, J = 8.03 Hz, 1H), 7.22 (br. s., 1H), 5.58 (d, J = 9.79 Hz, 1H), 4.07-4.34 (m, 2H), 3.90 (s, 3H), 2.45 (q, J = 14.31 Hz, 2H), 2.18-2.32 (m, 3H), 1.95 (d, J = 13.80 Hz, 1H), 1.50 (s, 9H), 1.22 (br. s., 6H). |
| 89b | (S)-5-(tert-butyl)-N-(2-(2-hydroxy-2-methylpropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 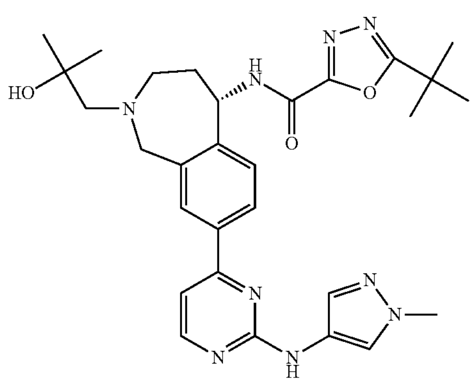 [SMILES: Cn1cc(Nc2nccc(-c3ccc4c(c3)CN(CC(C)(C)O)CC[C@@H]4NC(=O)c3nnc(C(C)(C)C)o3)n2)cn1] | LCMS: Rt 0.87 min, m/z 560.3. ¹H NMR (400 MHz, METHANOL-d4) δ: 8.43 (br. s., 1H), 8.02 (s, 3H), 7.64 (s, 1H), 7.47 (d, J = 8.03 Hz, 1H), 7.23 (br. s., 1H), 5.58 (d, J = 9.54 Hz, 1H), 4.05-4.38 (m, 2H), 3.90 (s, 3H), 2.45 (q, J = 14.06 Hz, 2H), 2.27 (d, J = 2.51 Hz, 1H), 1.95 (d, J = 13.80 Hz, 1H), 1.50 (s, 9H), 1.21 (s, 6H). |

-continued

| Compd No. | Chemical Name | Structure | $^1$H-NMR and MS |
|---|---|---|---|
| 90 | 5-(tert-butyl)-N-(2-(3-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 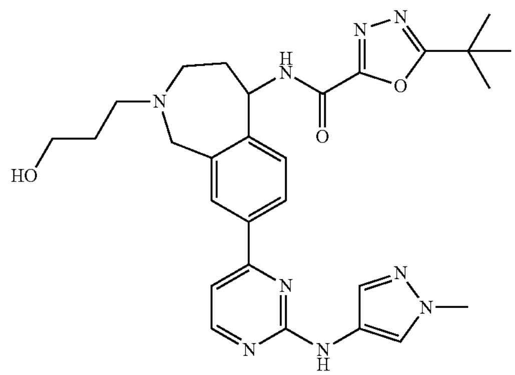 [SMILES: Cn1cc(Nc2nccc(-c3ccc4c(c3)CN(CCCO)CCC4NC(=O)c3nnc(C(C)(C)C)o3)n2)cn1] | ESI-MS (M + H)$^+$: 545.7. $^1$H NMR (400 MHz, CD$_3$OD) δ: 8.29 (d, J = 5.2 Hz, 1H), 7.91-7.88 (m, 2H), 7.85 (s, 1H), 7.53 (s, 1H), 7.35 (d, J = 8.0 Hz, 1H), 7.10 (d, J = 5.2 Hz, 1H), 5.46-5.42 (m, 1H), 4.02-3.93 (m, 2H), 3.78 (s, 3H), 3.51 (t, J = 6.0 Hz, 2H), 3.20-3.15 (m, 1H), 3.04-3.00 (m, 1H), 2.53-2.47 (m, 2H), 2.19-2.11 (m, 1H), 1.90-1.87 (m, 1H), 1.74-1.68 (m, 2H), 1.38 (s, 9H). |
| 91 | 5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,3,4-oxadiazole-2-carboxamide | 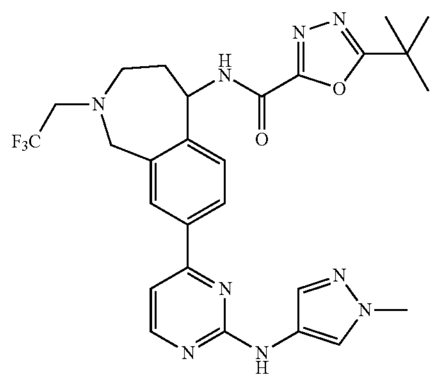 [SMILES: Cn1cc(Nc2nccc(-c3ccc4c(c3)CN(CC(F)(F)F)CCC4NC(=O)c3nnc(C(C)(C)C)o3)n2)cn1] | ESI-MS (M + H)$^+$: 570.2. $^1$H NMR (400 MHz, CDCl$_3$) δ: 8.37 (d, J = 5.2 Hz, 1H), 7.83-7.76 (m, 4H), 7.46 (s, 1H), 7.42 (d, J = 8.0 Hz, 1H), 6.99 (d, J = 5.2 Hz, 1H), 6.85 (s, 1H), 5.56-5.52 (m, 1H), 4.23-4.19 (m, 1H), 4.08-4.04 (m, 1H), 3.85 (s, 3H), 3.28-3.04 (m, 4H), 2.23-2.18 (m, 1H), 2.02-1.95 (m, 1H), 1.40 (s, 9H). |
| 92 | N-(8-(2-((1H-pyrazol-4-yl)amino)pyrimidin-4-yl)-2-(oxetan-3-yl)-2,3,4,5-tetrahydro-1H-benzo[c]azepin-5-yl)-5-(tert-butyl)-1,3,4-oxadiazole-2-carboxamide | 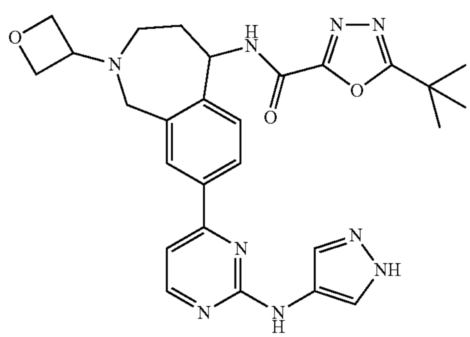 [SMILES: CC(C)(C)c1nnc(C(=O)NC2CCN(C3COC3)Cc3cc(-c4ccnc(Nc5cn[nH]c5)n4)ccc32)o1] | ESI-MS (M + H)$^+$: 530.3. $^1$H NMR (400 MHz, DMSO-d$_6$) δ: 9.83 (d, J = 8.4 Hz, 1H), 9.47 (s, 1H), 8.47 (d, J = 8.8 Hz, 1H), 7.99 (d, J = 8.8 Hz, 1H), 7.96 (s, 1H), 7.91 (s, 1H), 7.65 (s, 1H), 7.39 (d, J = 8.0 Hz, 1H), 7.27 (d, J = 5.2 Hz, 2H), 5.40 (t, J = 9.6 Hz, 1H), 4.58 (t, J = 6.4 Hz, 1H), 4.52-4.45 (m, 3H), 3.90-3.62 (m, 3H), 2.95-2.92 (m, 1H), 2.83-2.77 (m, 1H), 2.13-2.05 (m, 1H), 1.88-1.85 (m, 1H), 1.42 (s, 9H). |
| 93 | (R)-5-(tert-butyl)-N-(8-(2-((5,6-dihydro-4H-pyrrolo[1,2-b]pyrazol-3-yl)amino)pyrimidin-4-yl)-2-(2-hydroxyethyl)-2,3,4,5-tetrahydro-1H-benzo[c]azepin-5-yl)-1,3,4-oxadiazole-2-carboxamide | 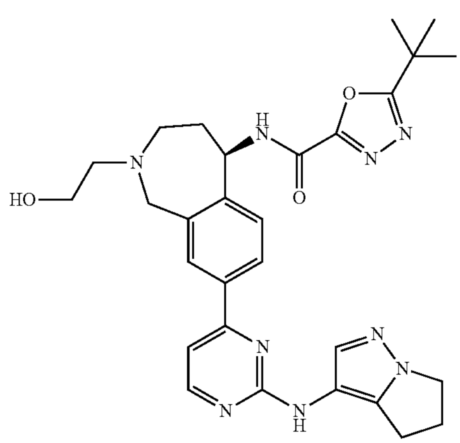 [SMILES: CC(C)(C)c1nnc(C(=O)N[C@@H]2CCN(CCO)Cc3cc(-c4ccnc(Nc5cnn6c5CCC6)n4)ccc32)o1] | ESI-MS (M + H)$^+$: 557.7. $^1$H NMR (400 MHz, CD$_3$OD) δ: 8.36 (d, J = 5.2 Hz, 1H), 8.04-8.02 (m, 2H), 7.69 (s, 1H), 7.48 (d, J = 8.0 Hz, 1H), 7.22 (d, J = 5.2 Hz, 1H), 5.60-5.57 (m, 1H), 4.29-4.13 (m, 4H), 3.77 (t, J = 6.0 Hz, 2H), 3.35-3.33 (m, 2H), 2.95 (t, J = 7.2 Hz, 2H), 2.78-2.76 (m, 2H), 2.66-2.62 (m, 2H), 2.34-2.28 (m, 1H), 2.08-2.01 (m, 1H), 1.50 (s, 9H). |

| Compd No. | Chemical Name | Structure | ¹H-NMR and MS |
|---|---|---|---|
| 94 | (R)-1-(tert-butyl)-N-(8-(2-((5,6-dihydro-4H-pyrrolo[1,2-b]pyrazol-3-yl)amino)pyrimidin-4-yl)-2-(2-hydroxyethyl)-2,3,4,5-tetrahydro-1H-benzo[c]azepin-5-yl)-1H-1,2,3-triazole-4-carboxamide | 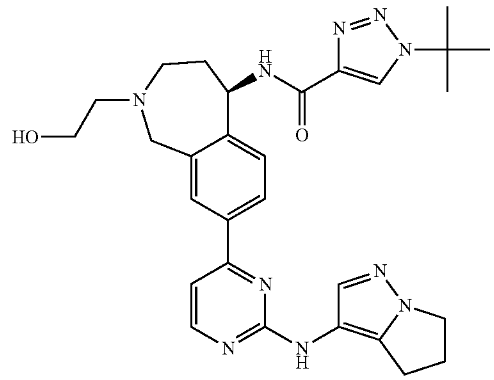 [SMILES: CC(C)(C)n1cc(C(=O)N[C@@H]2CCN(CCO)Cc3cc(-c4ccnc(Nc5cnn6c5CCC6)n4)ccc32)nn1] | ESI-MS (M + H)⁺: 556.7. ¹H NMR (400 MHz, CD₃OD) δ: 8.45 (s, 1H), 8.27 (d, J = 5.2 Hz, 1H), 7.91-7.87 (m, 2H), 7.59 (s, 1H), 7.37 (d, J = 8.0 Hz, 1H), 7.14 (d, J = 5.6 Hz, 1H), 5.49 (d, J = 9.6 Hz, 1H), 4.13-3.99 (m, 4H), 3.65 (t, J = 6.0 Hz, 2H), 3.20-3.05 (m, 2H), 2.86 (t, J = 7.2 Hz, 2H), 2.62-2.52 (m, 4H), 2.21-2.17 (m, 1H), 1.93-1.89 (m, 1H), 1.65 (s, 9H). |
| 95 | N-(2-methyl-8-(2-((1-methyl-1H-pyrazol-4-yl)amino)pyrimidin-4-yl)-2,3,4,5-tetrahydro-1H-benzo[c]azepin-5-yl)-5-(1-methylcyclopropyl)-1,3,4-oxadiazole-2-carboxamide | 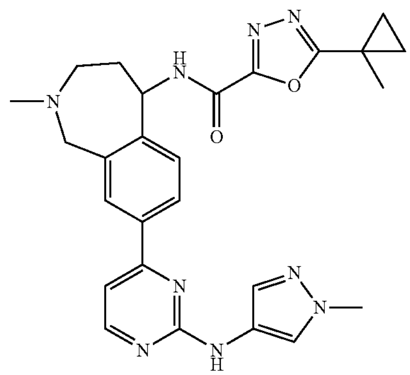 | ESI-MS (M + H)⁺: 530.2. ¹H NMR (400 MHz, CD₃OD) δ: 8.39 (d, J = 5.2 Hz, 1H), 8.00-7.97 (m, 3H), 7.63 (s, 1H), 7.44 (d, J = 8.0 Hz, 1H), 7.19 (d, J = 5.6 Hz, 1H), 5.53 (d, J = 10.0 Hz, 1H), 4.18-4.06 (m, 2H), 3.90 (s, 3H), 3.73 (t, J = 6.0 Hz, 2H), 3.28-3.19 (m, 2H), 2.67-2.62 (m, 2H), 2.28-2.24 (m, 1H), 1.98-1.95 (m, 1H), 1.61 (s, 3H), 1.45-1.42 (m, 2H), 1.13-1.10 (m, 2H). |
| 96 | 5-(tert-butyl)-N-(8-(2-((1-ethyl-1H-pyrazol-4-yl)amino)pyrimidin-4-yl)-2-(tetrahydrofuran-3-yl)-2,3,4,5-tetrahydro-1H-benzo[c]azepin-5-yl)-1,3,4-oxadiazole-2-carboxamide | 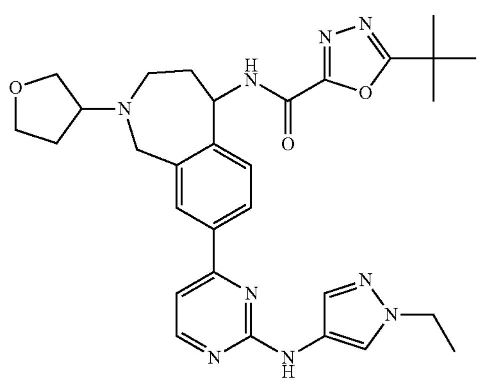 [SMILES: CCn1cc(Nc2nccc(-c3ccc4c(c3)CN(C3CCOC3)CCC4NC(=O)c3nnc(C(C)(C)C)o3)n2)cn1] | ESI-MS (M + H)⁺: 572.3. ¹H NMR (400 MHz, CD₃OD) δ: 8.42 (d, J = 5.2 Hz, 1H), 8.05-8.03 (m, 3H), 7.65 (s, 1H), 7.48 (d, J = 7.6 Hz, 1H), 7.24 (d, J = 5.2 Hz, 1H), 5.60-5.57 (m, 1H), 4.21-3.97 (m, 6H), 3.78-3.70 (m, 2H), 3.32-3.14 (m, 3H), 2.33-1.96 (m, 4H), 1.51-1.47 (m, 12H). |
| 97 | 5-(tert-butyl)-N-((R)-8-(2-((1-ethyl-1H-pyrazol-4-yl)amino)pyrimidin-4-yl)-2-((R*)-tetrahydrofuran-3-yl)-2,3,4,5-tetrahydro-1H-benzo[c]azepin-5-yl)-1,3,4-oxadiazole-2-carboxamide | 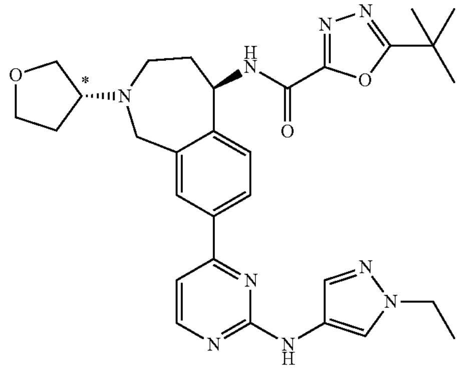 [SMILES: CCn1cc(Nc2nccc(-c3ccc4c(c3)CN([C@@H]3CCOC3)CC[C@H]4NC(=O)c3nnc(C(C)(C)C)o3)n2)cn1] | LCMS: Rt 0.90 min, m/z 572.10. ¹H NMR (300 MHz, METHANOL-d₄) δ: 8.41 (d, J = 5.3 Hz, 1H), 8.07-7.98 (m, 3H), 7.65 (s, 1H), 7.48 (d, J = 7.6 Hz, 1H), 7.22 (d, J = 5.3 Hz, 1H), 5.56 (br d, J = 9.1 Hz, 1H), 4.58 (s, 1H), 4.23-4.07 (m, 4H), 4.13-3.90 (m, 2H), 3.82-3.63 (m, 2H), 3.27-3.05 (m, 2H), 2.42-2.11 (m, 2H), 2.11-1.90 (m, 2H), 1.51-1.43 (m, 12H). |

-continued

| Compd No. | Chemical Name | Structure | $^1$H-NMR and MS |
|---|---|---|---|
| 98 | 5-(tert-butyl)-N-(8-(2-((1-ethyl-1H-pyrazol-4-yl)amino)pyrimidin-4-yl)-2-(2-hydroxyethyl)-2,3,4,5-tetrahydro-1H-benzo[c]azepin-5-yl)-1,3,4-oxadiazole-2-carboxamide | 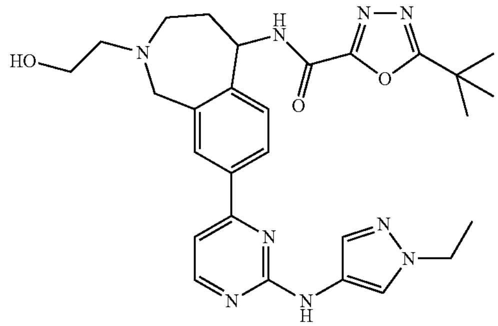 [SMILES: CCn1cc(Nc2nccc(-c3ccc4c(c3)CN(CCO)CCC4NC(=O)c3nnc(C(C)(C)C)o3)n2)cn1] | ESI-MS (M + H)$^+$: 545.7. $^1$H NMR (400 MHz, CD$_3$OD) δ: 8.42 (d, J = 5.2 Hz, 1H), 8.04-8.02 (m, 3H), 7.66 (s, 1H), 7.47 (d, J = 8.0 Hz, 1H), 7.23 (d, J = 5.2 Hz, 1H), 5.58-5.56 (m, 1H), 4.23-4.10 (m, 4H), 3.74 (t, J = 6.0 Hz, 1H), 3.25-3.22 (m, 2H), 2.71-2.63 (m, 2H), 2.32-2.27 (m, 1H), 2.02-1.98 (m, 1H), 1.40-1.47 (m, 12H). |
| 99 | 5-(tert-butyl)-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 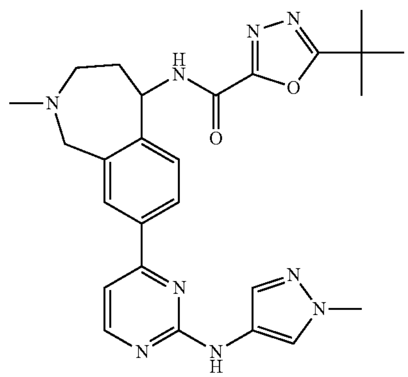 [SMILES: CN1CCC(NC(=O)c2nnc(C(C)(C)C)o2)c2ccc(-c3ccnc(Nc4cnn(C)c4)n3)cc2C1] | ESI-MS (M + H)$^+$: 502.2. $^1$H NMR (400 MHz, CD$_3$OD) δ: 8.43 (d, J = 5.2 Hz, 1H), 8.07-8.05 (m, 2H), 7.99 (s, 1H), 7.65 (s, 1H), 7.49 (d, J = 8.4 Hz, 1H), 7.25 (d, J = 5.6 Hz, 1H), 5.56 (d, J = 9.6 Hz, 1H), 4.13-4.09 (m, 1H), 3.97-3.93 (m, 1H), 3.90 (s, 3H), 3.21-3.18 (m, 1H), 3.10-3.05 (m, 1H), 2.42 (s, 3H), 2.30-2.26 (m, 1H), 2.05-2.01 (m, 1H), 1.52 (s, 9H). |
| 100 | (R)-5-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1,3,4-oxadiazole-2-carboxamide | 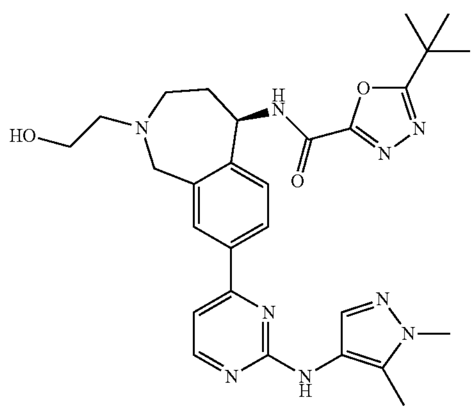 [SMILES: Cc1c(Nc2nccc(-c3ccc4c(c3)CN(CCO)CC[C@H]4NC(=O)c3nnc(C(C)(C)C)o3)n2)cnn1C] | ESI-MS (M + H)$^+$: 545.7. $^1$H NMR (400 MHz, CD$_3$OD) δ: 8.32 (d, J = 5.2 Hz, 1H), 8.01-7.99 (m, 2H), 7.60 (s, 1H), 7.44 (d, J = 8.0 Hz, 1H), 7.23 (d, J = 5.6 Hz, 1H), 5.57-5.54 (m, 1H), 4.21-4.07 (m, 2H), 3.82 (s, 3H), 3.73 (t, J = 6.0 Hz, 2H), 3.30-3.21 (m, 2H), 2.68-2.63 (m, 2H), 2.30-2.27 (m, 1H), 2.24 (s, 3H), 2.01-1.96 (m, 1H), 1.51 (s, 9H). |
| 101 | (R)-1-(tert-butyl)-N-(8-(2-((1,5-dimethyl-1H-pyrazol-4-yl)amino)pyrimidin-4-yl)-2-(2-hydroxyethyl)-2,3,4,5-tetrahydro-1H-benzo[c]azepin-5-yl)-1H-1,2,3-triazole-4-carboxamide | 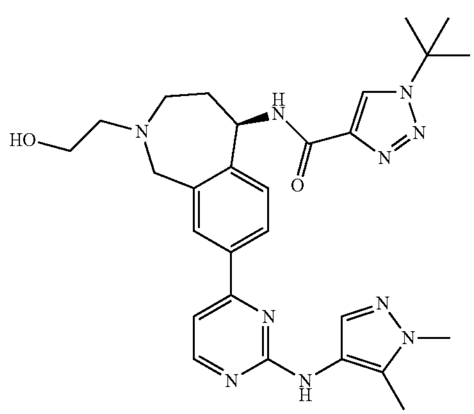 [SMILES: Cc1c(Nc2nccc(-c3ccc4c(c3)CN(CCO)CC[C@H]4NC(=O)c3cn(C(C)(C)C)nn3)n2)cnn1C] | ESI-MS (M + H)$^+$: 544.7. $^1$H NMR (400 MHz, CDCl$_3$) δ: 8.47 (br, 1H), 8.36 (d, J = 5.2 Hz, 1H), 8.16 (s, 1H), 7.80-7.78 (m, 2H), 7.67 (s, 1H), 7.45 (d, J = 7.6 Hz, 1H), 7.02 (d, J = 5.2 Hz, 1H), 6.45 (s, 1H), 5.59 (t, J = 8.8 Hz, 1H), 4.12-4.02 (m, 2H), 3.81 (s, 3H), 3.77-3.68 (m, 2H), 3.28-3.24 (m, 1H), 2.99-2.96 (m, 1H), 2.79-2.76 (m, 2H), 2.33-2.26 (m, 1H), 2.22 (s, 3H), 2.08-2.01 (m, 1H), 1.70 (s, 9H). |

| Compd No. | Chemical Name | Structure | ¹H-NMR and MS |
|---|---|---|---|
| 102 | (R)-5-(tert-butyl)-N-(8-(2-((1,3-dimethyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide | 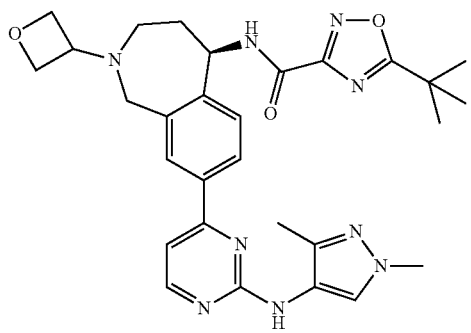 [SMILES: Cc1nn(C)cc1Nc1nccc(-c2ccc3c(c2)CN(C2COC2)CC[C@H]3NC(=O)c2noc(C(C)(C)C)n2)n1] | ESI-MS (M + H)⁺: 558.3. ¹H NMR (400 MHz, CD₃OD) δ: 8.38 (d, J = 5.6 Hz, 1H), 8.02 (d, J = 8.0 Hz, 1H), 7.95 (s, 1H), 7.84 (s, 1H), 7.46 (d, J = 8.0 Hz, 1H), 7.24 (d, J = 5.2 Hz, 1H), 5.61 (d, J = 9.2 Hz, 1H), 4.76 (t, J = 6.4 Hz, 1H), 4.70-4.66 (m, 3H), 3.96-3.81 (m, 3H), 3.84 (s, 3H), 3.08-3.02 (m, 1H), 2.87-2.81 (m, 1H), 2.27-2.24 (m, 1H), 2.22 (s, 3H), 2.07-2.03 (m, 1H), 1.15 (s, 9H). |
| 103 | (R)-1-(tert-butyl)-N-(8-(2-((1,3-dimethyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide | 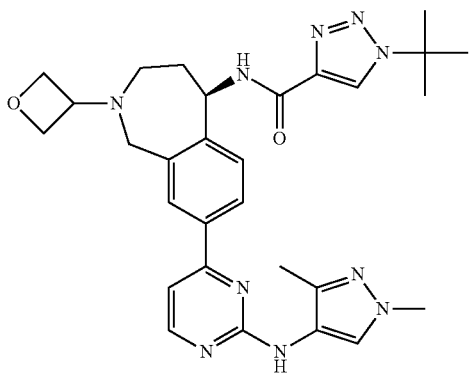 [SMILES: Cc1nn(C)cc1Nc1nccc(-c2ccc3c(c2)CN(C2COC2)CC[C@H]3NC(=O)c2cn(C(C)(C)C)nn2)n1] | ESI-MS (M + H)⁺: 557.3. ¹H NMR (400 MHz, CD₃OD) δ: 8.53 (s, 1H), 8.37 (d, J = 5.2 Hz, 1H), 8.00 (d, J = 7.6 Hz, 1H), 7.95 (s, 1H), 7.84 (s, 1H), 7.47 (d, J = 8.0 Hz, 1H), 7.24 (d, J = 5.6 Hz, 1H), 5.59 (d, J = 9.6 Hz, 1H), 4.76 (t, J = 6.4 Hz, 1H), 4.70-4.67 (m, 3H), 3.98-3.81 (m, 3H), 3.84 (s, 3H), 3.08-3.05 (m, 1H), 2.92-2.87 (m, 1H), 2.27-2.21 (m, 1H), 2.19 (s, 3H), 2.06-2.03 (m, 1H), 1.74 (s, 9H). |
| 104 | (R)-5-(tert-butyl)-N-(8-(2-((1,3-dimethyl-1H-pyrazol-4-yl)amino)pyrimidin-4-yl)-2-(2-hydroxyethyl)-2,3,4,5-tetrahydro-1H-benzo[c]azepin-5-yl)-1,2,4-oxadiazole-3-carboxamide | 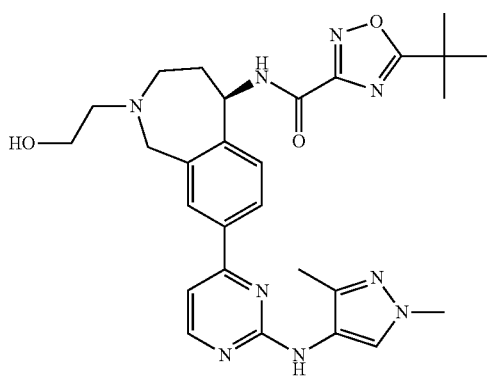 [SMILES: Cc1nn(C)cc1Nc1nccc(-c2ccc3c(c2)CN(CCO)CC[C@H]3NC(=O)c2noc(C(C)(C)C)n2)n1] | ESI-MS (M + H)⁺: 546.3. ¹H NMR (400 MHz, CD₃OD) δ: 8.37 (d, J = 4.8 Hz, 1H), 8.01 (s, 1H), 8.00 (d, J = 8.4 Hz, 1H), 7.85 (s, 1H), 7.44 (d, J = 8.0 Hz, 1H), 7.25 (d, J = 5.6 Hz, 1H), 5.59 (d, J = 9.6 Hz, 1H), 4.21-4.08 (m, 2H), 3.85 (s, 3H), 3.74 (t, J = 6.0 Hz, 2H), 3.27-3.17 (m, 2H), 2.71-2.63 (m, 2H), 2.30-2.25 (m, 1H), 2.22 (s, 3H), 1.99-1.96 (m, 1H), 1.52 (s, 9H). |
| 105 | (R)-1-(tert-butyl)-N-(2-(2-hydroxyethyl)-8-(2-((1-isopropyl-1H-pyrazol-4-yl)amino)pyrimidin-4-yl)-2,3,4,5-tetrahydro-1H-benzo[c]azepin-5-yl)-1H-1,2,3-triazole-4-carboxamide | 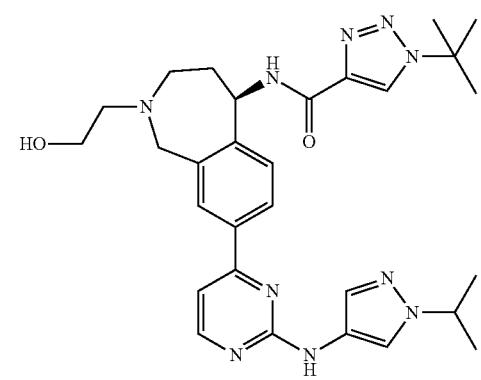 [SMILES: CC(C)n1cc(Nc2nccc(-c3ccc4c(c3)CN(CCO)CC[C@H]4NC(=O)c3cn(C(C)(C)C)nn3)n2)cn1] | ESI-MS (M + H)⁺: 559.3. ¹H NMR (400 MHz, CDCl₃) δ: 8.51 (br, 1H), 8.41 (d, J = 4.8 Hz, 1H), 8.17 (s, 1H), 7.95 (s, 1H), 7.83-7.82 (m, 2H), 7.56 (s, 1H), 7.48 (d, J = 8.4 Hz, 1H), 7.15 (s, 1H), 7.02 (d, J = 5.2 Hz, 1H), 5.61 (t, J = 8.0 Hz, 1H), 4.53-4.46 (m, 1H), 4.14-4.02 (m, 2H), 3.79-3.70 (m, 2H), 3.29-3.24 (m, 1H), 2.98-2.95 (m, 1H), 2.79-2.77 (m, 2H), 2.32-2.27 (m, 1H), 2.06-2.03 (m, 1H), 1.68 (s, 9H), 1.55 (d, J = 6.4 Hz, 6H). |

| Compd No. | Chemical Name | Structure | ¹H-NMR and MS |
|---|---|---|---|
| 106 | 5-(tert-butyl)-N-((R)-2-((R)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 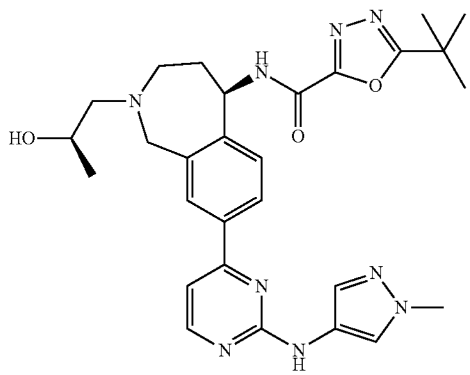 [SMILES: C[C@@H](O)CN1CC[C@@H](NC(=O)c2nnc(C(C)(C)C)o2)c2ccc(-c3ccnc(Nc4cnn(C)c4)n3)cc2C1] | ESI-MS (M + H)⁺: 546.3. ¹H NMR (400 MHz, CD₃OD) δ: 8.39 (d, J = 5.2 Hz, 1H), 8.00-7.97 (m, 3H), 7.64 (s, 1H), 7.45 (d, J = 8.0 Hz, 1H), 7.19 (d, J = 5.2 Hz, 1H), 5.57-5.55 (m, 1H), 4.21-4.09 (m, 2H), 3.99-3.97 (m, 1H), 3.90 (s, 3H), 3.28-3.23 (m, 2H), 2.40-2.37 (m, 2H), 2.28-2.25 (m, 1H), 1.97-1.94 (m, 1H), 1.48 (s, 9H), 1.13-1.12 (m, 3H). |
| 107 | (R)-5-(tert-butyl)-N-(2-(cyclopropylmethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 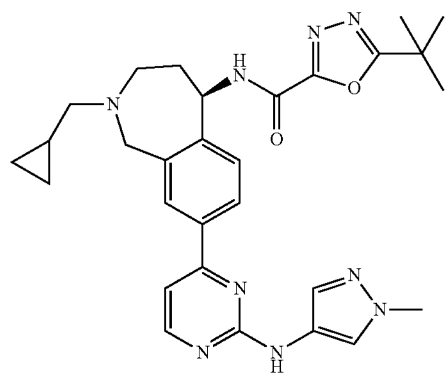 [SMILES: Cn1cc(Nc2nccc(-c3ccc4c(c3)CN(CC3CC3)CC[C@H]4NC(=O)c3nnc(C(C)(C)C)o3)n2)cn1] | ESI-MS (M + H)⁺: 542.1. ¹H NMR (300 MHz, METHANOL-d₄) δ: 8.45 (d, J = 5.3 Hz, 1H), 8.28-8.23 (m, 2H), 7.92 (s, 1H), 7.70-7.61 (m, 2H), 7.28 (d, J = 5.7 Hz, 1H), 5.72 (br s, 1H), 4.83-4.72 (m, 2H), 3.89 (s, 3H), 3.87-3.67 (m, 2H), 3.25-3.14 (m, 1H), 2.46 (br s, 2H), 1.50 (s, 10H), 1.32-1.17 (m, 1H), 0.85 (br s, 2H), 0.52 (br s, 2H). |
| 108 | 1-(tert-butyl)-N-((S)-8-(2-((1-methyl-1H-pyrazol-4-yl)amino)pyrimidin-4-yl)-2-((S*)-tetrahydrofuran-3-yl)-2,3,4,5-tetrahydro-1H-benzo[c]azepin-5-yl)-1H-1,2,3-triazole-4-carboxamide | 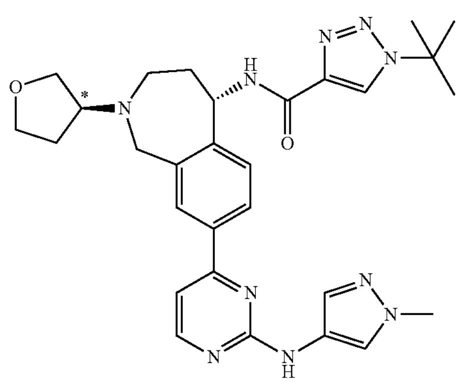 [SMILES: Cn1cc(Nc2nccc(-c3ccc4c(c3)CN([C@H]3CCOC3)CC[C@@H]4NC(=O)c3cn(C(C)(C)C)nn3)n2)cn1] | LCMS: Rt 0.82 min, m/z 557.00. ¹H NMR (400 MHz, METHANOL-d₄) δ: 8.51 (s, 1H), 8.41 (d, J = 5.4 Hz, 1H), 8.11-8.00 (m, 2H), 7.97 (s, 1H), 7.67-7.58 (m, 1H), 7.49 (d, J = 8.0 Hz, 1H), 7.23 (d, J = 5.3 Hz, 1H), 5.66-5.54 (m, 1H), 4.58 (br s, 1H), 4.28-4.108 (m, 2H), 4.03 (td, J = 8.7 Hz, 3.8 Hz, 1H), 3.99-3.93 (m, 1H), 3.89 (s, 3H), 3.86-3.70 (m, 2H), 3.47-3.38 (m, 1H), 3.27-3.17 (m, 1H), 2.37-2.17 (m, 2H), 2.16-1.96 (m, 2H), 1.73 (m, 9H). |
| 109 | 1-(tert-butyl)-N-((S)-8-(2-((1-methyl-1H-pyrazol-4-yl)amino)pyrimidin-4-yl)-2-((R*)-tetrahydrofuran-3-yl)-2,3,4,5-tetrahydro-1H-benzo[c]azepin-5-yl)-1H-1,2,3-triazole-4-carboxamide | 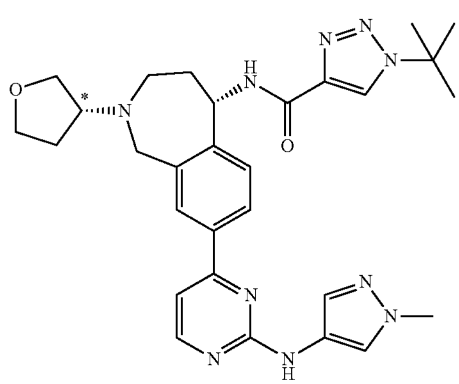 [SMILES: Cn1cc(Nc2nccc(-c3ccc4c(c3)CN([C@@H]3CCOC3)CC[C@@H]4NC(=O)c3cn(C(C)(C)C)nn3)n2)cn1] | LCMS: Rt 0.82 min, m/z 557.10. ¹H NMR (400 MHz, METHANOL-d₄) δ: 8.51 (s, 1H), 8.46-8.37 (m, 1H), 8.09-8.00 (m, 2H), 7.99 (s, 1H), 7.65-7.58 (m, 1H), 7.49 (d, J = 8.0 Hz, 1H), 7.22 (d, J = 5.3 Hz, 1H), 5.59 (br d, J = 9.5 Hz, 1H), 4.58 (s, 1H), 4.26-4.12 (m, 2H), 4.07-3.94 (m, 2H), 3.89 (s, 3H), 3.86-3.71 (m, 2H), 3.46-3.37 (m, 1H), 3.26-3.19 (m, 1H), 2.36-2.16 (m, 2H), 2.14-1.95 (m, 2H), 1.73 (s, 9H). |

| Compd No. | Chemical Name | Structure | ¹H-NMR and MS |
|---|---|---|---|
| 110 | (R)-5-(tert-butyl)-N-(8-(2-((1,3-dimethyl-1H-pyrazol-4-yl)amino)pyrimidin-4-yl)-2-(2,2,2-trifluoroethyl)-2,3,4,5-tetrahydro-1H-benzo[c]azepin-5-yl)-1,3,4-oxadiazole-2-carboxamide | 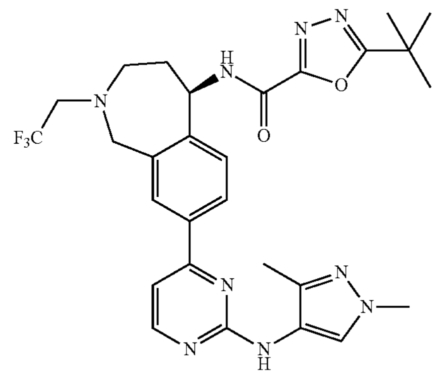 [SMILES: Cc1nn(C)cc1Nc1nccc(-c2ccc3c(c2)CN(CC(F)(F)F)CC[C@H]3NC(=O)c2nnc(C(C)(C)C)o2)n1] | ESI-MS (M + H)⁺: 584.3. ¹H NMR (400 MHz, CD₃OD) δ: 8.38 (d, J = 5.2 Hz, 1H), 8.03 (d, J = 8.4 Hz, 1H), 7.98 (s, 1H), 7.84 (s, 1H), 7.49 (d, J = 8.0 Hz, 1H), 7.25 (d, J = 5.6 Hz, 1H), 5.59 (d, J = 9.6 Hz, 1H), 4.37-4.34 (m, 1H), 4.13-4.10 (m, 1H), 3.84 (s, 3H), 3.46-3.41 (m, 2H), 3.15-3.08 (m, 2H), 2.25-2.17 (m, 1H), 2.22 (s, 3H), 1.97-1.93 (m, 1H), 1.51 (s, 9H). |
| 111 | 5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide | 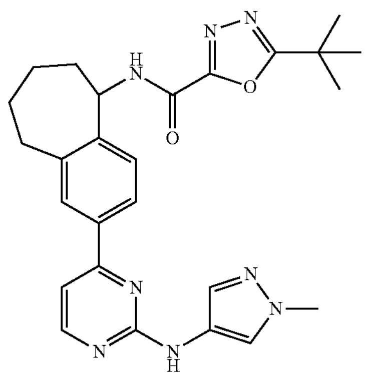 [SMILES: Cn1cc(Nc2nccc(-c3ccc4c(c3)CCCCC4NC(=O)c3nnc(C(C)(C)C)o3)n2)cn1] | LCMS: Rt 1.23 min.; (M + H)⁺ 487.0; ¹H NMR (400 MHz, METHANOL-d4) δ: 9.70 (br. s., 1H), 8.34 (d, J = 5.77 Hz, 1H), 8.02 (s, 2H), 7.97 (s, 1H), 7.69 (s, 1H), 7.47 (d, J = 8.53 Hz, 1H), 7.41 (s, 1H), 5.44 (t, J = 8.28 Hz, 1H), 3.93 (s, 3H), 2.87-3.22 (m, 2H), 1.77-2.28 (m, 4H), 1.51 (s, 11H). |
| 112 | N-(2-(2-((1H-pyrazol-4-yl)amino)pyrimidin-4-yl)-6,7,8,9-tetrahydro-5H-benzo[7]annulen-5-yl)-5-(tert-butyl)-1,2,4-oxadiazole-3-carboxamide | 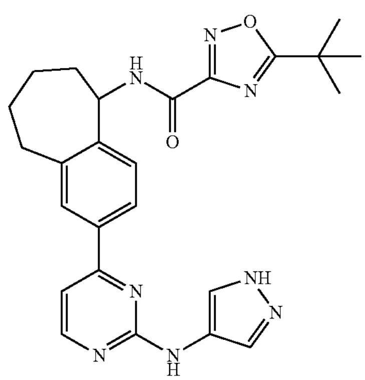 [SMILES: CC(C)(C)c1nc(C(=O)NC2CCCCc3cc(-c4ccnc(Nc5cn[nH]c5)n4)ccc32)no1] | ESI-MS (M + H)⁺: 473.1. ¹H NMR (400 MHz, CD₃OD) δ: 8.41 (d, J = 5.2 Hz, 1H), 8.07 (br, 1H), 7.96-7.95 (m, 2H), 7.76 (br, 1H), 7.40 (d, J = 8.4 Hz, 1H), 7.22 (d, J = 5.6 Hz, 1H), 5.44 (d, J = 9.6 Hz, 1H), 3.06-3.03 (m, 2H), 2.10-1.91 (m, 5H), 1.53 (s, 9H), 1.49-1.46 (m, 1H). |
| 113 | 5-(tert-butyl)-N-(2-(2-((5-methyl-4,5,6,7-tetrahydropyrazolo[1,5-a]pyrazin-3-yl)amino)pyrimidin-4-yl)-6,7,8,9-tetrahydro-5H-benzo[7]annulen-5-yl)-1,2,4-oxadiazole-3-carboxamide | 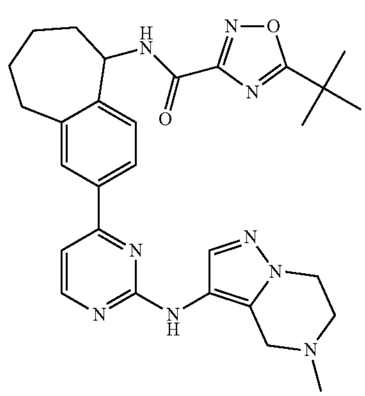 [SMILES: CN1CCn2ncc(Nc3nccc(-c4ccc5c(c4)CCCCC5NC(=O)c4noc(C(C)(C)C)n4)n3)c2C1] | ESI-MS (M + H)⁺: 542.2. ¹H NMR (400 MHz, CD₃OD) δ: 8.34 (d, J = 5.2 Hz, 1H), 7.94-7.91 (m, 2H), 7.70 (s, 1H), 7.38 (d, J = 8.0 Hz, 1H), 7.25 (d, J = 5.6 Hz, 1H), 5.45-5.42 (m, 1H), 4.23-4.21 (m, 2H), 3.67 (s, 2H), 3.02-2.99 (m, 4H), 2.49 (s, 3H), 2.06-1.92 (m, 5H), 1.54 (s, 9H), 1.51-1.42 (m, 1H). |

| Compd No. | Chemical Name | Structure | ¹H-NMR and MS |
|---|---|---|---|
| 114 | N-(2-(2-((1H-pyrazol-4-yl)amino)pyrimidin-4-yl)-6,7,8,9-tetrahydro-5H-benzo[7]annulen-5-yl)-5-(tert-butyl)-1,3,4-oxadiazole-2-carboxamide | 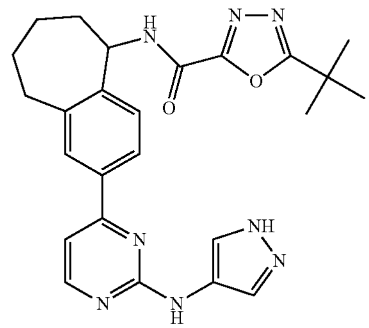 [SMILES: CC(C)(C)c1nnc(C(=O)NC2CCCCc3cc(-c4ccnc(Nc5cn[nH]c5)n4)ccc32)o1] | ESI-MS (M + H)⁺: 472.7. ¹H NMR (400 MHz, DMSO-d₆) δ: 12.46 (s, 1H), 9.89 (d, J = 8.0 Hz, 1H), 9.45 (s, 1H), 8.45 (d, J = 5.2 Hz, 1H), 7.96-7.91 (m, 3H), 7.63-7.62 (m, 1H), 7.37 (d, J = 8.0 Hz, 1H), 7.24 (d, J = 5.2 Hz, 1H), 5.28-5.24 (m, 1H), 2.97-2.96 (m, 2H), 2.00-1.77 (m, 5H), 1.42 (s, 9H), 1.33-1.30 (m, 1H). |
| 115 | 1-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1H-1,2,3-triazole-4-carboxamide | 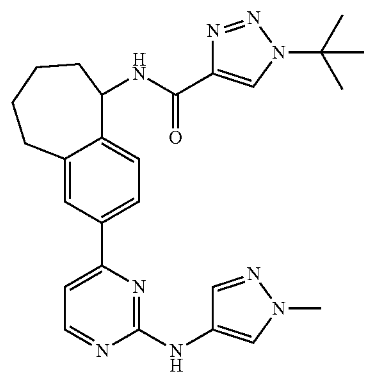 [SMILES: Cn1cc(Nc2nccc(-c3ccc4c(c3)CCCCC4NC(=O)c3cn(C(C)(C)C)nn3)n2)cn1] | ESI-MS (M + H)⁺: 486.2. ¹H NMR (400 MHz, CDCl₃) δ: 8.39 (d, J = 5.2 Hz, 1H), 8.16 (s, 1H), 7.90 (s, 1H), 7.81 (s, 1H), 7.79 (s, 1H), 7.68 (d, J = 8.4 Hz, 1H), 7.54 (s, 1H), 7.42 (d, J = 8.0 Hz, 1H), 7.05 (d, J = 5.2 Hz, 1H), 6.91 (s, 1H), 5.46-5.42 (m, 1H), 3.91 (s, 3H), 3.04-3.01 (m, 2H), 2.05-1.88 (m, 6H), 1.72 (s, 9H). |
| 116 | 5-(tert-butyl)-4-methyl-N-(2-(2-((1-methyl-1H-pyrazol-4-yl)amino)pyrimidin-4-yl)-6,7,8,9-tetrahydro-5H-benzo[7]annulen-5-yl)-4H-1,2,4-triazole-3-carboxamide | 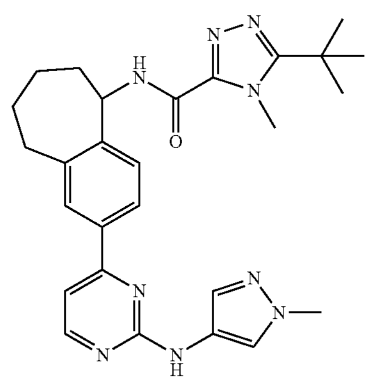 [SMILES: Cn1cc(Nc2nccc(-c3ccc4c(c3)CCCCC4NC(=O)c3nnc(C(C)(C)C)n3C)n2)cn1] | ESI-MS (M + H)⁺: 500.3. ¹H NMR (400 MHz, CD₃OD) δ: 8.27 (d, J = 5.2 Hz, 1H), 7.85-7.81 (m, 3H), 7.53 (s, 1H), 7.30 (d, J = 8.8 Hz, 1H), 7.08 (d, J = 5.2 Hz, 1H), 5.26-5.24 (m, 1H), 4.04 (s, 3H), 3.77 (s, 3H), 2.95-2.93 (m, 2H), 1.97-1.79 (m, 5H), 1.36-1.33 (m, 1H), 1.30 (s, 9H). |
| 117 | 2-isopropyl-N-(2-(2-((1-methyl-1H-pyrazol-4-yl)amino)pyrimidin-4-yl)-6,7,8,9-tetrahydro-5H-benzo[7]annulen-5-yl)-2H-1,2,3-triazole-4-carboxamide | 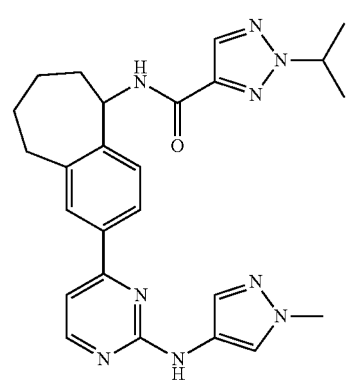 [SMILES: CC(C)n1ncc(C(=O)NC2CCCCc3cc(-c4ccnc(Nc5cnn(C)c5)n4)ccc32)n1] | ESI-MS (M + H)⁺: 472.2. ¹H NMR (400 MHz, CDCl₃) δ: 8.41 (d, J = 5.2 Hz, 1H), 8.06 (s, 1H), 7.87-7.81 (m, 3H), 7.55 (s, 1H), 7.40 (d, J = 7.6 Hz, 1H), 7.20-7.18 (m, 1H), 7.06 (d, J = 5.2 Hz, 1H), 6.99 (s, 1H), 5.45-5.41 (m, 1H), 4.91-4.85 (m, 1H), 3.91 (s, 3H), 3.08-2.96 (m, 2H), 2.03-1.86 (m, 5H), 1.67-1.66 (m, 1H), 1.63 (d, J = 6.8 Hz, 6H). |

| Compd No. | Chemical Name | Structure | ¹H-NMR and MS |
|---|---|---|---|
| 118a** | Racemic mixture of 5-(tert-butyl)-N-((5R,8S)-8-fluoro-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide and 5-(tert-butyl)-N-((5S,8R)-8-fluoro-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide | 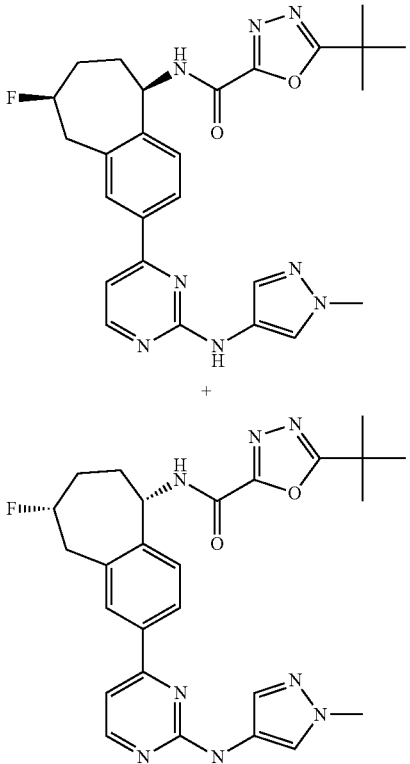 | ESI-MS (M + H)⁺: 505.2. ¹H NMR (400 MHz, CDCl₃) δ: 8.44 (d, J = 5.2 Hz, 1H), 7.90-7.88 (m, 3H), 7.60 (d, J = 7.6 Hz, 1H), 7.55 (s, 1H), 7.42 (d, J = 8.0 Hz, 1H), 7.08 (d, J = 5.2 Hz, 1H), 6.91 (s, 1H), 5.38 (d, J = 8.0 Hz, 1H), 4.91 (d, J = 47.2 Hz, 1H), 3.92 (s, 3H), 3.45-3.29 (m, 2H), 2.32-2.20 (m, 3H), 2.00-1.93 (m, 1H), 1.48 (s, 9H). |
| 118b** | Racemic mixture of 5-(tert-butyl)-N-((5R,8R)-8-fluoro-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide and 5-(tert-butyl)-N-((5S,8S)-8-fluoro-2-(2-((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide | 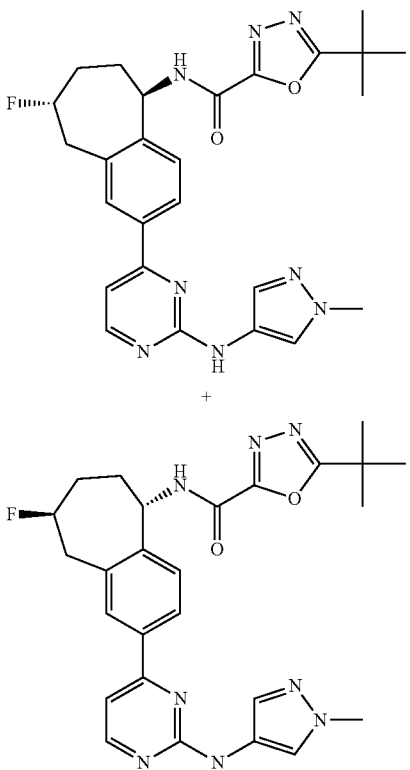 | ¹H NMR (400 MHz, CDCl₃) δ: 8.44 (d, J = 5.2 Hz, 1H), 7.92-7.88 (m, 3H), 7.56-7.54 (m, 2H), 7.40 (d, J = 8.0 Hz, 1H), 7.07 (d, J = 5.2 Hz, 1H), 6.89 (s, 1H), 5.40 (d, J = 9.6 Hz, 1H), 4.70 (d, J = 48.0 Hz, 1H), 3.92 (s, 3H), 3.45-3.28 (m, 2H), 2.37-2.30 (m, 1H), 2.22-2.17 (m, 2H), 1.95-1.92 (m, 1H), 1.49 (s, 9H). |

-continued

| Compd No. | Chemical Name | Structure | ¹H-NMR and MS |
|---|---|---|---|
| 119** | Racemic mixture of N-((5R,8S)-8-fluoro-2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide and N-((5S,8R)-8-fluoro-2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide | 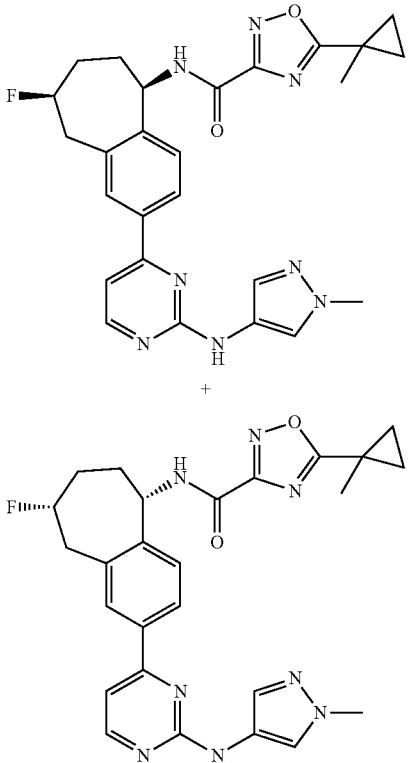 | ESI-MS (M + H)⁺: 503.2. ¹H NMR (400 MHz, CDCl₃) δ: 8.44 (d, J = 5.2 Hz, 1H), 7.90-7.88 (m, 3H), 7.55 (s, 1H), 7.40-7.35 (m, 2H), 7.07 (d, J = 5.2 Hz, 1H), 6.87 (s, 1H), 5.42 (d, J = 8.0 Hz, 1H), 4.90 (d, J = 48.8 Hz, 1H), 3.92 (s, 3H), 3.39-3.33 (m, 2H), 2.33-2.17 (m, 3H), 1.95-1.92 (m, 1H), 1.61 (s, 3H), 1.53-1.50 (m, 2H), 1.12-1.09 (m, 2H). |
| 120** | Racemic mixture of N-((5S,8S)-8-fluoro-2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide and N-((5R,8R)-8-fluoro-2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,2,4-oxadiazole-3-carboxamide | 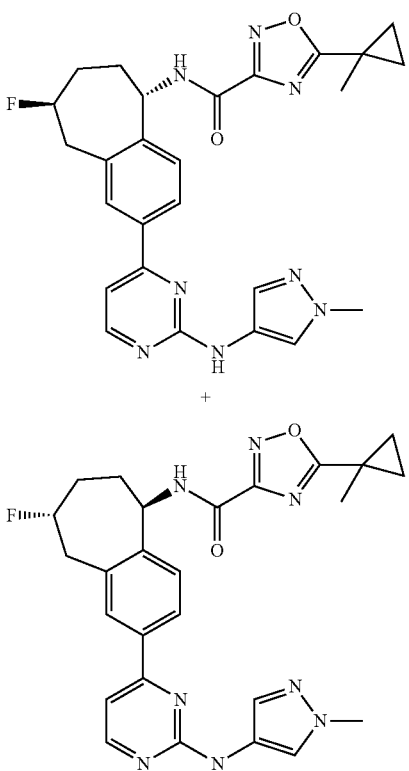 | ESI-MS (M + H)⁺: 503.2. ¹H NMR (400 MHz, CDCl₃) δ: 8.44 (d, J = 5.6 Hz, 1H), 7.91-7.87 (m, 3H), 7.55 (s, 1H), 7.36-7.30 (m, 2H), 7.07 (d, J = 5.2 Hz, 1H), 6.87 (s, 1H), 5.43 (d, J = 8.4 Hz, 1H), 4.67 (d, J = 47.2 Hz, 1H), 3.92 (s, 3H), 3.45-3.26 (m, 2H), 2.34-2.17 (m, 3H), 1.94-1.91 (m, 1H), 1.63 (s, 3H), 1.55-1.53 (m, 2H), 1.13-1.12 (m, 2H). |

| Compd No. | Chemical Name | Structure | 1H-NMR and MS |
|---|---|---|---|
| 121 | 1-(tert-butyl)-N-((5R)-8-(2-((1-methyl-1H-pyrazol-4-yl)amino)pyrimidin-4-yl)-2-(tetrahydrofuran-3-yl)-2,3,4,5-tetrahydro-1H-benzo[c]azepin-5-yl)-1H-1,2,3-triazole-4-carboxamide | 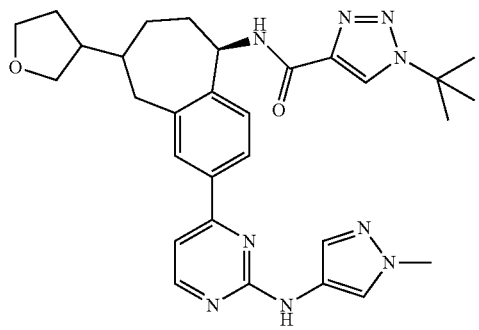 [SMILES: Cn1cc(Nc2nccc(-c3ccc4c(c3)CC(C3CCOC3)CC[C@H]4NC(=O)c3cn(C(C)(C)C)nn3)n2)cn1] | ESI-MS (M + H)+: 557.3. 1H NMR (400 MHz, CD3OD) δ: 8.53 (s, 1H), 8.42 (d, J = 5.2 Hz, 1H), 8.05-7.99 (m, 3H), 7.64 (s, 1H), 7.48 (d, J = 8.4 Hz, 1H), 7.23 (d, J = 5.2 Hz, 1H), 5.58 (d, J = 10.4 Hz, 1H), 4.16-4.09 (m, 2H), 4.02-3.96 (m, 2H), 3.90 (s, 3H), 3.79-3.71 (m, 2H), 3.31-3.24 (m, 2H), 3.15-3.10 (m, 1H), 2.31-2.17 (m, 2H), 2.07-1.97 (m, 2H), 1.74 (s, 9H). |
| 122 | (R)-N-(2-(2-((1-methyl-1H-pyrazol-4-yl)amino)pyrimidin-4-yl)-6,7,8,9-tetrahydro-5H-benzo[7]annulen-5-yl)-5-(1-methylcyclopropyl)-1,3,4-oxadiazole-2-carboxamide | 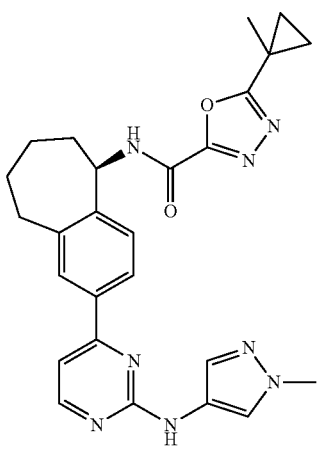 [SMILES: Cn1cc(Nc2nccc(-c3ccc4c(c3)CCCC[C@H]4NC(=O)c3nnc(C4(C)CC4)o3)n2)cn1] | ESI-MS (M + H)+: 485.2. 1H NMR (400 MHz, CD3OD) δ: 8.39 (d, J = 5.2 Hz, 1H), 7.97-7.92 (m, 3H), 7.65 (s, 1H), 7.40 (d, J = 8.8 Hz, 1H), 7.20 (d, J = 5.2 Hz, 1H), 5.42-5.39 (m, 1H), 3.89 (s, 3H), 3.07-3.02 (m, 2H), 2.10-1.86 (m, 5H), 1.62 (s, 3H), 1.47-1.43 (m, 3H), 1.13-1.10 (m, 2H). |
| 123 | 5-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 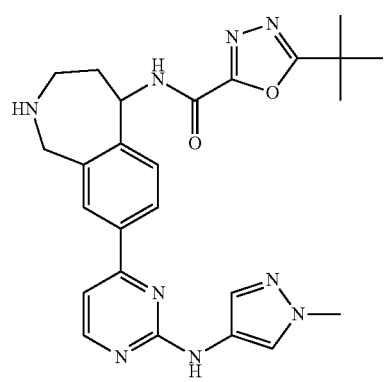 [SMILES: Cn1cc(Nc2nccc(-c3ccc4c(c3)CNCCC4NC(=O)c3nnc(C(C)(C)C)o3)n2)cn1] | ESI-MS (M + H)+: 488.3. 1H NMR (400 MHz, CD3OD) δ: 8.40 (d, J = 5.6 Hz, 1H), 8.02-7.98 (m, 3H), 7.64 (s, 1H), 7.47 (d, J = 8.4 Hz, 1H), 7.21 (d, J = 5.2 Hz, 1H), 5.60-5.58 (m, 1H), 4.12 (s, 2H), 3.89 (s, 3H), 3.39-3.37 (m, 1H), 3.28-3.21 (m, 2H), 2.15-2.09 (m, 2H), 1.51 (s, 9H). |
| 124* | 5-(tert-butyl)-N-((R)-8-(2-((1-ethyl-1H-pyrazol-4-yl)amino)pyrimidin-4-yl)-2-((S*)-tetrahydrofuran-3-yl)-2,3,4,5-tetrahydro-1H-benzo[c]azepin-5-yl)-1,3,4-oxadiazole-2-carboxamide | 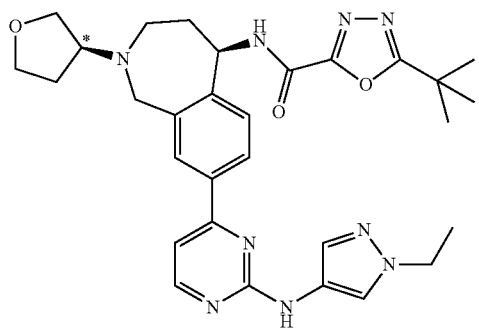 [SMILES: CCn1cc(Nc2nccc(-c3ccc4c(c3)CN([C@H]3CCOC3)CC[C@H]4NC(=O)c3nnc(C(C)(C)C)o3)n2)cn1] | LCMS: Rt 0.90 min, m/z 572.10. 1H NMR (300 MHz, METHANOL-d4) δ: 8.41 (d, J = 5.3 Hz, 1H), 8.07-7.98 (m, 3H), 7.65 (s, 1H), 7.48 (d, J = 7.6 Hz, 1H), 7.22 (d, J = 5.3 Hz, 1H), 5.56 (br d, J = 9.1 Hz, 1H), 4.58 (s, 1H), 4.23-4.09 (m, 4H), 4.00-3.92 (m, 2H), 3.78-3.69 (m, 2H), 3.27-3.05 (m, 2H), 2.36-2.20 (m, 2H), 2.16-1.91 (m, 2H), 1.51-1.43 (m, 12H). |

| Compd No. | Chemical Name | Structure | ¹H-NMR and MS |
|---|---|---|---|
| 125 | N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-5-(1-methylcyclopropyl)-1,3,4-oxadiazole-2-carboxamide | 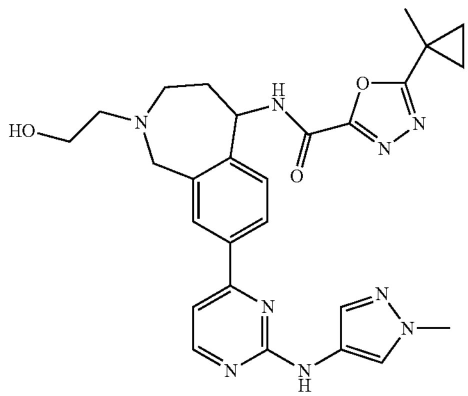 [SMILES: Cn1cc(Nc2nccc(-c3ccc4c(c3)CN(CCO)CCC4NC(=O)c3nnc(C4(C)CC4)o3)n2)cn1] | ESI-MS (M + H)⁺: 530.2. ¹H NMR (400 MHz, CD₃OD) δ: 8.39 (d, J = 5.2 Hz, 1H), 8.00-7.97 (m, 3H), 7.63 (s, 1H), 7.44 (d, J = 8.0 Hz, 1H), 7.19 (d, J = 5.6 Hz, 1H), 5.53 (d, J = 10.0 Hz, 1H), 4.18-4.06 (m, 2H), 3.90 (s, 3H), 3.73 (t, J = 6.0 Hz, 2H), 3.28-3.19 (m, 2H), 2.67-2.62 (m, 2H), 2.28-2.24 (m, 1H), 1.98-1.95 (m, 1H), 1.61 (s, 3H), 1.45-1.42 (m, 2H), 1.13-1.10 (m, 2H). |
| 126 | 5-cyclobutyl-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 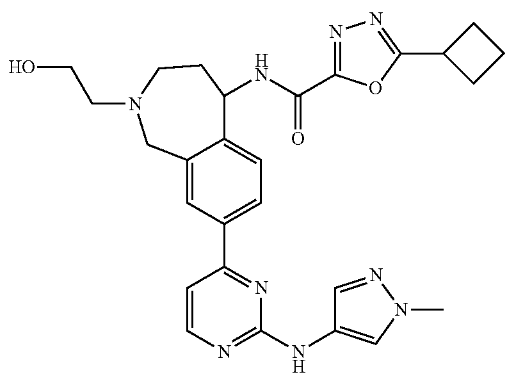 [SMILES: Cn1cc(Nc2nccc(-c3ccc4c(c3)CN(CCO)CCC4NC(=O)c3nnc(C4CCC4)o3)n2)cn1] | ESI-MS (M + H)⁺: 529.7. ¹H NMR (400 MHz, CDCl₃) δ: 8.80 (br, 1H), 8.43 (d, J = 5.2 Hz, 1H), 7.87 (s, 1H), 7.84-7.81 (m, 2H), 7.55 (s, 1H), 7.49 (d, J = 8.0 Hz, 1H), 7.05 (d, J = 5.2 Hz, 1H), 6.90 (s, 1H), 5.59 (t, J = 8.0 Hz, 1H), 4.13-4.04 (m, 2H), 3.91 (s, 3H), 3.81-3.69 (m, 3H), 3.27-3.20 (m, 1H), 2.96-2.91 (m, 1H), 2.81 (t, J = 4.8 Hz, 2H), 2.52-2.32 (m, 5H), 2.17-2.02 (m, 3H), 1.60 (s, 9H). |
| 127 | (R)-5-(tert-butyl)-N-(2-(2-ethoxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 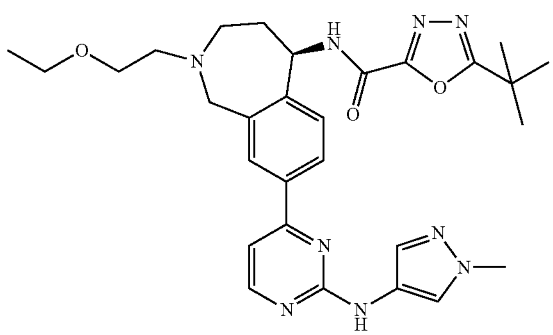 [SMILES: CCOCCN1CC[C@@H](NC(=O)c2nnc(C(C)(C)C)o2)c2ccc(-c3ccnc(Nc4cnn(C)c4)n3)cc2C1] | ESI-MS (M + H)⁺: 560.1. ¹H NMR (300 MHz, METHANOL-d₄) δ: 8.39 (d, J = 5.3 Hz, 1H), 8.02-7.95 (m, 3H), 7.62 (s, 1H), 7.45 (d, J = 7.9 Hz, 1H), 7.19 (d, J = 5.3 Hz, 1H), 5.54 (br d, J = 9.1 Hz, 1H), 4.15 (d, J = 4.9 Hz, 2H), 3.88 (s, 3H), 3.62 (t, J = 5.7 Hz, 2H), 3.50 (q, J = 6.8 Hz, 2H), 3.26-3.14 (m, 2H), 2.76-2.63 (m, 2H), 2.34-2.19 (m, 1H), 2.05-1.92 (m, 1H), 1.50-1.47 (m, 9H), 1.16 (t, J = 7.0 Hz, 3H). |
| 128 | (R)-5-(tert-butyl)-N-(7-(2-((1-methyl-1H-pyrazol-4-yl)amino)pyrimidin-4-yl)-3-(oxetan-3-yl)-2,3,4,5-tetrahydro-1H-benzo[d]azepin-1-yl)-1,3,4-oxadiazole-2-carboxamide | 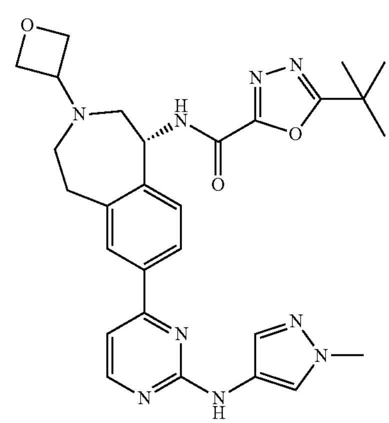 [SMILES: Cn1cc(Nc2nccc(-c3ccc4c(c3)CCN(C3COC3)C[C@@H]4NC(=O)c3nnc(C(C)(C)C)o3)n2)cn1] | LCMS: Rt 0.87 min, m/z 544.2. ¹H NMR (400 MHz, METHANOL-d₄) δ: 8.39 (br. s., 1H), 7.81-8.04 (m, 3H), 7.64 (br. s., 1H), 7.50 (d, J = 8.03 Hz, 1H), 7.17 (s, 1H), 5.25 (d, J = 6.53 Hz, 1H), 4.53-4.78 (m, 4H), 3.90 (br. s., 3H), 3.67-3.83 (m, 1H), 2.20-3.28 (m, 6H), 1.37-1.66 (m, 9H). |

| Compd No. | Chemical Name | Structure | ¹H-NMR and MS |
|---|---|---|---|
| 129 | 5-(tert-butyl)-N-(7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide | 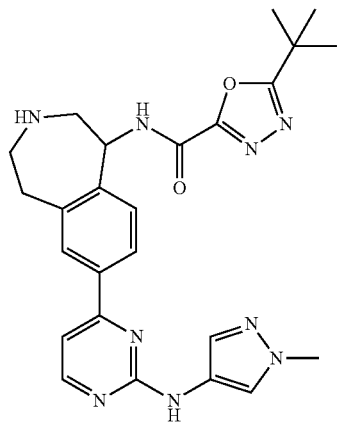 [SMILES: Cn1cc(Nc2nccc(-c3ccc4c(c3)CCNCC4NC(=O)c3nnc(C(C)(C)C)o3)n2)cn1] | ESI-MS (M + H)⁺: 488.00. ¹H NMR (400 MHz, DMSO-$d_6$) δ: 10.15 (d, J = 8.0 Hz, 1H), 9.53 (s, 1H), 9.21 (br s, 2H), 8.49 (d, J = 5.3 Hz, 1H), 8.09-7.99 (m, 2H), 7.91 (s, 1H), 7.57 (br s, 1H), 7.48 (d, J = 8.3 Hz, 1H), 7.27 (d, J = 5.3 Hz, 1H), 5.62 (br t, J = 8.4 Hz, 1H), 3.82 (s, 3H), 3.61-3.47 (m, 2H), 3.44-3.21 (m, 3H), 3.13 (br d, J = 9.0 Hz, 1H), 1.43 (s, 9H). |
| 130 | 1-(tert-butyl)-N-(7-(2-((1-methyl-1H-pyrazol-4-yl)amino)pyrimidin-4-yl)-3-(oxetan-3-yl)-2,3,4,5-tetrahydro-1H-benzo[d]azepin-1-yl)-1H-1,2,3-triazole-4-carboxamide | 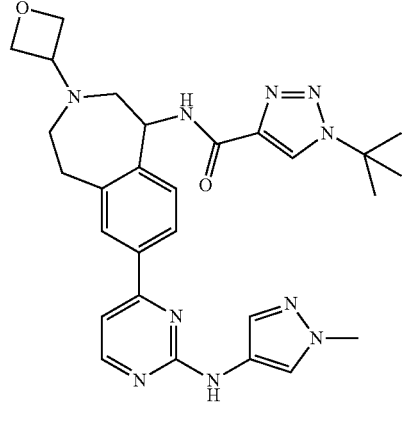 [SMILES: Cn1cc(Nc2nccc(-c3ccc4c(c3)CCN(C3COC3)CC4NC(=O)c3cn(C(C)(C)C)nn3)n2)cn1] | ESI-MS (M + H)⁺: 543.3. ¹H NMR (400 MHz, CD₃OD) δ: 8.44 (s, 1H), 8.41 (d, J = 5.2 Hz, 1H), 7.98-7.92 (m, 3H), 7.65 (s, 1H), 7.56 (d, J = 8.0 Hz, 1H), 7.21 (d, J = 5.2 Hz, 1H), 5.29-5.27 (m, 1H), 4.81-4.65 (m, 4H), 3.90 (s, 3H), 3.86-3.79 (m, 1H), 3.10-2.87 (m, 4H), 2.57-2.37 (m, 2H), 1.72 (s, 9H). |
| 131 | 5-(tert-butyl)-N-(8-(2-((1-methyl-1H-pyrazol-4-yl)amino)pyrimidin-4-yl)-2-(tetrahydrofuran-3-yl)-2,3,4,5-tetrahydro-1H-benzo[c]azepin-5-yl)-1,3,4-thiadiazole-2-carboxamide | 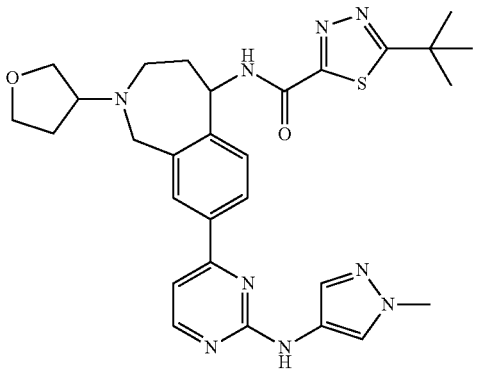 [SMILES: Cn1cc(Nc2nccc(-c3ccc4c(c3)CN(C3CCOC3)CCC4NC(=O)c3nnc(C(C)(C)C)s3)n2)cn1] | ESI-MS (M + H)⁺: 574.0. ¹H NMR (400 MHz, CDCl₃) δ: 8.42 (d, J = 5.2 Hz, 1H), 8.38 (brs, 1H), 7.89-7.81 (m, 3H), 7.53 (s, 1H), 7.48 (d, J = 7.6 Hz, 1H), 7.05 (d, J = 5.2 Hz, 1H), 6.96 (s, 1H), 5.62-5.56 (m, 1H), 4.09-3.92 (m, 4H), 3.91 (s, 3H), 3.81-3.73 (m, 2H), 3.48-3.40 (m, 1H), 3.23-3.08 (m, 1H), 2.99-2.95 (m, 1H), 2.35-2.28 (m, 1H), 2.19-2.06 (m, 2H), 2.00-1.95 (m, 1H), 1.51 (s, 9H). |

| Compd No. | Chemical Name | Structure | ¹H-NMR and MS |
|---|---|---|---|
| 132 | 5-(tert-butyl)-N-(3-methyl-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide | 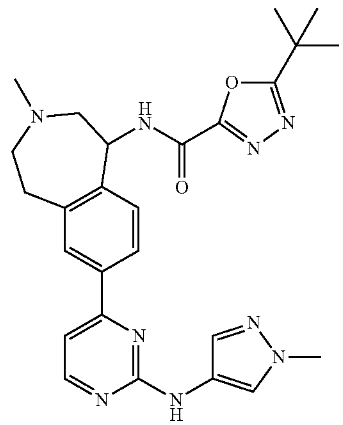 [SMILES: CN1CCc2cc(-c3ccnc(Nc4cnn(C)c4)n3)ccc2C(NC(=O)c2nnc(C(C)(C)C)o2)C1] | ESI-MS (M + H)⁺: 502.1. |
| 133 | (S)-5-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1,2,4-oxadiazole-3-carboxamide | 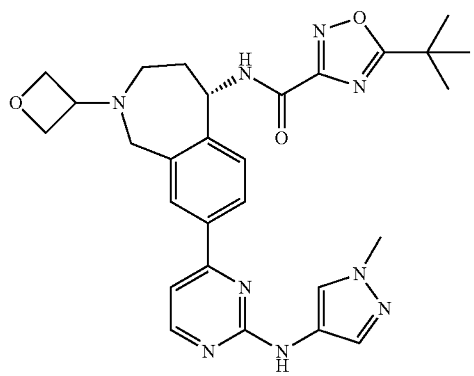 [SMILES: Cn1cc(Nc2nccc(-c3ccc4c(c3)CN(C3COC3)CC[C@@H]4NC(=O)c3noc(C(C)(C)C)n3)n2)cn1] | ESI-MS (M + H)⁺: 544.0. ¹H NMR (400 MHz, METHANOL-d4) δ: 8.40 (d, J = 5.02 Hz, 1H), 7.87-8.09 (m, 3H), 7.63 (s, 1H), 7.45 (d, J = 8.28 Hz, 1H), 7.20 (d, J = 5.27 Hz, 1H), 5.60 (s, 1H), 4.55-4.77 (m, 4H), 3.89 (s, 3H), 3.75-3.85 (m, 3H), 2.75-3.10 (m, 2H), 1.89-2.42 (m, 2H), 1.51 (s, 9H). |
| 134 | (S)-5-(tert-butyl)-N-(2-(3-hydroxycyclobutyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 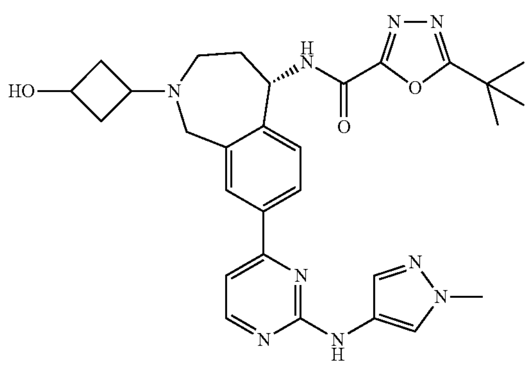 [SMILES: Cn1cc(Nc2nccc(-c3ccc4c(c3)CN(C3CC(O)C3)CC[C@@H]4NC(=O)c3nnc(C(C)(C)C)o3)n2)cn1] | LCMS: Rt 4.5 min, m/z 558.00. ¹H NMR (400 MHz, METHANOL-d₄) δ: 8.41 (d, J = 5.3 Hz, 1H), 8.03-7.98 (m, 3H), 7.62 (s, 1H), 7.47-7.45 (m, 1H), 7.22 (d, J = 5.3 Hz, 1H), 5.58-5.48 (m, 1H), 4.58 (br s, 1H), 3.99 (br s, 1H), 3.89 (s, 3H), 3.25-3.21 (m, 1H), 2.97-2.91 (m, 1H), 2.63-2.52 (m, 2H), 2.25-2.15 (m, 2H), 2.05-1.98 (m, 1H), 1.87-1.79 (m, 2H), 1.49 (s, 9H), 0.97-0.86 (m, 1H). |
| 135 | 5-(tert-butyl)-N-(2-(2-((1-methyl-1H-pyrazol-4-yl)amino)pyrimidin-4-yl)-6,7,8,9-tetrahydro-5H-benzo[7]annulen-5-yl)-1,3,4-thiadiazole-2-carboxamide | 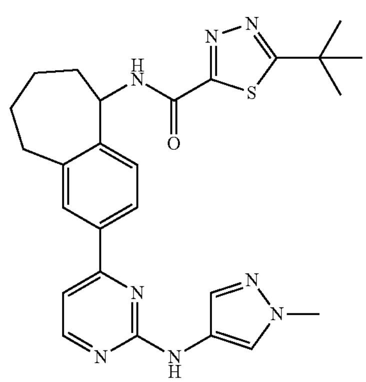 [SMILES: Cn1cc(Nc2nccc(-c3ccc4c(c3)CCCCC4NC(=O)c3nnc(C(C)(C)C)s3)n2)cn1] | ESI-MS (M + H)⁺: 503.2. ¹H NMR (400 MHz, CDCl₃) δ: 8.40 (d, J = 5.2 Hz, 1H), 7.89-7.80 (m, 4H), 7.54 (s, 1H), 7.40 (d, J = 8.0 Hz, 1H), 7.06 (d, J = 5.2 Hz, 1H), 6.92 (s, 1H), 5.41-5.39 (m, 1H), 3.91 (s, 3H), 3.03-3.00 (m, 2H), 2.00-1.84 (m, 6H), 1.53 (s, 9H). |

| Compd No. | Chemical Name | Structure | ¹H-NMR and MS |
|---|---|---|---|
| 136 | 5-(tert-butyl)-N-((S)-2-((S)-2-hydroxypropyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 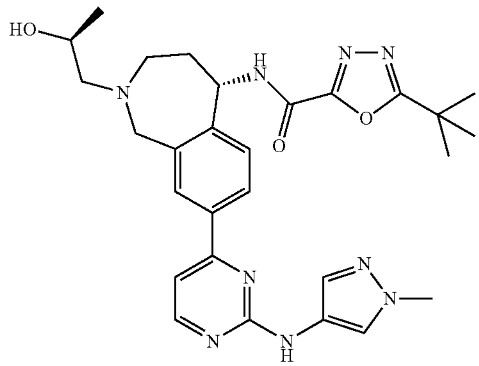 [SMILES: C[C@H](O)CN1CC[C@H](NC(=O)c2nnc(C(C)(C)C)o2)c2ccc(-c3ccnc(Nc4cnn(C)c4)n3)cc2C1] | LCMS: Rt 0.85 min, m/z 546.3. ¹H NMR (400 MHz, METHANOL-d4) δ: 8.41 (br. s., 1H), 7.91-8.12 (m, 3H), 7.64 (br. s., 1H), 7.46 (d, J = 7.53 Hz, 1H), 7.20 (br. s., 1H), 5.57 (d, J = 9.79 Hz, 1H), 4.08-4.36 (m, 2H), 4.00 (br. s., 1H), 3.83-3.92 (m, 3H), 3.47-3.75 (m, 4H), 3.28 (br. s., 2H), 2.37-2.62 (m, 2H), 2.26 (br. s., 1H), 1.84-2.07 (m, 1H), 1.50 (s, 9H), 0.95-1.24 (m, 4H). |
| 137 | (S)-5-(tert-butyl)-N-(8-(2-((1-methyl-1H-pyrazol-4-yl)amino)pyrimidin-4-yl)-2-(2,2,2-trifluoroethyl)-2,3,4,5-tetrahydro-1H-benzo[c]azepin-5-yl)-1,2,4-oxadiazole-3-carboxamide | 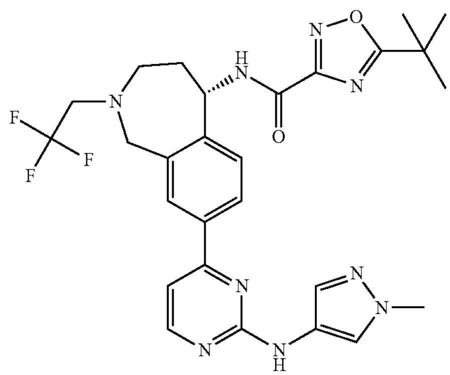 [SMILES: Cn1cc(Nc2nccc(-c3ccc4c(c3)CN(CC(F)(F)F)CC[C@@H]4NC(=O)c3noc(C(C)(C)C)n3)n2)cn1] | LCMS: Rt 1.36 min, m/z 570.3. ¹H NMR (400 MHz, METHANOL-d4) δ: 8.40 (br. s., 1H), 7.98 (d, J = 5.27 Hz, 3H), 7.62 (br. s., 1H), 7.46 (br. s., 1H), 7.18 (br. s., 1H), 5.60 (d, J = 8.78 Hz, 1H), 4.26-4.45 (m, 1H), 4.02-4.20 (m, 1H), 3.89 (br. s., 3H), 3.39 (br. s., 1H), 3.11 (br. s., 2H), 2.24 (br. s., 1H), 1.97 (br. s., 1H), 1.52 (s, 9H). |
| 138* | 5-(tert-butyl)-N-((S)-8-(2-((1-ethyl-1H-pyrazol-4-yl)amino)pyrimidin-4-yl)-2-((R*)-tetrahydrofuran-3-yl)-2,3,4,5-tetrahydro-1H-benzo[c]azepin-5-yl)-1,3,4-oxadiazole-2-carboxamide | 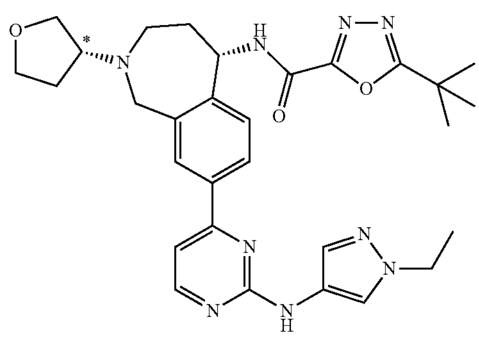 [SMILES: CCn1cc(Nc2nccc(-c3ccc4c(c3)CN([C@@H]3CCOC3)CC[C@@H]4NC(=O)c3nnc(C(C)(C)C)o3)n2)cn1] | LCMS: Rt 0.90 min, m/z 572.0. ¹H NMR (300 MHz, METHANOL-d4) δ: 8.41 (d, J = 5.3 Hz, 1H), 8.07-7.97 (m, 3H), 7.65 (s, 1H), 7.48 (d, J = 7.6 Hz, 1H), 7.22 (d, J = 5.3 Hz, 1H), 5.56 (br d, J = 8.7 Hz, 1H), 4.58 (s, 1H), 4.22-4.08 (m, 4H), 4.03-3.92 (m, 2H), 3.78-3.69 (m, 2H), 3.27-3.07 (m, 2H), 2.36-2.14 (m, 2H), 2.06-1.91 (m, 2H), 1.53-1.43 (m, 12H). |
| 139* | 5-(tert-butyl)-N-((S)-8-(2-((1-ethyl-1H-pyrazol-4-yl)amino)pyrimidin-4-yl)-2-((S*)-tetrahydrofuran-3-yl)-2,3,4,5-tetrahydro-1H-benzo[c]azepin-5-yl)-1,3,4-oxadiazole-2-carboxamide | 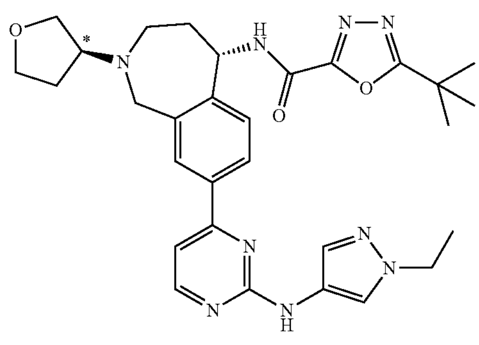 [SMILES: CCn1cc(Nc2nccc(-c3ccc4c(c3)CN([C@H]3CCOC3)CC[C@@H]4NC(=O)c3nnc(C(C)(C)C)o3)n2)cn1] | LCMS: Rt 0.90 min, m/z 572.0. ¹H NMR (300 MHz, METHANOL-d4) δ: 8.41 (d, J = 5.3 Hz, 1H), 8.04-8.01 (m, 3H), 7.63 (s, 1H), 7.47 (d, J = 7.6 Hz, 1H), 7.23 (d, J = 5.3 Hz, 1H), 5.57 (br d, J = 8.7 Hz, 1H), 4.58 (s, 1H), 4.23-4.10 (m, 4H), 4.04-3.93 (m, 2H), 3.78-3.70 (m, 2H), 3.25-3.07 (m, 2H), 2.35-2.13 (m, 2H), 2.07-1.90 (m, 2H), 1.51-1.43 (m, 12H). |

| Compd No. | Chemical Name | Structure | ¹H-NMR and MS |
|---|---|---|---|
| 140 | tert-butyl 1-(5-(tert-butyl)-1,3,4-oxadiazole-2-carboxamido)-7-(2-((1-methyl-1H-pyrazol-4-yl)amino)pyrimidin-4-yl)-1,2,4,5-tetrahydro-3H-benzo[d]azepine-3-carboxylate | 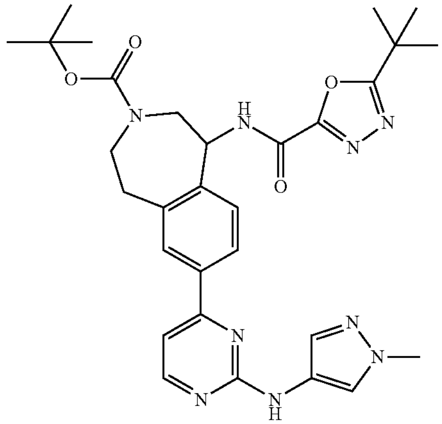 [SMILES: Cn1cc(Nc2nccc(-c3ccc4c(c3)CCN(C(=O)OC(C)(C)C)CC4NC(=O)c3nnc(C(C)(C)C)o3)n2)cn1] | ESI-MS (M + H)⁺: 588.10. ¹H NMR (400 MHz, CHLOROFORM-d) δ: 8.44 (d, J = 5.3 Hz, 1H), 7.94-7.79 (m, 3H), 7.62-7.50 (m, 2H), 7.06 (d, J = 5.3 Hz, 1H), 6.92 (s, 1H), 5.46-5.30 (m, 1H), 4.48 (br s, 1H), 4.37-4.18 (m, 1H), 3.92 (s, 3H), 3.44 (br d, J = 13.3 Hz, 1H), 3.31-3.11 (m, 2H), 3.05 (br dd, J = 6.5, 13.6 Hz, 1H), 1.56-1.33 (m, 18H). |
| 141 | (S)-5-(tert-butyl)-N-(7-(2-((1-methyl-1H-pyrazol-4-yl)amino)pyrimidin-4-yl)-3-(oxetan-3-yl)-2,3,4,5-tetrahydro-1H-benzo[d]azepin-1-yl)-1,3,4-oxadiazole-2-carboxamide | 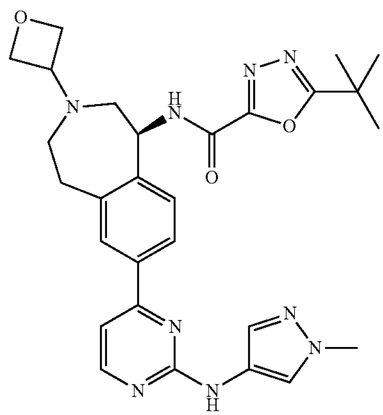 [SMILES: Cn1cc(Nc2nccc(-c3ccc4c(c3)CCN(C3COC3)C[C@H]4NC(=O)c3nnc(C(C)(C)C)o3)n2)cn1] | LCMS: Rt 0.87 min, m/z 544.3. ¹H NMR (400 MHz, METHANOL-d4) δ: 8.39 (d, J = 5.02 Hz, 1H), 7.85-8.03 (m, 3H), 7.64 (s, 1H), 7.51 (d, J = 8.03 Hz, 1H), 7.18 (d, J = 5.27 Hz, 1H), 5.26 (d, J = 6.78 Hz, 1H), 4.72 (d, J = 7.28 Hz, 4H), 3.89 (s, 3H), 3.79 (d, J = 6.27 Hz, 1H), 2.21-3.29 (m, 6H), 1.47 (s, 9H). |
| 142 | 5-(tert-butyl)-N-(7-(2-((1-methyl-1H-pyrazol-4-yl)amino)pyrimidin-4-yl)-3-(2,2,2-trifluoroethyl)-2,3,4,5-tetrahydro-1H-benzo[d]azepin-1-yl)-1,3,4-oxadiazole-2-carboxamide | 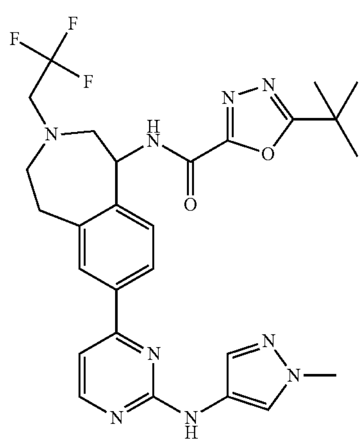 [SMILES: Cn1cc(Nc2nccc(-c3ccc4c(c3)CCN(CC(F)(F)F)CC4NC(=O)c3nnc(C(C)(C)C)o3)n2)cn1] | ESI-MS (M + H)⁺: 570.3. ¹H NMR (400 MHz, CD₃OD) δ: 8.29 (d, J = 5.2 Hz, 1H), 7.85-7.79 (m, 3H), 7.52 (s, 1H), 7.41 (d, J = 8.0 Hz, 1H), 7.08 (d, J = 5.2 Hz, 1H), 5.14-5.13 (m, 1H), 3.78 (s, 3H), 3.36-3.23 (m, 3H), 3.15-3.09 (m, 2H), 3.01-2.92 (m, 2H), 2.86-2.81 (m, 1H), 1.35 (s, 9H). |

-continued

| Compd No. | Chemical Name | Structure | $^1$H-NMR and MS |
|---|---|---|---|
| 143 | 5-(tert-butyl)-N-(3-((S)-2-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide | 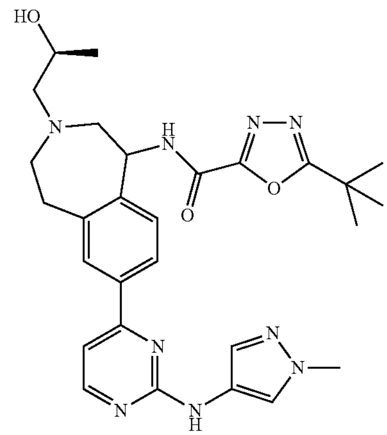 [SMILES: C[C@H](O)CN1CCc2cc(-c3ccnc(Nc4cnn(C)c4)n3)ccc2C(NC(=O)c2nnc(C(C)(C)C)o2)C1] | ESI-MS (M + H)$^+$: 546.3. $^1$H NMR (400 MHz, CDCl$_3$) δ: 8.95-8.79 (m, 1H), 8.41 (d, J = 5.2 Hz, 1H), 7.87-7.78 (m, 3H), 7.56-7.54 (m, 2H), 7.04 (d, J = 5.2 Hz, 1H), 6.97 (s, 1H), 5.18-5.14 (m, 1H), 3.92-3.91 (m, 1H), 3.90 (s, 3H), 3.39-2.43 (m, 8H), 1.43 (s, 9H), 1.23-1.21 (m, 3H). |
| 144 | 5-(tert-butyl)-N-(3-((R)-2-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide | 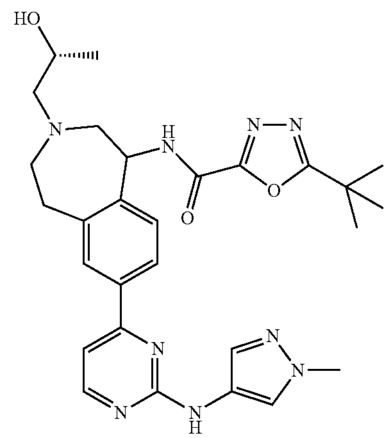 [SMILES: C[C@@H](O)CN1CCc2cc(-c3ccnc(Nc4cnn(C)c4)n3)ccc2C(NC(=O)c2nnc(C(C)(C)C)o2)C1] | ESI-MS (M + H)$^+$: 546.3. $^1$H NMR (400 MHz, CD$_3$OD) δ: 8.40 (d, J = 4.8 Hz, 1H), 7.97-7.90 (m, 3H), 7.64 (s, 1H), 7.51 (d, J = 8.0, 2.0 Hz, 1H), 7.20-7.18 (m, 1H), 5.26-5.24 (m, 1H), 4.01-3.98 (m, 1H), 3.90 (s, 3H), 3.27-3.21 (m, 2H), 3.14-3.03 (m, 2H), 2.85-2.80 (m, 1H), 2.70-2.56 (m, 3H), 1.46 (s, 9H), 1.26-1.23 (m, 3H). |
| 145 | 5-(tert-butyl)-N-(7-(2-((1-methyl-1H-pyrazol-4-yl)amino)pyrimidin-4-yl)-3-(tetrahydro-2H-pyran-4-yl)-2,3,4,5-tetrahydro-1H-benzo[d]azepin-1-yl)-1,3,4-oxadiazole-2-carboxamide | 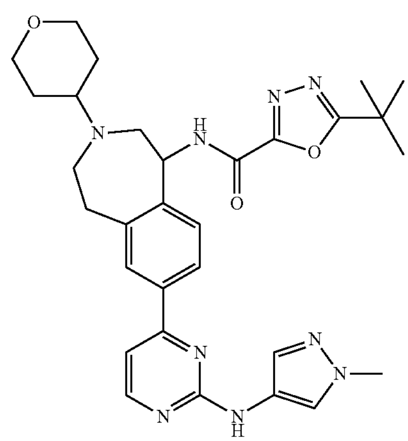 [SMILES: Cn1cc(Nc2nccc(-c3ccc4c(c3)CCN(C3CCOCC3)CC4NC(=O)c3nnc(C(C)(C)C)o3)n2)cn1] | ESI-MS (M + H)$^+$: 572.3. $^1$H NMR (400 MHz, CDCl$_3$) δ: 9.02 (d, J = 7.2 Hz, 1H), 8.41 (d, J = 5.2 Hz, 1H), 7.87 (s, 1H), 7.81 (dd, J = 8.0, 1.6 Hz, 1H), 7.76 (d, J = 1.6 Hz, 1H), 7.58 (d, J = 8.0 Hz, 1H), 7.53 (s, 1H), 7.03 (d, J = 5.2 Hz, 1H), 6.98 (s, 1H), 5.11-5.08 (m, 1H), 4.05-4.02 (m, 2H), 3.91 (s, 3H), 3.41-3.25 (m, 5H), 2.92-2.67 (m, 4H), 1.76-1.63 (m, 4H), 1.42 (s, 9H). |

| Compd No. | Chemical Name | Structure | ¹H-NMR and MS |
|---|---|---|---|
| 146 | 5-(tert-butyl)-N-(3-(3-hydroxypropyl)-7-(2-((1-methyl-1H-pyrazol-4-yl)amino)pyrimidin-4-yl)-2,3,4,5-tetrahydro-1H-benzo[d]azepin-1-yl)-1,3,4-oxadiazole-2-carboxamide | 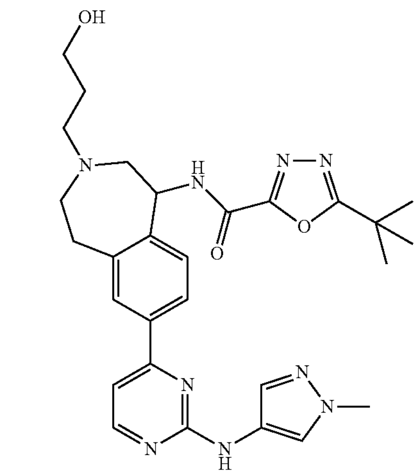 [SMILES: Cn1cc(Nc2nccc(-c3ccc4c(c3)CCN(CCCO)CC4NC(=O)c3nnc(C(C)(C)C)o3)n2)cn1] | ESI-MS (M + H)⁺: 545.7. ¹H NMR (400 MHz, CDCl₃) δ: 9.02 (d, J = 6.8 Hz, 1H), 8.40 (d, J = 5.2 Hz, 1H), 7.89-7.76 (m, 3H), 7.57-7.52 (m, 3H), 7.03 (d, J = 5.2 Hz, 1H), 5.13-5.10 (m, 1H), 3.94-3.84 (m, 5H), 3.32-3.15 (m, 3H), 2.90-2.67 (m, 5H), 2.45-2.42 (m, 1H), 1.83-1.81 (m, 2H), 1.43 (s, 9H). |
| 147 | 5-(3,3-difluorocyclobutyl)-N-(2-methyl-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 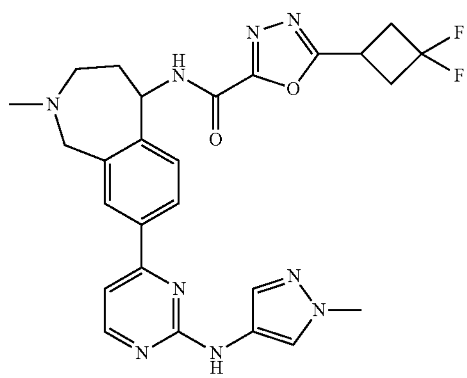 [SMILES: CN1CCC(NC(=O)c2nnc(C3CC(F)(F)C3)o2)c2ccc(-c3ccnc(Nc4cnn(C)c4)n3)cc2C1] | ESI-MS (M + H)⁺: 536.2. ¹H NMR (400 MHz, CDCl₃) δ: 8.43-8.42 (m, 2H), 7.87 (s, 1H), 7.85-7.82 (m, 2H), 7.55 (s, 1H), 7.46 (d, J = 8.0 Hz, 1H), 7.05 (d, J = 5.2 Hz, 1H), 6.94 (s, 1H), 5.60-5.56 (m, 1H), 3.98-3.88 (m, 5H), 3.69-3.61 (m, 1H), 3.13-3.05 (m, 5H), 2.87-2.81 (m, 1H), 2.52 (s, 3H), 2.36-2.28 (m, 1H), 2.10-2.03 (m, 1H). |
| 148 | 5-(3,3-difluorocyclobutyl)-N-(2-(2-hydroxyethyl)-8-(2-((1-methyl-1H-pyrazol-4-yl)amino)pyrimidin-4-yl)-2,3,4,5-tetrahydro-1H-benzo[c]azepin-5-yl)-1,3,4-oxadiazole-2-carboxamide | 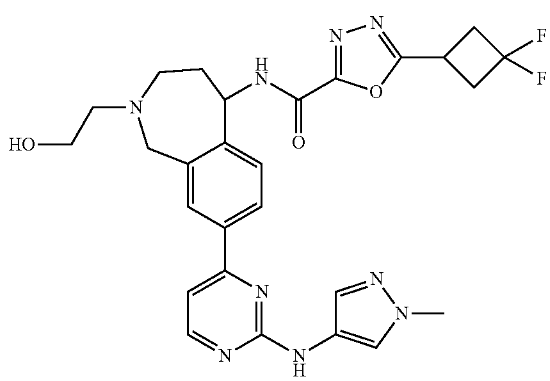 [SMILES: Cn1cc(Nc2nccc(-c3ccc4c(c3)CN(CCO)CCC4NC(=O)c3nnc(C4CC(F)(F)C4)o3)n2)cn1] | ESI-MS (M + H)⁺: 566.2. ¹H NMR (400 MHz, CDCl₃) δ: 8.88 (br, 1H), 8.42 (d, J = 5.2 Hz, 1H), 7.85 (s, 1H), 7.84-7.81 (m, 2H), 7.54 (s, 1H), 7.47 (d, J = 8.0 Hz, 1H), 7.05-7.02 (m, 2H), 5.61-5.57 (m, 1H), 4.12-4.03 (m, 2H), 3.91 (s, 3H), 3.81-3.60 (m, 3H), 3.38-3.04 (m, 6H), 2.95-2.78 (m, 3H), 2.39-2.31 (m, 1H), 2.12-2.05 (m, 1H). |

| Compd No. | Chemical Name | Structure | ¹H-NMR and MS |
|---|---|---|---|
| 149 | (R)-5-(tert-butyl)-N-(8-(2-((5,6-dihydro-4H-pyrrolo[1,2-b]pyrazol-3-yl)amino)pyrimidin-4-yl)-2-(2-hydroxyethyl)-2,3,4,5-tetrahydro-1H-benzo[c]azepin-5-yl)-1,2,4-oxadiazole-3-carboxamide | 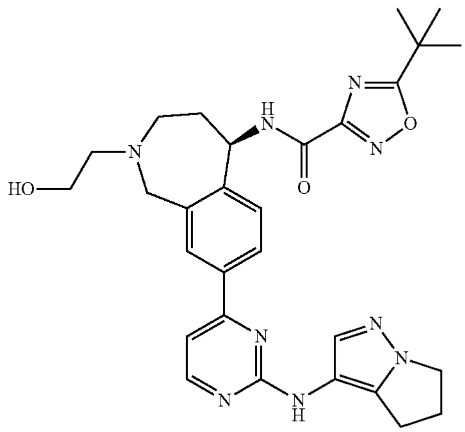 [SMILES: CC(C)(C)c1nc(C(=O)N[C@@H]2CCN(CCO)Cc3cc(-c4ccnc(Nc5cnn6c5CCC6)n4)ccc32)no1] | ESI-MS (M + H)⁺: 558.2. ¹H NMR (400 MHz, CD₃OD) δ: 8.35 (d, J = 5.2 Hz, 1H), 7.99-7.97 (m, 2H), 7.69 (s, 1H), 7.42 (d, J = 8.0 Hz, 1H), 7.21 (d, J = 5.2 Hz, 1H), 5.59-5.55 (m, 1H), 4.16-4.10 (m, 4H), 3.74 (t, J = 6.0 Hz, 2H), 3.27-3.13 (m, 2H), 2.96 (t, J = 7.2 Hz, 2H), 2.67-2.62 (m, 4H), 2.33-2.24 (m, 1H), 2.00-1.96 (m, 1H), 1.52 (s, 9H). |
| 150 | 5-(tert-butyl)-N-(8-hydroxy-2-(2-(((1-methyl-1H-pyrazol-4-yl)amino)pyrimidin-4-yl)-6,7,8,9-tetrahydro-5H-benzo[7]annulen-5-yl)-1,3,4-oxadiazole-2-carboxamide | 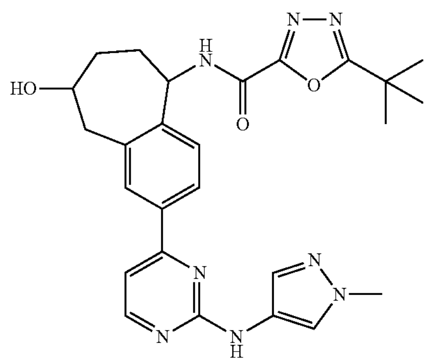 [SMILES: Cn1cc(Nc2nccc(-c3ccc4c(c3)CC(O)CCC4NC(=O)c3nnc(C(C)(C)C)o3)n2)cn1] | ESI-MS (M + H)⁺: 503.2. ¹H NMR (400 MHz, CDCl₃) δ: 8.74 (d, J = 4.8 Hz, 1H), 7.88-7.85 (m, 3H), 7.76-7.59 (m, 1H), 7.54 (s, 1H), 7.39-7.37 (m, 1H), 7.05-7.03 (m, 2H), 5.41-5.37 (m, 1H), 4.14-4.09 (m, 1H), 3.91 (s, 3H), 3.89-3.84 (m, 1H), 3.26-3.19 (m, 2H), 2.24-1.96 (m, 4H), 1.49-1.44 (m, 9H). |
| 151 | (R)-5-(tert-butyl)-N-(2-(2-(((1,5-dimethyl-1H-pyrazol-4-yl)amino)pyrimidin-4-yl)-6,7,8,9-tetrahydro-5H-benzo[7]annulen-5-yl)-1,2,4-oxadiazole-3-carboxamide | 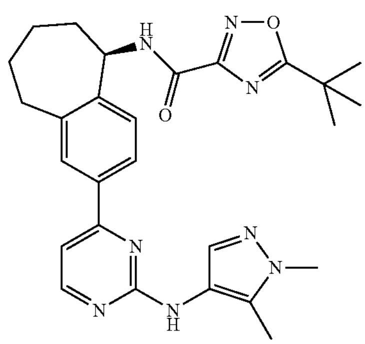 [SMILES: Cc1c(Nc2nccc(-c3ccc4c(c3)CCCC[C@H]4NC(=O)c3noc(C(C)(C)C)n3)n2)cnn1C] | ESI-MS (M + H)⁺: 501.3. ¹H NMR (400 MHz, CD₃OD) δ: 8.31 (d, J = 5.2 Hz, 1H), 7.93-7.91 (m, 2H), 7.60 (s, 1H), 7.38 (d, J = 8.0 Hz, 1H), 7.23 (d, J = 5.2 Hz, 1H), 5.44 (d, J = 10.0 Hz, 1H), 3.82 (s, 3H), 3.10-2.97 (m, 2H), 2.25 (s, 3H), 2.09-1.86 (m, 5H), 1.54 (s, 9H), 1.49-1.43 (m, 1H). |
| 152 | (R)-5-(tert-butyl)-N-(2-(2-((5,6-dihydro-4H-pyrrolo[1,2-b]pyrazol-3-yl)amino)pyrimidin-4-yl)-6,7,8,9-tetrahydro-5H-benzo[7]annulen-5-yl)-1,2,4-oxadiazole-3-carboxamide | 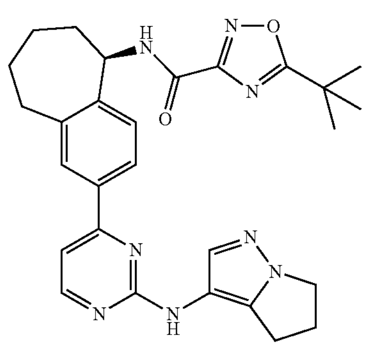 [SMILES: CC(C)(C)c1nc(C(=O)N[C@@H]2CCCCc3cc(-c4ccnc(Nc5cnn6c5CCC6)n4)ccc32)no1] | ESI-MS (M + H)⁺: 513.3. ¹H NMR (500 MHz, DMSO-d₆) δ: 9.57 (d, J = 7.94 Hz, 1H), 9.06 (s, 1H), 8.40 (d, J = 5.49 Hz, 1H), 7.93-7.84 (m, 2H), 7.62 (br s, 1H), 7.32 (d, J = 7.94 Hz, 1H), 7.21 (d, J = 4.88 Hz, 1H), 5.26 (t, J = 8.85 Hz, 1H), 4.05 (t, J = 7.33 Hz, 2H), 3.17 (s, 4H), 2.97-2.91 (m, 2H), 2.91-2.83 (m, 2H), 2.54-2.51 (m, 2H), 1.99-1.89 (m, 3H), 1.88-1.68 (m, 2H), 1.46 (s, 9H), 1.36-1.26 (m, 1H). |

-continued

| Compd No. | Chemical Name | Structure | $^1$H-NMR and MS |
|---|---|---|---|
| 153 | (R)-5-(tert-butyl)-N-(2-(2-((1-methyl-5-(trifluoromethyl)-1H-pyrazol-4-yl)amino)pyrimidin-4-yl)-6,7,8,9-tetrahydro-5H-benzo[7]annulen-5-yl)-1,2,4-oxadiazole-3-carboxamide | 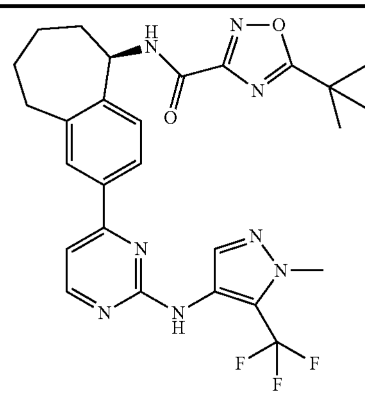 | ESI-MS (M + H)$^+$: 555.3. $^1$H NMR (500 MHz, DMSO-d$_6$) δ: 9.56 (d, J = 8.55 Hz, 1H), 8.93 (s, 1H), 8.43 (d, J = 5.49 Hz, 1H), 7.89 (s, 1H), 7.86 (dd, J = 8.2, 1.5 Hz, 1H), 7.79 (s, 1H), 7.37-7.28 (m, 2H), 5.25 (br t, J = 8.85 Hz, 1H), 3.95 (s, 3 H), 2.99-2.86 (m, 2H), 1.99-1.88 (m, 3H), 1.86-1.71 (m, 2H), 1.46 (s, 9H), 1.35-1.25 (m, 1H). |
| 154 | (R)-1-(tert-butyl)-N-(2-(2-((1-methyl-1H-pyrazol-4-yl)amino)pyridin-4-yl)-6,7,8,9-tetrahydro-5H-benzo[7]annulen-5-yl)-1H-1,2,3-triazole-4-carboxamide | 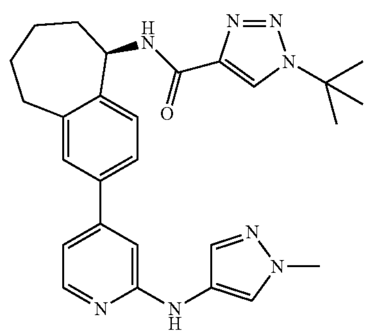 [SMILES: Cn1cc(Nc2cc(-c3ccc4c(c3)CCCC[C@H]4NC(=O)c3cn(C(C)(C)C)nn3)ccn2)cn1] | ESI-MS (M + H)$^+$: 485.3. $^1$H NMR (400 MHz, CDCl$_3$) δ: 8.17-8.15 (m, 1H), 7.66 (d, J = 8.4 Hz, 1H), 7.61 (s, 1H), 7.47 (s, 1H), 7.37-7.30 (m, 3H), 6.87-6.86 (m, 1H), 6.70 (s, 1H), 6.13-6.09 (m, 1H), 5.41-5.38 (m, 1H), 3.91 (s, 3H), 3.03-2.92 (m, 2H), 2.03-1.93 (m, 4H), 1.87-1.84 (m, 1H), 1.71 (s, 9H), 1.63-1.55 (m, 1H). |

*indicates that the stereochemistry at the chiral center is arbitrarily assigned.
**indicates that the relative stereochemistry at the two chiral centers for the racemic mixture is arbitrarily assigned, i.e., the trans- or cis-configuration at one chiral center relative to the other chiral center is arbitrarily assigned.

Example 155. In Vitro BTK Kinase Assay: BTK-POLYGAT-LS ASSAY

The purpose of the BTK in vitro assay is to determine compound potency against BTK through the measurement of IC$_{50}$. Compound inhibition is measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). For a typical assay, a 24 pL aliquot of a ATP/peptide master mix (final concentration; ATP 10 μM, polyGAT 100 nM) in kinase buffer (10 mM Tris-HCl pH 7.5, 10 mM MgCl2, 200 μM Na$_3$PO$_4$, 5 mM DTT, 0.01% Triton X-100, and 0.2 mg/ml casein) is added to each well. Next, 1 pL of a 4-fold, 40× compound titration in 100% DMSO solvent is added, followed by adding 15 uL of BTK enzyme mix in 1× kinase buffer (with a final concentration of 0.25 nM). The assay is incubated for 30 minutes before being stopped with 28 pL of a 50 mM EDTA solution. Aliquots (5 uL) of the kinase reaction are transferred to a low volume white 384 well plate (Corning 3674), and 5 pL of a 2× detection buffer (Invitrogen PV3574, with 4 nM Tb-PY20 antibody, Invitrogen PV3552) is added. The plate is covered and incubated for 45 minutes at room temperature. Time resolved fluorescence (TRF) on Molecular Devices M5 (332 nm excitation; 488 nm emission; 518 nm fluorescein emission) is measured. IC$_{50}$ values are calculated using a four parameter fit with 100% enzyme activity determined from the DMSO control and 0% activity from the EDTA control.

Table 1 shows the activity of selected compounds of this invention in the in vitro Btk kinase assay, wherein each compound number corresponds to the compound numbering set forth in Examples 1-154 herein. "†" represents an IC$_{50}$ of equal to or less than 1000 nM and greater than 10 nM; "††" represents an IC$_{50}$ of equal to or less than 10 nM and greater than 1 nM; and "†††" represents an IC$_{50}$ of equal to or less than 1 nM.

TABLE 1

| IC$_{50}$ (nM) | Compound No. |
|---|---|
| †††  | 1, 2, 3, 4, 5, 6, 7, 8, 9, 10, 11, 12, 13, 14a, 15, 16, 17, 18, 19, 20, 21, 22, 23, 24a, 25, 26a, 26b, 27, 28, 29, 30, 31, 32, 33, 34, 35, 36a, 37, 38, 39, 40, 41, 42a, 44, 54, 55, 58, 59, 68, 70, 71, 72, 73, 75, 76, 77, 78, 79, 80, 81, 82, 83, 84, 86, 87, 88, 89a, 90, 91, 92, 93, 96, 97, 98, 99, 101, 102, 105, 106, 107, 111, 112, 114, 117, 119a, 116, 121, 122, 124, 125, 127, 135, 149, 150, 152, 153, |
| †† | 43, 45, 46, 47, 49, 48, 50, 51, 52, 53, 56, 57, 60, 61, 62, 63, 64, 65, 66, 67, 69, 74, 94, 95, 100, 103, 110, 113, 115, 123, 126, 128, 129, 130, 131, |
| † | 14b, 24b, 36b, 85, 89b, 108, 109, 132, 133, 134, 136, 137, 138, 139, 141 |

Example 156. In Vitro PD Assay in Human Whole Blood

Human heparinized venous blood was purchased from Bioreclamation, Inc. or SeraCare Life Sciences and shipped overnight. Whole blood was aliquoted into 96-well plate and "spiked" with serial dilutions of test compound in DMSO or with DMSO without drug. The final concentration of DMSO in all wells was 0.1%. The plate was incubated at 37° C. for 30 min. Lysis buffer containing protease and phosphatase inhibitors was added to the drug-containing samples and one of the DMSO-only samples (+PPi, high control), while lysis buffer containing protease inhibitors was added to the other DMSO-only samples (-PPi, low control). All of the lysed whole blood samples were subjected to the total BTK capture and phosphotyrosine detection method described in US20160311802, incorporated herein by reference. ECL values were graphed in Prism and a best-fit curve with restrictions on the maximum and minimum defined by the +PPi high and PPi low controls was used to estimate the test compound concentration that results in 50% inhibition of ECL signal by interpolation.

Table 2 shows the activity of selected compounds of this invention in the pBTK assay, wherein each compound number corresponds to the compound numbering set forth in Examples 1-154 described herein. "†" represents an IC$_{50}$ of equal to or less than 10,000 nM but greater than 500 nM, "††" represents an IC$_{50}$ of equal to or less than 500 nM but greater than 100 nM; and "†††" represents an IC$_{50}$ of equal to or less than 100 nM.

What is claimed is:

1. A method of treating multiple sclerosis in a subject comprising administering to the subject an effective amount of a compound represented by the following formula:

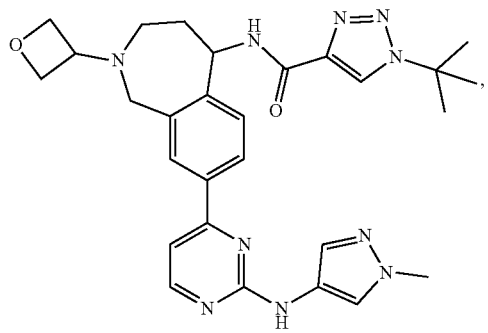 [SMILES: Cn1cc(Nc2nccc(-c3ccc4c(c3)CN(C3COC3)CCC4NC(=O)c3cn(C(C)(C)C)nn3)n2)cn1]

or a pharmaceutically acceptable salt thereof.

2. A method of treating multiple sclerosis in a subject comprising administering to the subject an effective amount of a compound represented by the following formula:

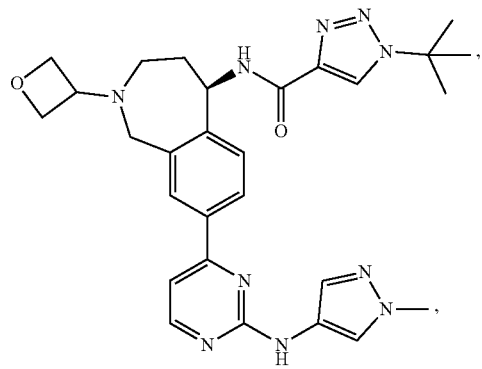 [SMILES: Cn1cc(Nc2nccc(-c3ccc4c(c3)CN(C3COC3)CC[C@H]4NC(=O)c3cn(C(C)(C)C)nn3)n2)cn1]

or a pharmaceutically acceptable salt thereof.

TABLE 2

| IC$_{50}$ (nM) | Compound No. |
|---|---|
| ††† | 2, 3, 4, 5, 6, 7, 8, 9, 10, 11, 12, 13, 14a, 15, 16, 17, 18, 19, 20, 21, 22, 23, 24a, 25, 26a, 26b, 27, 28, 29, 30, 31, 32, 33, 34, 35, 36a, 37, 39, 40, 41, 42a, 44, 56, 58, 60, 62, 63, 64, 65, 67, 68, 71, 72, 73, 75, 76, 77, 78, 79, 80, 81, 82, 83, 84, 86, 87, 88, 89a, 90, 91, 92, 93, 94, 95, 96, 97, 98, 99, 100, 101, 104, 105, 106, 107, 110, 111, 112, 113, 114, 119a, 120, 121, 122, 123, 124, 125, 126, 152, |
| †† | 38, 42b, 45, 46, 47, 48, 49, 51, 52, 53, 57, 59, 61, 66, 69, 70, 74, 102, 103, 115, 117, 118a, 118b, 127, 128, 129, 130, 131, 132 |
| † | 14b, 24b, 36b, 43, 50, 85, 89b, 108, 109, 116, 133, 134, 135, 136, 137, 138, 139, 140, 141, 153, |

3. The method of claim 2, wherein the compound is Crystalline Form A of the compound.

4. The method of claim 2, wherein the compound is Crystalline Form G of the compound.

5. The method of claim 1, wherein the subject is a human.

6. The method of claim 2, wherein the subject is a human.

* * * * *